US007569683B2

(12) United States Patent
Hansen et al.

(10) Patent No.: US 7,569,683 B2
(45) Date of Patent: Aug. 4, 2009

(54) **USPA2 NUCLEIC ACID OF *MORAXELLA CATARRHALIS***

(75) Inventors: Eric J. Hansen, Plano, TX (US); Christoph Aebi, Gasel (CH); Leslie D. Cope, Mesquite, TX (US); Isobel Maciver, Cottage Grove, WI (US); Michael J. Fiske, Rochester, NY (US); Ross A. Fredenburg, Rochester, NY (US)

(73) Assignees: Board of Regents, The University of Texas System, Austin, TX (US); Wyeth Holding Corporation, Wayne, NJ (US)

( * ) Notice: Subject to any disclaimer, the term of this patent is extended or adjusted under 35 U.S.C. 154(b) by 0 days.

(21) Appl. No.: 12/044,818

(22) Filed: Mar. 7, 2008

(65) Prior Publication Data

US 2009/0137788 A1 May 28, 2009

Related U.S. Application Data

(60) Division of application No. 10/872,769, filed on Jun. 21, 2004, now Pat. No. 7,344,724, which is a division of application No. 09/336,447, filed on Jun. 21, 1999, now Pat. No. 6,310,190, which is a continuation of application No. PCT/US97/23930, filed on Dec. 19, 1997.

(60) Provisional application No. 60/033,598, filed on Dec. 20, 1996.

(51) Int. Cl.
*C07H 21/04* (2006.01)

(52) U.S. Cl. .................. 536/23.7; 536/23.1; 536/24.3

(58) Field of Classification Search .................. None
See application file for complete search history.

(56) References Cited

U.S. PATENT DOCUMENTS

| 4,554,101 A | 11/1985 | Hopp | 530/324 |
|---|---|---|---|
| 6,335,018 B1 | 1/2002 | Sasaki et al. | 424/251.1 |

FOREIGN PATENT DOCUMENTS

| WO | WO 93/03761 | 3/1993 |
|---|---|---|
| WO | WO 96/34960 | 11/1996 |

OTHER PUBLICATIONS

Aebi et al., "A protective epitope of *Moraxella catarrhalis* is encoded by two different genes," *Infection and Immunity*, 65:4367-4377, 1997.
Chen et al., "Evaluation of purified UspA from *Moraxella catarrhalis* as vaccine in a murine model after active immunization," *Infection and Immunity*, 64:1900-1905, 1996.
Chen et al., *Abstracts of the General Meeting of the ASM.*, 95(O):290, May 21-25, 1995.
Chi et al., "Antibody response to P-protein in patients with *Moraxella catarrhalis* infections," *Amer. J. Med.*, 88(Supp5A):25s-27s, 1990.
Eliasson, "A protein antigen characteristic of *Moraxella catarrhalis*: serological indentification of the genus," *Acta Path. Microbiol. Scand.*, 88:281-286, 1980.
Helminen et al., "A large antigenically conserved protein on the surface of *Moraxella catarrhalis* is a target for protective antibodies," *J. of Infectious Diseases*, 170:867-872, 1994.
Helminen et al., "A major outer membrane protein of *Moraxella catarrhalis* is a target for antibodies that enhance pulmonary clearance of the pathogen in an animal model," *Infect. Immun.*, 61:2003-2010, 1993.
Klingman and Murphy, "Purification and characterization of a high-molecular-weight outer membrane protein of *Moraxella (Branhamella) catarrhali*," *Infection and Immunity*, 62:1150-1155, 1994.
Murphy et al., "Somatic antigens of *Haemophilus influenzae* of vaccine components," *Pediatric Infect. Dis. J.*, 8:S66-S68, 1989.
Office Communication issued in European Patent Application No. EP 97/953461, dated Apr. 28, 2006.
Vandermeid et al., *Abstracts of the General Meeting of the ASM.*, 90(O):290, May 19-23, 1996.
Yamanaka et al., "Antibody response to outer membrance protein of nontypeable *Haemophilus* influenzae in otitis-prone children," *J. Pediatrics.*, 122(2):212-218, 1993.

*Primary Examiner*—Jennifer E Graser
(74) *Attorney, Agent, or Firm*—Fulbright & Jaworski, LLP

(57) ABSTRACT

The present invention discloses the existence of two novel proteins UspA1 and UspA2, and their respective genes uspA1 and uspA2. Each protein encompasses a region that is conserved between the two proteins and comprises an epitope that is recognized by the MAb 17C7. One or more than one of these species may aggregate to form the very high molecular weight form (i.e. greater than 200 kDa) of the UspA antigen. Compositions and both diagnostic and therapeutic methods for the treatment and study of *M. catarrhalis* are disclosed.

2 Claims, 17 Drawing Sheets

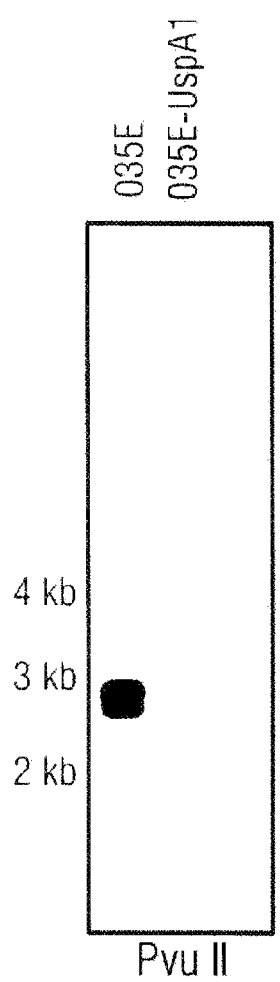 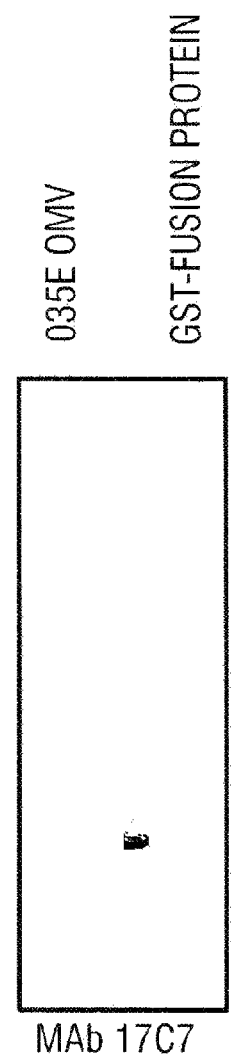
FIG. 3
FIG. 4

```
SEQUENCE LISTING

<160> NUMBER OF SEQ ID NOS: 98

<210> SEQ ID NO 1
<211> LENGTH: 831
<212> TYPE: PRT
<213> ORGANISM: Moraxella catarrhalis

<400> SEQUENCE: 1

Met Asn Lys Ile Tyr Lys Val Lys Lys Asn Ala Ala Gly His Leu Val
  1               5                  10                  15

Ala Cys Ser Glu Phe Ala Lys Gly His Thr Lys Lys Ala Val Leu Gly
             20                  25                  30

Ser Leu Leu Ile Val Gly Ala Leu Gly Met Ala Thr Thr Ala Ser Ala
         35                  40                  45
```

-continued

```
Gln Ala Thr Asn Ser Lys Gly Thr Gly Ala His Ile Gly Val Asn Asn
            50                  55                  60

Asn Asn Glu Ala Pro Gly Ser Tyr Ser Phe Ile Gly Ser Gly Gly Tyr
 65                  70                  75                  80

Asn Lys Ala Asp Arg Tyr Ser Ala Ile Gly Gly Leu Phe Asn Lys
                85                  90                  95

Ala Thr Asn Glu Tyr Ser Thr Ile Val Gly Gly Tyr Asn Lys Ala
            100                 105                 110

Glu Gly Arg Tyr Ser Thr Ile Gly Gly Ser Asn Asn Glu Ala Thr
            115                 120                 125

Asn Glu Tyr Ser Thr Ile Val Gly Gly Asp Asp Asn Lys Ala Thr Gly
130                 135                 140

Arg Tyr Ser Thr Ile Gly Gly Gly Asp Asn Asn Thr Arg Glu Gly Glu
145                 150                 155                 160

Tyr Ser Thr Val Ala Gly Gly Lys Asn Asn Gln Ala Thr Gly Thr Gly
                165                 170                 175

Ser Phe Ala Ala Gly Val Glu Asn Gln Ala Asn Ala Glu Asn Ala Val
            180                 185                 190

Ala Val Gly Lys Lys Asn Ile Ile Glu Gly Glu Asn Ser Val Ala Ile
            195                 200                 205

Gly Ser Glu Asn Thr Val Lys Thr Glu His Lys Asn Val Phe Ile Leu
            210                 215                 220

Gly Ser Gly Thr Thr Gly Val Thr Ser Asn Ser Val Leu Leu Gly Asn
225                 230                 235                 240

Glu Thr Ala Gly Lys Gln Ala Thr Thr Val Lys Asn Ala Glu Val Gly
                245                 250                 255

Gly Leu Ser Leu Thr Gly Phe Ala Gly Glu Ser Lys Ala Glu Asn Gly
            260                 265                 270

Val Val Ser Val Gly Ser Glu Gly Glu Arg Gln Ile Val Asn Val
            275                 280                 285

Gly Ala Gly Gln Ile Ser Asp Thr Ser Thr Asp Ala Val Asn Gly Ser
290                 295                 300

Gln Leu His Ala Leu Ala Thr Val Val Asp Asp Asn Gln Tyr Asp Ile
305                 310                 315                 320

Val Asn Asn Arg Ala Asp Ile Leu Asn Asn Gln Asp Asp Ile Lys Asp
                325                 330                 335

Leu Gln Lys Glu Val Lys Gly Leu Asp Asn Glu Val Gly Glu Leu Ser
            340                 345                 350

Arg Asp Ile Asn Ser Leu His Asp Val Thr Asp Asn Gln Gln Asp Asp
            355                 360                 365

Ile Lys Glu Leu Lys Arg Gly Val Lys Glu Leu Asp Asn Glu Val Gly
370                 375                 380

Val Leu Ser Arg Asp Ile Asn Ser Leu His Asp Asp Val Ala Asp Asn
385                 390                 395                 400

Gln Asp Asp Ile Ala Lys Asn Lys Ala Asp Ile Lys Gly Leu Asn Lys
                405                 410                 415

Glu Val Lys Glu Leu Asp Lys Glu Val Gly Val Leu Ser Arg Asp Ile
            420                 425                 430

Gly Ser Leu His Asp Asp Val Ala Thr Asn Gln Ala Asp Ile Ala Lys
            435                 440                 445

Asn Gln Ala Asp Ile Lys Thr Leu Glu Asn Asn Val Glu Glu Glu Leu
450                 455                 460
```

Leu Asn Leu Ser Gly Arg Leu Leu Asp Gln Lys Ala Asp Ile Asp Asn
465                 470                 475                 480

Asn Ile Asn Asn Ile Tyr Glu Leu Ala Gln Gln Asp Gln His Ser
        485                 490                 495

Ser Asp Ile Lys Thr Leu Lys Asn Asn Val Glu Glu Gly Leu Leu Asp
    500                 505                 510

Leu Ser Gly Arg Leu Ile Asp Gln Lys Ala Asp Ile Ala Lys Asn Gln
    515                 520                 525

Ala Asp Ile Ala Gln Asn Gln Thr Asp Ile Gln Asp Leu Ala Ala Tyr
    530                 535                 540

Asn Glu Leu Gln Asp Gln Tyr Ala Gln Lys Gln Thr Glu Ala Ile Asp
545                 550                 555                 560

Ala Leu Asn Lys Ala Ser Ser Glu Asn Thr Gln Asn Ile Ala Lys Asn
                565                 570                 575

Gln Ala Asp Ile Ala Asn Asn Ile Asn Asn Ile Tyr Glu Leu Ala Gln
            580                 585                 590

Gln Gln Asp Gln His Ser Ser Asp Ile Lys Thr Leu Ala Lys Val Ser
        595                 600                 605

Ala Ala Asn Thr Asp Arg Ile Ala Lys Asn Lys Ala Glu Ala Asp Ala
    610                 615                 620

Ser Phe Glu Thr Leu Thr Lys Asn Gln Asn Thr Leu Ile Glu Gln Gly
625                 630                 635                 640

Glu Ala Leu Val Glu Gln Asn Lys Ala Ile Asn Gln Glu Leu Glu Gly
                645                 650                 655

Phe Ala Ala His Ala Asp Ile Gln Asp Lys Gln Ile Leu Gln Asn Gln
            660                 665                 670

Ala Asp Ile Thr Thr Asn Lys Thr Ala Ile Glu Gln Asn Ile Asn Arg
    675                 680                 685

Thr Val Ala Asn Gly Phe Glu Ile Glu Lys Asn Lys Ala Gly Ile Ala
690                 695                 700

Thr Asn Lys Gln Glu Leu Ile Leu Gln Asn Asp Arg Leu Asn Arg Ile
705                 710                 715                 720

Asn Glu Thr Asn Asn Arg Gln Asp Gln Lys Ile Asp Gln Leu Gly Tyr
                725                 730                 735

Ala Leu Lys Glu Gln Gly Gln His Phe Asn Asn Arg Ile Ser Ala Val
            740                 745                 750

Glu Arg Gln Thr Ala Gly Gly Ile Ala Asn Ala Ile Ala Ile Ala Thr
    755                 760                 765

Leu Pro Ser Pro Ser Arg Ala Gly Glu His His Val Leu Phe Gly Ser
    770                 775                 780

Gly Tyr His Asn Gly Gln Ala Ala Val Ser Leu Gly Ala Ala Gly Leu
785                 790                 795                 800

Ser Asp Thr Gly Lys Ser Thr Tyr Lys Ile Gly Leu Ser Trp Ser Asp
                805                 810                 815

Ala Gly Gly Leu Ser Gly Gly Val Gly Gly Ser Tyr Arg Trp Lys
            820                 825                 830

<210> SEQ ID NO 2
<211> LENGTH: 3349
<212> TYPE: DNA
<213> ORGANISM: Moraxella catarrhalis

<400> SEQUENCE: 2
atcagcatgt gagcaaatga ctggcgtaaa tgactgatga gtgtctattt aatgaaagat          60

-continued

```
atcaatatat aaaagttgac tatagcgatg caatacagta aaatttgtta cggctaaaca      120
taacgacggt ccaagatggc ggatatcgcc atttaccaac ctgataatca gtttgatagc      180
cattagcgat ggcatcaagt tgtgttgttg tattgtcata taaacggtaa atttggtttg      240
gtggatgccc catctgattt accgtccccc taataagtga gggggggggg gagacccag       300 tcatttatta ggagactaag atgaataaaa tttataaagt gaagaaaaat gccgcaggtc      360
acttggtggc atgttctgaa tttgccaaag gtcataccaa aaaggcagtt ttgggcagtt      420
tattgattgt tggggcgttg ggcatggcaa cgacggcgtc tgcacaagca accaacagca      480
aaggcacagg cgcgcacatc ggtgttaaca ataacaacga agcccccaggc agttactctt     540 tcatcggtag tggcggttat aacaaagccg acagatactc tgccatcggt ggtggccttt      600
ttaacaaagc cacaaacgag tactctacca tcgttggtgg cggttataac aaagccgaag      660
gcagatactc taccatcggt ggtggcagta acaacgaagc cacaaacgag tactctacca      720
tcgttggtgg cgatgacaac aaagccacag gcagatactc taccatcggt ggtggcgata      780
acaacacacg cgaaggcgaa tactcaaccg tcgcagggg caagaataac caagccacag       840
gtacaggttc atttgccgca ggtgtagaga accaagccaa tgccgaaaac gccgtcgccg      900
tgggtaaaaa gaacattatc gaaggtgaaa actcagtagc catcggctct gagaataccg      960
ttaaaacaga acacaaaaat gtctttattc ttggctctgg cacaacaggt gtaacgagta     1020
actcagtgct actgggtaat gagaccgctg gcaaacaggc gaccactgtt aagaatgccg     1080
aagtgggtgg tctaagccta acaggatttg caggggagtc aaaagctgaa acggcgtag      1140 tttctgtggg tagtgaaggc ggtgagcgtc aaatcgttaa tgttggtgca ggtcagatca     1200
gtgacacctc aacagatgct gttaatggct cacagctaca tgctttggcc acagttgttg     1260
atgacaacca atatgacatt gttaacaacc gagctgacat tcttaacaac caagatgata     1320
tcaaagatct tcagaaggag gtgaaaggtc ttgataatga ggtgggtgaa ttaagccgag     1380
acattaattc acttcatgat gttactgaca accaacaaga tgacatcaaa gagcttaaga     1440 gggggggtaaa agagcttgat aatgaggtgg gtgtattaag ccgagacatt aattcacttc    1500
atgatgatgt tgctgacaac caagatgaca ttgctaaaaa caaagctgac atcaaaggtc     1560
ttaataagga ggtgaaagag cttgataagg aggtgggtgt attaagccga gacattggtt     1620
cacttcatga tgatgttgcc accaaccaag ctgacattgc taaaaaccaa gcggatatca     1680
aaacacttga aaacaatgtc gaagaagaat tattaaatct aagcggtcgc ctgcttgatc     1740
agaaagcgga tattgataat aacatcaaca atatctatga gctggcacaa cagcaagatc     1800
agcatagctc tgatatcaaa acacttaaaa acaatgtcga agaaggttta ttggatctaa     1860
gcggtcgcct cattgatcaa aaagcagata ttgctaaaaa ccaagctgac attgctcaaa     1920
accaaacaga catccaagat ctggccgctt acaatgagct acaagaccag tatgctcaaa     1980
agcaaaccga agcgattgac gctctaaata agcaagctc tgagaataca caaacattg      2040 ctaaaaacca agcggatatt gctaataaca tcaacaatat ctatgagctg cacaacagc      2100 aagatcagca tagctctgat atcaaaacct ggcaaaagt aagtgctgcc aatactgatc     2160
gtattgctaa aaacaaagct gaagctgatg caagttttga acgctcacc aaaaatcaaa      2220 atactttgat tgagcaaggt gaagcattgg ttgagcaaaa taagccatc aatcaagagc      2280 ttgaagggtt tgcggctcat gcagatattc aagataagca aattttacaa aaccaagctg     2340
atatcactac caataagacc gctattgaac aaaatatcaa tagaactgtt gccaatgggt     2400
ttgagattga gaaaaataaa gctggtattg ctaccaataa gcaagagctt attcttcaaa     2460
```

```
atgatcgatt aaatcgaatt aatgagacaa ataatcgtca ggatcagaag attgatcaat    2520
taggttatgc actaaaagag cagggtcagc attttaataa tcgtattagt gctgttgagc    2580
gtcaaacagc tggaggtatt gcaaatgcta tcgcaattgc aactttacca tcgcccagta    2640
gagcaggtga gcatcatgtc ttatttggtt caggttatca caatggtcaa gctgcggtat    2700
cattgggcgc ggctgggtta agtgatacag gaaaatcaac ttataagatt ggtctaagct    2760
ggtcagatgc aggtggatta tctggtggtg ttggtggcag ttaccgctgg aaataaagcc    2820
taaatttaac tgctgtgtca aaaaatatgg tctgtataaa cagaccatat ttttatccaa    2880
aaaaattatc ttaactttta taagtattaa taagccaaag ctgtaataat aagagatgtt    2940
gaaataagag atgttaaagc tgctagacaa tcggcttgcg acgataaaat aagatacctg    3000
gaatggacag ccccaaaacc aatgctgaga tgataaaaat cgcctcaaaa aaatgacgca    3060
tcataacgat aaataaatcc atatcaaatc caaatagcc aatttgtacc atgctaacca    3120
tggctttata ggcagcgatt cccggcatca tacaaatcaa gctaggtaca atcaaggctt    3180
taggtggcag gccatgacgc tgagcaaaat gtacacccaa aaagctaccc gccatcgccc    3240
caaagaatgt tgccacaacc aaatgcacac caaaaattac catcacttgt tttaaaccaa    3300
aaccaagtgg tgttaccatc atgcaatgca tgatgtattg ctttgtcaa                3349

<210> SEQ ID NO 3
<211> LENGTH: 573
<212> TYPE: PRT
<213> ORGANISM: Moraxella catarrhalis

<400> SEQUENCE: 3

Met Lys Leu Leu Pro Leu Lys Ile Ala Val Thr Ser Ala Met Ile Val
 1               5                  10                  15

Gly Leu Gly Ala Thr Ser Thr Val Asn Ala Gln Val Val Glu Gln Phe
            20                  25                  30

Phe Pro Asn Ile Phe Phe Asn Glu Asn His Asp Glu Leu Asp Asp Ala
        35                  40                  45

Tyr His Asn Met Ile Leu Gly Asp Thr Ala Ile Val Ser Asn Ser Gln
    50                  55                  60

Asp Asn Ser Thr Gln Leu Lys Phe Tyr Ser Asn Asp Glu Asp Ser Val
65                  70                  75                  80

Pro Asp Ser Leu Leu Phe Ser Lys Leu Leu His Glu Gln Gln Leu Asn
                85                  90                  95

Gly Phe Lys Ala Gly Asp Thr Ile Ile Pro Leu Asp Lys Asp Gly Lys
           100                 105                 110

Pro Val Tyr Thr Lys Asp Thr Arg Thr Lys Asp Gly Lys Val Glu Thr
       115                 120                 125

Val Tyr Ser Val Thr Thr Lys Ile Ala Thr Gln Asp Asp Val Glu Gln
   130                 135                 140

Ser Ala Tyr Ser Arg Gly Ile Gln Gly Asp Ile Asp Asp Leu Tyr Asp
145                 150                 155                 160

Ile Asn Arg Glu Val Asn Glu Tyr Leu Lys Ala Thr His Asp Tyr Asn
                165                 170                 175

Glu Arg Gln Thr Glu Ala Ile Asp Ala Leu Asn Lys Ala Ser Ser Ala
            180                 185                 190

Asn Thr Asp Arg Ile Asp Thr Ala Glu Glu Arg Ile Asp Lys Asn Glu
        195                 200                 205

Tyr Asp Ile Lys Ala Leu Glu Ser Asn Val Glu Glu Gly Leu Leu Glu
```

-continued

```
Leu Ser Gly His Leu Ile Asp Gln Lys Ala Asp Leu Thr Lys Asp Ile
225                 230                 235                 240

Lys Ala Leu Glu Ser Asn Val Glu Glu Gly Leu Leu Glu Leu Ser Gly
            245                 250                 255

His Leu Ile Asp Gln Lys Ala Asp Leu Thr Lys Asp Ile Lys Ala Leu
        260                 265                 270

Glu Ser Asn Val Glu Glu Gly Leu Leu Asp Leu Ser Gly Arg Leu Leu
    275                 280                 285

Asp Gln Lys Ala Asp Ile Ala Lys Asn Gln Ala Asp Ile Ala Gln Asn
290                 295                 300

Gln Thr Asp Ile Gln Asp Leu Ala Ala Tyr Asn Glu Leu Gln Asp Ala
305                 310                 315                 320

Tyr Ala Lys Gln Gln Thr Glu Ala Ile Asp Ala Leu Asn Lys Ala Ser
            325                 330                 335

Ser Glu Asn Thr Gln Asn Ile Ala Lys Asn Gln Ala Asp Ile Ala Asn
        340                 345                 350

Asn Ile Asn Asn Ile Tyr Glu Leu Ala Gln Gln Gln Asp Gln His Ser
    355                 360                 365

Ser Asp Ile Lys Thr Leu Ala Lys Ala Ser Ala Ala Asn Thr Asp Arg
370                 375                 380

Ile Ala Lys Asn Lys Ala Asp Ala Asp Ala Ser Phe Glu Thr Leu Thr
385                 390                 395                 400

Lys Asn Gln Asn Thr Leu Ile Glu Lys Asp Lys Glu His Asp Lys Leu
            405                 410                 415

Ile Thr Ala Asn Lys Thr Ala Ile Asp Ala Asn Lys Ala Ser Ala Asp
        420                 425                 430

Thr Lys Phe Ala Ala Thr Ala Asp Ala Ile Thr Lys Asn Gly Asn Ala
    435                 440                 445

Ile Thr Lys Asn Ala Lys Ser Ile Thr Asp Leu Gly Thr Lys Val Asp
450                 455                 460

Gly Phe Asp Gly Arg Val Thr Ala Leu Asp Thr Lys Val Asn Ala Leu
465                 470                 475                 480

Asp Thr Lys Val Asn Ala Phe Asp Gly Arg Ile Thr Ala Leu Asp Ser
            485                 490                 495

Lys Val Glu Asn Gly Met Ala Ala Gln Ala Ala Leu Ser Gly Leu Phe
        500                 505                 510

Gln Pro Tyr Ser Val Gly Lys Phe Asn Ala Thr Ala Ala Leu Gly Gly
    515                 520                 525

Tyr Gly Ser Lys Ser Ala Val Ala Ile Gly Ala Gly Tyr Arg Val Asn
530                 535                 540

Pro Asn Leu Ala Phe Lys Ala Gly Ala Ala Ile Asn Thr Ser Gly Asn
545                 550                 555                 560

Lys Lys Gly Ser Tyr Asn Ile Gly Val Asn Tyr Glu Phe
                565                 570
```

<210> SEQ ID NO 4
<211> LENGTH: 2596
<212> TYPE: DNA
<213> ORGANISM: Moraxella catarrhalis

<400> SEQUENCE: 4

```
ctggtggtcg caggggggcgt ctctgccaat cagtacacta cgccgcaccc tgaccgaaac      60
gctccgccaa atcgatgcgt cggtgtacca tgccccgacc gagctatgca cggataatgg     120
```

```
tgcgatgatc gcctatgctg gcttttgtcg gctaatccgt ggacagtcgg atgacttggt    180
ggttcgctgc attccccgat gggatatgac gacgcttggc gtatctgctc ataaatagcc    240
acatcaatca taccaaccaa atcataccaa ccaaatcgta caaacggttg atacatgcca    300
aaaataccat attgaaagta gggtttgggt attatttatg taacttatat ctaatttggt    360
gttgatactt tgataaagcc ttgctatact gtaacctaaa tggatatgat agagattttt    420
ccatttatgc cagcaaaaga gatagataga tagatagata gatagataga tagatagata    480
gatagataga tagatagata aaactctgtc ttttatctgt ccgctgatgc tttctgcctg    540
ccaccgatga tatcatttat ctgcttttta ggcatcagtt atttcaccgt gatgactgat    600
gtgatgactt aactaccaaa agagagtgct aaatgaaaac catgaaactt ctcccctaa     660
aaatcgctgt aaccagtgcc atgattgttg cttgggtgc gacatctact gtgaatgcac      720
aagtagtgga acagttttt ccgaatatct ttttaatga aaaccatgat gaattagatg       780
atgcatacca taatatgatc ttaggggata ctgcgattgt atctaattca caagataata    840
gtactcaatt gaaattttat tctaatgatg aagattcagt tcctgacagc ctactcttta    900
gtaaactact tcatgagcag caacttaatg gttttaaagc aggtgacaca atcattcctt    960
tggataagga tggcaaacct gtttatacaa aggacacgag aacaaaggat ggtaaagtag   1020
aaacagttta ttcggtcacc accaaaatcg ctacccaaga tgatgttgaa caaagtgcat   1080
attcacgagg cattcaaggt gatatcgatg atctgtatga cattaaccgt gaagtcaatg   1140
aatacttaaa agcaacacat gattataatg aaagacaaac tgaagcaatt gacgctctaa   1200
acaaagcaag ctctgcgaat actgatcgta ttgatactgc tgaagagcgt atcgataaaa   1260
acgaatatga cattaaagca cttgaaagca atgtcgaaga aggtttgttg gagctaagcg   1320
gtcacctcat tgatcaaaaa gcagatctta caaaagacat caaagcactt gaaagcaatg   1380
tcgaagaagg tttgttggag ctaagcggtc acctcattga tcaaaaagca gatcttacaa   1440
aagacatcaa agcacttgaa agcaatgtcg aagaaggttt gttggatcta agcggtcgtc   1500
tgcttgatca aaaagcagat atcgctaaaa accaagctga cattgctcaa aaccaaacag   1560
acatccaaga tctagccgct tacaacgagc tacaagatgc ctatgccaaa cagcaaaccg   1620
aagcgattga cgctctaaac aaagcaagct ctgagaatac acaaaacatt gctaaaaacc   1680
aagcggatat tgctaataac atcaacaata tctatgagct ggcacaacag caagatcagc   1740
atagctctga tatcaaaacc ttggcaaaag caagtgctgc caatactgat cgtattgcta   1800
aaacaaagc cgatgctgat gcaagttttg aaacgctcac caaaaatcaa aatactttga   1860
ttgaaaaaga taaagagcat gacaaattaa ttactgcaaa caaaactgcg attgatgcca   1920
ataaagcatc tgcggatacc aagtttgcag cgacagcaga cgccattacc aaaaatggaa   1980
atgctatcac taaaaacgca aaatctatca ctgatttggg tactaaagtg gatggttttg   2040
acggtcgtgt aactgcatta gacaccaaag tcaatgcctt agacaccaaa gtcaatgcct   2100
ttgatggtcg tatcacagct ttagacagta aagttgaaaa cggtatggct gcccaagctg   2160
ccctaagtgg tctattccag ccttatagcg ttggtaagtt taatgcgacc gctgcacttg   2220
gtggctatgg ctcaaaatct gcggttgcta tcggtgctgg ctatcgtgtg aatccaaatc   2280
tggcgtttaa agctggtgcg gcgattaata ccagtggtaa taaaaaaggc tcttataaca   2340
tcggtgtgaa ttcgagttt taattgtcta tcatcaccaa aaaaaagcag tcagtttact    2400
ggctgctttt ttatgggttt ttgtggcttt tggttgtgag tgatggataa aagcttatca   2460
```

```
agcgattgat gaatatcaat aaatgattgg taaatatcaa taaagcggtt tagggttttt    2520
ggatatcttt taataagttt aaaaacccct gcataaaata aagctgggca tcagagctgc    2580
gagtagcggc atacag                                                    2596

<210> SEQ ID NO 5
<211> LENGTH: 892
<212> TYPE: PRT
<213> ORGANISM: Moraxella catarrhalis

<400> SEQUENCE: 5

Met Asn Lys Ile Tyr Lys Val Lys Lys Asn Ala Ala Gly His Leu Val
  1               5                  10                  15

Ala Cys Ser Glu Phe Ala Lys Gly His Thr Lys Lys Ala Val Leu Gly
                 20                  25                  30

Ser Leu Leu Ile Val Gly Ala Leu Gly Met Ala Thr Thr Ala Ser Ala
             35                  40                  45

Gln Ala Thr Lys Gly Thr Gly Lys His Val Val Asp Asn Lys Asp Asn
         50                  55                  60

Lys Ala Lys Gly Asp Tyr Ser Thr Ala Ser Gly Gly Lys Asp Asn Glu
 65                  70                  75                  80

Ala Lys Gly Asn Tyr Ser Thr Val Gly Gly Asp Tyr Asn Glu Ala
                 85                  90                  95

Lys Gly Asn Tyr Ser Thr Val Gly Gly Ser Ser Asn Thr Ala Lys
                100                 105                 110

Gly Glu Lys Ser Thr Ile Gly Gly Asp Thr Asn Asp Ala Asn Gly
                115                 120                 125

Thr Tyr Ser Thr Ile Gly Gly Tyr Tyr Ser Arg Ala Ile Gly Asp
130                 135                 140

Ser Ser Thr Ile Gly Gly Tyr Tyr Asn Gln Ala Thr Gly Glu Lys
145                 150                 155                 160

Ser Thr Val Ala Gly Gly Arg Asn Asn Gln Ala Thr Gly Asn Asn Ser
                165                 170                 175

Thr Val Ala Gly Gly Ser Tyr Asn Gln Ala Thr Gly Asn Asn Ser Thr
                180                 185                 190

Val Ala Gly Gly Ser His Asn Gln Ala Thr Gly Glu Gly Ser Phe Ala
                195                 200                 205

Ala Gly Val Glu Asn Lys Ala Asn Ala Asn Asn Ala Val Ala Leu Gly
                210                 215                 220

Lys Asn Asn Thr Ile Asp Gly Asp Asn Ser Val Ala Ile Gly Ser Asn
225                 230                 235                 240

Asn Thr Ile Asp Ser Gly Lys Gln Asn Val Phe Ile Leu Gly Ser Ser
                245                 250                 255

Thr Asn Thr Thr Asn Ala Gln Ser Gly Ser Val Leu Leu Gly His Asn
                260                 265                 270

Thr Ala Gly Lys Lys Ala Thr Ala Val Ser Ser Ala Lys Val Asn Gly
                275                 280                 285

Leu Thr Leu Gly Asn Phe Ala Gly Ala Ser Lys Thr Gly Asn Gly Thr
                290                 295                 300

Val Ser Val Gly Ser Glu Asn Asn Glu Arg Gln Ile Val Asn Val Gly
305                 310                 315                 320

Ala Gly Asn Ile Ser Ala Asp Ser Thr Asp Ala Val Asn Gly Ser Gln
                325                 330                 335

Leu Tyr Ala Leu Ala Thr Ala Val Lys Ala Asp Ala Asp Glu Asn Phe
                340                 345                 350
```

```
Lys Ala Leu Thr Lys Thr Gln Asn Thr Leu Ile Glu Gln Gly Glu Ala
            355                 360                 365

Gln Asp Ala Leu Ile Ala Gln Asn Gln Thr Asp Ile Thr Ala Asn Lys
            370                 375                 380

Thr Ala Ile Glu Arg Asn Phe Asn Arg Thr Val Val Asn Gly Phe Glu
385                 390                 395                 400

Ile Glu Lys Asn Lys Ala Gly Ile Ala Lys Asn Gln Ala Asp Ile Gln
            405                 410                 415

Thr Leu Glu Asn Asn Val Gly Glu Glu Leu Leu Asn Leu Ser Gly Arg
            420                 425                 430

Leu Leu Asp Gln Lys Ala Asp Ile Asp Asn Asn Ile Asn Asn Ile Tyr
            435                 440                 445

Asp Leu Ala Gln Gln Gln Asp Gln His Ser Ser Asp Ile Lys Thr Leu
            450                 455                 460

Lys Lys Asn Val Glu Glu Gly Leu Leu Asp Leu Ser Gly Arg Leu Ile
465                 470                 475                 480

Asp Gln Lys Ala Asp Leu Thr Lys Asp Ile Lys Thr Leu Glu Asn Asn
            485                 490                 495

Val Glu Glu Gly Leu Leu Asp Leu Ser Gly Arg Leu Ile Asp Gln Lys
            500                 505                 510

Ala Asp Ile Ala Lys Asn Gln Ala Asp Ile Ala Gln Asn Gln Thr Asp
            515                 520                 525

Ile Gln Asp Leu Ala Ala Tyr Asn Glu Leu Gln Asp Gln Tyr Ala Gln
            530                 535                 540

Lys Gln Thr Glu Ala Ile Asp Ala Leu Asn Lys Ala Ser Ser Ala Asn
545                 550                 555                 560

Thr Asp Arg Ile Ala Thr Ala Glu Leu Gly Ile Ala Glu Asn Lys Lys
                565                 570                 575

Asp Ala Gln Ile Ala Lys Ala Gln Ala Asn Glu Asn Lys Asp Gly Ile
            580                 585                 590

Ala Lys Asn Gln Ala Asp Ile Gln Leu His Asp Lys Lys Ile Thr Asn
            595                 600                 605

Leu Gly Ile Leu His Ser Met Val Ala Arg Ala Val Gly Asn Asn Thr
            610                 615                 620

Gln Gly Val Ala Thr Asn Lys Ala Asp Ile Ala Lys Asn Gln Ala Asp
625                 630                 635                 640

Ile Ala Asn Asn Ile Lys Asn Ile Tyr Glu Leu Ala Gln Gln Gln Asp
                645                 650                 655

Gln His Ser Ser Asp Ile Lys Thr Leu Ala Lys Val Ser Ala Ala Asn
            660                 665                 670

Thr Asp Arg Ile Ala Lys Asn Lys Ala Glu Ala Asp Ala Ser Phe Glu
            675                 680                 685

Thr Leu Thr Lys Asn Gln Asn Thr Leu Ile Glu Gln Gly Glu Ala Leu
            690                 695                 700

Val Glu Gln Asn Lys Ala Ile Asn Gln Glu Leu Glu Gly Phe Ala Ala
705                 710                 715                 720

His Ala Asp Val Gln Asp Lys Gln Ile Leu Gln Asn Gln Ala Asp Ile
                725                 730                 735

Thr Thr Asn Lys Ala Ala Ile Glu Gln Asn Ile Asn Arg Thr Val Ala
            740                 745                 750

Asn Gly Phe Glu Ile Glu Lys Asn Lys Ala Gly Ile Ala Thr Asn Lys
            755                 760                 765
```

```
Gln Glu Leu Ile Leu Gln Asn Asp Arg Leu Asn Gln Ile Asn Glu Thr
    770                 775                 780
Asn Asn Arg Gln Asp Gln Lys Ile Asp Gln Leu Gly Tyr Ala Leu Lys
785                 790                 795                 800
Glu Gln Gly Gln His Phe Asn Asn Arg Ile Ser Ala Val Glu Arg Gln
                805                 810                 815
Thr Ala Gly Ile Ala Asn Ala Ile Ala Ile Ala Thr Leu Pro Ser
            820                 825                 830
Pro Ser Arg Ala Gly Glu His His Val Leu Phe Gly Ser Gly Tyr His
            835                 840                 845
Asn Gly Gln Ala Ala Val Ser Leu Gly Ala Ala Gly Leu Ser Asp Thr
    850                 855                 860
Gly Lys Ser Thr Tyr Lys Ile Gly Leu Ser Trp Ser Asp Ala Gly Gly
865                 870                 875                 880
Leu Ser Gly Gly Val Gly Gly Ser Tyr Arg Trp Lys
            885                 890
```

<210> SEQ ID NO 6
<211> LENGTH: 3381
<212> TYPE: DNA
<213> ORGANISM: Moraxella catarrhalis

<400> SEQUENCE: 6

```
tgtgagcaaa tgactggcgt aaatgactga tgaatgtcta tttaatgaaa gatatcaata      60
tataaaagtt gactatagcg atgcaataca gtaaaatttg ttacggctaa acataacgac     120
ggtccaagat ggcggatatc gccatttacc aacctgataa tcagtttgat agccattagc     180
gatggcatca agttgtgttg ttgtattgtc atataaacgg taaatttggt ttggtggatg     240
ccccatctga tttaccgtcc ccctaataag tgaggggggg ggagacccca gtcatttatt     300
aggagactaa gatgaacaaa atttataaag tgaaaaaaaa tgccgcaggt cacttggtgg     360
catgttctga atttgccaaa ggccatacca aaaaggcagt tttgggcagt ttattgattg     420
ttggggcatt gggcatggca acgacggcgt ctgcacaagc aaccaaaggc acaggcaagc     480
acgttgttga caataaggac aacaaagcca aaggcgatta ctctaccgcc agtggtggca     540
aggacaacga agccaaaggc aattactcta ccgtcggtgg tggcgattat aacgaagcca     600
aaggcaatta ctctaccgtc ggtggtggct ctagtaatac cgccaaaggc gagaaatcaa     660
ccatcggtgg tggcgatact aacgacgcca acggcacata ctctaccatc ggtggtggct     720
attatagccg agccataggc gatagctcta ccatcggtgg tggttattat aaccaagcca     780
caggcgagaa atcaacggtt gcaggggca ggaataacca agccacaggc aacaactcaa     840
cggttgcagg cggctcttat aaccaagcca caggcaacaa ctcaacggtt gcaggtggct     900
ctcataacca agccacaggt gaaggttcat tgcagcagg tgtagagaac aaagccaatg     960
ccaacaacgc cgtcgctcta ggtaaaaata caccatcga tggcgataac tcagtagcca    1020
tcggctctaa taataccatt gacagtggca acaaaatgt ctttattctt ggctctagca    1080
caaacacaac aaatgcacaa agcggctccg tgctgctggg tcataatacc gctggcaaaa    1140
aagcaaccgc tgttagcagt gccaaagtga acggcttaac cctaggaaat tttgcaggtg    1200
catcaaaaac tggtaatggt actgtatctg tcggtagtga gaataatgag cgtcaaatcg    1260
tcaatgttgg tgcaggtaat atcagtgctg attcaacaga tgctgttaat ggctcacagc    1320
tatatgcttt ggccacagct gtcaaagccg atgccgatga aaactttaaa gcactcacca    1380
aaactcaaaa tactttgatt gagcaaggtg aagcacaaga cgcattaatc gctcaaaatc    1440
```

```
aaactgacat cactgccaat aaaactgcca ttgagcgaaa ttttaataga actgttgtca   1500
atgggtttga gattgagaaa aataaagctg gtattgctaa aaaccaagcg gatatccaaa   1560
cgcttgaaaa caatgtcgga gaagaactat taaatctaag cggtcgcctg cttgatcaaa   1620
aagcggatat tgataataac atcaacaata tctatgatct ggcacaacag caagatcagc   1680
atagctctga tatcaaaaca cttaaaaaaa atgtcgaaga aggtttgttg gatctaagtg   1740
gtcgcctcat tgatcaaaaa gcagatctta cgaaagacat caaaacactt gaaaacaatg   1800
tcgaagaagg tttgttggat ctaagcggtc gcctcattga tcaaaaagca gatattgcta   1860
aaaaccaagc tgacattgct caaaaccaaa cagacatcca agatctggcc gcttacaacg   1920
agctacaaga ccagtatgct caaaagcaaa ccgaagcgat tgacgctcta aataaagcaa   1980
gctctgccaa tactgatcgt attgctactg ctgaattggg tatcgctgag aacaaaaaag   2040
acgctcagat cgccaaagca caagccaatg aaaataaaga cggcattgct aaaaaccaag   2100
ctgatatcca gttgcacgat aaaaaaatca ccaatctagg tatccttcac agcatggttg   2160
caagagcggt aggaaataac acacaaggtg ttgctaccaa taaagctgac attgctaaaa   2220
accaagcaga tattgctaat aacatcaaaa atatctatga gctggcacaa cagcaagatc   2280
agcatagctc tgatatcaaa accttggcaa aagtaagtgc tgccaatact gatcgtattg   2340
ctaaaaacaa agctgaagct gatgcaagtt ttgaaacgct caccaaaaat caaaatactt   2400
tgattgagca aggtgaagca ttggttgagc aaaaataaagc catcaatcaa gagcttgaag   2460
ggtttgcggc tcatgcagat gttcaagata agcaaatttt acaaaaccaa gctgatatca   2520
ctaccaataa ggccgctatt gaacaaaata tcaatagaac tgttgccaat gggtttgaga   2580
ttgagaaaaa taaagctggt attgctacca ataagcaaga gcttattctt caaaatgatc   2640
gattaaatca aattaatgag acaaataatc gtcaggatca gaagattgat caattaggtt   2700
atgcactaaa agagcagggt cagcattta ataatcgtat tagtgctgtt gagcgtcaaa    2760
cagctggagg tattgcaaat gctatcgcaa ttgcaacttt accatcgccc agtagagcag   2820
gtgagcatca tgtcttattt ggttcaggtt atcacaatgg tcaagctgcg gtatcattgg   2880
gtgcggctgg gttaagtgat acaggaaaat caacttataa gattggtcta agctggtcag   2940
atgcaggtgg attatctggt ggtgttggtg gcagttaccg ctggaaatag agcctaaatt   3000
taactgctgt atcaaaaaat atggtctgta taaacagacc atattttat ctaaaaactt    3060 atcttaactt ttatgaagca tcataagcca aagctgagta ataataagag atgttaaaat   3120
aagagatgtt aaaactgcta acaatcggc ttacgacgat aaaataaaat acctggaatg    3180
gacagcccca aaaccaatgc tgagatgata aaaatcgcct caaaaaaatg acgcatcata   3240
acgataaata aatccatatc aaatccaaaa tagccaattt gtaccatgct aaccatggct   3300
ttataggcag cgattcccgg catcatacaa atcaagctag gtacaatcaa ggctttaggc   3360
ggcaggccat gacgctgagc a                                             3381
```

<210> SEQ ID NO 7
<211> LENGTH: 624
<212> TYPE: PRT
<213> ORGANISM: Moraxella catarrhalis

<400> SEQUENCE: 7

```
Val Asn Lys Ile Tyr Lys Val Lys Lys Asn Ala Ala Gly His Ser Val
 1               5                  10                  15

Ala Cys Ser Glu Phe Ala Lys Gly His Thr Lys Lys Ala Val Leu Gly
```

```
                    20                  25                  30
Ser Leu Leu Ile Val Gly Ala Leu Gly Met Ala Thr Thr Ala Ser Ala
            35                  40                  45

Gln Thr Gly Ser Thr Asn Ala Ala Asn Gly Asn Ile Ile Ser Gly Val
        50                  55                  60

Gly Ala Tyr Val Gly Gly Val Ile Asn Gln Ala Lys Gly Asn Tyr
    65                  70                  75                  80

Pro Thr Val Gly Gly Phe Asp Asn Arg Ala Thr Gly Asn Tyr Ser
                85                  90                  95

Val Ile Ser Gly Gly Phe Asp Asn Gln Ala Lys Gly Glu His Ser Thr
                100                 105                 110

Ile Ala Gly Gly Glu Ser Asn Gln Ala Thr Gly Arg Asn Ser Thr Val
                115                 120                 125

Ala Gly Gly Ser Asn Asn Gln Ala Val Gly Thr Asn Ser Thr Val Ala
                130                 135                 140

Gly Gly Ser Asn Asn Gln Ala Lys Gly Ala Asn Ser Phe Ala Ala Gly
145                 150                 155                 160

Val Gly Asn Gln Ala Asn Thr Asp Asn Ala Val Ala Leu Gly Lys Asn
                165                 170                 175

Asn Thr Ile Asn Gly Asn Asn Ser Ala Ala Ile Gly Ser Glu Asn Thr
                180                 185                 190

Val Asn Glu Asn Gln Lys Asn Val Phe Ile Leu Gly Ser Asn Thr Thr
                195                 200                 205

Asn Ala Gln Ser Gly Ser Val Leu Leu Gly His Glu Thr Ser Gly Lys
                210                 215                 220

Glu Ala Thr Ala Val Ser Arg Ala Arg Val Asn Gly Leu Thr Leu Lys
225                 230                 235                 240

Asn Phe Ser Gly Val Ser Lys Ala Asp Asn Gly Thr Val Ser Val Gly
                245                 250                 255

Ser Gln Gly Lys Glu Arg Gln Ile Val His Val Gly Ala Gly Gln Ile
                260                 265                 270

Ser Asp Asp Ser Thr Asp Ala Val Asn Gly Ser Gln Leu Tyr Ala Leu
                275                 280                 285

Ala Thr Ala Val Asp Asp Asn Gln Tyr Asp Ile Glu Ile Asn Gln Asp
                290                 295                 300

Asn Ile Lys Asp Leu Gln Lys Glu Val Lys Gly Leu Asp Lys Glu Val
305                 310                 315                 320

Gly Val Leu Ser Arg Asp Ile Gly Ser Leu His Asp Asp Val Ala Asp
                325                 330                 335

Asn Gln Ala Asp Ile Ala Lys Asn Lys Ala Asp Ile Lys Glu Leu Asp
                340                 345                 350

Lys Glu Met Asn Val Leu Ser Arg Asp Ile Val Ser Leu Asn Asp Asp
                355                 360                 365

Val Ala Asp Asn Gln Ala Asp Ile Ala Lys Asn Gln Ala Asp Ile Lys
                370                 375                 380

Thr Leu Glu Asn Asn Val Glu Glu Gly Leu Leu Asp Leu Ser Gly Arg
385                 390                 395                 400

Leu Ile Asp Gln Lys Ala Asp Ile Asp Asn Asn Ile Asn His Ile Tyr
                405                 410                 415

Glu Leu Ala Gln Gln Gln Asp Gln His Ser Ser Asp Ile Lys Thr Leu
                420                 425                 430

Ala Lys Ala Ser Ala Ala Asn Thr Asp Arg Ile Ala Lys Asn Lys Ala
                435                 440                 445
```

```
Asp Ala Asp Ala Ser Phe Glu Thr Leu Thr Lys Asn Gln Asn Thr Leu
    450                 455                 460

Ile Glu Lys Asp Lys Glu His Asp Lys Leu Ile Thr Ala Asn Lys Thr
465                 470                 475                 480

Ala Ile Asp Ala Asn Lys Ala Ser Ala Asp Thr Lys Phe Ala Ala Thr
                485                 490                 495

Ala Asp Ala Ile Thr Lys Asn Gly Asn Ala Ile Thr Lys Asn Ala Lys
            500                 505                 510

Ser Ile Thr Asp Leu Gly Thr Lys Val Asp Gly Phe Asp Gly Arg Val
        515                 520                 525

Thr Ala Leu Asp Thr Lys Val Asn Ala Phe Asp Gly Arg Ile Thr Ala
    530                 535                 540

Leu Asp Ser Lys Val Glu Asn Gly Met Ala Ala Gln Ala Ala Leu Ser
545                 550                 555                 560

Gly Leu Phe Gln Pro Tyr Ser Val Gly Lys Phe Asn Ala Thr Ala Ala
                565                 570                 575

Leu Gly Gly Tyr Gly Ser Lys Ser Ala Val Ala Ile Gly Ala Gly Tyr
            580                 585                 590

Arg Val Asn Pro Asn Leu Ala Phe Lys Ala Gly Ala Ala Ile Asn Thr
        595                 600                 605

Ser Gly Asn Lys Lys Gly Ser Tyr Asn Ile Gly Val Asn Tyr Glu Phe
    610                 615                 620

<210> SEQ ID NO 8
<211> LENGTH: 3295
<212> TYPE: DNA
<213> ORGANISM: Moraxella catarrhalis

<400> SEQUENCE: 8
gccgcacctg accgagacgc tccgccaaat caatgcgtcg gtgtactatg ccccgaccga      60
gctatgcacg gataatggtg cgatgatcgc ctatgctggc ttttgtcggc taagccgtgg     120
acagtcggat gacttggcgg ttcgctgcat tccccgatgg gatatgacaa cgcttggtat     180
cgaatatgat aattaggctg tggtatttga gttttgagta atgtacctac taccactaat     240
ttatcataca atacataaac ataaaaaaca tcggtattgt taaaaaacaa tacccaagtt     300
aaaatagctc aatactttac catagcacaa agaaacttgt gaacgaaaca tttaataatt     360
gcccaaaatg tcactgcaca cactttgtaa aagcaggttt gggcaatggc aaacaacgat     420
acaaatgcaa aggttaccat cactattttt ctgtgaagca acgaagcaac caaaaaagta     480
atgacattaa aaaacaagc cattgataca aacagtaaac aaatcttagg ctttgtctgt     540
ggtaaaacag cactaacac cctttaaacga ctttatcagc agttaaatac ccataacatt     600
caactgtttt ttagtgacta ctggaaatct tatcgtcaag tcattttaaa gccaaaacat     660
ataacaagca aagctcaaac ttttaccata gaggactata atagtctcat gggcatttc      720 atagcaagat ttacaagaaa gtcaaagtat tattctaaat ccgaaaaaat gatagaaaac     780
acgttgaatt tattatttgc taagtggaat ggtagcttaa gatatgtatt ttaatttaac     840
aatgccaaaa acatcaatta cagtaagatt ttaggcgttt tgcagttgct actttagtaa     900
agctttgtta tactagctgt taatatactc aagcttgttt gtgtttgagc tatgtttatt     960
ttatagcagt agttggttat aaaatataaa taaagctaag ctcgagggtt tggtaatggt    1020
tttttatgtt tataatacca acagagtatc tatacagcta aaatagctaa taccttaggt    1080
gtattacaag taaaaatcct tgttaatcag gggagtgtat tatatgtata tttccttttgt   1140
```

```
atttggttat agcaatccct tggtaagaaa tcatatctat tttttattgt tcaattattc    1200
aggagactaa ggtgaacaaa atttataaag tgaaaaaaaa tgccgcaggt cattcggtgg    1260
catgttctga atttgccaaa ggccatacca aaaaggcagt tttgggcagt ttattgattg    1320
ttggggcatt gggcatggca acgacagcgt ctgcacaaac aggcagtaca aatgcagcca    1380
acggcaatat aatcagcggc gtaggcgcgt acgtcggtgg tggcgttata aaccaagcca    1440
aaggcaatta ccctaccgtc ggtggtggct ttgataaccg agccacaggc aattactctg    1500
tcatcagtgg tggctttgat aaccaagcca aaggcgagca ctctaccatc gcaggggggtg   1560 agagtaacca agctacaggt cgtaactcaa cggttgcagg gggttctaat aaccaagccg    1620
tgggtacaaa ctcaacggtt gcagggggtt ctaataacca agccaaaggt gcaaattcat    1680
ttgcagcagg tgtaggtaac caagccaata ccgacaacgc cgtcgctcta ggtaaaaata    1740
acaccatcaa tggcaataac tcagcagcca tcggctctga aataccgtt aacgaaaatc     1800 aaaaaaatgt ctttattctt ggctctaaca caacaaatgc acaaagcggc tcagtactgc    1860
taggtcatga aacctctggt aaagaagcga ccgctgttag cagagccaga gtgaacggct    1920
taaccctaaa aaattttttca ggcgtatcaa aagctgataa tggtactgta tctgtcggta   1980
gtcagggtaa agagcgtcaa atcgttcatg ttggtgcagg tcagatcagt gatgattcaa    2040
cagatgctgt taatggctca cagctatatg ctttggctac agctgttgat gacaaccaat    2100
atgacattga ataaaccaa gataatatca aagatcttca aaggaggtg aaaggtcttg      2160 ataaggaagt gggtgtatta agccgagaca ttggttcact tcatgatgat gttgctgaca    2220
accaagctga tattgctaaa aacaaagctg acatcaaaga gcttgataag gagatgaatg    2280
tattaagccg agacattgtc tcacttaatg atgatgttgc tgataaccaa gctgacattg    2340
ctaaaaacca agcggatatc aaaacacttg aaaacaatgt cgaagaaggt ttattggatc    2400
taagcggtcg cctcattgat caaaaagcag atattgataa taacatcaac catatctatg    2460
agctggcaca acagcaagat cagcatagct ctgatatcaa aaccttggca aaagcaagtg    2520
ctgccaatac tgatcgtatt gctaaaaaca agccgatgc tgatgcaagt tttgaaacac     2580
tcaccaaaaa tcaaaatact ttgattgaaa aagataaaga gcatgacaaa ttaattactg    2640
caaacaaaac tgcgattgat gccaataaag catctgcgga taccaagttt gcagcgacag    2700
cagacgccat taccaaaaat ggaaatgcta tcactaaaaa cgcaaaatct atcactgatt    2760
tgggtactaa agtggatggt tttgacggtc gtgtaactgc attagacacc aaagtcaatg    2820
cctttgatgg tcgcatcaca gctttagaca gtaaagttga aaacggtatg gctgcccaag    2880
ctgccctaag tggtctattc cagccttata gcgttggtaa gttaatgcg accgctgcac     2940 ttggtggcta tggctcaaaa tctgcggttg ctatcggtgc tggctatcgt gtgaatccaa    3000
atctggcgtt taaagctggt gcggcgatta taccagtgg caataaaaaa ggctcttata     3060
acatcggtgt gaattacgag ttctaattgt ctatcatcac caaaaaagc agtcagttta     3120 ctggctgctt ttttatgggt ttttatggct tttggttgtg agtgatggat aaaagcttat    3180
caagcgattg atgaatatca ataaatgatt ggtaaatatc aataaagcgg tttagggttt    3240
ttggatatct tttaataagt ttaaaaaccc ctgcataaaa taaagctggc atcag         3295
```

<210> SEQ ID NO 9
<211> LENGTH: 941
<212> TYPE: PRT
<213> ORGANISM: Moraxella catarrhalis

```
<400> SEQUENCE: 9

Met Asn Lys Ile Tyr Lys Val Lys Lys Asn Ala Ala Gly His Leu Val
 1               5                  10                  15

Ala Cys Ser Glu Phe Ala Lys Gly His Thr Lys Lys Ala Val Leu Gly
             20                  25                  30

Ser Leu Leu Ile Val Gly Ile Leu Gly Met Ala Thr Thr Ala Ser Ala
         35                  40                  45

Gln Met Ala Thr Thr Pro Ser Ala Gln Val Val Lys Thr Asn Asn Lys
     50                  55                  60

Lys Asn Gly Thr His Pro Phe Ile Gly Gly Asp Tyr Asn Thr Thr
 65                  70                  75                  80

Lys Gly Asn Tyr Pro Thr Ile Gly Gly His Phe Asn Thr Ala Glu
             85                  90                  95

Gly Asn Tyr Ser Thr Val Gly Gly Phe Thr Asn Glu Ala Ile Gly
            100                 105                 110

Lys Asn Ser Thr Val Gly Gly Phe Thr Asn Glu Ala Met Gly Glu
            115                 120                 125

Tyr Ser Thr Val Ala Gly Gly Ala Asn Asn Gln Ala Lys Gly Asn Tyr
    130                 135                 140

Ser Thr Val Gly Gly Gly Asn Gly Asn Lys Ala Ile Gly Asn Asn Ser
145                 150                 155                 160

Thr Val Val Gly Gly Ser Asn Asn Gln Ala Lys Gly Glu His Ser Thr
                165                 170                 175

Ile Ala Gly Gly Lys Asn Asn Gln Ala Thr Gly Asn Gly Ser Phe Ala
            180                 185                 190

Ala Gly Val Glu Asn Lys Ala Asp Ala Asn Asn Ala Val Ala Leu Gly
        195                 200                 205

Asn Lys Asn Thr Ile Glu Gly Thr Asn Ser Val Ala Ile Gly Ser Asn
    210                 215                 220

Asn Thr Val Lys Thr Gly Lys Glu Asn Val Phe Ile Leu Gly Ser Asn
225                 230                 235                 240

Thr Asn Thr Glu Asn Ala Gln Ser Gly Ser Val Leu Leu Gly Asn Asn
                245                 250                 255

Thr Ala Gly Lys Ala Ala Thr Thr Val Asn Asn Ala Glu Val Asn Gly
            260                 265                 270

Leu Thr Leu Glu Asn Phe Ala Gly Ala Ser Lys Ala Asn Ala Asn Asn
        275                 280                 285

Ile Gly Thr Val Ser Val Gly Ser Glu Asn Asn Glu Arg Gln Ile Val
    290                 295                 300

Asn Val Gly Ala Gly Gln Ile Ser Ala Thr Ser Thr Asp Ala Val Asn
305                 310                 315                 320

Gly Ser Gln Leu His Ala Leu Ala Lys Ala Val Ala Lys Asn Lys Ser
                325                 330                 335

Asp Ile Lys Gly Leu Asn Lys Gly Val Lys Glu Leu Asp Lys Glu Val
            340                 345                 350

Gly Val Leu Ser Arg Asp Ile Asn Ser Leu His Asp Asp Val Ala Asp
        355                 360                 365

Asn Gln Asp Ser Ile Ala Lys Asn Lys Ala Asp Ile Lys Gly Leu Asn
    370                 375                 380

Lys Glu Val Lys Glu Leu Asp Lys Glu Val Gly Val Leu Ser Arg Asp
385                 390                 395                 400

Ile Gly Ser Leu His Asp Asp Val Ala Asp Asn Gln Asp Ser Ile Ala
                405                 410                 415
```

-continued

Lys Asn Lys Ala Asp Ile Lys Gly Leu Asn Lys Glu Val Lys Glu Leu
            420                 425                 430

Asp Lys Glu Val Gly Val Leu Ser Arg Asp Ile Gly Ser Leu His Asp
        435                 440                 445

Asp Val Ala Thr Asn Gln Ala Asp Ile Ala Lys Asn Gln Ala Asp Ile
    450                 455                 460

Lys Thr Leu Glu Asn Asn Val Glu Glu Leu Leu Asn Leu Ser Gly
465                 470                 475                 480

Arg Leu Ile Asp Gln Lys Ala Asp Ile Asp Asn Asn Ile Asn Asn Ile
            485                 490                 495

Tyr Glu Leu Ala Gln Gln Gln Asp Gln His Ser Ser Asp Ile Lys Thr
        500                 505                 510

Leu Lys Asn Asn Val Glu Glu Gly Leu Leu Asp Leu Ser Gly Arg Leu
    515                 520                 525

Ile Asp Gln Lys Ala Asp Leu Thr Lys Asp Ile Lys Thr Leu Lys Asn
530                 535                 540

Asn Val Glu Glu Gly Leu Leu Asp Leu Ser Gly Arg Leu Ile Asp Gln
545                 550                 555                 560

Lys Ala Asp Ile Ala Lys Asn Gln Ala Asp Ile Ala Gln Asn Gln Thr
            565                 570                 575

Asp Ile Gln Asp Leu Ala Ala Tyr Asn Glu Leu Gln Asp Gln Tyr Ala
        580                 585                 590

Gln Lys Gln Thr Glu Ala Ile Asp Ala Leu Asn Lys Ala Ser Ser Ala
    595                 600                 605

Asn Thr Asp Arg Ile Ala Thr Ala Glu Leu Gly Ile Ala Glu Asn Lys
    610                 615                 620

Lys Asp Ala Gln Ile Ala Lys Ala Gln Ala Asn Glu Asn Lys Asp Gly
625                 630                 635                 640

Ile Ala Lys Asn Gln Ala Asp Ile Gln Leu His Asp Lys Lys Ile Thr
            645                 650                 655

Asn Leu Gly Ile Leu His Ser Met Val Ala Arg Ala Val Gly Asn Asn
        660                 665                 670

Thr Gln Gly Val Ala Thr Asn Lys Ala Asp Ile Ala Lys Asn Gln Ala
    675                 680                 685

Asp Ile Ala Asn Asn Ile Lys Asn Ile Tyr Glu Leu Ala Gln Gln Gln
    690                 695                 700

Asp Gln His Ser Ser Asp Ile Lys Thr Leu Ala Lys Val Ser Ala Ala
705                 710                 715                 720

Asn Thr Asp Arg Ile Ala Lys Asn Lys Ala Glu Ala Asp Ala Ser Phe
            725                 730                 735

Glu Thr Leu Thr Lys Asn Gln Asn Thr Leu Ile Glu Gln Gly Glu Ala
        740                 745                 750

Leu Val Glu Gln Asn Lys Ala Ile Asn Gln Glu Leu Glu Gly Phe Ala
    755                 760                 765

Ala His Ala Asp Val Gln Asp Lys Gln Ile Leu Gln Asn Gln Ala Asp
    770                 775                 780

Ile Thr Thr Asn Lys Thr Ala Ile Glu Gln Asn Ile Asn Arg Thr Val
785                 790                 795                 800

Ala Asn Gly Phe Glu Ile Glu Lys Asn Lys Ala Gly Ile Ala Thr Asn
            805                 810                 815

Lys Gln Glu Leu Ile Leu Gln Asn Asp Arg Leu Asn Gln Ile Asn Glu
        820                 825                 830

```
Thr Asn Asn His Gln Asp Gln Lys Ile Asp Gln Leu Gly Tyr Ala Leu
        835                 840                 845

Lys Glu Gln Gly Gln His Phe Asn Asn Arg Ile Ser Ala Val Glu Arg
    850                 855                 860

Gln Thr Ala Gly Gly Ile Ala Asn Ala Ile Ala Ile Ala Thr Leu Pro
865                 870                 875                 880

Ser Pro Ser Arg Ala Gly Glu His His Val Leu Phe Gly Ser Gly Tyr
                885                 890                 895

His Asn Gly Gln Ala Ala Val Ser Leu Gly Ala Ala Gly Leu Ser Asp
            900                 905                 910

Thr Gly Lys Ser Thr Tyr Lys Ile Gly Leu Ser Trp Ser Asp Ala Gly
        915                 920                 925

Gly Leu Ser Gly Gly Val Gly Gly Ser Tyr Arg Trp Lys
        930                 935                 940

<210> SEQ ID NO 10
<211> LENGTH: 3538
<212> TYPE: DNA
<213> ORGANISM: Moraxella catarrhalis

<400> SEQUENCE: 10
```

| | | | | | |
|---|---|---|---|---|---|
| ttctgtgagc | aaatgactgg | cgtaaatgac | tgatgagtgt | ctatttaatg | aaagatatca | 60 |
| atatataaaa | gttgactata | gcgatgcaat | acagtaaaat | ttgttacggc | taaacataac | 120 |
| gacggtccaa | gatggcggat | atcgccattt | accaacctga | taatcagttt | gatagccatt | 180 |
| agcgatggca | tcaagttgtg | ttgttgtatt | gtcatataaa | cggtaaattt | ggtttggtgg | 240 |
| atgccccatc | tgatttaccg | tcccctaat | aagtgagggg | gggggggaga | ccccagtcat | 300 |
| ttattaggag | actaagatga | acaaaattta | taaagtgaaa | aaaatgccg | caggtcactt | 360 |
| ggtggcgtgt | tctgaatttg | ccaaaggtca | taccaaaaag | gcagttttgg | gcagtttatt | 420 |
| gattgttgga | atattgggta | tggcaacgac | agcatctgca | caaatggcaa | cgacgccgtc | 480 |
| tgcacaagta | gtcaagacaa | acaataaaaa | aaacggcacg | cacccttca | tcggtggtgg | 540 |
| cgattataat | accaccaaag | gcaattaccc | taccatcggt | ggtggccatt | ttaataccgc | 600 |
| cgaaggcaat | tactctaccg | tcggtggtgg | ctttactaac | gaagccatag | caagaactc | 660 |
| taccgtcggt | ggtggcttta | ctaacgaagc | catgggcgaa | tactcaaccg | tcgcaggcgg | 720 |
| tgctaacaac | caagccaaag | gcaattactc | taccgtcggt | ggtggcaatg | caacaaagc | 780 |
| cataggcaac | aactcaacgg | ttgtaggtgg | ttctaacaac | caagccaaag | gcgagcactc | 840 |
| taccatcgca | gggggcaaga | taaccaagc | tacaggtaat | ggttcatttg | cagcaggtgt | 900 |
| agagaacaaa | gccgatgcta | caacgccgt | cgctctaggt | aacaagaaca | ccatcgaagg | 960 |
| tacaaactca | gtagccatcg | gctctaataa | taccgttaaa | actggcaaag | aaaatgtctt | 1020 |
| tattcttggc | tctaacacaa | acacagaaaa | tgcacaaagt | ggctccgtgc | tgctgggtaa | 1080 |
| taataccgct | ggcaaagcag | cgaccactgt | taacaatgcc | gaagtgaacg | gcttaaccct | 1140 |
| agaaaatttt | gcaggtgcat | caaaagctaa | tgctaataat | attggtactg | tatctgtcgg | 1200 |
| tagtgagaat | aatgagcgtc | aaatcgttaa | tgttggtgca | ggtcagatca | gtgccacctc | 1260 |
| aacagatgct | gttaatggct | cacagctaca | tgctttagcc | aaagctgttg | ctaaaaacaa | 1320 |
| atctgacatc | aaaggtctta | taaggggggt | gaaagagctt | gataaggagg | tgggtgtatt | 1380 |
| aagccgagac | attaattcac | ttcatgatga | tgttgctgac | aaccaagata | gcattgctaa | 1440 |
| aaacaaagct | gacatcaaag | gtcttaataa | ggaggtgaaa | gagcttgata | aggaggtggg | 1500 |

-continued

```
tgtattaagc cgagacattg gttcacttca tgatgatgtt gctgacaacc aagatagcat    1560
tgctaaaaac aaagctgaca tcaaaggtct taataaggag gtgaaagagc ttgataagga    1620
ggtgggtgta ttaagccgag acattggttc acttcatgat gatgttgcca ccaaccaagc    1680
tgacattgct aaaaaccaag cggatatcaa aacacttgaa aacaatgtcg aagaagaatt    1740
attaaatcta gcggtcgcc tcattgatca aaaagcggat attgataata acatcaacaa    1800
tatctatgag ctggcacaac agcaagatca gcatagctct gatatcaaaa cacttaaaaa    1860
caatgtcgaa gaaggtttgt tggatctaag cggtcgcctc attgatcaaa agcagatct    1920 tacgaaagac atcaaaacac ttaaaaacaa tgtcgaagaa ggtttattgg atctaagcgg    1980
tcgcctcatt gatcaaaaag cagatattgc taaaaaccaa gctgacattg ctcaaaacca    2040
aacagacatc caagatctgg ccgcttacaa cgagctacaa gaccagtatg ctcaaaagca    2100
aaccgaagcg attgacgctc taaataaagc aagctctgcc aatactgatc gtattgctac    2160
tgctgaattg ggtatcgctg agaacaaaaa agacgctcag atcgccaaag cacaagccaa    2220
tgaaaataaa gacggcattg ctaaaaacca agctgatatc cagttgcacg ataaaaaaat    2280
caccaatcta ggtatccttc acagcatggt tgcaagagcg gtaggaaata atacacaagg    2340
tgttgctacc aacaaagctg atattgctaa aaaccaagca gatattgcta ataacatcaa    2400
aaatatctat gagctggcac aacagcaaga tcagcatagc tctgatatca aaaccttggc    2460
aaaagtaagt gctgccaata ctgatcgtat tgctaaaaac aaagctgaag ctgatgcaag    2520
ttttgaaacg ctcaccaaaa atcaaaatac tttgattgag caaggtgaag cattggttga    2580
gcaaaataaa gccatcaatc aagagcttga agggtttgcg gctcatgcag atgttcaaga    2640
taagcaaatt ttacaaaacc aagctgatat cactaccaat aagaccgcta ttgaacaaaa    2700
tatcaataga actgttgcca atgggtttga gattgagaaa aataaagctg gtattgctac    2760
caataagcaa gagcttattc ttcaaaatga tcgattaaat caaattaatg agacaaataa    2820
tcatcaggat cagaagattg atcaattagg ttatgcacta aaagagcagg gtcagcattt    2880
taataatcgt attagtgctg ttgagcgtca aacagctgga ggtattgcaa atgctatcgc    2940
aattgcaact ttaccatcgc ccagtagagc aggtgagcat catgtcttat ttggttcagg    3000
ttatcacaat ggtcaagctg cggtatcatt gggcgcggct ggattaagtg atacaggaaa    3060
atcaacttat aagattggtc taagctggtc agatgcaggt ggattatctg gtggtgttgg    3120
tggcagttac cgctggaaat agagcctaaa tttaactgct gtatcaaaaa atatggtctg    3180
tataaacaga ccatattttt atctaaaaaa cttatcttaa ctttatgaa gcatcataag    3240 ccaaagctga gtaataataa agatgttaa aataagagat gttaaaactg ctaaacaatc    3300
ggcttgcgac gataaaataa aatacctgga atggacagcc ccaaaaccaa tgctgagatg    3360
ataaaaatcg cctcaaaaaa atgacgcatc ataacgataa ataaatccat atcaaatcca    3420
aaatagccaa tttgtaccat gctaaccatg gctttatagg cagcgattcc cggcatcata    3480
caaatcaagc taggtacaat caaggcttta ggcggcaggc catgacgctg agcaaaaa     3538
```

<210> SEQ ID NO 11
<211> LENGTH: 610
<212> TYPE: PRT
<213> ORGANISM: Moraxella catarrhalis

<400> SEQUENCE: 11

Met Lys Leu Leu Pro Leu Lys Ile Ala Val Thr Ser Ala Met Ile Ile
 1               5                  10                  15

-continued

```
Gly Leu Gly Ala Ala Ser Thr Ala Asn Ala Gln Ser Arg Asp Arg Ser
            20                  25                  30

Leu Glu Asp Ile Gln Asp Ser Ile Ser Lys Leu Val Gln Asp Asp Ile
        35                  40                  45

Asp Thr Leu Lys Gln Asp Gln Gln Lys Met Asn Lys Tyr Leu Leu Leu
    50                  55                  60

Asn Gln Leu Ala Asn Thr Leu Ile Thr Asp Glu Leu Asn Asn Asn Val
65                  70                  75                  80

Ile Lys Asn Thr Asn Ser Ile Glu Ala Leu Gly Asp Glu Ile Gly Trp
                85                  90                  95

Leu Glu Asn Asp Ile Ala Asp Leu Glu Gly Val Glu Glu Leu Thr
        100                 105                 110

Lys Asn Gln Asn Thr Leu Ile Glu Lys Asp Glu His Asp Arg Leu
        115                 120                 125

Ile Ala Gln Asn Gln Ala Asp Ile Gln Thr Leu Glu Asn Asn Val Val
    130                 135                 140

Glu Glu Leu Phe Asn Leu Ser Gly Arg Leu Ile Asp Gln Glu Ala Asp
145                 150                 155                 160

Ile Ala Lys Asn Asn Ala Ser Ile Glu Glu Leu Tyr Asp Phe Asp Asn
                165                 170                 175

Glu Val Ala Glu Arg Ile Gly Glu Ile His Ala Tyr Thr Glu Glu Val
            180                 185                 190

Asn Lys Thr Leu Glu Asn Leu Ile Thr Asn Ser Val Lys Asn Thr Asp
        195                 200                 205

Asn Ile Asp Lys Asn Lys Ala Asp Ile Asp Asn Asn Ile Asn His Ile
    210                 215                 220

Tyr Glu Leu Ala Gln Gln Asp Gln His Ser Ser Asp Ile Lys Thr
225                 230                 235                 240

Leu Lys Asn Asn Val Glu Glu Gly Leu Leu Glu Leu Ser Gly His Leu
                245                 250                 255

Ile Asp Gln Lys Ala Asp Leu Thr Lys Asp Ile Lys Ala Leu Glu Ser
            260                 265                 270

Asn Val Glu Glu Gly Leu Leu Asp Leu Ser Gly Arg Leu Leu Asp Gln
        275                 280                 285

Lys Ala Asp Leu Thr Lys Asp Ile Lys Ala Leu Glu Ser Asn Val Glu
    290                 295                 300

Glu Gly Leu Leu Asp Leu Ser Gly Arg Leu Leu Asp Gln Lys Ala Asp
305                 310                 315                 320

Ile Ala Gln Asn Gln Thr Asp Ile Gln Asp Leu Ala Ala Tyr Asn Glu
                325                 330                 335

Leu Gln Asp Gln Tyr Ala Gln Lys Gln Thr Glu Ala Ile Asp Ala Leu
            340                 345                 350

Asn Lys Ala Ser Ser Glu Asn Thr Gln Asn Ile Glu Asp Leu Ala Ala
        355                 360                 365

Tyr Asn Glu Leu Gln Asp Ala Tyr Ala Lys Gln Gln Thr Glu Ala Ile
    370                 375                 380

Asp Ala Leu Asn Lys Ala Ser Ser Glu Asn Thr Gln Asn Ile Ala Lys
385                 390                 395                 400

Asn Gln Ala Asp Ile Ala Asn Asn Ile Asn Asn Ile Tyr Glu Leu Ala
                405                 410                 415

Gln Gln Gln Asp Gln His Ser Ser Asp Ile Lys Thr Leu Ala Lys Ala
            420                 425                 430

Ser Ala Ala Asn Thr Asn Arg Ile Ala Thr Ala Glu Leu Gly Ile Ala
```

-continued

```
            435                 440                 445
Glu Asn Lys Lys Asp Ala Gln Ile Ala Lys Ala Gln Ala Asn Ala Asn
    450                 455                 460

Lys Thr Ala Ile Asp Glu Asn Lys Ala Ser Ala Asp Thr Lys Phe Ala
465                 470                 475                 480

Ala Thr Ala Asp Ala Ile Thr Lys Asn Gly Asn Ala Ile Thr Lys Asn
                485                 490                 495

Ala Lys Ser Ile Thr Asp Leu Gly Thr Lys Val Asp Gly Phe Asp Gly
            500                 505                 510

Arg Val Thr Ala Leu Asp Thr Lys Val Asn Ala Phe Asp Gly Arg Ile
            515                 520                 525

Thr Ala Leu Asp Ser Lys Val Glu Asn Gly Met Ala Ala Gln Ala Ala
            530                 535                 540

Leu Ser Gly Leu Phe Gln Pro Tyr Ser Val Gly Lys Phe Asn Ala Thr
545                 550                 555                 560

Ala Ala Leu Gly Gly Tyr Gly Ser Lys Ser Ala Val Ala Ile Gly Ala
                565                 570                 575

Gly Tyr Arg Val Asn Pro Asn Leu Ala Phe Lys Ala Gly Ala Ala Ile
            580                 585                 590

Asn Thr Ser Gly Asn Lys Lys Gly Ser Tyr Asn Ile Gly Val Asn Tyr
            595                 600                 605

Glu Phe
    610
```

<210> SEQ ID NO 12
<211> LENGTH: 2673
<212> TYPE: DNA
<213> ORGANISM: Moraxella catarrhalis

<400> SEQUENCE: 12

```
ccatcagtac atacgccgca cctgaccgag acgctccgcc aaatcaatgc gtcggtgtac      60
tacgccccga ccgagctatg cacggataat ggtgcgatga tcgcttacgc tggcttttgt     120
cggctaagcc gtggacagtc ggatgacttg gcggttcgct gcattcccg atgggatatg      180
acaacgcttg gcgtatctgc tcatagatag ccacatcaat cataccaacg atattggtat     240
ataccaaatt gatacctgcc aaaaatacca tattgaaagt agggtttggg tattatttat     300
gtaacttata tctaatttgg tgttgatact ttgataaagc cttgctatac tgtaacctaa     360
atggatatga tagagatttt tccatttatg ccagcaaaag agatagatag atagatagat     420
agatagatag atagatagat agatagatag atagataaaa ctctgtcttt tatctgtcca     480
ctgatgcttt ctgcctgcca ccgatgatat cgtttatctg ctttttagg catcagttat      540
ttcaccgtga tgactgatgt gatgacttaa ccaccaaaag agagtgctaa atgaaaacca     600
tgaaacttct ccctctaaaa atcgctgtaa ccagtgccat gattattggt ttgggtgcgg     660
catctactgc gaatgcacag tctcgggata gatctttaga agatatacaa gattcaatta     720
gtaaacttgt tcaagatgat atagatacac taaaacaaga tcagcagaag atgaacaagt     780
atctgttgct caaccagtta gctaatactt taattacaga cgagctcaac aataatgtta     840
taaaaaacac caattctatt gaagctcttg gtgatgagat tggatggctt gaaaatgata     900
ttgcagactt ggaagaaggt gttgaagaac tcaccaaaaa ccaaaatact ttgattgaaa     960
aagatgaaga gcatgacaga ttaatcgctc aaaatcaagc tgtatatcca acacttgaaa    1020
acaatgtcgt agaagaacta ttcaatctaa gcggtcgcct aattgatcaa gaagcggata    1080
```

```
ttgctaaaaa taatgcttct attgaagagc tttatgattt tgataatgag gttgcagaaa    1140
ggataggtga gatacatgct tatactgaag aggtaaaata aactcttgaa aacttgataa    1200
caaacagtgt taagaatact gataatattg acaaaaacaa agctgatatt gataataaca    1260
tcaaccatat ctatgagctg cacaacagc aagatcagca tagctctgat atcaaaacac     1320
ttaaaaacaa tgtcgaagaa ggtttgttgg agctaagcgg tcacctcatt gatcaaaaag    1380
cggatcttac aaaagacatc aaagcacttg aaagcaatgt cgaagaaggt ttgttggatc    1440
taagcggtcg tctgcttgat caaaaagcgg atcttacaaa agacatcaaa gcacttgaaa    1500
gcaatgtcga gaaggtttg ttggatctaa gcggtcgtct gcttgatcaa aaagcggata     1560
ttgctcaaaa ccaaacagac atccaagatc tggccgctta caacgagcta caagaccagt    1620
atgctcaaaa gcaaaccgaa gcgattgacg ctctaaataa agcaagctct gagaatacac    1680
aaaacatcga agatctggcc gcttacaatg agctacaaga tgcctatgcc aaacagcaaa    1740
ccgaagcgat tgacgctcta aataaagcaa gctctgagaa tacacaaaac attgctaaaa    1800
accaagcgga tattgctaat aacatcaaca atatctatga gctggcacaa cagcaagatc    1860
agcatagctc tgatatcaaa accttggcaa aagcaagtgc tgccaatact aatcgtattg    1920
ctactgctga attgggcatc gctgagaaca aaaagacgc tcagatcgcc aaagcacaag     1980
cgaatgccaa caaactgcg attgatgaaa acaaagcatc tgcggatacc aagtttgcag     2040
caacagcaga cgccattacc aaaaatggaa atgctatcac taaaaacgca aaatctatca    2100
ctgatttggg cactaaagtg gatggttttg acggtcgtgt aactgcatta gacaccaaag    2160
tcaatgcctt tgatggtcgt atcacagctt tagacagtaa agttgaaaac ggtatggctg    2220
cccaagctgc cctaagtggt ctattccagc cttatagcgt tggtaagttt aatgcgaccg    2280
ctgcacttgg tggctatggc tcaaaatctg cggttgctat cggtgctggc tatcgtgtga    2340
atccaaatct ggcgttaaa gctggtgcgg cgattaatac cagtggcaat aaaaaaggct     2400
cttataacat cggtgtgaat tacgagttct aattgtctat catcaccaaa aaagcagtc    2460 agtttactgg ctgcttttt atgggttttt gtggcttttg ttgtgagtg atggataaaa      2520 gcttatcaag cgattgatga atatcaataa atgattggta aatatcaata aagcggttta    2580 gggttttttgg atatctttta ataagtttaa aaacccctgc ataaaataaa gctgggcatc    2640
agagctgcga gtagcggcat acagcgggag atc                                 2673
```

<210> SEQ ID NO 13
<211> LENGTH: 873
<212> TYPE: PRT
<213> ORGANISM: Moraxella catarrhalis

<400> SEQUENCE: 13

```
Met Asn Lys Ile Tyr Lys Val Lys Lys Asn Ala Ala Gly His Leu Val
  1               5                  10                  15

Ala Cys Ser Glu Phe Ala Lys Gly His Thr Lys Lys Ala Val Leu Gly
                 20                  25                  30

Ser Leu Leu Ile Val Gly Ile Leu Gly Met Ala Thr Thr Ala Ser Ala
         35                  40                  45

Gln Gln Thr Ile Ala Arg Gln Gly Lys Gly Met His Ser Ile Ile Gly
     50                  55                  60

Gly Gly Asn Asp Asn Glu Ala Asn Gly Asp Tyr Ser Thr Val Ser Gly
 65                  70                  75                  80

Gly Asp Tyr Asn Glu Ala Lys Gly Asp Ser Ser Thr Ile Gly Gly Gly
                 85                  90                  95
```

```
Tyr Tyr Asn Glu Ala Asn Gly Asp Ser Ser Thr Ile Gly Gly Gly Phe
            100                 105                 110

Tyr Asn Glu Ala Lys Gly Glu Ser Ser Thr Ile Gly Gly Gly Asp Asn
        115                 120                 125

Asn Ser Ala Thr Gly Met Tyr Ser Thr Ile Gly Gly Gly Asp Asn Asn
    130                 135                 140

Ser Ala Thr Gly Arg Tyr Ser Thr Ile Ala Gly Gly Trp Leu Asn Gln
145                 150                 155                 160

Ala Thr Gly His Ser Ser Thr Val Ala Gly Gly Trp Leu Asn Gln Ala
                165                 170                 175

Thr Asn Glu Asn Ser Thr Val Gly Gly Gly Arg Phe Asn Gln Ala Thr
            180                 185                 190

Gly Arg Asn Ser Thr Val Ala Gly Gly Tyr Lys Asn Lys Ala Thr Gly
        195                 200                 205

Val Asp Ser Thr Ile Ala Gly Gly Arg Asn Asn Gln Ala Asn Gly Ile
    210                 215                 220

Gly Ser Phe Ala Ala Gly Ile Asp Asn Gln Ala Asn Ala Asn Asn Thr
225                 230                 235                 240

Val Ala Leu Gly Asn Lys Asn Ile Ile Lys Gly Lys Asp Ser Val Ala
                245                 250                 255

Ile Gly Ser Asn Asn Thr Val Glu Thr Gly Lys Glu Asn Val Phe Ile
            260                 265                 270

Leu Gly Ser Asn Thr Lys Asp Ala His Ser Asn Ser Val Leu Leu Gly
        275                 280                 285

Asn Glu Thr Thr Gly Lys Ala Ala Thr Thr Val Glu Asn Ala Lys Val
    290                 295                 300

Gly Gly Leu Ser Leu Thr Gly Phe Val Gly Ala Ser Lys Ala Asn Thr
305                 310                 315                 320

Asn Asn Gly Thr Val Ser Val Gly Lys Gln Gly Lys Glu Arg Gln Ile
                325                 330                 335

Val Asn Val Gly Ala Gly Gln Ile Arg Ala Asp Ser Thr Asp Ala Val
            340                 345                 350

Asn Gly Ser Gln Leu His Ala Leu Ala Thr Ala Val Asp Ala Glu Phe
        355                 360                 365

Arg Thr Leu Thr Gln Thr Gln Asn Ala Leu Ile Glu Gln Gly Glu Ala
    370                 375                 380

Ile Asn Gln Glu Leu Glu Gly Leu Ala Asp Tyr Thr Asn Ala Gln Asp
385                 390                 395                 400

Glu Lys Ile Leu Lys Asn Gln Thr Asp Ile Thr Ala Asn Lys Thr Ala
                405                 410                 415

Ile Glu Gln Asn Phe Asn Arg Thr Val Thr Asn Gly Phe Glu Ile Glu
            420                 425                 430

Lys Asn Lys Ala Gly Ile Ala Lys Asn Gln Ala Asp Ile Gln Thr Leu
        435                 440                 445

Glu Asn Asp Val Gly Lys Glu Leu Leu Asn Leu Ser Gly Arg Leu Leu
    450                 455                 460

Asp Gln Lys Ala Asp Ile Asp Asn Asn Ile Asn Asn Ile Tyr Glu Leu
465                 470                 475                 480

Ala Gln Gln Gln Asp Gln His Ser Ser Asp Ile Lys Thr Leu Lys Asn
                485                 490                 495

Asn Val Glu Glu Gly Leu Leu Asp Leu Ser Gly Arg Leu Ile Asp Gln
            500                 505                 510
```

```
Lys Ala Asp Leu Thr Lys Asp Ile Lys Ala Leu Glu Asn Asn Val Glu
            515                 520                 525

Glu Gly Leu Leu Asp Leu Ser Gly Arg Leu Ile Asp Gln Lys Ala Asp
        530                 535                 540

Ile Ala Lys Asn Gln Ala Asp Ile Gln Asp Leu Ala Ala Tyr Asn Glu
545                 550                 555                 560

Leu Gln Asp Gln Tyr Ala Gln Lys Gln Thr Glu Ala Ile Asp Ala Leu
                565                 570                 575

Asn Lys Ala Ser Ser Ala Asn Thr Asp Arg Ile Ala Thr Ala Glu Leu
            580                 585                 590

Gly Ile Ala Glu Asn Lys Lys Asp Ala Gln Ile Ala Lys Ala Gln Ala
        595                 600                 605

Asn Glu Asn Lys Asp Gly Ile Ala Lys Asn Gln Ala Asp Ile Ala Asn
    610                 615                 620

Asn Ile Lys Asn Ile Tyr Glu Leu Ala Gln Gln Gln Asp Gln His Ser
625                 630                 635                 640

Ser Asp Ile Lys Thr Leu Ala Lys Val Ser Ala Ala Asn Thr Asp Arg
                645                 650                 655

Ile Ala Lys Asn Lys Ala Glu Ala Asp Ala Ser Phe Glu Thr Leu Thr
            660                 665                 670

Lys Asn Gln Asn Thr Leu Ile Glu Gln Gly Glu Ala Leu Val Glu Gln
        675                 680                 685

Asn Lys Ala Ile Asn Gln Glu Leu Glu Gly Phe Ala Ala His Ala Asp
    690                 695                 700

Val Gln Asp Lys Gln Ile Leu Gln Asn Gln Ala Asp Ile Thr Ala Asn
705                 710                 715                 720

Lys Thr Ala Ile Glu Gln Asn Ile Asn Arg Thr Val Ala Asn Gly Phe
                725                 730                 735

Glu Ile Glu Lys Asn Lys Ala Gly Ile Ala Thr Asn Lys Gln Glu Leu
            740                 745                 750

Ile Leu Gln His Asp Arg Leu Asn Arg Ile Asn Glu Thr Asn Asn Arg
        755                 760                 765

Gln Asp Gln Lys Ile Asp Gln Leu Gly Tyr Ala Leu Lys Glu Gln Gly
    770                 775                 780

Gln His Phe Asn Asn Arg Ile Ser Ala Val Glu Arg Gln Thr Ala Gly
785                 790                 795                 800

Gly Ile Ala Asn Ala Ile Ala Ile Ala Thr Leu Pro Ser Pro Ser Arg
                805                 810                 815

Ala Gly Glu His His Val Leu Phe Gly Ser Gly Tyr His Asn Gly Gln
            820                 825                 830

Ala Ala Val Ser Leu Gly Ala Ala Gly Leu Ser Asp Thr Gly Lys Ser
        835                 840                 845

Thr Tyr Lys Ile Gly Leu Ser Trp Ser Asp Ala Gly Gly Leu Ser Gly
    850                 855                 860

Gly Val Gly Gly Ser Tyr Arg Trp Lys
865                 870

<210> SEQ ID NO 14
<211> LENGTH: 3292
<212> TYPE: DNA
<213> ORGANISM: Moraxella catarrhalis

<400> SEQUENCE: 14
gtaaatgact gatgagtgtc tatttaatga aagatacaat atataaaagt tgactatagc    60
```

```
gatgcaatac agtaaaattt gttacggcta aacataacga cggtccaaga tggcggatat      120
cgccatttac caacctgata atcagtttga tagccattag cgatggcatc aagttgtgtt      180
gttgtattgt catataaacg gtaaatttgg tttggtggat gccccatctg atttaccgtc      240
cccctaataa gtgagagggg ggggagacc ccagtcattt attaggagac taagatgaac       300
aaaatttata aagtgaaaaa aaatgccgca ggtcacttgg tggcatgttc tgaatttgcc      360
aaaggccata ccaagaaggc agttttgggc agtttattga ttgttggaat attgggtatg     420
gcaacgacag catctgcaca acaaacaatc gcacgccaag gcaaaggcat gcactctatc     480
atcggtggtg gcaatgacaa cgaagccaac ggcgattact ctaccgtcag tggtggcgat      540
tataacgaag ccaaggcga tagctctacc atcggtggtg gctattataa cgaagccaac       600
ggcgatagct ctaccatcgg tggtggcttt tataacgaag ccaaggcga gagctctacc       660 atcggtggtg gcgataacaa ctcagccaca ggcatgtact ctaccatcgg tggtggcgat      720
aacaactcag ccacaggcag gtactctacc atcgcagggg gttggcttaa ccaagctaca     780
ggtcatagct caacggttgc aggggggttgg cttaaccaag ctacaaacga gaattctacc     840
gttggtggcg gcaggtttaa ccaagctaca ggtcgtaact caacggttgc agggggctat     900
aaaaacaaag ccacaggcgt agactctacc atcgcagggg gcaggaataa ccaagccaac     960
ggtataggtt catttgcagc aggtatagac aaccaagcca atgccaacaa caccgtcgct    1020
ctaggtaaca agaacatcat caaaggtaaa gactcagtag ccatcggctc taataatacc    1080
gttgaaactg gcaaagaaaa tgtctttatt cttggctcta acacaaaaga tgcacatagt    1140
aactcagtgc tactgggtaa tgagaccact ggcaaagcag cgaccactgt tgagaatgcc    1200
aaagtgggtg gtctaagcct aacaggattt gtaggtgcat caaaagctaa tactaataat    1260
ggtactgtat ctgtcggtaa gcagggtaaa gagcgtcaaa tcgttaatgt tggtgcaggt    1320
cagatccgtg ctgattcaac agatgctgtt aatggctcac agctacatgc tttggccaca    1380
gctgtcgatg cagaatttag aacactcacc caaactcaaa atgctttgat tgagcaaggt    1440
gaagccatca atcaagagct tgaaggtttg gcagattata caaatgctca agatgagaaa    1500
attctaaaaa accaaactga catcactgcc aataaaactg ctattgagca aaattttaat    1560
agaactgtta ccaatgggtt tgagattgag aaaaataaag ctggtattgc taaaaaccaa    1620
gcggatatcc aaacacttga aaacgatgtc ggaaaagaac tattaaatct aagcggtcgc    1680
ctgcttgatc aaaaagcaga tattgataat aacatcaaca atatctatga gctggcacaa    1740
cagcaagatc agcatagctc tgatatcaaa acacttaaaa acaatgtcga agaaggtttg    1800
ttggatctaa gcggtcgcct cattgatcaa aaagcagatc ttacgaaaga catcaaagca    1860
cttgaaaaca atgtcgaaga aggtttattg gatctaagcg gtcgcctcat tgatcaaaaa    1920
gcagatattg ctaaaaacca agcagacatc aagatttgg ccgcttacaa cgagctacaa     1980
gaccagtatg ctcaaaagca aaccgaagcg attgacgctc taaataaagc aagctctgcc    2040
aatactgatc gtattgctac tgctgaattg ggtatcgctg agaacaaaaa agacgctcag    2100
atcgccaaag cacaagccaa tgaaaataaa gacggcattg ctaaaaacca agcagatatt    2160
gctaataaca tcaaaaatat ctatgagctg gcacaacagc aagatcagca tagctctgat    2220
atcaaaacct tggcaaaagt aagtgctgcc aatactgatc gtattgctaa aaacaaagct    2280
gaagctgatg caagttttga aacgctcacc aaaaatcaaa atactttgat tgagcaaggt    2340
gaagcattgg ttgagcaaaa taagccatc aatcaagagc ttgaagggtt tgcggctcat    2400
gcagatgttc aagataagca aatttttacaa aaccaagctg atatcactgc caataagacc    2460
```

```
gctattgaac aaaatatcaa tagaactgtt gccaatgggt ttgagattga gaaaaataaa    2520
gctggtattg ctaccaataa gcaagagctt attcttcaac atgatcgatt aaatcgaatt    2580
aatgagacaa ataatcgtca ggatcagaag attgatcaat taggttatgc actaaaagag    2640
cagggtcagc attttaataa tcgtattagt gctgttgagc gtcaaacagc tggaggtatt    2700
gcaaatgcta tcgcaattgc aactttacca tcgcccagta gagcaggtga gcatcatgtc    2760
ttatttggtt caggttatca caatggtcaa gctgcggtat cattgggtgc ggctgggtta    2820
agtgatacag gaaaatcaac ttataagatt ggtctaagct ggtcagatgc aggtggatta    2880
tctggtggtg ttggtggtag ttaccgctgg aaatagagcc taaatttaac tgctgtatca    2940
aaaaatatgg tctgtataaa cagaccatat ttttatctaa aaacttatct taacttttat    3000
gaagcatcat aagccaaagc tgagtaataa taagagatgt taaataagaa gatgttaaaa    3060
ctgctaaaca atcggcttac gacgataaaa taaaatacct ggaatggaca gccccaaaac    3120
caatgctgag atgataaaaa tcgcctcaaa aaaatgacgc atcataacga taaataaatc    3180
catatcaaat ccaaaatagc caatttgtac catgctaacc atggctttat aggcagcgat    3240
tcccggcatc atacaaatca agctaggtac aatcaaggct ttaggcggca gg            3292
```

<210> SEQ ID NO 15
<211> LENGTH: 889
<212> TYPE: PRT
<213> ORGANISM: Moraxella catarrhalis

<400> SEQUENCE: 15

```
Val Asn Lys Ile Tyr Lys Val Lys Lys Asn Ala Ala Gly His Leu Val
  1               5                  10                  15

Ala Cys Ser Glu Phe Ala Lys Gly His Thr Lys Lys Ala Val Leu Gly
             20                  25                  30

Ser Leu Leu Ile Val Gly Ala Leu Gly Met Ala Thr Thr Ala Ser Ala
         35                  40                  45

Gln Pro Leu Val Ser Thr Asn Lys Pro Asn Gln Gln Val Lys Gly Tyr
     50                  55                  60

Trp Ser Ile Ile Gly Ala Gly Arg His Asn Asn Val Gly Gly Ser Ala
 65                  70                  75                  80

His His Ser Gly Ile Leu Gly Gly Trp Lys Asn Thr Val Asn Gly Tyr
                 85                  90                  95

Thr Ser Ala Ile Val Gly Gly Tyr Gly Asn Glu Thr Gln Gly Asp Tyr
            100                 105                 110

Thr Phe Val Gly Gly Gly Tyr Lys Asn Leu Ala Lys Gly Asn Tyr Thr
        115                 120                 125

Phe Val Gly Gly Gly Tyr Lys Asn Leu Ala Glu Gly Asp Asn Ala Thr
    130                 135                 140

Ile Ala Gly Gly Phe Ala Asn Leu Ala Glu Gly Asp Asn Ala Thr Ile
145                 150                 155                 160

Ala Gly Gly Phe Glu Asn Arg Ala Glu Gly Ile Asp Ser Val Val Ser
                165                 170                 175

Gly Gly Tyr Ala Asn Gln Ala Thr Gly Glu Ser Ser Thr Val Ala Gly
            180                 185                 190

Gly Ser Asn Asn Leu Ala Glu Gly Lys Ser Ser Ala Ile Gly Gly Gly
        195                 200                 205

Arg Gln Asn Glu Ala Ser Gly Asp Arg Ser Thr Val Ser Gly Gly Tyr
    210                 215                 220
```

-continued

```
Asn Asn Leu Ala Glu Gly Lys Ser Ala Ile Gly Gly Glu Phe
225                 230                 235                 240

Asn Leu Ala Leu Gly Asn Asn Ala Thr Ile Ser Gly Gly Arg Gln Asn
            245                 250                 255

Glu Ala Ser Gly Asp Arg Ser Thr Val Ala Gly Gly Glu Gln Asn Gln
            260                 265                 270

Ala Ile Gly Lys Tyr Ser Thr Ile Ser Gly Gly Arg Gln Asn Glu Ala
            275                 280                 285

Ser Gly Asp Arg Ser Thr Val Ala Gly Gly Glu Gln Asn Gln Ala Ile
            290                 295                 300

Gly Lys Tyr Ser Thr Val Ser Gly Gly Tyr Arg Asn Gln Ala Thr Gly
305                 310                 315                 320

Lys Gly Ser Phe Ala Ala Gly Ile Asp Asn Lys Ala Asn Ala Asp Asn
                325                 330                 335

Ala Val Ala Leu Gly Asn Lys Asn Thr Ile Glu Gly Glu Asn Ser Val
                340                 345                 350

Ala Ile Gly Ser Asn Asn Thr Val Lys Lys Asn Gln Lys Asn Val Phe
                355                 360                 365

Ile Leu Gly Ser Asn Thr Asp Thr Lys Asp Ala Gln Ser Gly Ser Val
                370                 375                 380

Leu Leu Gly Asp Asn Thr Ser Gly Lys Ala Ala Thr Ala Val Glu Asp
385                 390                 395                 400

Ala Thr Val Gly Asp Leu Ser Leu Thr Gly Phe Ala Gly Val Ser Lys
                405                 410                 415

Ala Asn Ser Gly Thr Val Ser Val Gly Ser Glu Gly Lys Glu Arg Gln
                420                 425                 430

Ile Val His Val Gly Ala Gly Arg Ile Ser Asn Asp Ser Thr Asp Ala
                435                 440                 445

Val Asn Gly Ser Gln Leu Tyr Ala Leu Ala Ala Val Asp Asp Asn
450                 455                 460

Gln Tyr Asp Ile Glu Lys Asn Gln Asp Ile Ala Lys Asn Gln Ala
465                 470                 475                 480

Asp Ile Ala Lys Asn Gln Ala Asp Ile Gln Thr Leu Glu Asn Asp Val
                485                 490                 495

Gly Lys Glu Leu Leu Asn Leu Ser Gly Arg Leu Ile Asp Gln Lys Ala
                500                 505                 510

Asp Ile Asp Asn Asn Ile Asn His Ile Tyr Glu Leu Ala Gln Gln Gln
            515                 520                 525

Asp Gln His Ser Ser Asp Ile Lys Thr Leu Lys Lys Asn Val Glu Glu
            530                 535                 540

Gly Leu Leu Glu Leu Ser Gly His Leu Ile Asp Gln Lys Ala Asp Leu
545                 550                 555                 560

Thr Lys Asp Ile Lys Ala Leu Glu Ser Asn Val Glu Glu Gly Leu Leu
                565                 570                 575

Asp Leu Ser Gly Arg Leu Ile Asp Gln Lys Ala Asp Ile Ala Gln Asn
            580                 585                 590

Gln Ala Asn Ile Gln Asp Leu Ala Ala Tyr Asn Glu Leu Gln Asp Gln
        595                 600                 605

Tyr Ala Gln Lys Gln Thr Glu Ala Ile Asp Ala Leu Asn Lys Ala Ser
        610                 615                 620

Ser Glu Asn Thr Gln Asn Ile Glu Asp Leu Ala Ala Tyr Asn Glu Leu
625                 630                 635                 640

Gln Asp Ala Tyr Ala Lys Gln Gln Thr Glu Ala Ile Asp Ala Leu Asn
```

```
                       645                 650                 655
Lys Ala Ser Ser Glu Asn Thr Gln Asn Ile Ala Lys Asn Gln Ala Asp
            660                 665                 670

Ile Ala Asn Asn Ile Asn Asn Ile Tyr Glu Leu Ala Gln Gln Gln Asp
            675                 680                 685

Gln His Ser Ser Asp Ile Lys Thr Leu Ala Lys Ala Ser Ala Ala Asn
            690                 695                 700

Thr Asp Arg Ile Ala Lys Asn Lys Ala Asp Ala Asp Ala Ser Phe Glu
705                 710                 715                 720

Thr Leu Thr Lys Asn Gln Asn Thr Leu Ile Glu Lys Asp Lys Glu His
                725                 730                 735

Asp Lys Leu Ile Thr Ala Asn Lys Thr Ala Ile Asp Ala Asn Lys Ala
                740                 745                 750

Ser Ala Asp Thr Lys Phe Ala Ala Thr Ala Asp Ala Ile Thr Lys Asn
            755                 760                 765

Gly Asn Ala Ile Thr Lys Asn Ala Lys Ser Ile Thr Asp Leu Gly Thr
770                 775                 780

Lys Val Asp Gly Phe Asp Gly Arg Val Thr Ala Leu Asp Thr Lys Val
785                 790                 795                 800

Asn Ala Phe Asp Gly Arg Ile Thr Ala Leu Asp Ser Lys Val Glu Asn
            805                 810                 815

Gly Met Ala Ala Gln Ala Ala Leu Ser Gly Leu Phe Gln Pro Tyr Ser
            820                 825                 830

Val Gly Lys Phe Asn Ala Thr Ala Ala Leu Gly Gly Tyr Gly Ser Lys
            835                 840                 845

Ser Ala Val Ala Ile Gly Ala Gly Tyr Arg Val Asn Pro Asn Leu Ala
            850                 855                 860

Phe Lys Ala Gly Ala Ala Ile Asn Thr Ser Gly Asn Lys Lys Gly Ser
865                 870                 875                 880

Tyr Asn Ile Gly Val Asn Tyr Glu Phe
            885

<210> SEQ ID NO 16
<211> LENGTH: 4228
<212> TYPE: DNA
<213> ORGANISM: Moraxella catarrhalis

<400> SEQUENCE: 16
gccgcaccct gaccgagacg ctccgccaaa tcgatgcgtc ggtgtactat gccccgaccg      60
agctatgcac ggataatggt gcgatgatcg cctatgctgg cttttgtcgg ctaagccgtg     120
gacagtcgga tgacttggtg gttcgctgta ttccccgatg ggatatgacg acgcttggta     180
tcgaatatga taattaggct gtggtatttg agttttgagt aatgtaccta ctaccactaa     240
tttatcatac aatacataaa cataaaaaac atcggtattg ttaaaaaaca atacccaagt     300
taaaatagct caatacttta ccatagcaca agaaacttg tgaacgaaac atttaataat     360
tgcccaaaat gttactgcac acactttgta aagcaggct gggcaatgg caaacaacga     420 tacaaatgca aaggttgcca tcactatttt tctgtgaagc aacgaagcaa ccaaaaaagt     480
aatgacatta aaaaacaag ccattgatac aaacagtaaa caaatcttag gctttgtctg     540
tggtaaaaca gacactaaca cctttaaacg actttatcag cagttaaata cccatagcat     600
tcaactgttt tttagtgact actgaaatc ttatcgtcaa gtcatttaa agccaaaaca     660 tataacaagc aaagctcaaa cttttaccat agagggctat aatagtctca ttaggcattt     720
```

```
catagcaaga tttacaagaa agtcaaagtg ttattctaaa tccgaaaaaa tgatagaaaa    780
cacgttgaat ttattatttg ctaagtggaa tggtagctta agatatgtat tttaatttaa    840
caatgccaaa aacatcaatt acagtaagat tttaggcgtt ttgcagttgc tactttagta    900
aagctttgtt atactagctg ttagtatact caagcttgtt tgtgtttgag ctatatttat    960
tttatagcag tagttggtta taaaatataa ataaagctaa gctcgagggt ttggtaatgg   1020
tttttttatgt ttataatacc aacagagtct atacagctaa aatagctaat accttaggtg   1080
tattacaagt aaaaatcctt tggttaatca gggggtgtat tatatgtata tttcctttgt   1140
atttggttat agcaatccct tggtaagaaa tcatatctat tttttattgt tcaattattt   1200
aggagactaa ggtgaacaaa atttataaag tgaaaaaaaa tgccgcaggt cacttggtgg   1260
catgttctga atttgccaaa ggccatacca aaaaggcagt tttgggcagt ttattgattg   1320
ttggggcgtt gggcatggca acgacggcgt ctgcacagcc attagtaagt acaaataagc   1380
ctaatcagca ggtaaagggt tattggtcta ttattggtgc aggtcgtcat aataacgtag   1440
gtggatccgc tcatcactca gggattcttg gtggttggaa aaatacagtc aatggctata   1500
cctcagccat tgtaggtggt tatggtaacg aaactcaggg tgattataca ttcgtcggtg   1560
gtggttataa aaacttggca aagggtaatt atacattcgt cggtggtggt tataaaaact   1620
tggcagaggg tgataatgca accatcgctg gtggttttgc aaacttggca gagggtgata   1680
atgcaaccat cgctggtggt tttgaaaacc gtgcagaggg tatcgactca gtagtttctg   1740
gtggttatgc caaccaagct acaggagaaa gctcaaccgt cgcaggtggt tctaataacc   1800
tagcagaggg caaaagctca gccattggtg gtggccgtca aaatgaggcg tctggtgacc   1860
gatctactgt ctcaggtggt tataataacc tagcagaggg caaaagctca gccattggtg   1920
gcggtgagtt taacttagca ttagggaata acgctaccat tagtggtggc cgtcaaaatg   1980
aggcgtctgg tgaccgatct actgtcgcag gtggtgaaca aaaccaagcc ataggcaagt   2040
attctaccat tagtggtggc cgtcaaaatg aggcgtctgg tgaccgatct actgtcgcag   2100
gtggtgaaca aaaccaagcc ataggcaagt attctaccgt tagtggtggc tatcgaaacc   2160
aagccacagg taaaggttca tttgcagcag gtatagataa caaagccaat gccgacaacg   2220
ccgtcgctct aggtaacaag aacaccatcg aaggtgaaaa ctcagtagcc atcggctcta   2280
ataataccgt taaaaaaaat caaaaaaatg tctttattct tggctctaac acagacacaa   2340
aagatgcaca aagcggctca gtactgctag gtgataatac ctctggtaaa gcagcgaccg   2400
ctgttgagga tgccacagtg ggtgatctaa gcctaacagg atttgcaggc gtatcaaaag   2460
ctaatagtgg tactgtatct gtcggtagtg agggtaaaga gcgtcaaatc gttcatgttg   2520
gtgcaggtcg gatcagtaat gattcaacag atgctgttaa tggctcacag ctatatgctt   2580
tggccgcagc tgttgatgac aaccaatatg acattgaaaa aaaccaagat gacattgcta   2640
aaaaccaagc tgacattgct aaaaaccaag ctgacatcca aacacttgaa aacgatgtcg   2700
gaaaagaact attaaatcta agcggtcgcc tcattgatca aaaagcagat attgataata   2760
acatcaacca tatctatgag ctggcacaac agcaagatca gcatagctct gatatcaaaa   2820
cacttaaaaa aaatgtcgaa gaaggttttgt tggagctaag cggtcacctc attgatcaaa   2880
aagcagatct tacaaaagac atcaaagcac ttgaaagcaa tgtcgaagaa ggtttgttgg   2940
atctaagcgg tcgcctcatt gatcaaaaag cagatattgc tcaaaaccaa gctaacatcc   3000
aagatttggc tgcttacaac gagctacaag accagtatgc tcaaaagcaa accgaagcga   3060
ttgacgctct aaataaagca agctctgaga atacacaaaa catcgaagat ctggccgctt   3120
```

```
acaacgagct acaagatgcc tatgccaaac agcaaaccga agccattgac gctctaaata    3180
aagcaagctc tgagaataca caaaacattg ctaaaaacca agcggatatt gctaataaca    3240
tcaacaatat ctatgagcta gcacaacagc aagatcagca tagctctgat atcaaaacct    3300
tggcaaaagc aagtgctgcc aatactgatc gtattgctaa aaacaaagcc gatgctgatg    3360
caagttttga aacgctcacc aaaaatcaaa atactttgat tgaaaaagat aaagagcatg    3420
acaaattaat tactgcaaac aaaactgcga ttgatgccaa taaagcatct gcggatacca    3480
agtttgcagc gacagcagac gccattacca aaaatggaaa tgctatcact aaaaacgcaa    3540
aatctatcac tgatttgggt actaaagtgg atggttttga cggtcgtgta actgcattag    3600
acaccaaagt caatgccttt gatggtcgta tcacagcttt agacagtaaa gttgaaaacg    3660
gtatggctgc ccaagctgcc ctaagtggtc tattccagcc ttatagcgtt ggtaagttta    3720
atgcgaccgc tgcacttggt ggctatggct caaaatctgc ggttgctatc ggtgctggct    3780
atcgtgtgaa tccaaatctg cgtttaaag ctggtgcggc gattaatacc agtggcaata    3840
aaaaaggctc ttataacatc ggtgtgaatt acgagttcta attgtctatc atcaccaaaa    3900
aaagcagtca gtttactggc tgctttttta tgggttttg tggcttttgg ttgtgagtga    3960
tggataaaag cttgtcaagc gattgatgaa tatcaataaa tgattggtaa atatcaataa    4020
agcggtttag ggttttgga tatcttttaa taagtttaaa acccctgca taaaataaag    4080 ctggcatcag agctgcgaag tagcggcata cagctggcaa tgcacgcctg tgcctagggg    4140
gcgtgagacc acccagcctt tgcgttcgta ttctaaaatt acccaatcag gcagagcggc    4200
aactccatgt tcggaggcga ccagctga                                       4228
```

<210> SEQ ID NO 17
<211> LENGTH: 7
<212> TYPE: PRT
<213> ORGANISM: Moraxella catarrhalis

<400> SEQUENCE: 17

Ala Gln Gln Gln Asp Gln His
  1               5

<210> SEQ ID NO 18
<211> LENGTH: 10
<212> TYPE: PRT
<213> ORGANISM: Moraxella catarrhalis

<400> SEQUENCE: 18

Tyr Glu Leu Ala Gln Gln Gln Asp Gln His
  1               5                  10

<210> SEQ ID NO 19
<211> LENGTH: 10
<212> TYPE: PRT
<213> ORGANISM: Moraxella catarrhalis

<400> SEQUENCE: 19

Tyr Asp Leu Ala Gln Gln Gln Asp Gln His
  1               5                  10

<210> SEQ ID NO 20
<211> LENGTH: 22
<212> TYPE: DNA
<213> ORGANISM: Moraxella catarrhalis

<400> SEQUENCE: 20

```
gacgctcaac agcactaata cg                                              22

<210> SEQ ID NO 21
<211> LENGTH: 19
<212> TYPE: DNA
<213> ORGANISM: Moraxella catarrhalis

<400> SEQUENCE: 21
ccaagctgat atcactacc                                                  19

<210> SEQ ID NO 22
<211> LENGTH: 18
<212> TYPE: DNA
<213> ORGANISM: Moraxella catarrhalis

<400> SEQUENCE: 22
tcaatgcctt tgatggtc                                                   18

<210> SEQ ID NO 23
<211> LENGTH: 21
<212> TYPE: DNA
<213> ORGANISM: Moraxella catarrhalis

<400> SEQUENCE: 23
tgtatgccgc tactcgcagc t                                               21

<210> SEQ ID NO 24
<211> LENGTH: 14
<212> TYPE: PRT
<213> ORGANISM: Moraxella catarrhalis
<220> FEATURE:
<221> NAME/KEY: MOD_RES
<222> LOCATION: (2)..(13)
<223> OTHER INFORMATION: Xaa = any natural occurring amino acid

<400> SEQUENCE: 24

Asn Xaa Ala Xaa Xaa Tyr Ser Xaa Ile Gly Gly Gly Xaa Asn
 1               5                  10

<210> SEQ ID NO 25
<211> LENGTH: 4
<212> TYPE: PRT
<213> ORGANISM: Moraxella catarrhalis

<400> SEQUENCE: 25

Gln Ala Asp Ile
 1

<210> SEQ ID NO 26
<211> LENGTH: 30
<212> TYPE: PRT
<213> ORGANISM: Moraxella catarrhalis

<400> SEQUENCE: 26

Ala Ala Gln Ala Ala Leu Ser Gly Leu Phe Val Pro Tyr Ser Val Gly
 1               5                  10                  15

Lys Phe Asn Ala Thr Ala Ala Leu Gly Gly Tyr Gly Ser Lys
             20                  25                  30

<210> SEQ ID NO 27
<211> LENGTH: 13
<212> TYPE: PRT
<213> ORGANISM: Moraxella catarrhalis
```

```
<400> SEQUENCE: 27

Gly Lys Ile Thr Lys Asn Ala Ala Arg Gln Glu Asn Gly
 1               5                   10

<210> SEQ ID NO 28
<211> LENGTH: 9
<212> TYPE: PRT
<213> ORGANISM: Moraxella catarrhalis

<400> SEQUENCE: 28

Val Ile Gly Asp Leu Gly Arg Lys Val
 1               5

<210> SEQ ID NO 29
<211> LENGTH: 10
<212> TYPE: PRT
<213> ORGANISM: Moraxella catarrhalis
<220> FEATURE:
<221> NAME/KEY: MOD_RES
<222> LOCATION: (4)
<223> OTHER INFORMATION: Xaa = any natural occurring amino acid

<400> SEQUENCE: 29

Ala Leu Glu Xaa Asn Val Glu Glu Gly Leu
 1               5                   10

<210> SEQ ID NO 30
<211> LENGTH: 14
<212> TYPE: PRT
<213> ORGANISM: Moraxella catarrhalis
<220> FEATURE:
<221> NAME/KEY: MOD_RES
<222> LOCATION: (11)..(12)
<223> OTHER INFORMATION: Xaa = any natural occurring amino acid

<400> SEQUENCE: 30

Ala Leu Glu Ser Asn Val Glu Glu Gly Leu Xaa Xaa Leu Ser
 1               5                   10

<210> SEQ ID NO 31
<211> LENGTH: 7
<212> TYPE: PRT
<213> ORGANISM: Moraxella catarrhalis

<400> SEQUENCE: 31

Ala Leu Glu Phe Asn Gly Glu
 1               5

<210> SEQ ID NO 32
<211> LENGTH: 9
<212> TYPE: PRT
<213> ORGANISM: Moraxella catarrhalis
<220> FEATURE:
<221> NAME/KEY: MOD_RES
<222> LOCATION: (7)
<223> OTHER INFORMATION: Xaa = any natural occurring amino acid

<400> SEQUENCE: 32

Ser Ile Thr Asp Leu Gly Xaa Lys Val
 1               5

<210> SEQ ID NO 33
<211> LENGTH: 15
<212> TYPE: PRT
<213> ORGANISM: Moraxella catarrhalis
<220> FEATURE:
<221> NAME/KEY: MOD_RES
```

```
<222> LOCATION: (13)..(15)
<223> OTHER INFORMATION: Xaa = any natural occurring amino acid

<400> SEQUENCE: 33

Ser Ile Thr Asp Leu Gly Thr Ile Val Asp Gly Phe Xaa Xaa Xaa
1               5                   10                  15

<210> SEQ ID NO 34
<211> LENGTH: 10
<212> TYPE: PRT
<213> ORGANISM: Moraxella catarrhalis

<400> SEQUENCE: 34

Ser Ile Thr Asp Leu Gly Thr Ile Val Asp
1               5                   10

<210> SEQ ID NO 35
<211> LENGTH: 20
<212> TYPE: PRT
<213> ORGANISM: Moraxella catarrhalis
<220> FEATURE:
<221> NAME/KEY: MOD_RES
<222> LOCATION: (5)..(19)
<223> OTHER INFORMATION: Xaa = any natural occurring amino acid

<400> SEQUENCE: 35

Val Asp Ala Leu Xaa Thr Lys Val Asn Ala Leu Asp Xaa Lys Val Asn
1               5                   10                  15

Ser Asp Xaa Thr
            20

<210> SEQ ID NO 36
<211> LENGTH: 15
<212> TYPE: PRT
<213> ORGANISM: Moraxella catarrhalis

<400> SEQUENCE: 36

Leu Leu Ala Glu Gln Gln Leu Asn Gly Lys Thr Leu Thr Pro Val
1               5                   10                  15

<210> SEQ ID NO 37
<211> LENGTH: 14
<212> TYPE: PRT
<213> ORGANISM: Moraxella catarrhalis

<400> SEQUENCE: 37

Ala Lys His Asp Ala Ala Ser Thr Glu Lys Gly Lys Met Asp
1               5                   10

<210> SEQ ID NO 38
<211> LENGTH: 15
<212> TYPE: PRT
<213> ORGANISM: Moraxella catarrhalis

<400> SEQUENCE: 38

Ala Leu Glu Ser Asn Val Glu Glu Gly Leu Leu Asp Leu Ser Gly
1               5                   10                  15

<210> SEQ ID NO 39
<211> LENGTH: 12
<212> TYPE: PRT
<213> ORGANISM: Moraxella catarrhalis

<400> SEQUENCE: 39

Asn Gln Asn Thr Leu Ile Glu Lys Thr Ala Asn Lys
```

```
          1               5                  10
```

<210> SEQ ID NO 40
<211> LENGTH: 9
<212> TYPE: PRT
<213> ORGANISM: Moraxella catarrhalis

<400> SEQUENCE: 40

```
Ile Asp Lys Asn Glu Tyr Ser Ile Lys
  1               5
```

<210> SEQ ID NO 41
<211> LENGTH: 8
<212> TYPE: PRT
<213> ORGANISM: Moraxella catarrhalis

<400> SEQUENCE: 41

```
Ser Ile Thr Asp Leu Gly Thr Lys
  1               5
```

<210> SEQ ID NO 42
<211> LENGTH: 8
<212> TYPE: PRT
<213> ORGANISM: Moraxella catarrhalis

<400> SEQUENCE: 42

```
Asn Gln Asn Thr Leu Ile Glu Lys
  1               5
```

<210> SEQ ID NO 43
<211> LENGTH: 12
<212> TYPE: PRT
<213> ORGANISM: Moraxella catarrhalis

<400> SEQUENCE: 43

```
Ala Leu His Glu Gln Gln Leu Glu Thr Leu Thr Lys
  1               5                  10
```

<210> SEQ ID NO 44
<211> LENGTH: 4
<212> TYPE: PRT
<213> ORGANISM: Moraxella catarrhalis

<400> SEQUENCE: 44

```
Asn Ser Ser Asp
  1
```

<210> SEQ ID NO 45
<211> LENGTH: 14
<212> TYPE: PRT
<213> ORGANISM: Moraxella catarrhalis

<400> SEQUENCE: 45

```
Asn Lys Ala Asp Ala Asp Ala Ser Phe Glu Thr Leu Thr Lys
  1               5                  10
```

<210> SEQ ID NO 46
<211> LENGTH: 10
<212> TYPE: PRT
<213> ORGANISM: Moraxella catarrhalis

<400> SEQUENCE: 46

```
Phe Ala Ala Thr Ala Ile Ala Lys Asp Lys
  1               5                  10
```

```
<210> SEQ ID NO 47
<211> LENGTH: 12
<212> TYPE: PRT
<213> ORGANISM: Moraxella catarrhalis

<400> SEQUENCE: 47

Lys Ala Ser Ser Glu Asn Thr Gln Asn Ile Ala Lys
 1               5                  10

<210> SEQ ID NO 48
<211> LENGTH: 6
<212> TYPE: PRT
<213> ORGANISM: Moraxella catarrhalis

<400> SEQUENCE: 48

Arg Leu Leu Asp Gln Lys
 1               5

<210> SEQ ID NO 49
<211> LENGTH: 12
<212> TYPE: PRT
<213> ORGANISM: Moraxella catarrhalis
<220> FEATURE:
<221> NAME/KEY: MOD_RES
<222> LOCATION: (12)
<223> OTHER INFORMATION: Xaa = any natural occurring amino acid

<400> SEQUENCE: 49

Ala Ala Thr Ala Asp Ala Ile Thr Lys Asn Gly Xaa
 1               5                  10

<210> SEQ ID NO 50
<211> LENGTH: 10
<212> TYPE: PRT
<213> ORGANISM: Moraxella catarrhalis
<220> FEATURE:
<221> NAME/KEY: MOD_RES
<222> LOCATION: (4)..(8)
<223> OTHER INFORMATION: Xaa = any natural occurring amino acid

<400> SEQUENCE: 50

Ala Lys Ala Xaa Ala Ala Asn Xaa Asp Arg
 1               5                  10

<210> SEQ ID NO 51
<211> LENGTH: 22
<212> TYPE: PRT
<213> ORGANISM: Moraxella catarrhalis

<400> SEQUENCE: 51

Asn Gln Ala Asp Ile Ala Gln Asn Gln Thr Asp Ile Gln Asp Leu Ala
 1               5                  10                  15

Ala Tyr Asn Glu Leu Gln
            20

<210> SEQ ID NO 52
<211> LENGTH: 21
<212> TYPE: PRT
<213> ORGANISM: Moraxella catarrhalis

<400> SEQUENCE: 52

Asn Gln Ala Asp Ile Ala Asn Asn Ile Asn Asn Ile Tyr Glu Leu Ala
 1               5                  10                  15

Gln Gln Gln Asp Gln
            20
```

<210> SEQ ID NO 53
<211> LENGTH: 13
<212> TYPE: PRT
<213> ORGANISM: Moraxella catarrhalis

<400> SEQUENCE: 53

Tyr Asn Glu Arg Gln Thr Glu Ala Ile Asp Ala Leu Asn
 1               5                  10

<210> SEQ ID NO 54
<211> LENGTH: 13
<212> TYPE: PRT
<213> ORGANISM: Moraxella catarrhalis

<400> SEQUENCE: 54

Ile Leu Gly Asp Thr Ala Ile Val Ser Asn Ser Gln Asp
 1               5                  10

<210> SEQ ID NO 55
<211> LENGTH: 17
<212> TYPE: PRT
<213> ORGANISM: Moraxella catarrhalis

<400> SEQUENCE: 55

Lys Ala Leu Glu Ser Asn Val Glu Glu Gly Leu Leu Asp Leu Ser Gly
 1               5                  10                  15

Arg

<210> SEQ ID NO 56
<211> LENGTH: 21
<212> TYPE: PRT
<213> ORGANISM: Moraxella catarrhalis

<400> SEQUENCE: 56

Ala Leu Glu Ser Asn Val Glu Glu Gly Leu Leu Glu Leu Ser Gly Arg
 1               5                  10                  15

Thr Ile Asp Gln Arg
            20

<210> SEQ ID NO 57
<211> LENGTH: 22
<212> TYPE: PRT
<213> ORGANISM: Moraxella catarrhalis
<220> FEATURE:
<221> NAME/KEY: MOD_RES
<222> LOCATION: (11)
<223> OTHER INFORMATION: Xaa = any natural occurring amino acid

<400> SEQUENCE: 57

Asn Gln Ala His Ile Ala Asn Asn Ile Asn Xaa Ile Tyr Glu Leu Ala
 1               5                  10                  15

Gln Gln Gln Asp Gln Lys
            20

<210> SEQ ID NO 58
<211> LENGTH: 22
<212> TYPE: PRT
<213> ORGANISM: Moraxella catarrhalis

<400> SEQUENCE: 58

Asn Gln Ala Asp Ile Ala Gln Asn Gln Thr Asp Ile Gln Asp Leu Ala
 1               5                  10                  15

Ala Tyr Asn Glu Leu Gln
            20

<210> SEQ ID NO 59
<211> LENGTH: 12
<212> TYPE: PRT
<213> ORGANISM: Moraxella catarrhalis

<400> SEQUENCE: 59

Ala Thr His Asp Tyr Asn Glu Arg Gln Thr Glu Ala
1               5                   10

<210> SEQ ID NO 60
<211> LENGTH: 12
<212> TYPE: PRT
<213> ORGANISM: Moraxella catarrhalis

<400> SEQUENCE: 60

Lys Ala Ser Ser Glu Asn Thr Gln Asn Ile Ala Lys
1               5                   10

<210> SEQ ID NO 61
<211> LENGTH: 23
<212> TYPE: PRT
<213> ORGANISM: Moraxella catarrhalis

<400> SEQUENCE: 61

Met Ile Leu Gly Asp Thr Ala Ile Val Ser Asn Ser Gln Asp Asn Lys
1               5                   10                  15

Thr Gln Leu Lys Phe Tyr Lys
            20

<210> SEQ ID NO 62
<211> LENGTH: 14
<212> TYPE: PRT
<213> ORGANISM: Moraxella catarrhalis
<220> FEATURE:
<221> NAME/KEY: MOD_RES
<222> LOCATION: (12)..(13)
<223> OTHER INFORMATION: Xaa = any natural occurring amino acid

<400> SEQUENCE: 62

Ala Gly Asp Thr Ile Ile Pro Leu Asp Asp Xaa Xaa Pro
1               5                   10

<210> SEQ ID NO 63
<211> LENGTH: 10
<212> TYPE: PRT
<213> ORGANISM: Moraxella catarrhalis
<220> FEATURE:
<221> NAME/KEY: MOD_RES
<222> LOCATION: (8)
<223> OTHER INFORMATION: Xaa = any natural occurring amino acid

<400> SEQUENCE: 63

Leu Leu His Glu Gln Gln Leu Xaa Gly Lys
1               5                   10

<210> SEQ ID NO 64
<211> LENGTH: 6
<212> TYPE: PRT
<213> ORGANISM: Moraxella catarrhalis
<220> FEATURE:
<221> NAME/KEY: MOD_RES
<222> LOCATION: (5)
<223> OTHER INFORMATION: Xaa = any natural occurring amino acid -continued

```
<400> SEQUENCE: 64

Ile Phe Phe Asn Xaa Gly
  1               5

<210> SEQ ID NO 65
<211> LENGTH: 23
<212> TYPE: PRT
<213> ORGANISM: Moraxella catarrhalis

<400> SEQUENCE: 65

Asn Asn Ile Asn Asn Ile Tyr Glu Leu Ala Gln Gln Gln Asp Gln His
  1               5                  10                  15

Ser Ser Asp Ile Lys Thr Leu
             20

<210> SEQ ID NO 66
<211> LENGTH: 21
<212> TYPE: DNA
<213> ORGANISM: Moraxella catarrhalis

<400> SEQUENCE: 66
ggtgcaggtc agatcagtga c                                           21

<210> SEQ ID NO 67
<211> LENGTH: 18
<212> TYPE: DNA
<213> ORGANISM: Moraxella catarrhalis

<400> SEQUENCE: 67
gccaccaacc aagctgac                                               18

<210> SEQ ID NO 68
<211> LENGTH: 21
<212> TYPE: DNA
<213> ORGANISM: Moraxella catarrhalis

<400> SEQUENCE: 68
agcggtcgcc tgcttgatca g                                           21

<210> SEQ ID NO 69
<211> LENGTH: 21
<212> TYPE: DNA
<213> ORGANISM: Moraxella catarrhalis

<400> SEQUENCE: 69
ctgatcaagc aggcgaccgc t                                           21

<210> SEQ ID NO 70
<211> LENGTH: 20
<212> TYPE: DNA
<213> ORGANISM: Moraxella catarrhalis

<400> SEQUENCE: 70
caagatctgg ccgcttacaa                                             20

<210> SEQ ID NO 71
<211> LENGTH: 20
<212> TYPE: DNA
<213> ORGANISM: Moraxella catarrhalis

<400> SEQUENCE: 71
ttgtaagcgg ccagatcttg                                             20
```

-continued

<210> SEQ ID NO 72
<211> LENGTH: 18
<212> TYPE: DNA
<213> ORGANISM: Moraxella catarrhalis

<400> SEQUENCE: 72
tgcatgagcc gcaaaccc                                                 18

<210> SEQ ID NO 73
<211> LENGTH: 9
<212> TYPE: PRT
<213> ORGANISM: Moraxella catarrhalis

<400> SEQUENCE: 73

Leu Leu Ala Glu Gln Gln Leu Asn Gly
 1               5

<210> SEQ ID NO 74
<211> LENGTH: 10
<212> TYPE: PRT
<213> ORGANISM: Moraxella catarrhalis

<400> SEQUENCE: 74

Ala Leu Glu Ser Asn Val Glu Glu Gly Leu
 1               5                  10

<210> SEQ ID NO 75
<211> LENGTH: 14
<212> TYPE: PRT
<213> ORGANISM: Moraxella catarrhalis

<400> SEQUENCE: 75

Ala Leu Glu Ser Asn Val Glu Glu Gly Leu Leu Asp Leu Ser
 1               5                  10

<210> SEQ ID NO 76
<211> LENGTH: 3788
<212> TYPE: PRT
<213> ORGANISM: Moraxella catarrhalis
<220> FEATURE:
<221> NAME/KEY: MOD_RES
<222> LOCATION: (1036)..(3786)
<223> OTHER INFORMATION: Xaa = any natural occurring amino acid

<400> SEQUENCE: 76

Thr His Glu Phe Ile Arg Ser Thr Ser Glu Gln Glu Asn Cys Glu Ser
 1               5                  10                  15

Ala Arg Glu Asn Thr His Glu Asp Ile Ser Lys Glu Thr Thr Glu Ser
                20                  25                  30

Ala Asn Asp Ala Thr Leu Glu Ala Ser Thr Ser Met Glu Phe Thr His
            35                  40                  45

Glu Ser Glu Ala Leu Arg Glu Ala Asp Tyr Asn Thr His Glu Thr Asp
        50                  55                  60

Arg Ile Val Glu Cys His Glu Cys Lys Trp Ile Thr His Gly Glu Arg
 65                  70                  75                  80

Arg Ile Thr His Glu Ser Glu Ser Glu Gln Glu Asn Cys Glu Ser Ala
                85                  90                  95

Arg Glu Asn Ala Met Glu Asp Asn Thr His Glu Asp Ile Ser Lys Glu
               100                 105                 110

Thr Thr Glu Ser Ala Asn Asp His Ala Arg Asp Cys Pro Ile Glu Ser
           115                 120                 125

```
Ala Thr Thr Ala Cys His Glu Asp Ala Ser Phe Leu Leu Trp Ser Ala
        130                 135                 140

Asn Asp Asp Asn Thr His Ala Val Glu Ala Asn Tyr Ser Pro Glu Cys
145                 150                 155                 160

Ile Ala Leu Cys His Ala Arg Ala Cys Thr Glu Arg Ser Asp Asn Thr
                165                 170                 175

Thr Arg Ala Asn Ser Leu Ala Thr Glu Ala Asn Tyr Ser Glu Gln Glu
            180                 185                 190

Asn Cys Glu Ser Thr His Ala Thr Ile Ser Thr His Glu Arg Glu Ile
        195                 200                 205

Ser Asn Ser Thr Ala Arg Thr Cys Asp Asn Ser Glu Gln Ile Asp Asn
210                 215                 220

Phe Ile Leu Glu Asn Ala Met Glu Thr Tyr Pro Glu Ser Thr Arg Ala
225                 230                 235                 240

Asn Asp Thr Pro Leu Gly Tyr Ser Glu Gln Ile Asp Asn Glu Ser Pro
                245                 250                 255

Ala Ala Ala Pro Arg Thr Glu Ile Asn Asn Ala Leu Ile Asn Glu Ala
                260                 265                 270

Arg Ser Glu Gln Ile Asp Asn Glu Ser Pro Ala Asn Ala Asp Asn Ala
                275                 280                 285

Asp Asx Leu Glu Leu Ile Asn Glu Ala Arg Ser Glu Gln Ile Asp Asn
        290                 295                 300

Glu Ser Pro Ala Ala Ala Pro Arg Thr Glu Ile Asn Asn Ala Leu Ile
305                 310                 315                 320

Asn Glu Ala Arg Ser Glu Gln Ile Asp Asn Glu Ser Pro Ala Asn Ala
                325                 330                 335

Asp Asn Ala Asp Asx Leu Glu Leu Ile Asn Glu Ala Arg Ser Glu Gln
            340                 345                 350

Ile Asp Asn Glu Ser Pro Ala Ala Ala Pro Ala Thr Pro Arg Thr Glu
            355                 360                 365

Ile Asn Asn Ala Leu Ile Asn Glu Ala Arg Ser Glu Gln Ile Asp Asn
        370                 375                 380

Glu Ser Pro Ala Asn Ala Pro Ala Thr Asp Asn Ala Asp Asx Leu Glu
385                 390                 395                 400

Leu Ile Asn Glu Ala Arg Ser Glu Gln Ile Asp Asn Glu Ser Pro Ala
                405                 410                 415

Ala Ala Pro Ala Thr Pro Arg Thr Glu Ile Asn Asn Ala Leu Ile Asn
            420                 425                 430

Glu Ala Arg Ser Glu Gln Ile Asp Asn Glu Ser Pro Ala Asn Ala Pro
        435                 440                 445

Ala Thr Asp Asn Ala Asp Asx Leu Glu Leu Ile Asn Glu Ala Arg Ser
    450                 455                 460

Glu Gln Ile Asp Asn Thr Thr Ala Ser Pro Ala Ala Pro Ala Thr
465                 470                 475                 480

Pro Arg Thr Glu Ile Asn Asn Ala Leu Ile Asn Glu Ala Arg Ser Glu
                485                 490                 495

Gln Ile Asp Asn Thr Thr Ala Ser Pro Ala Asn Ala Pro Ala Thr Asp
            500                 505                 510

Asn Ala Asp Asx Leu Glu Leu Ile Asn Glu Ala Arg Ser Glu Gln Ile
        515                 520                 525

Asp Asn Thr Thr Ala Ser Pro Ala Ala Ala Pro Ala Thr Pro Arg Thr
    530                 535                 540

Glu Ile Asn Asn Ala Leu Ile Asn Glu Ala Arg Ser Glu Gln Ile Asp
```

```
                545                 550                 555                 560
Asn Thr Thr Ala Ser Pro Ala Asn Ala Pro Ala Thr Asp Asn Ala Asp
                565                 570                 575
Asx Leu Glu Leu Ile Asn Glu Ala Arg Ser Glu Gln Ile Asp Asn Thr
                580                 585                 590
Thr Ala Ser Pro Ala Ala Pro Ala Thr Pro Arg Thr Glu Ile Asn
                595                 600                 605
Asn Ala Leu Ile Asn Glu Ala Arg Ser Glu Gln Ile Asp Asn Thr Thr
                610                 615                 620
Ala Ser Pro Ala Asn Ala Pro Ala Thr Asp Asn Ala Asp Asx Leu Glu
625                 630                 635                 640
Leu Ile Asn Glu Ala Arg Ser Glu Gln Ile Asp Asn Thr Thr Ala Ser
                645                 650                 655
Pro Ala Ala Pro Ala Thr Pro Arg Thr Glu Ile Asn Asn Ala Leu
                660                 665                 670
Ile Asn Glu Ala Arg Ser Glu Gln Ile Asp Asn Thr Thr Ala Ser Pro
                675                 680                 685
Ala Asn Ala Pro Ala Thr Asp Asn Ala Asp Asx Leu Glu Leu Ile Asn
690                 695                 700
Glu Ala Arg Ser Glu Gln Ile Asp Asn Thr His Arg Gly His Ser Glu
705                 710                 715                 720
Gln Ile Asp Asn Ile Ser Gly Ile Val Glu Asn Asx Glu Leu Trp Ala
                725                 730                 735
Asn Asp Ala Arg Glu Asn Thr Asn Thr His Glu Asp Ile Ser Lys Glu
                740                 745                 750
Thr Thr Glu Ser Ser Glu Gln Glu Asn Cys Glu Ser Glu Gln Ile Asp
                755                 760                 765
Asn Thr Tyr Pro Glu Thr Pro Leu Gly Tyr Ser Thr Arg Ala Asn Asp
                770                 775                 780
Ser Pro Glu Cys Ile Ala Leu Ala Gln Gln Asp Gln His Ser Glu
785                 790                 795                 800
Gln Ile Asp Asn Pro Arg Thr Glu Ile Asn Leu Ile Asn Glu Ala Arg
                805                 810                 815
Asn Ala Tyr Glu Leu Ala Gln Gln Gln Asp Gln His Ser Glu Gln Ile
                820                 825                 830
Asp Asn Pro Arg Thr Glu Ile Asn Leu Ile Asn Glu Ala Arg Asn Ala
                835                 840                 845
Tyr Asp Leu Ala Gln Gln Gln Asp Gln His Ser Glu Gln Ile Asp Asn
                850                 855                 860
Pro Arg Thr Glu Ile Asn Leu Ile Asn Glu Ala Arg Asn Ala Gly Ala
865                 870                 875                 880
Cys Gly Cys Thr Cys Ala Ala Cys Ala Gly Cys Ala Cys Thr Ala Ala
                885                 890                 895
Thr Ala Cys Gly Ser Glu Gln Ile Asp Asn Asp Asn Ala Leu Ile Asn
                900                 905                 910
Glu Ala Arg Asp Asx Leu Glu Cys Cys Ala Ala Gly Cys Thr Gly Ala
                915                 920                 925
Thr Ala Thr Cys Ala Cys Thr Ala Cys Ser Glu Gln Ile Asp Asn
                930                 935                 940
Asp Asn Ala Leu Ile Asn Glu Ala Arg Asp Asx Leu Glu Thr Cys Ala
945                 950                 955                 960
Ala Thr Gly Cys Cys Thr Thr Gly Ala Thr Gly Gly Thr Cys Ser
                965                 970                 975
```

```
Glu Gln Ile Asp Asn Asp Asn Ala Leu Ile Asn Glu Ala Arg Asp Asx
            980                 985                 990

Leu Glu Thr Gly Thr Ala Thr Gly Cys Cys Gly Cys Thr Ala Cys Thr
        995                 1000                1005

Cys Gly Cys Ala Gly Cys Thr Ser Glu Gln Ile Asp Asn Asp Asn Ala
    1010                1015                1020

Leu Ile Asn Glu Ala Arg Asp Asx Leu Glu Asn Xaa Ala Xaa Xaa Tyr
1025                1030                1035                1040

Ser Xaa Ile Gly Gly Gly Xaa Asn Ser Glu Gln Ile Asp Asn Pro Arg
        1045                1050                1055

Thr Glu Ile Asn Leu Ile Asn Glu Ala Arg Asn Ala Xaa Ala Asn Tyr
    1060                1065                1070

Ala Thr Pro Ser Ile Thr Ile Asn Ser Gln Ala Asp Ile Ser Glu Gln
        1075                1080                1085

Ile Asp Asn Pro Arg Thr Glu Ile Asn Leu Ile Asn Glu Ala Arg Asn
    1090                1095                1100

Ala Ala Ala Gln Ala Ala Leu Ser Gly Leu Phe Val Pro Tyr Ser Val
1105                1110                1115                1120

Gly Lys Phe Asn Ala Thr Ala Ala Leu Gly Gly Tyr Gly Ser Lys Ser
            1125                1130                1135

Glu Gln Ile Asp Asn Pro Arg Thr Glu Ile Asn Leu Ile Asn Glu Ala
        1140                1145                1150

Arg Asn Ala Gly Lys Ile Thr Lys Asn Ala Ala Arg Gln Glu Asn Gly
    1155                1160                1165

Ser Glu Gln Ile Asp Asn Pro Arg Thr Glu Ile Asn Leu Ile Asn Glu
    1170                1175                1180

Ala Arg Asn Ala Val Ile Gly Asp Leu Gly Arg Lys Val Ser Glu Gln
1185                1190                1195                1200

Ile Asp Asn Pro Arg Thr Glu Ile Asn Leu Ile Asn Glu Ala Arg Asn
        1205                1210                1215

Ala Ala Leu Glu Xaa Asn Val Glu Glu Gly Leu Ser Glu Gln Ile Asp
    1220                1225                1230

Asn Pro Arg Thr Glu Ile Asn Leu Ile Asn Glu Ala Arg Asn Ala Xaa
    1235                1240                1245

Ala Asn Tyr Ala Thr Pro Ser Ile Thr Ile Asn Ala Leu Glu Ser Asn
    1250                1255                1260

Val Glu Glu Gly Leu Xaa Xaa Leu Ser Ser Glu Gln Ile Asp Asn Pro
1265                1270                1275                1280

Arg Thr Glu Ile Asn Leu Ile Asn Glu Ala Arg Asn Ala Xaa Ala Asn
        1285                1290                1295

Tyr Ala Thr Pro Ser Ile Thr Ile Asn Ser Ala Leu Glu Phe Asn Gly
        1300                1305                1310

Glu Ser Glu Gln Ile Asp Asn Pro Arg Thr Glu Ile Asn Leu Ile Asn
        1315                1320                1325

Glu Ala Arg Asn Ala Ser Ile Thr Asp Leu Gly Xaa Lys Val Ser Glu
    1330                1335                1340

Gln Ile Asp Asn Pro Arg Thr Glu Ile Asn Leu Ile Asn Glu Ala Arg
1345                1350                1355                1360

Asn Ala Xaa Ala Asn Tyr Ala Thr Pro Ser Ile Thr Ile Asn Ser Ile
        1365                1370                1375

Thr Asp Leu Gly Thr Ile Val Asp Gly Phe Xaa Xaa Xaa Ser Glu Gln
        1380                1385                1390
```

```
Ile Asp Asn Pro Arg Thr Glu Ile Asn Leu Ile Asn Glu Ala Arg Asn
    1395                1400                1405

Ala Xaa Ala Asn Tyr Ala Thr Pro Ser Ile Thr Ile Asn Ser Ser Ile
    1410                1415                1420

Thr Asp Leu Gly Thr Ile Val Asp Ser Glu Gln Ile Asp Asn Pro Arg
1425                1430                1435                1440

Thr Glu Ile Asn Leu Ile Asn Glu Ala Arg Asn Ala Val Asp Ala Leu
            1445                1450                1455

Xaa Thr Lys Val Asn Ala Leu Asp Xaa Lys Val Asn Ser Asp Xaa Thr
        1460                1465                1470

Ser Glu Gln Ile Asp Asn Pro Arg Thr Glu Ile Asn Leu Ile Asn Glu
    1475                1480                1485

Ala Arg Asn Ala Xaa Ala Asn Tyr Ala Thr Pro Ser Ile Thr Ile Asn
    1490                1495                1500

Ser Leu Leu Ala Glu Gln Gln Leu Asn Gly Lys Thr Leu Thr Pro Val
1505                1510                1515                1520

Ser Glu Gln Ile Asp Asn Pro Arg Thr Glu Ile Asn Leu Ile Asn Glu
            1525                1530                1535

Ala Arg Asn Ala Ala Lys His Asp Ala Ala Ser Thr Glu Lys Gly Lys
        1540                1545                1550

Met Asp Ser Glu Gln Ile Asp Asn Pro Arg Thr Glu Ile Asn Leu Ile
    1555                1560                1565

Asn Glu Ala Arg Asn Ala Ala Leu Glu Ser Asn Val Glu Glu Gly Leu
    1570                1575                1580

Leu Asp Leu Ser Gly Ser Glu Gln Ile Asp Asn Pro Arg Thr Glu Ile
1585                1590                1595                1600

Asn Leu Ile Asn Glu Ala Arg Asn Ala Asn Gln Asn Thr Leu Ile Glu
            1605                1610                1615

Lys Thr Ala Asn Lys Ser Glu Gln Ile Asp Asn Pro Arg Thr Glu Ile
        1620                1625                1630

Asn Leu Ile Asn Glu Ala Arg Asn Ala Ile Asp Lys Asn Glu Tyr Ser
    1635                1640                1645

Ile Lys Ser Glu Gln Ile Asp Asn Pro Arg Thr Glu Ile Asn Leu Ile
    1650                1655                1660

Asn Glu Ala Arg Asn Ala Ser Ile Thr Asp Leu Gly Thr Lys Ser Glu
1665                1670                1675                1680

Gln Ile Asp Asn Pro Arg Thr Glu Ile Asn Leu Ile Asn Glu Ala Arg
            1685                1690                1695

Asn Ala Asn Gln Asn Thr Leu Ile Glu Lys Ser Glu Gln Ile Asp Asn
        1700                1705                1710

Pro Arg Thr Glu Ile Asn Leu Ile Asn Glu Ala Arg Asn Ala Ala Leu
    1715                1720                1725

His Glu Gln Gln Leu Glu Thr Leu Thr Lys Ser Glu Gln Ile Asp Asn
    1730                1735                1740

Pro Arg Thr Glu Ile Asn Leu Ile Asn Glu Ala Arg Asn Ala Asn Ser
1745                1750                1755                1760

Ser Asp Ser Glu Gln Ile Asp Asn Pro Arg Thr Glu Ile Asn Leu Ile
            1765                1770                1775

Asn Glu Ala Arg Asn Ala Asn Lys Ala Asp Ala Asp Ala Ser Phe Glu
        1780                1785                1790

Thr Leu Thr Lys Ser Glu Gln Ile Asp Asn Pro Arg Thr Glu Ile Asn
    1795                1800                1805

Leu Ile Asn Glu Ala Arg Asn Ala Phe Ala Ala Thr Ala Ile Ala Lys
```

-continued

```
                1810                1815                1820
Asp Lys Ser Glu Gln Ile Asp Asn Pro Arg Thr Glu Ile Asn Leu Ile
1825                1830                1835                1840

Asn Glu Ala Arg Asn Ala Lys Ala Ser Ser Glu Asn Thr Gln Asn Ile
                1845                1850                1855

Ala Lys Ser Glu Gln Ile Asp Asn Pro Arg Thr Glu Ile Asn Leu Ile
            1860                1865                1870

Asn Glu Ala Arg Asn Ala Arg Leu Leu Asp Gln Lys Ser Glu Gln Ile
        1875                1880                1885

Asp Asn Pro Arg Thr Glu Ile Asn Leu Ile Asn Glu Ala Arg Asn Ala
    1890                1895                1900

Ala Ala Thr Ala Asp Ala Ile Thr Lys Asn Gly Xaa Ser Glu Gln Ile
1905                1910                1915                1920

Asp Asn Pro Arg Thr Glu Ile Asn Leu Ile Asn Glu Ala Arg Asn Ala
                1925                1930                1935

Ala Lys Ala Xaa Ala Ala Asn Xaa Asp Arg Ser Glu Gln Ile Asp Asn
            1940                1945                1950

Pro Arg Thr Glu Ile Asn Leu Ile Asn Glu Ala Arg Asn Ala Xaa Ala
        1955                1960                1965

Asn Tyr Ala Thr Pro Ser Ile Thr Ile Asn Ser Asn Gln Ala Asp Ile
    1970                1975                1980

Ala Gln Asn Gln Thr Asp Ile Gln Asp Leu Ala Ala Tyr Asn Glu Leu
1985                1990                1995                2000

Gln Ser Glu Gln Ile Asp Asn Pro Arg Thr Glu Ile Asn Leu Ile Asn
                2005                2010                2015

Glu Ala Arg Asn Ala Asn Gln Ala Asp Ile Ala Asn Asn Ile Asn Asn
            2020                2025                2030

Ile Tyr Glu Leu Ala Gln Gln Asp Gln Ser Glu Gln Ile Asp Asn
        2035                2040                2045

Pro Arg Thr Glu Ile Asn Leu Ile Asn Glu Ala Arg Asn Ala Tyr Asn
    2050                2055                2060

Glu Arg Gln Thr Glu Ala Ile Asp Ala Leu Asn Ser Glu Gln Ile Asp
2065                2070                2075                2080

Asn Pro Arg Thr Glu Ile Asn Leu Ile Asn Glu Ala Arg Asn Ala Ile
                2085                2090                2095

Leu Gly Asp Thr Ala Ile Val Ser Asn Ser Gln Asp Ser Glu Gln Ile
            2100                2105                2110

Asp Asn Pro Arg Thr Glu Ile Asn Leu Ile Asn Glu Ala Arg Asn Ala
        2115                2120                2125

Lys Ala Leu Glu Ser Asn Val Glu Glu Gly Leu Leu Asp Leu Ser Gly
    2130                2135                2140

Arg Ser Glu Gln Ile Asp Asn Pro Arg Thr Glu Ile Asn Leu Ile Asn
2145                2150                2155                2160

Glu Ala Arg Asn Ala Ala Leu Glu Ser Asn Val Glu Glu Gly Leu Leu
                2165                2170                2175

Glu Leu Ser Gly Arg Thr Ile Asp Gln Arg Ser Glu Gln Ile Asp Asn
            2180                2185                2190

Pro Arg Thr Glu Ile Asn Leu Ile Asn Glu Ala Arg Asn Ala Asn Gln
        2195                2200                2205

Ala His Ile Ala Asn Asn Ile Asn Xaa Ile Tyr Glu Leu Ala Gln Gln
    2210                2215                2220

Gln Asp Gln Lys Ser Glu Gln Ile Asp Asn Pro Arg Thr Glu Ile Asn
2225                2230                2235                2240
```

-continued

```
Leu Ile Asn Glu Ala Arg Asn Ala Xaa Ala Asn Tyr Ala Thr Pro Ser
        2245                2250                2255

Ile Thr Ile Asn Asn Gln Ala Asp Ile Ala Gln Asn Gln Thr Asp Ile
        2260                2265                2270

Gln Asp Leu Ala Ala Tyr Asn Glu Leu Gln Ser Glu Gln Ile Asp Asn
        2275                2280                2285

Pro Arg Thr Glu Ile Asn Leu Ile Asn Glu Ala Arg Asn Ala Ala Thr
        2290                2295                2300

His Asp Tyr Asn Glu Arg Gln Thr Glu Ala Ser Glu Gln Ile Asp Asn
2305                2310                2315                2320

Pro Arg Thr Glu Ile Asn Leu Ile Asn Glu Ala Arg Asn Ala Lys Ala
        2325                2330                2335

Ser Ser Glu Asn Thr Gln Asn Ile Ala Lys Ser Glu Gln Ile Asp Asn
        2340                2345                2350

Pro Arg Thr Glu Ile Asn Leu Ile Asn Glu Ala Arg Asn Ala Met Ile
        2355                2360                2365

Leu Gly Asp Thr Ala Ile Val Ser Asn Ser Gln Asp Asn Lys Thr Gln
        2370                2375                2380

Leu Lys Phe Tyr Lys Ser Glu Gln Ile Asp Asn Pro Arg Thr Glu Ile
2385                2390                2395                2400

Asn Leu Ile Asn Glu Ala Arg Asn Ala Ala Gly Asp Thr Ile Ile Pro
        2405                2410                2415

Leu Asp Asp Asp Xaa Xaa Pro Ser Glu Gln Ile Asp Asn Pro Arg Thr
        2420                2425                2430

Glu Ile Asn Leu Ile Asn Glu Ala Arg Asn Ala Xaa Ala Asn Tyr Ala
        2435                2440                2445

Thr Pro Ser Ile Thr Ile Asn Ser Leu Leu His Glu Gln Gln Leu Xaa
        2450                2455                2460

Gly Lys Ser Glu Gln Ile Asp Asn Pro Arg Thr Glu Ile Asn Leu Ile
2465                2470                2475                2480

Asn Glu Ala Arg Asn Ala Xaa Ala Asn Tyr Ala Thr Pro Ser Ile Thr
        2485                2490                2495

Ile Asn Ile Phe Phe Asn Xaa Gly Ser Glu Gln Ile Asp Asn Pro Arg
        2500                2505                2510

Thr Glu Ile Asn Leu Ile Asn Glu Ala Arg Asn Ala Xaa Ala Asn Tyr
        2515                2520                2525

Ala Thr Pro Ser Ile Thr Ile Asn Asn Asn Ile Asn Asn Ile Tyr Glu
        2530                2535                2540

Leu Ala Gln Gln Gln Asp Gln His Ser Ser Asp Ile Lys Thr Leu Ser
2545                2550                2555                2560

Glu Gln Ile Asp Asn Pro Arg Thr Glu Ile Asn Leu Ile Asn Glu Ala
        2565                2570                2575

Arg Asn Ala Gly Gly Thr Gly Cys Ala Gly Gly Thr Cys Ala Gly Ala
        2580                2585                2590

Thr Cys Ala Gly Thr Gly Ala Cys Ser Glu Gln Ile Asp Asn Asp Asn
        2595                2600                2605

Ala Leu Ile Asn Glu Ala Arg Asp Asx Leu Glu Gly Cys Cys Ala Cys
        2610                2615                2620

Cys Ala Ala Cys Cys Ala Ala Gly Cys Thr Gly Ala Cys Ser Glu Gln
2625                2630                2635                2640

Ile Asp Asn Asp Asn Ala Leu Ile Asn Glu Ala Arg Asp Asx Leu Glu
        2645                2650                2655
```

```
Ala Gly Cys Gly Gly Thr Cys Gly Cys Cys Thr Gly Cys Thr Thr Gly
            2660                2665                2670

Ala Thr Cys Ala Gly Ser Glu Gln Ile Asp Asn Asp Asn Ala Leu Ile
        2675                2680                2685

Asn Glu Ala Arg Asp Asx Leu Glu Cys Thr Gly Ala Thr Cys Ala Ala
    2690                2695                2700

Gly Cys Ala Gly Gly Cys Gly Ala Cys Cys Gly Cys Thr Ser Glu Gln
2705                2710                2715                2720

Ile Asp Asn Asp Asn Ala Leu Ile Asn Glu Ala Arg Asp Asx Leu Glu
        2725                2730                2735

Cys Ala Ala Gly Ala Thr Cys Thr Gly Gly Cys Gly Cys Thr Thr
        2740                2745                2750

Ala Cys Ala Ala Ser Glu Gln Ile Asp Asn Asp Asn Ala Leu Ile Asn
        2755                2760                2765

Glu Ala Arg Asp Asx Leu Glu Thr Thr Gly Thr Ala Ala Gly Cys Gly
        2770                2775                2780

Gly Cys Cys Ala Gly Ala Thr Cys Thr Thr Gly Ser Glu Gln Ile Asp
2785                2790                2795                2800

Asn Asp Asn Ala Leu Ile Asn Glu Ala Arg Asp Asx Leu Glu Thr Gly
        2805                2810                2815

Cys Ala Thr Gly Ala Gly Cys Cys Gly Cys Ala Ala Ala Cys Cys Cys
        2820                2825                2830

Ser Glu Gln Ile Asp Asn Asp Asn Ala Leu Ile Asn Glu Ala Arg Asp
        2835                2840                2845

Asx Leu Glu Leu Leu Ala Glu Gln Gln Leu Asn Gly Ser Glu Gln Ile
    2850                2855                2860

Asp Asn Pro Arg Thr Glu Ile Asn Leu Ile Asn Glu Ala Arg Asn Ala
2865                2870                2875                2880

Ala Leu Glu Ser Asn Val Glu Glu Gly Leu Ser Glu Gln Ile Asp Asn
        2885                2890                2895

Pro Arg Thr Glu Ile Asn Leu Ile Asn Glu Ala Arg Asn Ala Ala Leu
    2900                2905                2910

Glu Ser Asn Val Glu Glu Gly Leu Leu Asp Leu Ser Ser Glu Gln Ile
    2915                2920                2925

Asp Asn Pro Arg Thr Glu Ile Asn Leu Ile Asn Glu Ala Arg Asn Ala
    2930                2935                2940

Asn Ala Lys Ala Ser Ala Ala Asn Thr Asp Arg Ser Glu Gln Ile Asp
2945                2950                2955                2960

Asn Pro Arg Thr Glu Ile Asn Leu Ile Asn Glu Ala Arg Asn Ala Ala
        2965                2970                2975

Ala Thr Ala Ala Asp Ala Ile Thr Lys Asn Gly Asn Ser Glu Gln Ile
            2980                2985                2990

Asp Asn Pro Arg Thr Glu Ile Asn Leu Ile Asn Glu Ala Arg Asn Ala
    2995                3000                3005

Ser Ile Thr Asp Leu Gly Thr Lys Val Asp Gly Phe Asp Gly Arg Ser
    3010                3015                3020

Glu Gln Ile Asp Asn Pro Arg Thr Glu Ile Asn Leu Ile Asn Glu Ala
3025                3030                3035                3040

Arg Asn Ala Val Asp Ala Leu Xaa Thr Lys Val Asn Ala Leu Asp Xaa
            3045                3050                3055

Lys Val Asn Ser Glu Gln Ile Asp Asn Pro Arg Thr Glu Ile Asn Leu
        3060                3065                3070

Ile Asn Glu Ala Arg Asn Ala Xaa Ala Asn Tyr Ala Thr Pro Ser Ile
```

-continued

```
                3075                3080                3085
Thr Ile Asn Ser Ala Ala Gln Ala Ala Leu Ser Gly Leu Phe Val Pro
        3090                3095                3100
Tyr Ser Val Gly Lys Phe Asn Ala Thr Ala Ala Leu Gly Gly Tyr Gly
3105                3110                3115                3120
Ser Lys Ser Glu Gln Ile Asp Asn Pro Arg Thr Glu Ile Asn Leu Ile
            3125                3130                3135
Asn Glu Ala Arg Asn Ala Ser Gly Arg Leu Leu Asp Gln Lys Ala Asp
                3140                3145                3150
Ser Glu Gln Ile Asp Asn Pro Arg Thr Glu Ile Asn Leu Ile Asn Glu
            3155                3160                3165
Ala Arg Asn Ala Gln Lys Ala Asp Ile Asp Asn Asn Ile Asn Ser Glu
        3170                3175                3180
Gln Ile Asp Asn Pro Arg Thr Glu Ile Asn Leu Ile Asn Glu Ala Arg
3185                3190                3195                3200
Asn Ala Asn Asn Ile Asn Asn Ile Tyr Glu Leu Ala Ser Glu Gln Ile
            3205                3210                3215
Asp Asn Pro Arg Thr Glu Ile Asn Leu Ile Asn Glu Ala Arg Asn Ala
        3220                3225                3230
Asn Asn Ile Tyr Glu Leu Ala Gln Gln Gln Ser Glu Gln Ile Asp Asn
            3235                3240                3245
Pro Arg Thr Glu Ile Asn Leu Ile Asn Glu Ala Arg Asn Ala Ala Gln
        3250                3255                3260
Gln Gln Asp Gln His Ser Ser Asp Ser Glu Gln Ile Asp Asn Pro Arg
3265                3270                3275                3280
Thr Glu Ile Asn Leu Ile Asn Glu Ala Arg Asn Ala Gln Asp Gln His
            3285                3290                3295
Ser Ser Asp Ile Lys Thr Ser Glu Gln Ile Asp Asn Pro Arg Thr Glu
            3300                3305                3310
Ile Asn Leu Ile Asn Glu Ala Arg Asn Ala His Ser Ser Asp Ile Lys
        3315                3320                3325
Thr Leu Lys Asn Ser Glu Gln Ile Asp Asn Pro Arg Thr Glu Ile Asn
        3330                3335                3340
Leu Ile Asn Glu Ala Arg Asn Ala Asp Ile Lys Thr Leu Lys Asn Asn
3345                3350                3355                3360
Val Glu Ser Glu Gln Ile Asp Asn Pro Arg Thr Glu Ile Asn Leu Ile
            3365                3370                3375
Asn Glu Ala Arg Asn Ala Thr Leu Lys Asn Asn Val Glu Glu Gly Leu
            3380                3385                3390
Ser Glu Gln Ile Asp Asn Pro Arg Thr Glu Ile Asn Leu Ile Asn Glu
            3395                3400                3405
Ala Arg Asn Ala Glu Glu Gly Leu Leu Asp Leu Ser Gly Arg Ser Glu
        3410                3415                3420
Gln Ile Asp Asn Pro Arg Thr Glu Ile Asn Leu Ile Asn Glu Ala Arg
3425                3430                3435                3440
Asn Ala Leu Ser Gly Arg Leu Ile Asp Gln Lys Ala Ser Glu Gln Ile
            3445                3450                3455
Asp Asn Pro Arg Thr Glu Ile Asn Leu Ile Asn Glu Ala Arg Asn Ala
        3460                3465                3470
Asp Gln Lys Ala Asp Ile Ala Lys Asn Gln Ser Glu Gln Ile Asp Asn
        3475                3480                3485
Pro Arg Thr Glu Ile Asn Leu Ile Asn Glu Ala Arg Asn Ala Ala Lys
        3490                3495                3500
```

```
Asn Gln Ala Asp Ile Ala Gln Asn Ser Glu Gln Ile Asp Asn Pro Arg
    3505                3510                3515                3520

Thr Glu Ile Asn Leu Ile Asn Glu Ala Arg Asn Ala Ile Ala Gln Asn
            3525                3530                3535

Gln Thr Asp Ile Gln Asp Ser Glu Gln Ile Asp Asn Pro Arg Thr Glu
        3540                3545                3550

Ile Asn Leu Ile Asn Glu Ala Arg Asn Ala Asp Ile Gln Asp Leu Ala
        3555                3560                3565

Ala Tyr Asn Glu Ser Glu Gln Ile Asp Asn Pro Arg Thr Glu Ile Asn
    3570                3575                3580

Leu Ile Asn Glu Ala Arg Asn Ala Cys Gly Gly Gly Ala Thr Cys Cys
3585                3590                3595                3600

Gly Thr Gly Ala Ala Gly Ala Ala Ala Ala Thr Gly Cys Cys Gly
        3605                3610                3615

Cys Ala Gly Gly Thr Ser Glu Gln Ile Asp Asn Asp Asn Ala Leu Ile
        3620                3625                3630

Asn Glu Ala Arg Asp Asx Leu Glu Cys Gly Gly Gly Ala Thr Cys Cys
        3635                3640                3645

Cys Gly Thr Cys Gly Cys Ala Ala Gly Cys Cys Gly Ala Thr Thr Gly
    3650                3655                3660

Ser Glu Gln Ile Asp Asn Asp Asn Ala Leu Ile Asn Glu Ala Arg Asp
3665                3670                3675                3680

Asx Leu Glu Ser Gly Arg Leu Leu Asp Gln Lys Ala Asp Ile Asp Asn
            3685                3690                3695

Asn Ile Asn Asn Ile Tyr Glu Leu Ala Gln Gln Gln Asp Gln His Ser
        3700                3705                3710

Ser Asp Ile Lys Thr Leu Lys Asn Asn Val Glu Gly Leu Leu Asp
        3715                3720                3725

Leu Ser Gly Arg Leu Ile Asp Gln Lys Ala Asp Ile Ala Lys Asn Gln
        3730                3735                3740

Ala Asp Ile Ala Gln Asn Gln Thr Asp Ile Gln Asp Leu Ala Ala Tyr
3745                3750                3755                3760

Asn Glu Ser Glu Gln Ile Asp Asn Pro Arg Thr Glu Ile Asn Leu Ile
            3765                3770                3775

Asn Glu Ala Arg Asn Ala Ala Trp Glx Xaa Asp Cys
        3780                3785

<210> SEQ ID NO 77
<211> LENGTH: 13
<212> TYPE: PRT
<213> ORGANISM: Moraxella catarrhalis

<400> SEQUENCE: 77

Ala Ala Thr Ala Ala Asp Ala Ile Thr Lys Asn Gly Asn
1               5                   10

<210> SEQ ID NO 78
<211> LENGTH: 15
<212> TYPE: PRT
<213> ORGANISM: Moraxella catarrhalis

<400> SEQUENCE: 78

Ser Ile Thr Asp Leu Gly Thr Lys Val Asp Gly Phe Asp Gly Arg
1               5                   10                  15

<210> SEQ ID NO 79
```

```
<211> LENGTH: 16
<212> TYPE: PRT
<213> ORGANISM: Moraxella catarrhalis
<220> FEATURE:
<221> NAME/KEY: MOD_RES
<222> LOCATION: (5)..(13)
<223> OTHER INFORMATION: Xaa = any natural occurring amino acid

<400> SEQUENCE: 79

Val Asp Ala Leu Xaa Thr Lys Val Asn Ala Leu Asp Xaa Lys Val Asn
 1               5                  10                  15

<210> SEQ ID NO 80
<211> LENGTH: 30
<212> TYPE: PRT
<213> ORGANISM: Moraxella catarrhalis

<400> SEQUENCE: 80

Ala Ala Gln Ala Ala Leu Ser Gly Leu Phe Val Pro Tyr Ser Val Gly
 1               5                  10                  15

Lys Phe Asn Ala Thr Ala Ala Leu Gly Gly Tyr Gly Ser Lys
            20                  25                  30

<210> SEQ ID NO 81
<211> LENGTH: 10
<212> TYPE: PRT
<213> ORGANISM: Moraxella catarrhalis

<400> SEQUENCE: 81

Ser Gly Arg Leu Leu Asp Gln Lys Ala Asp
 1               5                  10

<210> SEQ ID NO 82
<211> LENGTH: 10
<212> TYPE: PRT
<213> ORGANISM: Moraxella catarrhalis

<400> SEQUENCE: 82

Gln Lys Ala Asp Ile Asp Asn Asn Ile Asn
 1               5                  10

<210> SEQ ID NO 83
<211> LENGTH: 10
<212> TYPE: PRT
<213> ORGANISM: Moraxella catarrhalis

<400> SEQUENCE: 83

Asn Asn Ile Asn Asn Ile Tyr Glu Leu Ala
 1               5                  10

<210> SEQ ID NO 84
<211> LENGTH: 10
<212> TYPE: PRT
<213> ORGANISM: Moraxella catarrhalis

<400> SEQUENCE: 84

Asn Asn Ile Tyr Glu Leu Ala Gln Gln Gln
 1               5                  10

<210> SEQ ID NO 85
<211> LENGTH: 10
<212> TYPE: PRT
<213> ORGANISM: Moraxella catarrhalis

<400> SEQUENCE: 85
```

Ala Gln Gln Gln Asp Gln His Ser Ser Asp
1               5                   10

<210> SEQ ID NO 86
<211> LENGTH: 10
<212> TYPE: PRT
<213> ORGANISM: Moraxella catarrhalis

<400> SEQUENCE: 86

Gln Asp Gln His Ser Ser Asp Ile Lys Thr
1               5                   10

<210> SEQ ID NO 87
<211> LENGTH: 10
<212> TYPE: PRT
<213> ORGANISM: Moraxella catarrhalis

<400> SEQUENCE: 87

His Ser Ser Asp Ile Lys Thr Leu Lys Asn
1               5                   10

<210> SEQ ID NO 88
<211> LENGTH: 10
<212> TYPE: PRT
<213> ORGANISM: Moraxella catarrhalis

<400> SEQUENCE: 88

Asp Ile Lys Thr Leu Lys Asn Asn Val Glu
1               5                   10

<210> SEQ ID NO 89
<211> LENGTH: 10
<212> TYPE: PRT
<213> ORGANISM: Moraxella catarrhalis

<400> SEQUENCE: 89

Thr Leu Lys Asn Asn Val Glu Glu Gly Leu
1               5                   10

<210> SEQ ID NO 90
<211> LENGTH: 10
<212> TYPE: PRT
<213> ORGANISM: Moraxella catarrhalis

<400> SEQUENCE: 90

Glu Glu Gly Leu Leu Asp Leu Ser Gly Arg
1               5                   10

<210> SEQ ID NO 91
<211> LENGTH: 10
<212> TYPE: PRT
<213> ORGANISM: Moraxella catarrhalis

<400> SEQUENCE: 91

Leu Ser Gly Arg Leu Ile Asp Gln Lys Ala
1               5                   10

<210> SEQ ID NO 92
<211> LENGTH: 10
<212> TYPE: PRT
<213> ORGANISM: Moraxella catarrhalis

<400> SEQUENCE: 92

Asp Gln Lys Ala Asp Ile Ala Lys Asn Gln
1               5                   10

```
<210> SEQ ID NO 93
<211> LENGTH: 10
<212> TYPE: PRT
<213> ORGANISM: Moraxella catarrhalis

<400> SEQUENCE: 93

Ala Lys Asn Gln Ala Asp Ile Ala Gln Asn
 1               5                  10

<210> SEQ ID NO 94
<211> LENGTH: 10
<212> TYPE: PRT
<213> ORGANISM: Moraxella catarrhalis

<400> SEQUENCE: 94

Ile Ala Gln Asn Gln Thr Asp Ile Gln Asp
 1               5                  10

<210> SEQ ID NO 95
<211> LENGTH: 10
<212> TYPE: PRT
<213> ORGANISM: Moraxella catarrhalis

<400> SEQUENCE: 95

Asp Ile Gln Asp Leu Ala Ala Tyr Asn Glu
 1               5                  10

<210> SEQ ID NO 96
<211> LENGTH: 29
<212> TYPE: DNA
<213> ORGANISM: Moraxella catarrhalis

<400> SEQUENCE: 96
cgggatccgt gaagaaaaat gccgcaggt                                      29

<210> SEQ ID NO 97
<211> LENGTH: 24
<212> TYPE: DNA
<213> ORGANISM: Moraxella catarrhalis

<400> SEQUENCE: 97
cgggatcccg tcgcaagccg attg                                           24

<210> SEQ ID NO 98
<211> LENGTH: 79
<212> TYPE: PRT
<213> ORGANISM: Moraxella catarrhalis

<400> SEQUENCE: 98

Ser Gly Arg Leu Leu Asp Gln Lys Ala Asp Ile Asp Asn Asn Ile Asn
 1               5                  10                  15

Asn Ile Tyr Glu Leu Ala Gln Gln Gln Asp Gln His Ser Ser Asp Ile
             20                  25                  30

Lys Thr Leu Lys Asn Asn Val Glu Glu Gly Leu Leu Asp Leu Ser Gly
         35                  40                  45

Arg Leu Ile Asp Gln Lys Ala Asp Ile Ala Lys Asn Gln Ala Asp Ile
     50                  55                  60

Ala Gln Asn Gln Thr Asp Ile Gln Asp Leu Ala Ala Tyr Asn Glu
 65                  70                  75
```

USPA2 NUCLEIC ACID OF *MORAXELLA CATARRHALIS*

The present application is a Divisional application of U.S. patent application Ser. No. 10/872,769 filed on Jun. 21, 2004, which issued as U.S. Pat. No. 7,344,724 on Jun. 21, 2004, which is a Divisional of Ser. No. 09/336,447 filed Jun. 21, 1999, which issued as U.S. Pat. No. 6,310,190, on Oct. 30, 2001, which is a Continuation of International Application No. PCT/US97/23930, filed Dec. 19, 1997, which claimed priority to U.S. Provisional Application Ser. No. 60/033,598 filed Dec. 20, 1996. The entire text of the above-referenced disclosures are specifically incorporated herein by reference without disclaimer.

BACKGROUND OF THE INVENTION

1. Field of the Invention

The present invention relates generally to the fields of microbiology, and clinical bacteriology. More particularly, it concerns sequences of the uspA1 and uspA2 genes which encode the proteins UspA1 and UspA2, respectively, both of which encode an epitope reactive with monoclonal antibody (MAb) 17C7 and provide useful epitopes for immunodiagnosis and immunoprophylaxis.

2. Description of Related Art

It was previously thought that *Moraxella catarrhalis*, previously known as *Branhamella catarrhalis* or *Neisseria catarrhalis*, was a harmless saprophyte of the upper respiratory tract (Catlin, 1990; Berk, 1990). However, during the previous decade, it has been determined that this organism is an important human pathogen. Indeed, it has been established that this Gram-negative diplococcus is the cause of a number of human infections (Murphy, 1989). *M. catarrhalis* is now known to be the third most common cause of both acute and chronic otitis media (Catlin, 1990; Faden et al., 1990; 1991; Marchant, 1990), the most common disease for which infants and children receive health care according to the 1989 Consensus Report. This organism also causes acute maxillary sinusitis, generalized infections of the lower respiratory tract (Murphy and Loeb, 1989) and is an important cause of bronchopulmonary infections in patients with underlying chronic lung disease and, less frequently, of systemic infections in immunocompromised patients (Melendez and Johnson, 1990; Sarubbi et al., 1990; Schonheyder and Ejlertsen, 1989; Wright and Wallace, 1989).

The 1989 Consensus Report further concluded that prevention of otitis media is an important health care goal due to both its occurrence in infants and children, as well as certain populations of all age groups. In fact, the total financial burden of otitis media has been estimated to be at least $2.5 billion annually. Vaccines were identified as the most desired approach to prevent this disease for a number of reasons. For example, it was estimated that if vaccines could reduce the incidence of otitis media by 30%, then the annual health care savings would be at least $400 million. However, while some progress has been made in the development of vaccines for 2 of the 3 common otitis media pathogens, *Streptococcus pneumoniae* and *Haemophilus influenzae*, there is no indication that similar progress has been made with respect to *M. catarrhalis*. This is particularly troublesome in that *M. catarrhalis* now accounts for approximately 17-20% of all otitis media infection (Murphy, 1989). In addition, *M. catarrhalis* is also a significant cause of sinusitis (van Cauwenberge et al., 1993) and persistent cough (Gottfarb and Brauner, 1994) in children. In the elderly, it infects patients with predisposing conditions such as chronic obstructive pulmonary disease (COPD) and other chronic cardiopulmonary conditions (Boyle et al., 1991; Davies and Maesen, 1988; Hager et al., 1987).

Despite its recognized virulence potential, little is known about the mechanisms employed by *M. catarrhalis* in the production of disease or about host factors governing immunity to this pathogen. An antibody response to *M. catarrhalis* otitis media has been documented by means of an ELISA system using whole *M. catarrhalis* cells as antigen and acute and convalescent sera or middle ear fluid as the source of antibody (Leinonen et al., 1981). The development of serum bactericidal antibody during *M. catarrhalis* infection in adults was shown to be dependent on the classical complement pathway (Chapman et al., 1985). And more recently, it was reported that young children with *M. catarrhalis* otitis media develop an antibody response in the middle ear but fail to develop a systemic antibody response in a uniform manner (Faden et al., 1992).

Previous attempts have been made to identify and characterize *M. catarrhalis* antigens that would serve as potentially important targets of the human immune response to infection (Murphy, 1989; Goldblatt et al., 1990; Murphy et al., 1990). Generally speaking, the surface of *M. catarrhalis* is composed of outer membrane proteins (OMPs), lipooligosaccharide (LOS) and fimbriae. *M. catarrhalis* appears to be somewhat distinct from other Gram-negative bacteria in that attempts to isolate the outer membrane of this organism using detergent fractionation of cell envelopes has generally proven to be unsuccessful in that the procedures did not yield consistent results (Murphy, 1989; Murphy and Loeb, 1989). Moreover, preparations were found to be contaminated with cytoplasmic membranes, suggesting an unusual characteristic of the *M. catarrhalis* cell envelope.

Passive immunization with polyclonal antisera raised against outer membrane vesicles of the *M. catarrhalis* strain O35E was also found to protect against pulmonary challenge by the heterologous *M. catarrhalis* strain TTA24. In addition, active immunization with *M. catarrhalis* outer membrane vesicles resulted in enhanced clearance of this organism from the lungs after challenge. The positive effect of immunization in pulmonary clearance indicates that antibodies play a major role in immunoprotection from this pathogen. In addition, the protection observed against pulmonary challenge with a heterologous *M. catarrhalis* strain demonstrates that one or more conserved surface antigens are targets for antibodies which function to enhance clearance of *M. catarrhalis* from the lungs.

Outer membrane proteins (OMPs) constitute major antigenic determinants of this unencapsulated organism (Bartos and Murphy, 1988) and different strains share remarkably similar OMP profiles (Bartos and Murphy, 1988; Murphy and Bartos, 1989). At least three different surface-exposed outer membrane antigens have been shown to be well-conserved among *M. catarrhalis* strains; these include the 81 kDa CopB OMP (Helminen et al, 1993b), the heat-modifiable CD OMP (Murphy et al., 1993) and the high-molecular weight UspA antigen (Helminen et al., 1994). Of these three antigens, both the CopB protein and UspA antigen have been shown to bind antibodies which exert biological activity against *M. catarrhalis* in an animal model (Helminen et al., 1994; Murphy et al., 1993).

The MAb, designated 17C7, was described as binding to UspA, a very high molecular weight protein that migrated with an apparent molecular weight (in SDS-PAGE) of at least 250 kDa (Helminen et al, 1994; Klingman and Murphy, 1994). MAb 17C7 enhanced pulmonary clearance of *M. catarrhalis* from the lungs of mice when used in passive immunization studies and, in colony blot radioimmunoassay analysis, bound to every isolate of *M. catarrhalis* examined. This same MAb also reacted, although less intensely, with another antigen band of approximately 100 kDa, as described in U.S. Pat. No. 5,552,146 (incorporated herein by reference). A recombinant bacteriophage that contained a fragment of *M. catarrhalis* chromosomal DNA that expressed a protein product that bound MAb 17C7 was also identified and migrated at a rate similar or indistinguishable from that of the native UspA antigen from *M. catarrhalis* (Helminen et al., 1994).

With the rising importance of this pathogen in respiratory tract infections, identification of the surface components of this bacterium involved in virulence expression and immunity is becoming more important. To date, there are no vaccines available, against any other OMP, LOS or fimbriae, that induce protective antibodies against *M. catarrhalis*. Thus, it is clear that there remains a need to identify and characterize useful antigens and which can be employed in the preparation of immunoprophylactic reagents. Additionally, once such an antigen or antigens is identified, there is a need for providing methods and compositions which will allow the preparation of vaccines and in quantities that will allow their use on a wide scale basis in prophylactic protocols.

SUMMARY OF THE INVENTION

It is, therefore, an object of the present invention to provide new UspA1 and UspA2 proteins and genes coding therefor. It also is an object of the present invention to provide methods of using these new proteins, for example, in the preparation of agents for the treatment and inhibition of *M. catarrhalis* infection. It also is contemplated that through the use of other technologies such as antibody treatment and immunoprophylaxis that one can inhibit or even prevent *M. catarrhalis* infections.

In satisfying these goals, there are provided epitopic core sequences of UspA1 and UspA2 which can serve as the basis for the preparation of therapeutic or prophylactic compositions or vaccines which comprise peptides of 7, 10, 20, 30, 40, 50 or even 60 amino acids in length that elicit an antigenic reaction and a pharmaceutically acceptable buffer or diluent. These peptides may be coupled to a carrier, adjuvant, another peptide or other molecule such that an effective antigenic response to *M. catarrhalis* is retained or even enhanced. Alternatively, these peptides may act as carriers themselves when coupled to another peptide or other molecule that elicits an antigenic response to *M. catarrhalis* or another pathogen. For example, UspA2 can serve as a carrier for an oligosaccharide.

In one embodiment, the epitopic core sequences of UspA1 and UspA2 comprise one or more isolated peptides of 7, 10, 20, 30, 40, 50 or even 60 amino acids in length having the amino acid sequence AQQQDQH (SEQ ID NO:17).

In another embodiment, there are provided nucleic acids, uspA1 and uspA2, which encode the UspA1 and the UspA2 antigens, respectively, as well as the amino acid sequences of the UspA1 and UspA2 antigens of the *M. catarrhalis* isolates O35E, TTA24, TTA37, and O46E. It is envisioned that nucleic acid segments and fragments of the genes uspA1 and uspA2 and the UspA1 and UspA2 antigens will be of value in the preparation and use of therapeutic or prophylactic compositions or vaccines for treating, inhibiting or even preventing *M. catarrhalis* infections.

In another embodiment, there is provided a method for inducing an immune response in a mammal comprising the step of providing to the mammal an antigenic composition that comprises an isolated peptide of about 20 to about 60 amino acids that contains the identified epitopic core sequence and a pharmaceutically acceptable buffer or diluent.

In another embodiment, there is provided a method for diagnosing *M. catarrhalis* infection which comprises the step of determining the presence, in a sample, of an *M. catarrhalis* amino acid sequence corresponding to residues of the epitopic core sequences of either the UspA1 or UspA2 antigen. This method may comprise PCR™ detection of the nucleotide sequences or alternatively an immunologic reactivity of an antibody to either a UspA1 or UspA2 antigen.

In a further embodiment, there is provided a method for treating an individual having an *M. catarrhalis* infection which comprises providing to the individual an isolated peptide of about 20 to about 60 amino acids that comprises at least about 10 consecutive residues of the amino acid sequence identified as an epitopic core sequence of UspA1 or UspA2.

In a still further embodiment, there is provided a method for preventing or limiting an *M. catarrhalis* infection that comprises providing to a subject an antibody that reacts immunologically with the identified epitopic core region of either UspA1 or UspA2 of *M. catarrhalis*.

In another embodiment, there is provided a method for screening a peptide for reactivity with an antibody that binds immunologically to UspA1, UspA2 or both which comprises the steps of providing the peptide and contacting the peptide with the antibody and then determining the binding of the antibody to the peptide. This method may comprise an immunoassay such as a western blot, an ELISA, an RIA or an immunoaffinity separation.

In a still further embodiment, there is provided a method for screening a UspA1 or UspA2 peptide for its ability to induce a protective immune response against *M. catarrhalis* by providing the peptide, administering it in a suitable form to an experimental animal, challenging the animal with *M. catarrhalis* and then assaying for an *M. catarrhalis* infection in the animal. It is envisioned that the animal used will be a mouse that is challenged by a pulmonary exposure to *M. catarrhalis* and that the assaying comprises assessing the degree of pulmonary clearance by the mouse.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3. Southern blot analysis of chromosomal DNA from the wild-type M. catarrhalis strain O35E and the isogenic uspA1 mutant. Chromosomal DNA was digested with PvuII and probed with a 0.6 kb BglII-PvuII fragment from the uspA1 gene. The wild-type strain is listed as O35E at the top of this figure and the mutant strain is listed as O35E-uspA1⁻. Kilobase position markers are present on the left side.

FIG. 4. Western blot reactivity of proteins in M. catarrhalis strain O35E outer membrane vesicles (labeled O35E OMV) and the MF-4-1 GST fusion protein (labeled GST fusion protein) with MAb 17C7.

FIG. 6A. Coomassie blue stained gel of purified UspA2 (lane 2). FIG. 6B. Coomassie blue stained gel of purified UspA1 prepared without heating of sample (lane 4), heated for 3 min at 100° C. (lane 5), heated for 5 min at 100° C. (lane 6), and heated for 10 min at 100° C. (lane 7). FIG. 6C. Western of the purified UspA2 (lane 9) and purified UspA1 (lane 10) probed with the 17C7 MAb. Both proteins were heated 10 min. The molecular size markers in lanes 1, 3, and 8 are as indicated in kilodaltons.

FIG. 10A shows titers toward UspA1 and FIG. 10B shows titers to UspA2.

P3 (5'-GACGCTCAACAGCACTAATACG-3') (SEQ ID NO:20)/P4

(5'-CCAAGCTGATATCACTACC-3') (SEQ ID NO:21) and

P5 (5'-TCAATGCCTTTGATGGTC-3') (SEQ ID NO:22)/P6

(5'-TGTATGCCGCTACTCGCAGCT-3') (SEQ ID NO:23), respectively.

Figure 15A:
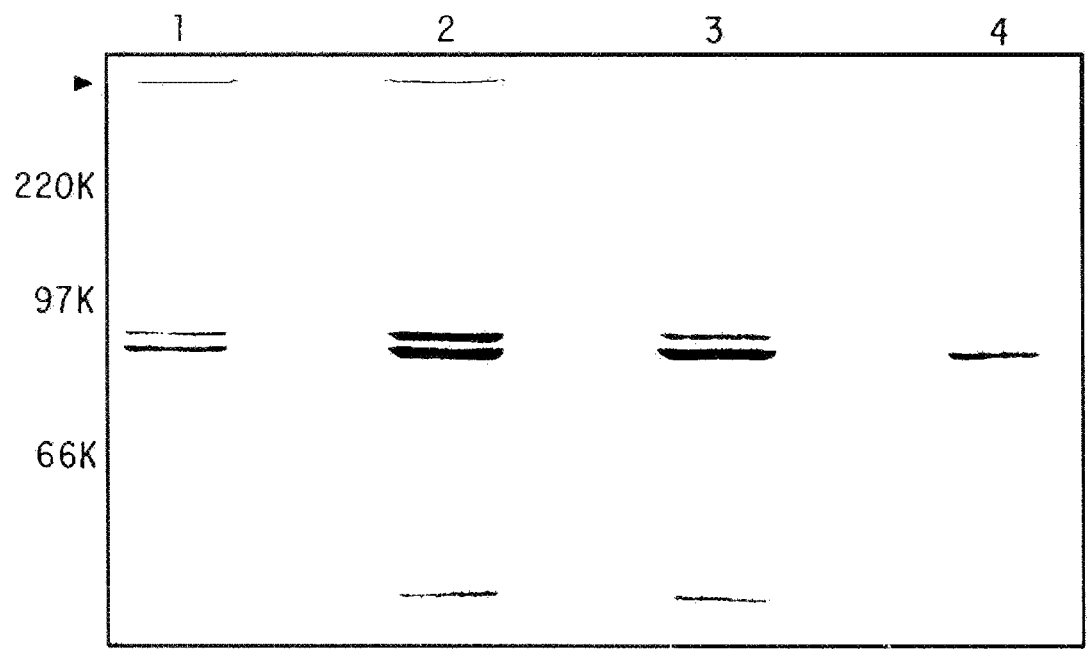
Figure 15B:

FIG. 15A-15B. Detection of the UspA1 and UspA2 proteins in wild-type and mutant strains of M. catarrhalis O35E. Proteins present in EDTA-extracted outer membrane vesicles from the wild-type strain (lane 1), the uspA1 mutant strain O35E.1 (lane 2), the uspA2 mutant strain O35E.2 (lane 3), and the isogenicuspA1 uspA2 double mutant strain O35E.12 (lane 4) were resolved by SDS-PAGE, and either stained with Coomassie blue (FIG. 15A) or transferred to nitrocellulose and probed with MAb 17C7 followed by radioiodinated goat anti-mouse immunoglobulin in western blot analysis. In FIG. 15A, the closed arrow indicates the very high molecular weight form of the UspA antigen which is comprised of both UspA1 and UspA2. In FIG. 15B, the bracket on the left indicates the very high molecular weight forms of the UspA1 and UspA2 proteins that bind MAb 17C7. The open arrow indicates the 120 kDa, putative monomeric form of UspA1. The closed arrow indicates the 85 kDa, putative monomeric form of UspA2. Molecular weight position markers (in kilodaltons) are present on the left.

Figure 16:
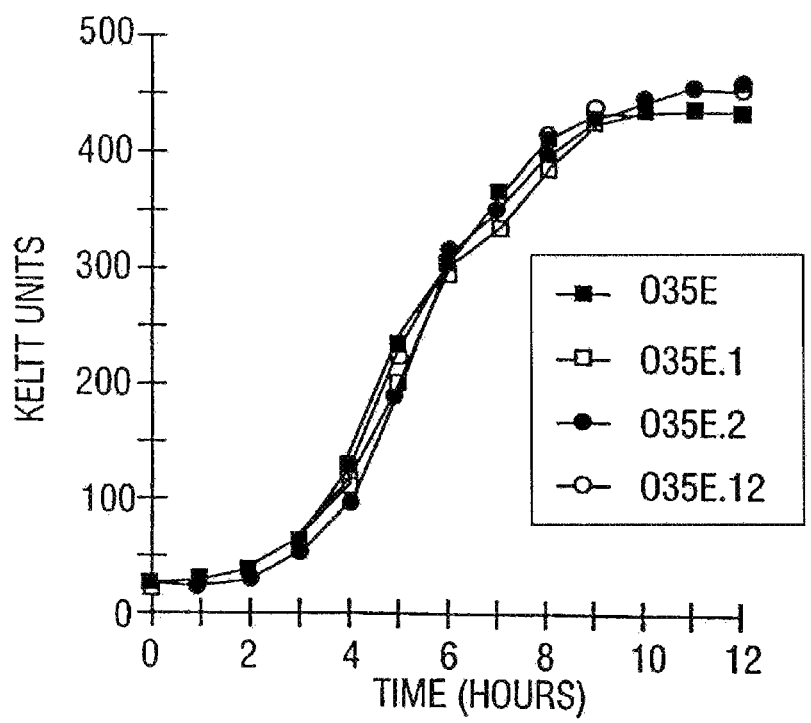

FIG. 16. Comparison of the rate and extent of growth of the wild-type and mutant strains of *M. catarrhalis*. The wild-type strain O35E (closed squares), the uspA1 mutant O35E.1 (open squares), the uspA2 mutant O35E.2 (closed circles), and the uspA1 uspA2 double mutant O35E.12 (open circles) of *M. catarrhalis* O35E from overnight broth cultures were diluted to a density of 35 Klett units in BHI broth and subsequently allowed to grow at 37° with shaking. Growth was followed by means of turbidity measurements.

Figure 17:
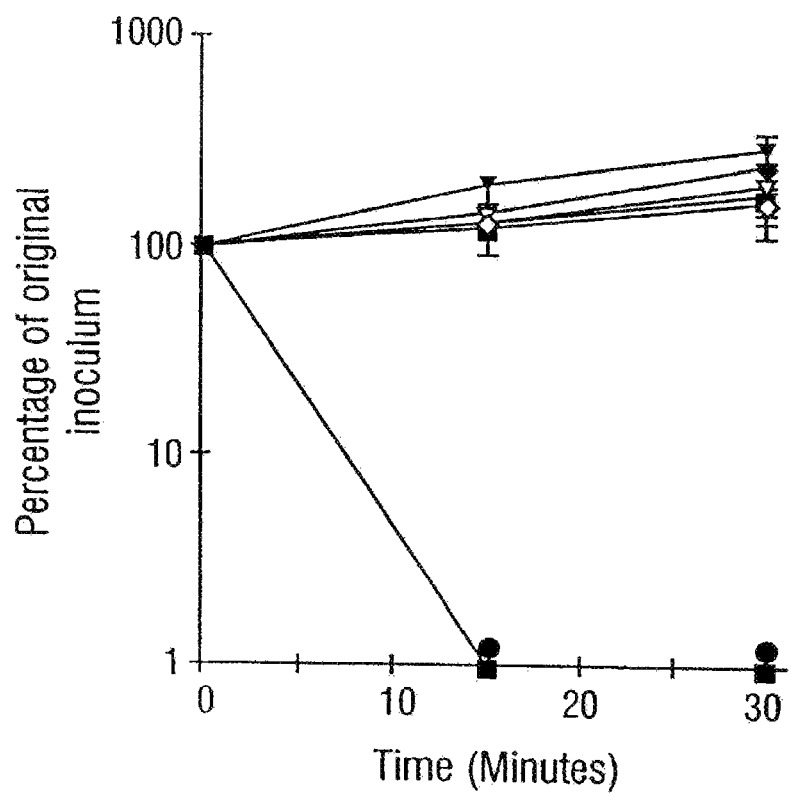

FIG. 17. Susceptibility of wild-type and mutant strains of *M. catarrhalis* to killing by normal human serum. Cells of the wild-type parent strain O35E (diamonds), uspA1 mutant O35E.1 (triangles), uspA2 mutant O35E.2 (circles), and uspA1 uspA2 double mutant O35E.12 (squares) from logarithmic-phase BHI broth cultures were incubated in the presence of 10% (v/v) normal human serum (closed symbols) or heat-inactivated normal human serum (open symbols). Data are presented as the percentage of the original inoculum remaining at each time point.

DESCRIPTION OF ILLUSTRATIVE EMBODIMENTS

The present invention relates to the identification of epitopes useful for developing potential vaccines against *M. catarrhalis*. Early work was directed at determining the molecular nature of the UspA antigen and characterize the epitope which is recognized by the MAb 17C7. Preliminary work indicated that MAb 17C7 recognizes a single antigenic epitope and it was believed that this epitope was encoded by a single gene. However, isolation of the protein which contained the epitope yielded unexpected results. MAb 17C7 recognized a single epitope, but the characteristics of the protein associated with the epitope suggested the existence of not one but two separate proteins. Further careful analyses led to a surprising discovery. A single epitope of the UspA antigen is recognized by the MAb 17C7, but this epitope is present in two different proteins, UspA1 and UspA2, which are encoded by two different genes uspA1 and uspA2, respectively, and only have 43% identity to each other. The present invention provides the nucleotide sequences of the genes uspA1 and uspA2, their respective protein products, UspA1 and UspA2, and the shared epitope recognized by MAb 17C7.

In addition, the present invention provides insights into the antigenic structure of the UspA protein based on the analysis of the sequences of the UspA1 and UspA2 proteins which comprise the protein. Characterization of the epitopic region of the molecule that is targeted by the MAb 17C7 permits the development of agents that will be useful in protecting against *M. catarrhalis* infections, e.g., in the preparation of prophylactic reagents. Particular embodiments relate to the amino acid and nucleic acids corresponding to the UspA1 and UspA2 proteins, peptides and antigenic compositions derived therefrom, and methods for the diagnosis and treatment of *M. catarrhalis* disease.

As stated previously, *M. catarrhalis* infections present a serious health challenge, especially to the young. Thus, there is a clear need to develop compositions and methods that will aid in the treatment and diagnosis of this disease. The present invention, by virtue of new information regarding the structure of the UspA antigen of *M. catarrhalis*, and discovery of the two new and distinct proteins UspA1 and UspA2 provides such improved compositions and methods. UspA1 and UspA2 represent important antigenic determinants, as the MAb 17C7 has been shown to protect experimental animals, as measured in a pulmonary clearance model, when provided in passive immunizations.

In a first embodiment, the present invention provides for the identification of the proteins UspA1 and UspA2 from *M. catarrhalis* strain O35E. The UspA1 protein comprises about 831 amino acid residues and has a predicted mass of about 88,271 daltons (SEQ ID NO:1). The UspA2 protein comprises about 576 residues and has a predicted mass of about 62,483 daltons (SEQ ID NO:3). UspA2 is not a truncated or processed form of UspA1.

In a second embodiment, the present invention has identified the specific epitope to which MAb 17C7 binds. A common peptide sequence, designated as the "3Q" peptide, found between amino acid residues 480-502 and 582-604 of the UspA1 protein (SEQ ID NO:1) and residues 355-377 of the UspA2 protein (SEQ ID NO:3) of *M. catarrhalis* strain O35E, encompasses the region which appears to be recognized by MAb 17C7. (Note that numbering of the amino acid residues is based upon strain O35E as provided in SEQ ID NO:3.) It is envisioned that this region plays an important role in the biology of the pathogen and, from this information, one will deduce amino acids residues that are critical in MAb 17C7 antibody binding. It also is envisioned that, based upon this information, one will be able to design epitopic regions that have either a higher or lower affinity for the MAb 17C7 or other antibodies. Further embodiments of the present invention are discussed below.

In another preferred embodiment, the present invention provides DNA segments, vectors and the like comprising at least one isolated gene, DNA segment or coding region that encodes a *M. catarrhalis* UspA1 or UspA2 protein, polypeptide, domain, peptide or any fusion protein thereof. Herein are provided at least an isolated gene, DNA segment or coding region that encodes a *M. catarrhalis* uspA1 gene comprising about 2493 base pairs (bp) (SEQ ID NO:2) of strain O35E, about 3381 bp (SEQ ID NO:6) of strain O46E, about 3538 bp (SEQ ID NO:10) of strain TTA24, or about 3292 bp (SEQ ID NO:14) of strain TTA37. Further provided are at least an isolated gene, DNA segment or coding region that encodes a *M. catarrhalis* uspA2 gene comprising about 1728 bp (SEQ ID NO:4) of strain O35E, about 3295 bp (SEQ ID NO:8) of strain O46E, about 2673 bp (SEQ ID NO:12), or about 4228 bp (SEQ ID NO:16) of strain TTA37. It is envisioned that the uspA1 and uspA2 genes will be useful in the preparation of proteins, antibodies, screening assays for potential candidate drugs and the like to treat or inhibit, or even prevent, *M. catarrhalis* infections.

The present invention also provides for the use of the UspA1 or UspA2 proteins or peptides as immunogenic carriers of other agents which are useful for the treatment, inhibition or even prevention of other bacterial, viral or parasitic infections. It is envisioned that either the UspA1 or UspA2 antigen, or portions thereof, will be coupled, bonded, bound, conjugated or chemically-linked to one or more agents via linkers, polylinkers or derivatized amino acids such that a bispecific or multivalent composition or vaccine which is useful for the treatment, inhibition or even prevention of infection by *M. catarrhalis* and another pathogen(s) is prepared. It is further envisioned that the methods used in the preparation of these compositions will be familiar to those of skill in the art and, for example, similar to those used to prepare conjugates to keyhole limpet hemocyannin (KLH) or bovine serum albumin (BSA).

It is important to note that screening methods for diagnosis and prophylaxis are readily available, as set forth below. Thus, the ability to (i) test peptides, mutant peptides and antibodies for their reactivity with each other and (ii) test peptides and antibodies for the ability to prevent infections in vivo, provide powerful tools to develop clinically important reagents.

1. UspA PROTEINS, PEPTIDES AND POLYPEPTIDES

The present invention, in one embodiment, encompasses the two new protein sequences, UspA1 and UspA2, and the peptide sequence AQQQDQH (SEQ ID NO:17) identified as the target epitope of MAb 17C7. In addition, inspection of the amino acid sequences of the UspA1 and UspA2 proteins from four strains of M. catarrhalis indicated that each protein contained at least one copy of the peptide YELAQQQDQH (SEQ ID NO:18) which binds Mab 17C7 or, in one instance, a peptide nearly identical and having the amino acid sequence YDLAQQQDQH (SEQ ID NO:19).

The peptide (YELAQQQDQH, SEQ ID NO:18) occurs twice in UspA1 from strain O35E at residues 486-495 and 588-597 (SEQ ID NO:1) and once in UspA2 from strain O35E at residues 358-367 (SEQ ID NO:3). It occurs once in UspA1 from strain TTA24 at residues 497-506 (SEQ ID NO:9) and twice in UspA2 from strain TTA24 at residues 225-234 and 413-422 (SEQ ID NO:11). The peptide YDLAQQQDQH (SEQ ID NO:19) occurs once in UspA1 from strain O46E at residues 448-457 (SEQ ID NO:5) whereas the peptide YELAQQQDQH (SEQ ID NO:18) occurs once in this same protein at residues 649-658 (SEQ ID NO:5). The peptide YELAQQQDQH (SEQ ID NO:18) occurs once in UspA2 from strain O46E at residues 416-425 (SEQ ID NO:7). The peptide YELAQQQDQH (SEQ ID NO:18) occurs twice in UspA1 from strain TTA37 at residues 478-487 and 630-639 (SEQ ID NO:13) and twice in UspA2 from strain TTA37 at residues 522-531 and 681-690 (SEQ ID NO:15).

Also encompassed in the present invention are hybrid molecules containing portions from one UspA protein, for example the UspA1 protein, fused with portions of the other UspA protein, in this example the UspA2 protein, or fused with other proteins which are useful for identification, such as kanamycin-resistance, or other purposes in the screening of potential vaccines or further characterization of the UspA1 and UspA2 proteins. For example, one may fuse residues 1-350 of any UspA1 with residues 351-576 of any UspA2. Alternatively, a fusion could be generated with sequences from three, four or even five peptide regions represented in a single UspA antigen. Also encompassed are fragments of the disclosed UspA1 and UspA2 molecules, as well as insertion, deletion or replacement mutants in which non-UspA sequences are introduced, UspA sequences are removed, or UspA sequences are replaced with non-UspA sequences, respectively.

UspA1 and UspA2 proteins, according to the present invention, may be advantageously cleaved into fragments for use in further structural or functional analysis, or in the generation of reagents such as UspA-related polypeptides and UspA-specific antibodies. This can be accomplished by treating purified or unpurified UspA1 and/or UspA2 with a peptidase such as endoproteinase glu-C (Boehringer, Indianapolis, Ind.). Treatment with CNBr is another method by which UspA1 and/or UspA2 fragments may be produced from their natural respective proteins. Recombinant techniques also can be used to produce specific fragments of UspA1 or UspA2.

More subtle modifications and changes may be made in the structure of the encoded UspA1 or UspA2 polypeptides of the present invention and still obtain a molecule that encodes a protein or peptide with characteristics of the natural UspA antigen. The following is a discussion based upon changing the amino acids of a protein to create an equivalent, or even an improved, second-generation molecule. The amino acid changes may be achieved by changing the codons of the DNA sequence, according to the following codon table:

TABLE I

| Amino Acid Names and abbreviations | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It is known that certain amino acids may be substituted for other amino acids in a protein structure in order to modify or improve its antigenic or immunogenic activity (see, e.g., Kyte & Doolittle, 1982; Hopp, U.S. Pat. No. 4,554,101, incorporated herein by reference). For example, through the substitution of alternative amino acids, small conformational changes may be conferred upon a polypeptide which result in increased activity or stability. Alternatively, amino acid substitutions in certain polypeptides may be utilized to provide residues which may then be linked to other molecules to provide peptide-molecule conjugates which retain enough antigenicity of the starting peptide to be useful for other purposes. For example, a selected UspA1 or UspA2 peptide bound to a solid support might be constructed which would have particular advantages in diagnostic embodiments.

The importance of the hydropathic index of amino acids in conferring interactive biological function on a protein has been discussed generally by Kyte & Doolittle (1982), wherein it is found that certain amino acids may be substituted for other amino acids having a similar hydropathic index or core and still retain a similar biological activity. As displayed in Table II below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules. Preferred substitutions which result in an antigenically equivalent peptide or protein will generally involve amino acids having index scores within ±2 units of one another, and more preferably within ±1 unit, and even more preferably, within ±0.5 units.

TABLE II

| Amino Acid | Hydropathic Index |
|---|---|
| Isoleucine | 4.5 |
| Valine | 4.2 |

TABLE II-continued

| Amino Acid | Hydropathic Index |
| --- | --- |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, will preferably be exchanged with an amino acid such as valine (+4.2) or leucine (+3.8). Alternatively, at the other end of the scale, lysine (−3.9) will preferably be substituted for arginine (−4.5), and so on.

Substitution of like amino acids may also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with an important biological property of the protein.

As detailed in U.S. Pat. No. 4,554,101, each amino acid has also been assigned a hydrophilicity value. These values are detailed below in Table III.

TABLE III

| Amino Acid | Hydrophilic Index |
| --- | --- |
| arginine | +3.0 |
| lysine | +3.0 |
| aspartate | +3.0 ± 1 |
| glutamate | +3.0 ± 1 |
| serine | +0.3 |
| asparagine | +0.2 |
| glutamine | +0.2 |
| glycine | 0 |
| threonine | −0.4 |
| alanine | −0.5 |
| histidine | −0.5 |
| proline | −0.5 ± 1 |
| cysteine | −1.0 |
| methionine | −1.3 |
| valine | −1.5 |
| leucine | −1.8 |
| isoleucine | −1.8 |
| tyrosine | −2.3 |
| phenylalanine | −2.5 |
| tryptophan | −3.4 |

It is understood that one amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

Accordingly, these amino acid substitutions are generally based on the relative similarity of R-group substituents, for example, in terms of size, electrophilic character, charge, and the like. In general, preferred substitutions which take various of the foregoing characteristics into consideration will be known to those of skill in the art and include, for example, the following combinations: arginine and lysine; glutamate and aspartate; serine and threonine; glutamine and asparagine; and valine, leucine and isoleucine.

In addition, peptides derived from these polypeptides, including peptides of at least about 6 consecutive amino acids from these sequences, are contemplated. Alternatively, such peptides may comprise about 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 consecutive residues. For example, a peptide that comprises 6 consecutive amino acid residues may comprise residues 1 to 6, 2 to 7, 3 to 8 and so on of the UspA1 or UspA2 protein. Such peptides may be represented by the formula $x$ to $(x+n)=5'$ to $3'$ the positions of the first and last consecutive residues where x is equal to any number from 1 to the full length of a UspA1 or UspA2 protein and n is equal to the length of the peptide minus 1. So, for UspA1, x=1 to 831, for UspA2, x=1 to 576. Where the peptide is 10 residues long (n=10−1), the formula represents every 10-mer possible for each antigen. For example, where x is equal to 1 the peptide would comprise residues 1 to (1+[10−1]), or 1 to 10. Where x is equal to 2, the peptide would comprise residues 2 to (2+[10−2]), or 2 to 11, and so on.

Syntheses of peptides are readily achieved using conventional synthetic techniques such as the solid phase method (e.g., through the use of a commercially available peptide synthesizer such as an Applied Biosystems Model 430A Peptide Synthesizer). Peptides synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of 7.0 to 7.5. Moreover, it may be desirable to include agents which will inhibit microbial growth, such as sodium azide or Merthiolate. For extended storage in an aqueous state it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled, deionized) or buffer prior to use.

Of particular interest are peptides that represent epitopes that lie within the UspA antigen and are encompassed by the UspA1 and UspA2 proteins of the present invention. An "epitope" is a region of a molecule that stimulates a response from a T-cell or B-cell, and hence, elicits an immune response from these cells. An epitopic core sequence, as used herein, is a relatively short stretch of amino acids that is structurally "complementary" to, and therefore will bind to, binding sites on antibodies or T-cell receptors. It will be understood that, in the context of the present disclosure, the term "complementary" refers to amino acids or peptides that exhibit an attractive force towards each other. Thus, certain epitopic core sequences of the present invention may be operationally defined in terms of their ability to compete with or perhaps displace the binding of the corresponding UspA antigen to the corresponding UspA-directed antisera.

The identification of epitopic core sequences is known to those of skill in the art. For example U.S. Pat. No. 4,554,101 teaches identification and preparation of epitopes from amino acid sequences on the basis of hydrophilicity, and by Chou-Fasman analyses. Numerous computer programs are available for use in predicting antigenic portions of proteins, examples of which include those programs based upon Jameson-Wolf analyses (Jameson and Wolf, 1988; Wolf et al., 1988), the program PepPlot® (Brutlag et al., 1990; Weinberger et al., 1985), and other new programs for protein tertiary structure prediction (Fetrow & Bryant, 1993) that can be used in conjunction with computerized peptide sequence analysis programs.

In general, the size of the polypeptide antigen is not believed to be particularly crucial, so long as it is at least large enough to carry the identified core sequence or sequences. The smallest useful core sequence anticipated by the present disclosure would be on the order of about 6 amino acids in length. Thus, this size will generally correspond to the smallest peptide antigens prepared in accordance with the invention. However, the size of the antigen may be larger where desired, so long as it contains a basic epitopic core sequence.

2. UspA1 AND UspA2 NUCLEIC ACIDS

In addition to polypeptides, the present invention also encompasses nucleic acids encoding the UspA1 (SEQ ID NO:2, SEQ ID NO:6, SEQ ID NO:10 and SEQ ID NO:14) and UspA2 (SEQ ID NO:4, SEQ ID NO:8, SEQ ID NO:12 and SEQ ID NO:16) proteins from the exemplary *M. catarrhalis* strains O35E, O46E, TTA24 and TTA37, respectively. Because of the degeneracy of the genetic code, many other nucleic acids also may encode a given UspA1 or UspA2 protein. For example, four different three-base codons encode the amino acids alanine, glycine, proline, threonine and valine, while six different codons encode arginine, leucine and serine. Only methionine and tryptophan are encoded by a single codon. Table I provides a list of amino acids and their corresponding codons for use in such embodiments. In order to generate any nucleic acid encoding UspA1 or UspA2, one need only refer to the codon table provided herein. Substitution of the natural codon with any codon encoding the same amino acid will result in a distinct nucleic acid that encodes UspA1 or UspA2. As a practical matter, this can be accomplished by site-directed mutagenesis of an existing uspA1 or uspA2 gene or de novo chemical synthesis of one or more nucleic acids.

These observations regarding codon selection, site-directed mutagenesis and chemical synthesis apply with equal force to the discussion of substitutional mutant UspA1 or UspA2 peptides and polypeptides, as set forth above. More specifically, substitutional mutants generated by site-directed changes in the nucleic acid sequence that are designed to alter one or more codons of a given polypeptide or epitope may provide a more convenient way of generating large numbers of mutants in a rapid fashion. The nucleic acids of the present invention provide for a simple way to generate fragments (e.g., truncations) of UspA1 or UspA2, UspA1-UspA2 fusion molecules (discussed above) and UspA1 or UspA2 fusions with other molecules. For example, utilization of restriction enzymes and nuclease in the uspA1 or uspA2 gene permits one to manipulate the structure of these genes, and the resulting gene products.

The nucleic acid sequence information provided by the present disclosure also allows for the preparation of relatively short DNA (or RNA) sequences that have the ability to specifically hybridize to gene sequences of the selected uspA1 or uspA2 gene. In these aspects nucleic acid probes of an appropriate length are prepared based on a consideration of the coding sequence of the uspA1 or uspA2 gene, or flanking regions near the uspA1 or uspA2 gene, such as regions downstream and upstream in the *M. catarrhalis* chromosome. The ability of such nucleic acid probes to specifically hybridize to either uspA1 or uspA2 gene sequences lends them particular utility in a variety of embodiments. For example, the probes can be used in a variety of diagnostic assays for detecting the presence of pathogenic organisms in a given sample. In addition, these oligonucleotides can be inserted, in frame, into expression constructs for the purpose of screening the corresponding peptides for reactivity with existing antibodies or for the ability to generate diagnostic or therapeutic reagents.

To provide certain of the advantages in accordance with the invention, the preferred nucleic acid sequence employed for hybridization studies or assays includes sequences that are complementary to at least a 10 to 20, or so, nucleotide stretch of the sequence, although sequences of 30 to 60 or so nucleotides are also envisioned to be useful. A size of at least 9 nucleotides in length helps to ensure that the fragment will be of sufficient length to form a duplex molecule that is both stable and selective. Though molecules having complementary sequences over stretches greater than 10 bases in length are generally preferred, in order to increase stability and selectivity of the hybrid, and thereby improve the quality and degree of the specific hybrid molecules obtained. Thus, one will generally prefer to design nucleic acid molecules having either uspA1 or uspA2 gene-complementary stretches of 15 to 20 nucleotides, or even longer, such as 30 to 60, where desired. Such fragments may be readily prepared by, for example, directly synthesizing the fragment by chemical means, by application of nucleic acid reproduction technology, such as the PCR™ technology of U.S. Pat. No. 4,603,102, or by introducing selected sequences into recombinant vectors for recombinant production.

The probes that would be useful may be derived from any portion of the sequences of SEQ ID NO:2 or SEQ ID NO:4 or SEQ ID NO:6 or SEQ ID NO:8 or SEQ ID NO:10 or SEQ ID NO:12 or SEQ ID NO:14 or SEQ ID NO:16. Therefore, probes are specifically contemplated that comprise nucleotides 1 to 9, or 2 to 10, or 3 to 11 and so forth up to a probe comprising the last 9 nucleotides of the nucleotide sequence of SEQ ID NO:2 or SEQ ID NO:4 or SEQ ID NO:6 or SEQ ID NO:8 or SEQ ID NO:10 or SEQ ID NO:12 or SEQ ID NO:14 or SEQ ID NO:16. Thus, each probe would comprise at least about 9 linear nucleotides of the nucleotide sequence of SEQ ID NO:2 or SEQ ID NO:4 or SEQ ID NO:6 or SEQ ID NO:8 or SEQ ID NO:10 or SEQ ID NO:12 or SEQ ID NO:14 or SEQ ID NO:16, designated by the formula "n to n+8," where n is an integer from 1 to the number of nucleotides in the sequence. Longer probes that hybridize to the uspA1 or uspA2 gene under low, medium, medium-high and high stringency conditions are also contemplated, including those that comprise the entire nucleotide sequence of SEQ ID NO:2 or SEQ ID NO:4 or SEQ ID NO:6 or SEQ ID NO:8 or SEQ ID NO:10 or SEQ ID NO:12 or SEQ ID NO:14 or SEQ ID NO:16. This hypothetical may be repeated for probes having lengths of about 10, 11, 12, 13, 14, 15, 16, 17, 18, 19, 20, 25, 30, 35, 40, 45, 50, 60, 70, 80, 90, 100 and greater bases.

In that the UspA antigenic epitopes of the present invention are believed to be indicative of pathogenic *Moraxella* species as exemplified by strains O35E, O46E, TTA24 and TTA37, the probes of the present invention will find particular utility as the basis for diagnostic hybridization assays for detecting UspA1 or UspA2 DNA in clinical samples. Exemplary clinical samples that can be used in the diagnosis of infections are thus any samples which could possibly include *Moraxella* nucleic acid, including middle ear fluid, sputum, mucus, bronchoalveolar fluid, amniotic fluid or the like. A variety of hybridization techniques and systems are known which can be used in connection with the hybridization aspects of the invention, including diagnostic assays such as those described in Falkow et al., U.S. Pat. No. 4,358,535. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M-0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15M-0.9M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and the method of choice will generally depend on the desired results.

In certain embodiments, one may desire to employ nucleic acid probes to isolate variants from clone banks containing mutated clones. In particular embodiments, mutant clone colonies growing on solid media which contain variants of the UspA1 and/or UspA2 sequence could be identified on duplicate filters using hybridization conditions and methods, such as those used in colony blot assays, to obtain hybridization only between probes containing sequence variants and nucleic acid sequence variants contained in specific colonies. In this manner, small hybridization probes containing short variant sequences of either the uspA1 or uspA2 gene may be utilized to identify those clones growing on solid media which contain sequence variants of the entire uspA1 or uspA2 gene. These clones can then be grown to obtain desired quantities of the variant UspA1 or UspA2 nucleic acid sequences or the corresponding UspA antigen.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as urease, alkaline phosphatase or peroxidase, instead of radioactive or other environmental undesirable reagents. In the case of enzyme tags, calorimetric indicator substrates are known which can be employed to provide a means visible to the human eye or spectrophotometrically, to identify specific hybridization with pathogen nucleic acid-containing samples.

In general, it is envisioned that the hybridization probes described herein will be useful both as reagents in solution hybridizations as well as in embodiments employing a solid phase. In embodiments involving a solid phase, the test DNA (or RNA) from suspected clinical samples, such as exudates, body fluids (e.g., amniotic fluid, middle ear effusion, bronchoalveolar lavage fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

The nucleic acid sequences which encode for the UspA1 and/or UspA2 epitopes, or their variants, may be useful in conjunction with PCR™ methodology to detect *M. catarrhalis*. In general, by applying the PCR™ technology as set out, e.g., in U.S. Pat. No. 4,603,102, one may utilize various portions of either the uspA1 or uspA2 sequence as oligonucleotide probes for the PCR™ amplification of a defined portion of a uspA1 or uspA2 nucleic acid in a sample. The amplified portion of the uspA1 or uspA2 sequence may then be detected by hybridization with a hybridization probe containing a complementary sequence. In this manner, extremely small concentrations of *M. catarrhalis* nucleic acid may detected in a sample utilizing uspA1 or uspA2 sequences.

3. VECTORS, HOST CELLS AND CULTURES FOR PRODUCING UspA1 AND/OR UspA2 ANTIGENS

In order to express a UspA1 and/or UspA2 polypeptide, it is necessary to provide an uspA1 and/or uspA2 gene in an expression cassette. The expression cassette contains a UspA1 and/or UspA2-encoding nucleic acid under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. Those promoters most commonly used in prokaryotic recombinant DNA construction include the B-lactamase (penicillinase) and lactose promoter systems (Chang et al., 1978; Itakura et al., 1977; Goeddel et al., 1979) and a tryptophan (trp) promoter system (Goeddel et al., 1980; EPO Appl. Publ. No. 0036776). While these are the most commonly used, other microbial promoters have been discovered and utilized, and details concerning their nucleotide sequences have been published, enabling a skilled worker to ligate them functionally with plasmid vectors (EPO Appl. Publ. No. 0036776). Additional examples of useful promoters are provided in Table IV below.

TABLE IV

| Promoters | References |
|---|---|
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ a and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| a-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_{1\text{-}Antitrypain}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a, b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987; Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

The appropriate expression cassette can be inserted into a commercially available expression vector by standard subcloning techniques. For example, the *E. coli* vectors pUC or pBluescript™ may be used according to the present invention to produce recombinant UspA1 and/or UspA2 polypeptide in vitro. The manipulation of these vectors is well known in the art. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as a transforming vector in connection with these hosts. For example, the phage lambda GEM™-11 may be utilized in making recombinant phage vector which can be used to transform host cells, such as E. coli LE392.

In one embodiment, the UspA antigen is expressed as a fusion protein by using the pGEX4T-2 protein fusion system (Pharmacia LKB, Piscataway, N.J.), allowing characterization of the UspA antigen as comprising both the UspA1 and UspA2 proteins. Additional examples of fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.). Some of these fusion systems produce recombinant protein bearing only a small number of additional amino acids, which are unlikely to affect the functional capacity of the recombinant protein. For example, both the FLAG system and the 6×His system add only short sequences, both of which are known to be poorly antigenic and which do not adversely affect folding of the protein to its native conformation. Other fusion systems produce proteins where it is desirable to excise the fusion partner from the desired protein. In another embodiment, the fusion partner is linked to the recombinant protein by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

E. coli is a preferred prokaryotic host. For example, E. coli strain RR1 is particularly useful. Other microbial strains which may be used include E. coli strains such as E. coli LE392, E. coli B, and E. coli X 1776 (ATCC No. 31537). The aforementioned strains, as well as E. coli W3110 (F-, lambda-, prototrophic, ATCC No. 273325), bacilli such as Bacillus subtilis, or other enterobacteriaceae such as Salmonella typhimurium or Serratia marcescens, and various Pseudomonas species may be used. These examples are, of course, intended to be illustrative rather than limiting. Recombinant bacterial cells, for example E. coli, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed.

If the recombinant protein is expressed in the inclusion bodies, as is the case in many instances, these can be washed in any of several solutions to remove some of the contaminating host proteins, then solubilized in solutions containing high concentrations of urea (e.g. 8M) or chaotropic agents such as guanidine hydrochloride in the presence of reducing agents such as β-mercaptoethanol or DTT (dithiothreitol).

Under some circumstances, it may be advantageous to incubate the polypeptide for several hours under conditions suitable for the protein to undergo a refolding process into a conformation which more closely resembles that of the native protein. Such conditions generally include low protein concentrations less than 500 µg/ml, low levels of reducing agent, concentrations of urea less than 2 M and often the presence of reagents such as a mixture of reduced and oxidized glutathione which facilitate the interchange of disulfide bonds within the protein molecule.

The refolding process can be monitored, for example, by SDS-PAGE or with antibodies which are specific for the native molecule (which can be obtained from animals vaccinated with the native molecule isolated from bacteria). Following refolding, the protein can then be purified further and separated from the refolding mixture by chromatography on any of several supports including ion exchange resins, gel permeation resins or on a variety of affinity columns.

There are a variety of other eukaryotic vectors that provide a suitable vehicle in which recombinant UspA proteins can be produced. In various embodiments of the invention, the expression construct may comprise a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40 (SV40), bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccina virus (Ridgeway, 1988) adeno-associated virus (Ridgeway, 1988) and herpes simplex virus (HSV) (Glorioso et al., 1995). Such vectors may be used to (i) transform cell lines in vitro for the purpose of expressing proteins of interest or (ii) to transform cells in vitro or in vivo to provide therapeutic polypeptides in a gene therapy scenario.

With respect to eukaryotic vectors, the term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Preferred promoters include those derived from HSV, including the α4 promoter. Another preferred embodiment is the tetracycline controlled promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose. Table IV lists several promoters which may be employed, in the context of the present invention, to regulate the expression of a transgene. This list is not intended to be exhaustive of all the possible elements involved in the promotion of transgene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. Table V lists several enhancers, of course, this list is not meant to be limiting but exemplary.

TABLE V

| Enhancer | Inducer | References |
| --- | --- | --- |
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | poly(rI)X poly(rc) | Tavernier et al., 1983 |
| Adenovirus 5 E2 | Ela | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| a-2-Macroglobulin | IL-6 | Kunz et al., 1989 |
| Vimentin | Serum | Rittling et al., 1989 |
| MHC Class I Gene H-2kb | Interferon | Blanar et al., 1989 |
| HSP70 | Ela, SV40 Large T Antigen | Taylor et al., 1989; Taylor and Kingston, 1990a, b |
| Proliferin | Phorbol Ester-TPA | Mordacq and Linzer, 1989 |
| Tumor Necrosis Factor | FMA | Hensel et al., 1989 |
| Thyroid Stimulating Hormone a Gene | Thyroid Hormone | Chatterjee et al., 1989 |

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Host cells include eukaryotic microbes, such as yeast cultures may also be used. *Saccharomyces cerevisiae*, or common baker's yeast is the most commonly used among eukaryotic microorganisms, although a number of other strains are commonly available. For expression in *Saccharomyces*, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to eukaryotic microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Tissue Culture*, 1973). Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

4. PREPARATION OF ANTIBODIES TO UspA PROTEINS

Antibodies to UspA1 or UspA2 peptides or polypeptides may be readily prepared through use of well-known techniques, such as those exemplified in U.S. Pat. No. 4,196,265. Typically, this technique involves immunizing a suitable animal with a selected immunogen composition, e.g., purified or partially purified protein, synthetic protein or fragments thereof, as discussed in the section on vaccines. Animals to be immunized are mammals such as cats, dogs and horses, although there is no limitation other than that the subject be capable of mounting an immune response of some kind. The immunizing composition is administered in a manner effective to stimulate antibody producing cells. Rodents such as mice and rats are preferred animals, however, the use of rabbit, sheep or frog cells is possible. The use of rats may provide certain advantages, but mice are preferred, with the BALB/c mouse being most preferred as the most routinely used animal and one that generally gives a higher percentage of stable fusions.

For generation of monoclonal antibodies (MAbs), following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of the animal with the highest antibody titer removed. Spleen lymphocytes are obtained by homogenizing the spleen with a syringe. Typically, a spleen from an immunized mouse contains approximately $5 \times 10^7$ to $2 \times 10^8$ lymphocytes.

The antibody-producing B cells from the immunized animal are then fused with cells of an immortal myeloma cell line, generally one of the same species as the animal that was immunized. Myeloma cell lines suited for use in hybridoma-producing fusion procedures preferably are non-antibody-producing, have high fusion efficiency and enzyme deficiencies that render them incapable of growing in certain selective media which support the growth of only the desired fused cells, called "hybridomas."

Any one of a number of myeloma cells may be used and these are known to those of skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell line is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al. (1977). The use of electrically induced fusion methods is also appropriate.

Fusion procedures usually produce viable hybrids at low frequencies, about $1 \times 10^{-6}$ to $1 \times 10^{-8}$. This does not pose a problem, however, as the viable, fused hybrids are differentiated from the parental, unfused cells (particularly the unfused myeloma cells that would normally continue to divide indefinitely) by culture in a selective medium. The selective medium generally is one that contains an agent that blocks the de novo synthesis of nucleotides in the tissue culture media. Exemplary and preferred agents are aminopterin, methotrexate and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks.

Therefore, the only cells that can survive in the selective media are those hybrids formed from myeloma and B cells.

This culturing provides a population of hybridomas from which specific hybridomas are selected. Typically, selection of hybridomas is performed by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide MAbs. The cell lines may be exploited for MAb production in two basic ways. A sample of the hybridoma can be injected, usually in the peritoneal cavity, into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

Monoclonal antibodies of the present invention also include anti-idiotypic antibodies produced by methods well-known in the art. Monoclonal antibodies according to the present invention also may be monoclonal heteroconjugates, i.e., hybrids of two or more antibody molecules. In another embodiment, monoclonal antibodies according to the invention are chimeric monoclonal antibodies. In one approach, the chimeric monoclonal antibody is engineered by cloning recombinant DNA containing the promoter, leader, and variable-region sequences from a mouse antibody producing cell and the constant-region exons from a human antibody gene. The antibody encoded by such a recombinant gene is a mouse-human chimera. Its antibody specificity is determined by the variable region derived from mouse sequences. Its isotype, which is determined by the constant region, is derived from human DNA.

In another embodiment, the monoclonal antibody according to the present invention is a "humanized" monoclonal antibody, produced by techniques well-known in the art. That is, mouse complementary determining regions ("CDRs") are transferred from heavy and light V-chains of the mouse Ig into a human V-domain, followed by the replacement of some human residues in the framework regions of their murine counterparts. "Humanized" monoclonal antibodies in accordance with this invention are especially suitable for use in in vivo diagnostic and therapeutic methods for treating *Moraxella* infections.

As stated above, the monoclonal antibodies and fragments thereof according to this invention can be multiplied according to in vitro and in vivo methods well-known in the art. Multiplication in vitro is carried out in suitable culture media such as Dulbecco's modified Eagle medium or RPMI 1640 medium, optionally replenished by a mammalian serum such as fetal calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, e.g., in an airlift reactor or in a continuous stirrer reactor or immobilized or entrapped cell culture.

Large amounts of the monoclonal antibody of the present invention also may be obtained by multiplying hybridoma cells in vivo. Cell clones are injected into mammals which are histocompatible with the parent cells, e.g., syngeneic mice, to cause growth of antibody-producing tumors. Optionally, the animals are primed with a hydrocarbon, especially oils such as Pristane (tetramethylpentadecane) prior to injection.

In accordance with the present invention, fragments of the monoclonal antibody of the invention can be obtained from monoclonal antibodies produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer, or they may be produced manually using techniques well known in the art.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents, or by reaction with an isothiocyanate. Conjugates with metal chelates are similarly produced. Other moieties to which antibodies may be conjugated include radionuclides such as $^{3}$H, $^{125}$I, $^{131}$I $^{32}$P, $^{35}$S, $^{14}$C, $^{51}$Cr, $^{36}$Cl, $^{57}$Co, $^{58}$Co, $^{59}$Fe, $^{75}$Se, $^{152}$Eu, and $^{99}$mTc, are other useful labels which can be conjugated to antibodies. Radio-labeled monoclonal antibodies of the present invention are produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$m by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as $SNCl_2$, a buffer solution such as sodium-potassium phthalate solution, and the antibody.

5. USE OF PEPTIDES AND MONOCLONAL ANTIBODIES IN IMMUNOASSAYS

It is proposed that the monoclonal antibodies of the present invention will find useful application in standard immunochemical procedures, such as ELISA and western blot methods, as well as other procedures which may utilize antibodies specific to CopB epitopes. While ELISAs are preferred, it will be readily appreciated that such assays include RIAs and other non-enzyme linked antibody binding assays or procedures. Additionally, it is proposed that monoclonal antibodies specific to the particular UspA epitope may be utilized in other useful applications. For example, their use in immunoabsorbent protocols may be useful in purifying native or recombinant UspA proteins or variants thereof.

It also is proposed that the disclosed UspA1 and UspA2 peptides of the invention will find use as antigens for raising antibodies and in immunoassays for the detection of anti-UspA antigen-reactive antibodies. In a variation on this embodiment, UspA1 and UspA2 mutant peptides may be screened, in immunoassay format, for reactivity against UspA1- or UspA2-specific antibodies, such as MAb 17C7. In this way, a mutational analysis of various epitopes may be performed. Results from such analyses may then be used to determine which additional UspA1 or UspA2 epitopes may be recognized by antibodies and useful in the preparation of potential vaccines for *Moraxella*.

Diagnostic immunoassays include direct culturing of bodily fluids, either in liquid culture or on a solid support such as nutrient agar. A typical assay involves collecting a sample of bodily fluid from a patient and placing the sample in conditions optimum for growth of the pathogen. The determination can then be made as to whether the microbe exists in the sample. Further analysis can be carried out to determine the hemolyzing properties of the microbe.

Immunoassays encompassed by the present invention include, but are not limited to those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays, in their most simple and direct sense, are binding assays. Certain preferred immunoassays are the various types of enzyme linked immunosorbent assays (ELISAs) and radioimmunoassays (RIAs) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the anti-UspA antibodies of the invention are immobilized onto a selected surface exhibiting protein affinity, such as a well in a polystyrene microtiter plate. Then, a test composition suspected of containing the desired antigen, such as a clinical sample, is added to the wells. After binding and washing to remove non-specifically bound immune complexes, the bound antigen may be detected. Detection is generally achieved by the addition of another antibody, specific for the desired antigen, that is linked to a detectable label. This type of ELISA is a simple "sandwich ELISA". Detection may also be achieved by the addition of a second antibody specific for the desired antigen, followed by the addition of a third antibody that has binding affinity for the second antibody, with the third antibody being linked to a detectable label.

In another exemplary ELISA, the samples suspected of containing the UspA antigen are immobilized onto the well surface and then contacted with the anti-UspA antibodies. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Further methods include the detection of primary immune complexes by a two step approach. A second binding ligand, such as an antibody, that has binding affinity for the primary antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

Competition ELISAs are also possible in which test samples compete for binding with known amounts of labeled antigens or antibodies. The amount of reactive species in the unknown sample is determined by mixing the sample with the known labeled species before or during incubation with coated wells. (Antigen or antibodies may also be linked to a solid support, such as in the form of beads, dipstick, membrane or column matrix, and the sample to be analyzed applied to the immobilized antigen or antibody.) The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a second antibody having specificity for the first. Of course, in that the test sample will typically be of human origin, the second antibody will preferably be an antibody having specificity in general for human IgG. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer. Alternatively, the label may be a chemilluminescent one. The use of such labels is described in U.S. Pat. Nos. 5,310,687, 5,238,808 and 5,221,605.

6. PROPHYLACTIC USE OF UspA PEPTIDES AND UspA-SPECIFIC ANTIBODIES

In a further embodiment of the present invention, there are provided methods for active and passive immunoprophylaxis. Active immunoprophylaxis will be discussed first, followed by a discussion on passive immunoprophylaxis. It should be noted that the discussion of formulating vaccine compositions in the context of active immunotherapy is relevant to the raising antibodies in experimental animals for passive immunotherapy and for the generation of diagnostic methods.

6.1. Active Immunotherapy

According to the present invention, UspA1 or UspA2 polypeptides or UspA1- or UspA2-derived peptides, as discussed above, may be used as vaccine formulations to generate protective anti-*M. catarrhalis* antibody responses in vivo. By protective, it is only meant that the immune system of a treated individual is capable of generating a response that reduces, to any extent, the clinical impact of the bacterial infection. This may range from a minimal decrease in bacterial burden to outright prevention of infection. Ideally, the treated subject will not exhibit the more serious clinical manifestations of *M. catarrhalis* infection.

Generally, immunoprophylaxis involves the administration, to a subject at risk, of a vaccine composition. In the instant case, the vaccine composition will contain a UspA1 and/or UspA2 polypeptide or immunogenic derivative thereof in a pharmaceutically acceptable carrier, diluent or excipient. As stated above, those of skill in the art are able, through a variety of mechanisms, to identify appropriate antigenic characteristics of UspA1 and UspA2 and, in so doing, develop vaccines that will achieve generation of immune responses against *M. catarrhalis*.

The stability and immunogenicity of UspA1 and UspA2 antigens may vary and, therefore, it may be desirable to couple the antigen to a carrier molecule. Exemplary carriers are KLH, BSA, human serum albumin, myoglobin, β-galactosidase, penicillinase, $CRM_{197}$ and bacterial toxoids, such as diphtheria toxoid and tetanus toxoid. Those of skill in the art are aware of proper methods by which peptides can be linked to carriers without destroying their immunogenic value. Synthetic carriers such as multi-poly-DL-alanyl-poly-L-lysine and poly-L-lysine also are contemplated. Coupling generally is accomplished through amino or carboxyl-terminal residues of the antigen, thereby affording the peptide or polypeptide the greatest chance of assuming a relatively "native" conformation following coupling.

It is recognized that other protective agents could be coupled with either a UspA1 or UspA2 antigen such that the UspA1 or UspA2 antigen acts as the carrier molecule. For example, agents which protect against other pathogenic organisms, such as bacteria, viruses or parasites, could be coupled to either a UspA1 or UspA2 antigen to produce a multivalent vaccine or pharmaceutical composition which would be useful for the treatment or inhibition of both *M. catarrhalis* infection and other pathogenic infections. In particular, it is envisioned that either UspA1 or UspA2 proteins or peptides could serve as immunogenic carriers for other vaccine components, for example, saccharides of pneumococcus, menigococcus or hemophylus influenza and could even be covalently coupled to these other components.

It also may be desirable to include in the composition any of a number of different substances referred to as adjuvants, which are known to stimulate the appropriate portion of the immune system of the vaccinated animal. Suitable adjuvants for the vaccination of subjects (including experimental animals) include, but are not limited to oil emulsions such as Freund's complete or incomplete adjuvant (not suitable for livestock use), Marcol 52:Montanide 888 (Marcol is a Trademark of Esso, Montanide is a Trademark of SEPPIC, Paris), squalane or squalene, Adjuvant 65 (containing peanut oil, mannide monooleate and aluminum monostearate), MPL™ (3-O-deacylated monophosphoryl lipid A; RIBI ImmunoChem Research Inc., Hamilton, Utah), Stimulon™ (QS-21; Aquila Biopharmaceuticals Inc., Wooster, Mass.), mineral gels such as aluminum hydroxide, aluminum phosphate, calcium phosphate and alum, surfactants such as hexadecylamine, octadecylamine, lysolecithin, dimethyl-dioctadecylammonium bromide, N,N-dioctadecyl-N,N'-bis(2-hydroxyethyl)-propanediamine, methoxyhexadecylglycerol and pluronic polyols, polyanions such as pyran, dextran sulfate, polyacrylic acid and carbopol, peptides and amino acids such as muramyl dipeptide, dimethylglycine, tuftsin and trehalose dimycolate. Agents include synthetic polymers of sugars (Carbopol), emulsion in physiologically acceptable oil vehicles such as mannide mono-oleate (Aracel A) or emulsion with 20 percent solution of a perfluorocarbon (Fluosol-DA) also may be employed.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: Solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The vaccine preparations of the present invention also can be administered following incorporation into non-toxic carriers such as liposomes or other microcarrier substances, or after conjugation to polysaccharides, proteins or polymers or in combination with Quil-A to form "iscoms" (immunostimulating complexes). These complexes can serve to reduce the toxicity of the antigen, delay its clearance from the host and improve the immune response by acting as an adjuvant. Other suitable adjuvants for use this embodiment of the present invention include INF, IL-2, IL-4, IL-8, IL-12 and other immunostimulatory compounds. Further, conjugates comprising the immunogen together with an integral membrane protein of prokaryotic origin, such as TraT (see PCT/AU87/00107) may prove advantageous.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10-95% of active ingredient, preferably 25-70%.

The peptides may be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1-5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

6.2. Passive Immunotherapy

Passive immunity is defined, for the purposes of this application, as the transfer to an organism of an immune response effector that was generated in another organism. The classic example of establishing passive immunity is to transfer antibodies produced in one organism into a second, immunologically compatible animal. By "immunologically compatible," it is meant that the antibody can perform at least some of its immune functions in the new host animal. More recently, as a better understanding of cellular immune functions has evolved, it has become possible to accomplish passive immunity by transferring other effectors, such as certain kinds of lymphocytes, including cytotoxic and helper T cells, NK cells and other immune effector cells. The present invention contemplates both of these approaches.

Antibodies, antisera and immune effector cells are raised using standard vaccination regimes in appropriate animals, as discussed above. The primary animal is vaccinated with at least a microbe preparation or one bacterial product or by-product according to the present invention, with or without an adjuvant, to generate an immune response. The immune response may be monitored, for example, by measurement of the levels of antibodies produced, using standard ELISA methods.

Once an adequate immune response has been generated, immune effector cells can be collected on a regular basis, usually from blood draws. The antibody fraction can be purified from the blood by standard means, e.g., by protein A or protein G chromatography. In an alternative preferred embodiment, monoclonal antibody-producing hybridomas are prepared by standard means (Coligan et al., 1991). Monoclonal antibodies are then prepared from the hybridoma cells by standard means. If the primary host's monoclonal antibodies are not compatible with the animal to be treated, it is possible that genetic engineering of the cells can be employed to modify the antibody to be tolerated by the animal to be treated. In the human context, murine antibodies, for example, may be "humanized" in this fashion.

Antibodies, antisera or immune effector cells, prepared as set forth above, are injected into hosts to provide passive immunity against microbial infestation. For example, an antibody composition is prepared by mixing, preferably homogeneously mixing, at least one antibody with at least one pharmaceutically or veterinarally acceptable carrier, diluent, or excipient using standard methods of pharmaceutical or veterinary preparation. The amount of antibody required to produce a single dosage form will vary depending upon the microbial species being vaccinated against, the individual to be treated and the particular mode of administration. The specific dose level for any particular individual will depend upon a variety of factors including the age, body weight, general health, sex, and diet of the individual, time of administration, route of administration, rate of excretion, drug combination and the severity of the microbial infestation.

The antibody composition may be administered intravenously, subcutaneously, intranasally, orally, intramuscularly, vaginally, rectally, topically or via any other desired route. Repeated dosings may be necessary and will vary, for example, depending on the clinical setting, the particular microbe, the condition of the patient and the use of other therapies.

6.3 DNA Immunization

The invention also relates to a vaccine comprising a nucleic acid molecule encoding a UspA1, UspA2 protein or a peptide comprising SEQ ID NO:17 wherein said UspA 1, UspA2 protein or peptide retains immunogenicity and, when incorporated into an immunogenic composition or vaccine and administered to a vertebrate, provides protection without inducing enhanced disease upon subsequent infection of the vertebrate with *M. catarrhalis*, and a physiologically acceptable vehicle. Such a vaccine is referred to herein as a nucleic acid vaccine or DNA vaccine and is useful for the genetic immunization of vertebrates.

The term, "genetic immunization", as used herein, refers to inoculation of a vertebrate, particularly a mammal such as a mouse or human, with a nucleic acid vaccine directed against a pathogenic agent, particularly M. catarrhalis, resulting in protection of the vertebrate against M. catarrhalis. A "nucleic acid vaccine" or "DNA vaccine" as used herein, is a nucleic acid construct comprising a nucleic acid molecule encoding UspA1, UspA2 or an immunogenic epitope comprising SEQ ID NO:17. The nucleic acid construct can also include transcriptional promoter elements, enhancer elements, splicing signals, termination and polyadenylation signals, and other nucleic acid sequences.

The nucleic acid vaccine can be produced by standard methods. For example, using known methods, a nucleic acid (e.g., DNA) encoding UspA1 or UspA2 can be inserted into an expression vector to construct a nucleic acid vaccine (see Maniatis et al., 1989). The individual vertebrate is inoculated with the nucleic acid vaccine (i.e., the nucleic acid vaccine is administered), using standard methods. The vertebrate can be inoculated subcutaneously, intravenously, intraperitoneally, intradermally, intramuscularly, topically, orally, rectally, nasally, buccally, vaginally, by inhalation spray, or via an implanted reservoir in dosage formulations containing conventional non-toxic, physiologically acceptable carriers or vehicles. Alternatively, the vertebrate is inoculated with the nucleic acid vaccine through the use of a particle acceleration instrument (a "gene gun"). The form in which it is administered (e.g., capsule, tablet, solution, emulsion) will depend in part on the route by which it is administered. For example, for mucosal administration, nose drops, inhalants or suppositories can be used.

The nucleic acid vaccine can be administered in conjunction with any suitable adjuvant. The adjuvant is administered in a sufficient amount, which is that amount that is sufficient to generate an enhanced immune response to the nucleic acid vaccine. The adjuvant can be administered prior to (e.g., 1 or more days before) inoculation with the nucleic acid vaccine; concurrently with (e.g., within 24 hours of) inoculation with the nucleic acid vaccine; contemporaneously (simultaneously) with the nucleic acid vaccine (e.g., the adjuvant is mixed with the nucleic acid vaccine, and the mixture is administered to the vertebrate); or after (e.g., 1 or more days after) inoculation with the nucleic acid vaccine. The adjuvant can also be administered at more than one time (e.g., prior to inoculation with the nucleic acid vaccine and also after inoculation with the nucleic acid vaccine). As used herein, the term "in conjunction with" encompasses any time period, including those specifically described herein and combinations of the time periods specifically described herein, during which the adjuvant can be administered so as to generate an enhanced immune response to the nucleic acid vaccine (e.g., an increased antibody titer to the antigen encoded by the nucleic acid vaccine, or an increased antibody titer to M. catarrhalis). The adjuvant and the nucleic acid vaccine can be administered at approximately the same location on the vertebrate; for example, both the adjuvant and the nucleic acid vaccine are administered at a marked site on a limb of the vertebrate.

In a particular embodiment, the nucleic acid construct is co-administered with a transfection-facilitating agent. In a preferred embodiment, the transfection-facilitating agent is dioctylglycylspermine (DOGS) (as exemplified in published PCT application publication no. WO 96/21356 and incorporated herein by reference). In another embodiment, the transfection-facilitating agent is bupivicaine (as exemplified in U.S. Pat. No. 5,593,972 and incorporated herein by reference).

6.4. Animal Model for Testing Efficacy of Therapies

The evaluation of the functional significance of antibodies to surface antigens of M. catarrhalis has been hampered by the lack of a suitable animal model. The relative lack of virulence of this organism for animals rendered identification of an appropriate model system difficult (Doern, 1986). Attempts to use rodents, including chinchillas, to study middle ear infections caused by M. catarrhalis were unsuccessful, likely because this organism cannot grow or survive in the middle ear of these hosts (Doyle, 1989).

Murine short-term pulmonary clearance models have now been developed (Unhanand et al., 1992; Verghese et al., 1990) which permit an evaluation of the interaction of M. catarrhalis with the lower respiratory tract as well as assessment of pathologic changes in the lungs. This model reproducibly delivers an inoculum of bacteria to a localized peripheral segment of the murine lung. Bacteria multiply within the lung, but are eventually cleared as a result of (i) resident defense mechanisms, (ii) the development of an inflammatory response, and/or (iii) the development of a specific immune response. Using this model, it has been demonstrated that serum IgG antibody can enter the alveolar spaces in the absence of an inflammatory response and enhance pulmonary clearance of nontypable H. influenzae (McGehee et al., 1989), a pathogen with a host range and disease spectrum nearly identical to those of M. catarrhalis.

7. SCREENING ASSAYS

In still further embodiments, the present invention provides methods for identifying new M. catarrhalis inhibitory compounds, which may be termed as "candidate substances," by screening for immunogenic activity with peptides that include one or more mutations to the identified immunogenic epitopic region. It is contemplated that such screening techniques will prove useful in the general identification of any compound that will serve the purpose of inhibiting, or even killing, *M. catarrhalis*, and in preferred embodiments, will provide candidate vaccine compounds.

It is further contemplated that useful compounds in this regard will in no way be limited to proteinaceous or peptidyl compounds. In fact, it may prove to be the case that the most useful pharmacological compounds for identification through application of the screening assays will be non-peptidyl in nature and, e.g., which will serve to inhibit bacterial protein transcription through a tight binding or other chemical interaction. Candidate substances may be obtained from libraries of synthetic chemicals, or from natural samples, such as rain forest and marine samples.

To identify a *M. catarrhalis* inhibitor, one would simply conduct parallel or otherwise comparatively controlled immunoassays and identify a compound that inhibits the phenotype of *M. catarrhalis*. Those of skill in the art are familiar with the use of immunoassays for competitive screenings (for example refer to Sambrook et al. 1989).

Once a candidate substance is identified, one would measure the ability of the candidate substance to inhibit *M. catarrhalis* in the presence of the candidate substance. In general, one will desire to measure or otherwise determine the activity of *M. catarrhalis* in the absence of the added candidate substance relative to the activity in the presence of the candidate substance in order to assess the relative inhibitory capability of the candidate substance.

7.1 Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. as will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

7.2. Second Generation Inhibitors

In addition to the inhibitory compounds initially identified, the inventor also contemplates that other sterically similar compounds may be formulated to mimic the key portions of the structure of the inhibitors. Such compounds, which may include peptidomimetics of peptide inhibitors, may be used in the same manner as the initial inhibitors.

Certain mimetics that mimic elements of protein secondary structure are designed using the rationale that the peptide backbone of proteins exists chiefly to orientate amino acid side chains in such a way as to facilitate molecular interactions. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of computer-based chemical modeling is now well known. Using such methods, a chemical that specifically inhibits viral transcription elongation can be designed, and then synthesized, following the initial identification of a compound that inhibits RNA elongation, but that is not specific or sufficiently specific to inhibit viral RNA elongation in preference to human RNA elongation. It will be understood that all such sterically similar constructs and second generation molecules fall within the scope of the present invention.

8. DIAGNOSING *M. catarrhalis* INFECTIONS

8.1 Amplification and PCR™

Nucleic acid sequence used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a cDNA.

Pairs of primers that selectively hybridize to nucleic acids corresponding to UspA1 or UspA2 protein or a mutant thereof are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ (RT-PCR™) amplification procedure may be performed in order to quantify the amount of mRNA amplified or to prepare cDNA from the desired mRNA. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR™-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

All the essential materials and reagents required for detecting P-TEFb or kinase protein markers in a biological sample may be assembled together in a kit. This generally will comprise preselected primers for specific markers. Also included may be enzymes suitable for amplifying nucleic acids including various polymerases (RT, Taq, etc.), deoxynucleotides and buffers to provide the necessary reaction mixture for amplification.

Such kits generally will comprise, in suitable means, distinct containers for each individual reagent and enzyme as well as for each marker primer pair. Preferred pairs of primers for amplifying nucleic acids are selected to amplify the sequences specified in SEQ ID NO:2 or SEQ ID NO:4 or SEQ ID NO:6 or SEQ ID NO:8 or SEQ ID NO:10 or SEQ ID NO:12 or SEQ ID NO:14 or SEQ ID NO:16 such that, for example, nucleic acid fragments are prepared that include a contiguous stretch of nucleotides identical to for example about 15, 20, 25, 30, 35, etc.; 48, 49, 50, 51, etc.; 75, 76, 77, 78, 79, 80 etc.; 100, 101, 102, 103 etc.; 118, 119, 120, 121 etc.; 127, 128, 129, 130, 131, etc.; 316, 317, 318, 319, etc.; 322, 323, 324, 325, 326, etc.; 361, 362, 363, 364, etc.; 372, 373, 374, 375, etc. of SEQ ID NO:2 or SEQ ID NO:4 or SEQ ID NO:6 or SEQ ID NO:8 or SEQ ID NO:10 or SEQ ID NO:12 or SEQ ID NO:14 or SEQ ID NO:16, so long as the selected contiguous stretches are from spatially distinct regions. Similar fragments may be prepared which are identical or complimentary to, for example, SEQ ID NO:1 such that the fragments do not hybridize to, for example, SEQ ID NO:3.

In another embodiment, such kits will comprise hybridization probes specific for UspA1 or UspA2 proteins chosen from a group including nucleic acids corresponding to the sequences specified in SEQ ID NO:2 or SEQ ID NO:4 or SEQ ID NO:6 or SEQ ID NO:8 or SEQ ID NO:10 or SEQ ID NO:12 or SEQ ID NO:14 or SEQ ID NO:16 or to intermediate lengths of the sequences specified. Such kits generally will comprise, in suitable means, distinct containers for each individual reagent and enzyme as well as for each marker hybridization probe.

8.2 Other Assays

Other methods for genetic screening to accurately detect *M. catarrhalis* infections that alter normal cellular production and processing, in genomic DNA, cDNA or RNA samples may be employed, depending on the specific situation.

For example, one method of screening for genetic variation is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. After the RNase cleavage reaction, the RNase is inactivated by proteolytic digestion and organic extraction, and the cleavage products are denatured by heating and analyzed by electrophoresis on denaturing polyacrylamide gels. For the detection of mismatches, the single-stranded products of the RNaseA treatment, electrophoretically separated according to size, are compared to similarly treated control duplexes. Samples containing smaller fragments (cleavage products) not seen in the control duplex are scored as +.

Currently available RNase mismatch cleavage assays, including those performed according to U.S. Pat. No. 4,946,773, require the use of radiolabeled RNA probes. Myers and Maniatis in U.S. Pat. No. 4,946,773 describe the detection of base pair mismatches using RNase A. Other investigators have described the use of *E. coli* enzyme, RNase I, in mismatch assays. Because it has broader cleavage specificity than RNase A, RNase I would be a desirable enzyme to employ in the detection of base pair mismatches if components can be found to decrease the extent of non-specific cleavage and increase the frequency of cleavage of mismatches. The use of RNase I for mismatch detection is described in literature from Promega Biotech. Promega markets a kit containing RNase I that is shown in their literature to cleave three out of four known mismatches, provided the enzyme level is sufficiently high.

The RNase protection assay was first used to detect and map the ends of specific mRNA targets in solution. The assay relies on being able to easily generate high specific activity radiolabeled RNA probes complementary to the mRNA of interest by in vitro transcription. Originally, the templates for in vitro transcription were recombinant plasmids containing bacteriophage promoters. The probes are mixed with total cellular RNA samples to permit hybridization to their complementary targets, then the mixture is treated with RNase to degrade excess unhybridized probe. Also, as originally intended, the RNase used is specific for single-stranded RNA, so that hybridized double-stranded probe is protected from degradation. After inactivation and removal of the RNase, the protected probe (which is proportional in amount to the amount of target mRNA that was present) is recovered and analyzed on a polyacrylamide gel.

The RNase Protection assay was adapted for detection of single base mutations. In this type of RNase A mismatch cleavage assay, radiolabeled RNA probes transcribed in vitro from wild type sequences, are hybridized to complementary target regions derived from test samples. The test target generally comprises DNA (either genomic DNA or DNA amplified by cloning in plasmids or by PCR™), although RNA targets (endogenous mRNA) have occasionally been used. If single nucleotide (or greater) sequence differences occur between the hybridized probe and target, the resulting disruption in Watson-Crick hydrogen bonding at that position ("mismatch") can be recognized and cleaved in some cases by single-strand specific ribonuclease. To date, RNase A has been used almost exclusively for cleavage of single-base mismatches, although RNase I has recently been shown as useful also for mismatch cleavage. There are recent descriptions of using the MutS protein and other DNA-repair enzymes for detection of single-base mismatches.

9. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Sequence Analysis and Characterization of uspA1

Bacterial strains and culture conditions. *M. catarrhalis* strains O35E, O46E, TTA24, 012E, FR2682, and B21 have been previously described (Helminen et al., 1993a; Helminen et al., 1994; Unhanand et al., 1992). *M. catarrhalis* strains FR3227 and FR2336 were obtained from Richard Wallace, University of Texas Health Center, Tyler, Tex. *M. catarrhalis* strain B6 was obtained from Elliot Juni, University of Michigan, Ann Arbor, Mich. *M. catarrhalis* strain TTA1 was obtained from Steven Berk, East Tennessee State University, Johnson City, Tenn. *M. catarrhalis* strain 25240 was obtained from the American Type Culture Collection, Rockville, Md. *M. catarrhalis* strains were routinely cultured in Brain Heart Infusion (BHI) broth (Difco Laboratories, Detroit, Mich.) at 37° C. or on BHI agar plates in an atmosphere of 95% air-5% $CO_2$. *Escherichia coli* strains LE392 and XL1-Blue MRF' (Stratagene, La Jolla, Calif.) were grown on Lubria-Bertani medium (Maniatis et al., 1982) supplemented with maltose (0.2% w/v) and 10 mM $MgSO_4$ at 37° C., with antimicrobial supplementation as necessary.

Monoclonal antibodies (MAbs). MAb 17C7 is a murine IgG antibody reactive with the UspA proteinaceous material of all *M. catarrhalis* strains tested to date (Helminen et al., 1994). Additional MAbs specific for UspA material (i.e., 16A7, 17B1, and 5C12) were produced for this study by fusing spleen cells from mice immunized with outer membrane vesicles from *M. catarrhalis* O35E with the SP2/0-Ag14 plasmacytoma cell line, as described (Helminen et al., 1993a). These MAbs were used in the form of hybridoma culture supernatant fluid in western blot and dot blot analyses.

Cloning vectors. Plasmid and bacteriophage cloning vectors utilized in this work and the recombinant derivatives of these vectors are listed in Table VI.

TABLE VI

Bacteriophages And Plasmids

| Bacteriophage or plasmid | Description | Source |
|---|---|---|
| Bacteriophage | | |
| LambdaGEM-11 | Cloning vector | Promega Corp. (Madison, WI) |
| MEH200 | LambdaGEM-11 containing an 11 kb insert of *M. catarrhalis* strain 035E DNA encoding the UspA proteinaceous material | (Helminen et al., 1994) |
| ZAP Express | Cloning vector | Stratagene |
| USP100 | ZAP Express with a 2.7 kb fragment of DNA (containing the uspA1) amplified from the chromosome of *M. catarrhalis* strain 035E | This study |
| Plasmids | | |
| pBluescript II SK+ (pBS) | Cloning vector, $Amp^R$ | Stratagene |
| pJL501.6 | pBS containing the 1.6 kb BglII-EcoRI fragment from MEH200 | This study |
| pJL500.5 | pBS containing the 600-bp BglII fragment from MEH200 | This study |

MEH200, the original recombinant bacteriophage clone that produced plaques reactive with the UspA-specific MAb 17C7, has been described previously (Helminen et al., 1994).

Genetic techniques. Standard recombinant DNA techniques including plasmid isolation, restriction enzyme digestions, DNA modifications, ligation reactions and transformation of *E. coli* are familiar to those of skill in the art and were performed as previously described (Maniatis et al., 1982; Sambrook et al., 1989).

Polymerase Chain Reaction (PCR™). PCR™ was performed using the GeneAmp kit (Perkin-Elmer, Branchberg, N.J.). All reaction were carried out according to the manufacturer's instructions. To amplify products from total genomic DNA, 1 μg of *M. catarrhalis* chromosomal DNA and 100 ng of each primer were used in each 100 μl reaction.

Nucleotide sequence analysis. Nucleotide sequence analysis of DNA fragments in recombinant plasmids, in bacteriophage, or derived by PCR™ was performed using an Applied Biosystems Model 373A automated DNA sequencer (Applied Biosystems, Foster City, Calif.). DNA sequence information was analyzed using the Intelligenetics suite package and programs from the University of Wisconsin Genetics Computer Group software analysis package (Devereux et al., 1984). Analysis of protein hydrophilicity using the method of Kyte and Doolittle (1982) and analysis of repeated amino acid sequences within the UspA protein was performed using the MacVector™ software protein matrix analysis package (Eastman Kodak Company, Rochester, N.Y.).

Identification of recombinant bacteriophage. Lysates were generated from E. coli cells infected with recombinant bacteriophage by using the plate lysis method as described (Helminen et al., 1994). MAb-based screening of plaques formed by recombinant ZAP Express bacteriophage on E. coli XL1-Blue MRF' cells was performed according to the manufacturer's instructions (Stratagene, La Jolla, Calif.). Briefly, nitrocellulose filters soaked in 10 mM IPTG were applied to the surface of agar plates five hours after bacteriophage infection of the bacterial lawn. After overnight incubation at 37° C., the nitrocellulose pads were removed, washed with PBS containing 0.5% (v/v) Tween 20 and 5% (w/v) skim milk (PBS-T) and incubated with hybridoma culture supernatant containing the MAb for 4 hours at room temperature. After four washes with PBS-T, PBS-T containing $^{125}$I-labeled goat anti-mouse IgG was applied to each pad. After overnight incubation at 4° C., the pads were washed four times with PBS-T, blotted dry, and exposed to film.

Characterization of M. catarrhalis protein antigens. Outer membrane vesicles were prepared from BHI broth-grown M. catarrhalis cells by the EDTA-buffer method (Murphy and Loeb, 1989). Proteins present in these vesicles were resolved by sodium dodecyl sulfate (SDS)-polyacrylamide gel electrophoresis (PAGE) using 7.5% (w/v) polyacrylamide separating gels. These SDS-PAGE-resolved proteins were electrophoretically transferred to nitrocellulose and western blot analysis was performed as described using MAb 17C7 as the primary antibody (Kimura et al., 1985). For western blot analysis of proteins encoded by DNA inserts in recombinant bacteriophage, one part of a lysate from bacteriophage-infected E. coli cells was mixed with one part SDS-digestion buffer (Kimura et al., 1985) and this mixture was incubated at 37° C. for 15 minutes prior to SDS-PAGE.

Features of the uspA1 gene and its encoded protein product. The nucleotide sequence of the M. catarrhalis O35E uspA1 gene and the deduced amino acid sequence of the UspA1 protein are provided in SEQ ID NO:2 and SEQ ID NO:1, respectively. The open reading frame (ORF), containing 2,493 nucleotides, encoded a protein product of 831 amino acids, with a calculated molecular mass of 88,271 daltons.

The predicted protein product of the uspA1 ORF had a pI or 4.7, was highly hydrophilic, and was characterized by extensively repeated motifs. The first motif consists of the consensus sequence NXAXXYSXIGGGXN (SEQ ID NO:24), which is extensively repeated between amino acid residues 80 and 170. The second region, from amino acid residues 320 to 460, contains a long sequence which is repeated three times in its entirety, but which also contains smaller units which are repeated several times themselves. This "repeat within a repeat" arrangement is also true of the third region, which extends from amino acid residues 460 to 600. This last motif consists of many repeats of the small motif QADI (SEQ ID NO:25) and two large repeats which contain the QADI (SEQ ID NO:25) motif within themselves.

Similarity of UspA1 to other proteins. A BLAST-X search (Altschul et al., 1990; Gish and States, 1993) of the available databases for proteins with significant homology to UspA1 indicated that the prokaryotic proteins that were most similar to this M. catarrhalis antigen were a putative adhesin of H. influenzae Rd (GenBank accession number U32792) (Fleischmann et al., 1995), the Hia adhesin from nontypable H. influenzae (GenBank accession number U38617) (Barenkamp and St. Geme III, 1996), and the YadA invasin of Yersinia enterocolitica (Skurnik and Wolf-Watz, 1989) (SwissProt:P31489). When the GAP alignment program (Devereux et al., 1984) was used to compare the UspA1 sequence to that of these and closely related bacterial adhesins, UspA1 proved to be 25% identical and 47% similar to the E. coli AIDA-I adhesin from enteropathogenic E. coli (Benz and Schmidt, 1989; Benz and Schmidt, 1992b), 23% identical and 46% similar to Hia (Barenkamp and St. Geme III, 1996), and 24% identical and 43% similar to YadA (Skurnik and Wolf-Watz, 1989). Other proteins retrieved from database searches as having homology with UspA1 included myosin heavy chains from a number of species.

Example II

Two Genes Encode the Proteins UspA1 and UspA2

MAb 17C7 binds to a very high molecular weight proteinaceous material of M. catarrhalis, designated UspA, that migrates with an apparent molecular weight (in SDS-PAGE) of at least 250 kDa. This same MAb also reacts with another antigen band of approximately 100 kDa, as described in U.S. Pat. No. 5,552,146 and incorporated herein by reference, and it is bound by a phage lysate from E. coli infected by a recombinant bacteriophage that contained a fragment of M. catarrhalis chromosomal DNA. The M. catarrhalis proteinaceous material in the phage lysate that binds this MAb migrates at a rate similar or indistinguishable from that of the native UspA material (Helminen et al, 1994).

Analysis of uspA1. Nucleotide sequence analysis of the M. catarrhalis strain O35E gene expressed by the recombinant bacteriophage, designated uspA1, revealed the presence of an ORF encoding a predicted protein product with a molecular mass of 88,271 (SEQ ID NO:1). The use of the uspA1 ORF in an in vitro DNA-directed protein expression system revealed that the protein encoded by the uspA1 gene migrated in SDS-PAGE with an apparent molecular weight of about 120 kDa. (Those of skill in the art will be aware that denaturing processes, such as SDS-PAGE, can alter the migration rate of proteins such that the apparent molecular weight of the denatured protein is somewhat different than the predicted molecular weight of the non-denatured protein.) In addition, when the uspA1 ORF was introduced into a bacteriophage vector, the recombinant E. coli strain containing this recombinant phage expressed a protein that migrated in SDS-PAGE apparently at the same rate as the native UspA protein from M. catarrhalis.

Southern blot analysis of chromosomal DNA from several M. catarrhalis strains, using a 0.6 kb BglII-PvuII fragment derived from the cloned uspA1 gene as the probe, revealed that, with several strains, there were two distinct restriction fragments that bound this uspA1-derived probe (FIG. 1), indicating that M. catarrhalis possessed a second gene had some similarity to the uspA1 gene.

Native very high molecular weight UspA proteinaceous material from M. catarrhalis strain O35E was resolved by SDS PAGE, electroeluted, and digested with a protease. N-terminal acid sequence analysis of some of the resultant peptides revealed that the amino acid sequences of several peptides did not match that of the deduced amino acid sequence of UspA1. Other peptides obtained from this experiment were similar to those present in the deduced amino acid sequence but not identical.

Protease and cyanogen bromide (CNBr) Cleavage of High Molecular Weight UspA Proteinaceous Material: Three tenths (0.3) mg of purified very high molecular weight UspA proteinaceous material (at the time of the purification this material was thought to be a single protein) was precipitated with 90% ethanol and the pellet was resuspended in 100 ml of 88% formic acid containing 12M urea. Following resuspension, 100 ml of 88% formic acid containing 2M CNBr was added and the mixture was incubated in the dark overnight at room temperature. One ml (2.0 mg) of purified UspA material was added directly to a vial containing 25 mg of either trypsin or chymotrypsin. The reaction mixtures were incubated for ~48 hours. at 37° C. One ml (2.0 mg) of purified UspA material was added directly to a vial containing 15 mg of endoproteinase Lys-C. The reaction mixtures were incubated for about 48 hours at 37° C.

The cleavage reaction mixtures were clarified by centrifugation in an Eppendorf™ centrifuge at 12,000 rpm for 5 minutes. The clarified supernatant was loaded directly onto a Vydac C4 HPLC column using a mobile phase of 0.1% (v/v) aqueous trifluoroacetic acid (Solvent A) and acetonitrile:H$_2$O:trifluoroacetic acid, 80:20:0.1 (v/v/v) (Solvent B) at a flow rate of 1.0 ml/min. The reaction mixtures were washed onto the column with 100% Solvent A followed by elution of cleavage fragments using a 30 minutes linear gradient (0-100%) of Solvent B. Fractions were collected manually, dried overnight in a Speed-Vac and resuspended in House Pure Water. The resuspended HPLC-separated fractions were subjected to SDS-PAGE analysis using 10-18% gradient gels in a Tris-Tricine buffer system. The fractions which exhibited a single peptide band were submitted for direct N-terminal sequence analysis. Fractions displaying multiple peptide bands were transferred from SDS-PAGE onto a PVDF membrane and individual bands excised and submitted for N-terminal sequence analysis.

The N-terminal amino acid sequences of these fragments then were determined using an Applied Biosystems Model 477A PTH Analyzer (Applied Biosystems, Foster City, Calif., U.S.A.). A summary of these sequences is given in Table VII. About half of the sequences were found to match the sequence deduced from the uspA1 gene, while the other half did not. Attempts at shifting the reading frame of the uspA1 gene sequence failed to account for the non-matching peptide sequences, indicating that the high molecular weight UspA protein may comprise either a multimer of more than one distinct protein or distinct multimers of two different proteins.

TABLE VII

Summary of the N-terminal Sequences of Internal Peptide Fragments

| Digest | Sequence[a] |
|---|---|
| CNBr | AAQAALSGLFVPYSVGKFNATAALGGYGSK SEQ ID NO:26 |
| | GKITKNAARQENG SEQ ID NO:27 |
| LysC Digest #1 | VIGDLGRKV SEQ ID NO:28 |
| | ALEXNVEEGL SEQ ID NO:29 |
| | ALESNVEEGLXXLS SEQ ID NO:30 |
| | ALEFNGE SEQ ID NO:31 |
| LysC Digest #2 | SITDLGXKV SEQ ID NO:32 |
| | SITDLGTIVDGFXXX SEQ ID NO:33 |
| | SITDLGTIVD SEQ ID NO:34 |
| Trypsin | VDALXTKVNALDXKVNSDXT SEQ ID NO:35 |
| | LLAEQQLNGKTLTPV SEQ ID NO:36 |
| | AKHDAASTEKGKMD SEQ ID NO:37 |
| | ALESNVEEGLLDLSG SEQ ID NO:38 |
| Trypsin Digest #1 | NQNTLIEKTANK SEQ ID NO:39 |
| | IDKNEYSIK SEQ ID NO:40 |
| | SITDLGTK SEQ ID NO:41 |
| Trypsin Digest #2 | NQNTLIEK SEQ ID NO:42 |
| | ALHEQQLETLTK SEQ ID NO:43 |
| | NSSD SEQ ID NO:44 |
| | NKADADASFETLTK SEQ ID NO:45 |
| | FAATAIAKDK SEQ ID NO:46 |
| | KASSENTQNIAK SEQ ID NO:47 |
| | RLLDQK SEQ ID NO:48 |
| Chymotrypsin | AATADAITKNGX SEQ ID NO:49 |
| | AKAXAANXDR SEQ ID NO:50 |
| Digest of research grade UspA with cys-C-endopeptidase | NQADIAQNQTDIQDLAAYNELQ SEQ ID NO:51 |
| | NQADIANNINNIYELAQQQDQ SEQ ID NO:52 |
| | YNERQTEAIDALN SEQ ID NO:53 |
| | ILGDTAIVSNSQD SEQ ID NO:54 |

[a]Certain residues of several peptides could not be verified and these ambiguities are shown by an "X" in SEQ ID NO:29, SEQ ID NO:30, SEQ ID NO:32, SEQ ID NO:33, SEQ ID NO:35, SEQ ID NO:49 and SEQ ID NO:50. In SEQ ID NO:29 the ambiguous residue is likely to be a serine; in SEQ ID NO:33, position 13 is likely to be aspartic acid, position 14 is likely to be glycine and position 15 is likely to be arginine; in SEQ ID NO:35 both positions 13 and 19 are likely to be serines; in SEQ ID NO:49 the ambiguous residue is likely to be an asparagine; and in SEQ ID NO:50 position 4 is likely to be serine and position 8 is likely to be threonine.

Additional attempts to resolve the very high molecular weight UspA protein band from *M. catarrhalis* strain O35E by SDS-PAGE, followed by electroelution and digestion with proteases or with cyanogen bromide, again yielded a number of peptides which were sequenced. Several peptides (peptides 1-6, Table VIII) were obtained. The amino acid sequence of which was identical or very similar to that deduced from the nucleotide sequence of the uspA1 gene. However, several additional peptides, peptides 7-10, Table VIII, were not present in the deduced amino acid sequence. This finding substantiated the suggestion that a second protein was present in the UspA antigen preparation.

TABLE VIII

| Peptide # | Amino acid sequence | |
|---|---|---|
| Matching or closely matching peptides: | | |
| Peptide 1 | KALESNVEEGLLDLSGR | (SEQ ID NO:55) |
| Peptide 2 | ALESNVEEGLLELSGRTIDQR | (SEQ ID NO:56) |
| Peptide 3 | NQAHIANNINXIYELAQQQDQK | (SEQ ID NO:57) |
| Peptide 4 | NQADIAQNQTDIQDLAAYNELQ | (SEQ ID NO:58) |
| Peptide 5 | ATHDYNERQTEA | (SEQ ID NO:59) |
| Peptide 6 | KASSENTQNIAK | (SEQ ID NO:60) |
| Nonmatching peptides: | | |
| Peptide 7 | MILGDTAIVSNSQDNKTQLKFYK | (SEQ ID NO:61) |
| Peptide 8 | AGDTIIPLDDDXXP | (SEQ ID NO:62) |
| Peptide 9 | LLHEQQLXGK | (SEQ ID NO:63) |
| Peptide 10 | IFFNXG | (SEQ ID NO:64) |

$^a$Certain residues of several peptides could not be verified and these ambiguities are shown by an "X" in SEQ ID NO:57, SEQ ID NO:62, SEQ ID NO:63 and SEQ ID NO:64.

Further evidence corroborating the assertion that the high molecular weight UspA proteinaceous material was either a multimer of more than one distinct protein or distinct multimers of two different proteins was derived from earlier electrospray mass spectroscopic analysis which predicted that a monomer of the UspA material had a molecular weight of 59,500. This approximately 60 kDa protein reacted immunogenically with the MAbs 17C7, 45-2, 13-1, and 29-31, in contrast to the UspA1 protein which only cross-reacted with MAb 17C7. The fact that MAb 17C7 reacted with both isolated proteins suggested that this Mab recognized an epitope common to both proteins.

Preparation of mutant uspA1 construct. The nucleotide sequence of the cloned uspA1 gene was used to construct an isogenic uspA1 mutant. Oligonucleotide primers (BamHI-ended P1 and P16 in Table IX) were used to amplify a truncated version of the uspA1 ORF from M. catarrhalis strain O35E chromosomal DNA; this PCR™ product was cloned into the BamHI site of the plasmid vector pBluescript II SK+. A 0.6 kb BglII fragment from the middle of this cloned fragment was excised and was replaced by a BamHI-ended cassette encoding kanamycin resistance. This new plasmid was grown in E. coli DH5α, purified by column chromatography, linearized by digestion with EcoRI, precipitated, and then dissolved in water. This linear DNA molecule was used to electroporate the wild-type M. catarrhalis strain O35E, using a technique described previously (Helminen et al., 1993b). Approximately 5,000 kanamycin-resistant transformants were obtained; several picked at random were found to be still reactive with MAb 17C7. One of these kanamycin-resistant clones was randomly chosen for further examination and Southern blot analysis confirmed that this mutant was isogenic.

Figure 2A:
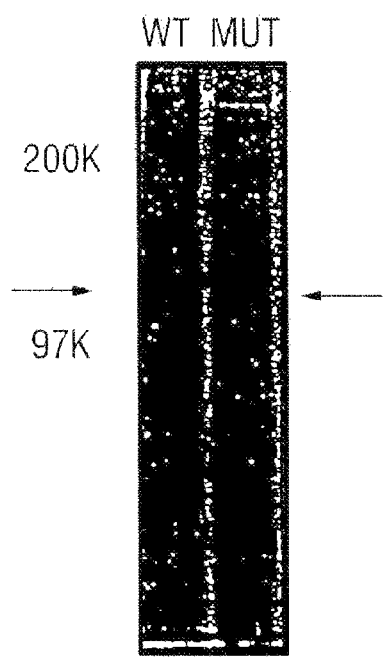
FIG. 2A. Proteins present in whole cell lysates of the wild-type strain O35E and the isogenic uspA1 mutant strain. These proteins were resolved by SDS-PAGE and stained with Coomassie blue. The left lane (WT) contains the wild-type strain and right lane (MUT) contains the mutant. The arrows indicate the protein, approximately 120 kDa in size, that is present in the wild-type and missing in the mutant. Kilodalton position markers are on the left.
Figure 2B:
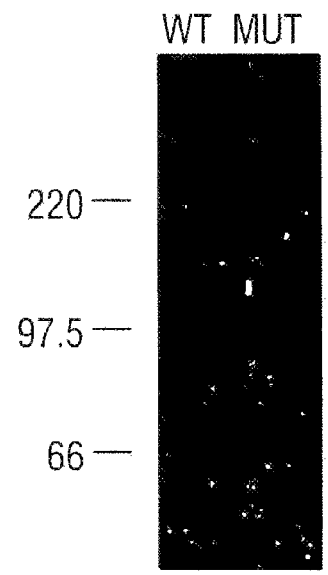
FIG. 2B. Western blot analysis of whole cell lysates of the wild-type strain O35E and the isogenic uspA1 mutant strain. These proteins were resolved by SDS-PAGE and probed with MAb 17C7 in western blot analysis. The left lane (WT) contains the wild-type strain and the right lane (MUT) contains the mutant. Kilodalton position markers are on the left. It can been seen that both strains possess the very high molecular weight band reactive with MAb 17C7 whereas only the wild-type strain also has a band of approximately 120 kDa that binds this MAb.

Analysis of products expressed by the UspA mutant. When whole cell lysates of both the wild-type M. catarrhalis strain and this mutant were subjected to SDS-PAGE, both the wild-type strain and the mutant strain still expressed the very high-molecular-weight band originally designated as UspA. However, a protein of approximately 120 kDa was found to be missing in the mutant strain (FIG. 2A). The fact that both this mutant and the wild-type parent strain still expressed a very high molecular weight antigen reactive with MAb 17C7 (FIG. 2B) indicated that there had to be a second gene in M. catarrhalis strain O35E that encoded a MAb 17C7-reactive antigen. Furthermore, it should be noted that EDTA-extracted outer membrane vesicles of both the wild-type strain (FIG. 2C, lanes 5 and 7) and mutant strain (FIG. 2C, lanes 6 and 8) possessed a protein of approximately 70-80 kDa that was reactive with MAb 17C7. This approximately 70-80 kDa band likely represents one form, perhaps the monomeric form, of the product of a second gene encoding the MAb 17C7-reactive epitope.

It is important to note that, when chromosomal DNA from both the wild-type parent strain and the mutant were digested with PvuII and probed in Southern blot analysis with a 0.6 kb BglII-PvuII fragment derived from the uspA1 gene, the wild-type strain exhibited a 2.6 kb band and a 2.8 kb band which bound this probe (FIG. 3). In contrast, the mutant strain had a 2.6 kb band and a 3.4 kb band that bound this probe. The presence of the 3.4 kb band was the result of the insertion of the kan cartridge into the deletion site in the uspA1 gene.

Example III

Characterization of UspA2 and uspA2

Construction of fusion proteins. The epitope which binds MAb 17C7 was localized by using the nucleotide sequence of the uspA1 gene described above to construct fusion proteins. First, fusion proteins containing five peptides spanning the UspA1 protein were constructed by using the pGEX4T-2 protein fusion system (Pharmacia LKB). The oligonucleotide primers used in PCR™ to amplify the desired nucleotide sequences from M. catarrhalis strain O35E chromosomal DNA are listed in Table IX. Each of these had either a BamHI site or a XhoI site at the 5' end, thereby allowing directional in-frame cloning of the amplified product into the BamHI- and XhoI-digested vector. When recombinant E. coli strains expressing each of these five fusion proteins were used in a colony blot radioimmunoassay, only fusion protein MF-4 readily bound MAb 17C7. Further analysis of the uspA1-derived nucleotide sequence in the MF-4 fusion construct involved the production of fusion proteins containing 79 amino acid residues (MF-4-1) and 123 amino acid residues (MF-4-2) derived from the MF-4 fusion protein (Table IX). These two fusion proteins both bound MAb 17C7 (Table IX). FIG. 4 depicts the western blot reactivity of MAb 17C7 with the MF-4-1 fusion protein. These two fusion proteins had in common only a 23-residue region NNINNIYE-LAQQQDQHSSDIKTL (SEQ ID NO:65), suggesting that this 23-residue region, designated as the "3Q" peptide, contains the epitope that binds MAb 17C7.

TABLE IX

PCR™ primers used for the production of usp Al gene fragments for use in the construction of fusion proteins and mutagenesis and the reactivity of the resulting fusion protein with MAb 17C7.

| Fragment Generated: | Primer Pair$^a$ | Reactivity with MAb 17C7 |
|---|---|---|
| MF-3 | P5-P8 | – |
| MF-4 | P6-P13 | + |
| MF-4.1 | P7-P12 | + |
| MF-4.2 | P11-P13 | + |

$^a$primer sequences are as follows:
| | | |
|---|---|---|
| P5 | GGTGCAGGTCAGATCAGTGAC | SEQ ID NO:66 |
| P6 | GCCACCAACCAAGCTGAC | SEQ ID NO:67 |
| P7 | AGCGGTCGCCTGCTTGATCAG | SEQ ID NO:68 |
| P8 | CTGATCAAGCAGGCGACCGCT | SEQ ID NO:69 |

TABLE IX-continued

PCR ™ primers used for the production of uspAl gene fragments for use in the construction of fusion proteins and mutagenesis and the reactivity of the resulting fusion protein with MAb 17C7.

| Fragment Generated: | Primer Pair[a] | Reactivity with MAb 17C7 |
|---|---|---|
| P11 | CAAGATCTGGCCGCTTACAA | SEQ ID NO:70 |
| P12 | TTGTAAGCGGCCAGATCTTG | SEQ ID NO:71 |
| P13 | TGCATGAGCCGCAAACCC | SEQ ID NO:72 |

Elucidation of the MAb 17C7 Epitope. It is important to note that the nucleotide sequence encoding this 23-residue polypeptide (i.e., the 3Q peptide) was present in the 0.6 kb BglII-PvuII fragment used in the Southern blot analysis described in Example II. This finding suggested that the epitope that bound MAb 17C7 might be encoded by DNA present in both the 2.6 and 2.8 kb PvuII fragments, with the 2.8 kb PvuII fragment being derived from the cloned uspA1 gene and the 2.6 kb PvuII fragment representing all or part of another gene encoding this same epitope.

Figure 5:
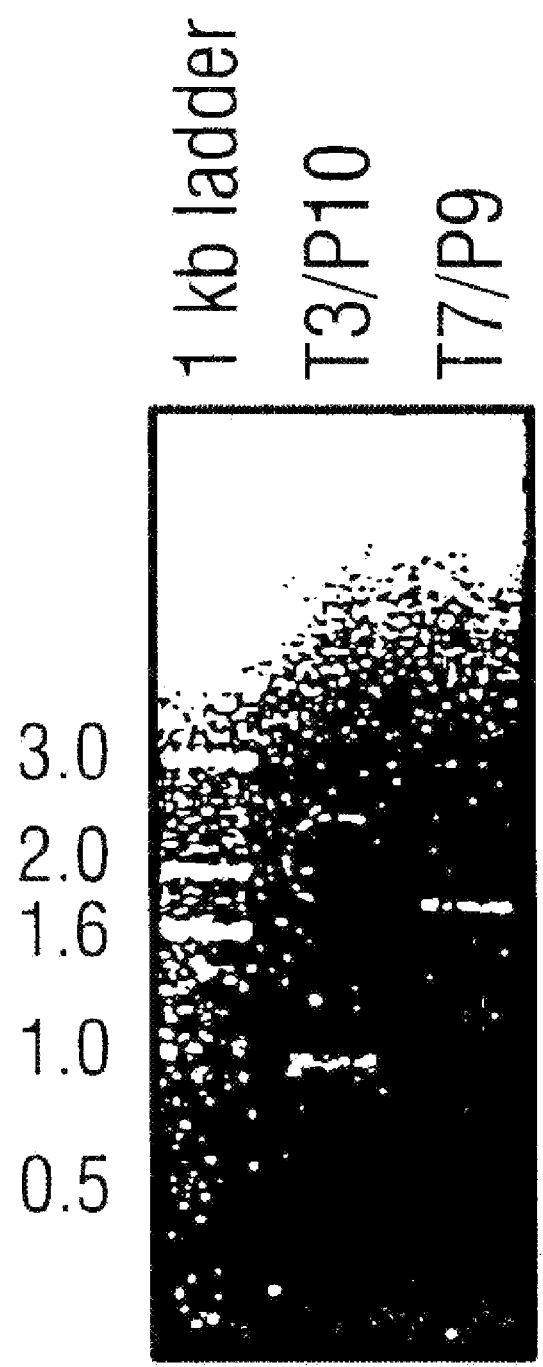
FIG. 5. PCR™ products obtained by the use of the T3 and P10 primers (middle lane—0.9 kb product) and the T7 and P9 primers (right lane—1.7 kb product) when used in a PCR™ amplification with chromosomal DNA from the uspA1 mutant. A kb ladder is present in the first lane; several kb position markers are listed on the left side of this figure.

A ligation-based PCR™ system was used to verify this finding. Chromosomal DNA from the mutant strain was digested to completion with PvuII and was resolved by agarose gel electrophoresis. Fragments ranging in size from 2-3 kb were excised from the agarose, blunt-ended, and ligated into the EcoRV site in pBluescript II SK+ This ligation reaction mixture was precipitated and used in a PCR™ amplification reaction. Each PCR™ reaction contained either the T3 or T7 primer derived from the DNA encoding the 3Q peptide. This approach yielded a 1.7 kb product with the T3 and P10 primers and a 0.9 kb product from the T7 and P9 primers (FIG. 5). The sum of these two bands is the same as the 2.6 kb size of the desired DNA fragment.

Nucleotide sequence analysis of these two PCR™ products revealed two incomplete ORFs which, when joined at the region encoding the 3Q peptide, formed a 1,728-bp ORF encoding a protein with a calculated molecular weight of 62,483 daltons (SEQ ID NO:3). The amino acid sequence of this protein had 43% identity with that of UspA1. Closer examination revealed that a region extending from amino acids 278-411 in this second protein, designated UspA2, was nearly identical to the region in UspA1 between amino acids 505-638 (SEQ ID NO:1). Furthermore, these two regions both contain the 23-mer (the 3Q peptide) that likely contains the epitope that binds MAb 17C7. It should also be noted that the four peptides from Table IX (Peptides 7-10) that were not found in UspA1 were found to be identical or very similar to peptides in the deduced amino acid sequence of UspA2. In addition, the first six peptides listed in Table IX, which matched or were very similar to peptides in the deduced amino acid sequence of UspA1, also matched peptides found in the deduced amino acid sequence of UspA2.

Oligonucleotide primers P1 and P2 (Table IX) were used to amplify a 2.5-2.6 kb fragment from M. catarrhalis strain O35E chromosomal DNA. Nucleotide sequence analysis of this PCR™ product was used to confirm the nucleotide sequence of the uspA2 ORF determined from the ligation-based PCR™ study. These results proved that M. catarrhalis strain O35E contains two different ORFs (i.e., uspA1 and uspA2) which encode the same peptide (i.e., the 3Q peptide) which likely binds MAb 17C7. This 3Q peptide appears twice in UspA1 and once in UspA2 (SEQ ID NO:1 and SEQ ID NO:3).

The nucleotide sequences of the two DNA segments encoding these 3Q peptides in uspA1 are nearly identical, with three nucleotides being different. These nucleotide differences did not cause a change in the amino acid sequence. The nucleotide sequence of the DNA segment encoding the 3Q peptide in uspA2 is identical to the DNA encoding the first 3Q peptide in UspA1.

Figure 1:
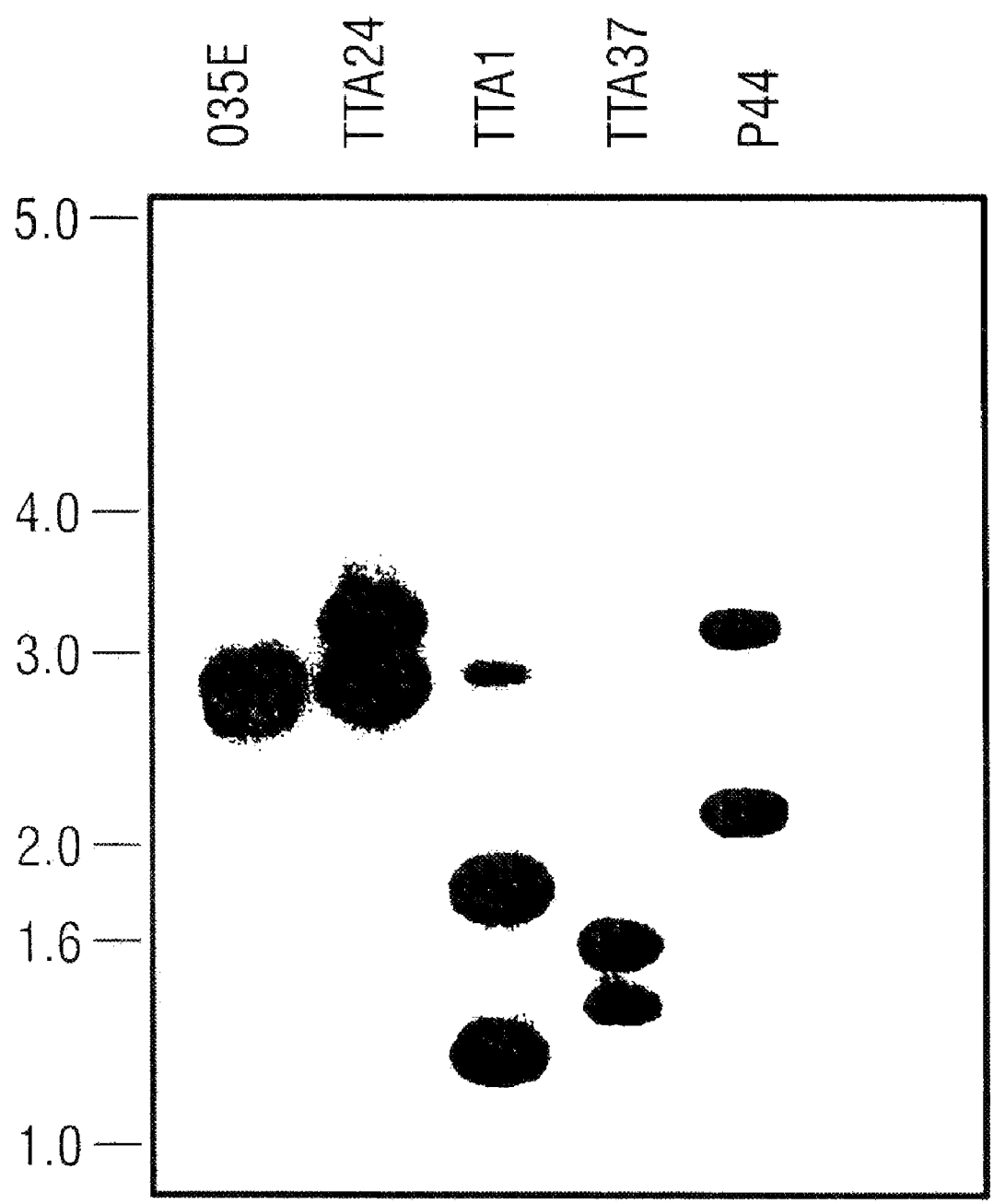
FIG. 1. Southern blot analysis of PvuII-digested chromosomal DNA from strains of *M. catarrhalis* using a probe from the uspA1 gene. Bacterial strain designations are at the top; kilobase (kb) position markers are on the left.
Figure 2C:
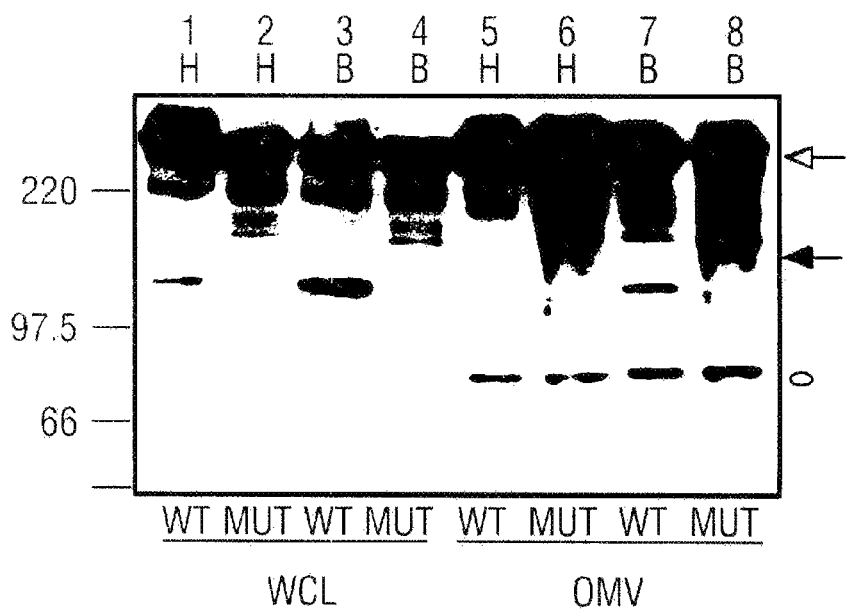
FIG. 2C. Western blot analysis of whole cell lysate (WCL) and EDTA-extracted outer membrane vesicles (OMV) from the wild-type strain O35E (WT) and the isogenic uspA1 mutant (MUT) using MAb 17C7. Samples were either heated at 37° C. for 15 minutes (H) or at 100° C. for 5 minutes (B) prior to SDS-PAGE. Molecular weight position markers (in kilodaltons) are indicated on the left. The open arrow indicates the position of the very high molecular weight form of the MAb 17C7-reactive antigen; the closed arrow indicates the position of the approximately 120 kDa protein; the open circle indicates the position of the approximately 70-80 kDa protein.

As seen in FIG. 2C, lane 7, the three dominant MAb 17C7-reactive bands present in M. catarrhalis strain O35E outer membrane vesicles have apparent molecular weights of greater than 200 kDa, approximately 120 kDa, and approximately 70-80 kDa. It should be noted that the existence of several MAb 17C7-reactive bands, with apparent molecular weights of greater than 200 kDa, approximately 120 kDa, and approximately 70-80 kDa was also apparent in U.S. Pat. No. 5,552,146 (FIG. 1, lane H). Therefore, the existence of at least more than one M. catarrhalis antigens reactive with MAb 17C7 was apparent as early as 1991. It is now apparent that the approximately 120 kDa band likely represents the monomeric form of the UspA1 antigen and the approximately 70-80 kDa band likely represents the monomeric form of the UspA2 antigen from M. catarrhalis strain O35E. One or more than one of these species may aggregate to form the very high molecular weight proteinaceous material (i.e. greater than 200 kDa) of the UspA antigen.

A new M. catarrhalis strain O35E genomic library was constructed in the bacteriophage vector ZAP Express (Stratagene, La Jolla, Calif.). Chromosomal DNA from this strain was partially digested with Sau3A1 and 4-9 kb DNA fragments were ligated into the vector arms according to the instructions obtained from the manufacturer. This library was amplified in E. coli MRF'. An aliquot of this library was diluted and plated and the resultant plaques were screened for reactivity with MAb 17C7. Approximately 24 plaques which bound this MAb were detected; the responsible recombinant bacteriophage were purified by the single plaque isolation method, and the DNA insert from one of these bacteriophage was subjected to nucleotide sequence analysis. Nucleotide sequence of the 2.6 kb DNA fragment present in this recombinant bacteriophage revealed that, on one end, it contained an incomplete ORF that encoded the 3Q peptide. Until its truncation by the vector cloning site, the sequence of this incomplete ORF was identical or nearly identical to that of the uspA2 ORF derived from the ligation-based PCR™ study described immediately above, providing further evidence that two genes which share a common epitope encode the UspA antigen.

Example IV

Purification of and Immunological Properties of the Proteins UspA1 and UspA2

Materials and Methods

Bacteria. TTA24 and O35E isolates were as previously described in Example I. Additional isolates were obtained from the University of Rochester and the American Type Culture Collection (ATCC). The bacteria were routinely passaged on Mueller-Hinton agar (Difco, Detroit, Mich.) incubated at 35° C. with 5% carbon dioxide. The bacteria used for the purification of the protein were grown in sterile broth containing 10 g casamino acids (Difco, Detroit, Mich.) and 15 g yeast extract (BBL, Cockeysville, Md.) per liter. The isolates were stored at −70° C. in Mueller-Hinton broth containing 40% glycerol.

Purification of UspA2. Bacterial cells (~400 g wet wt. of M. catarrhalis O35E) were washed twice with 2 liters of pH 6.0, 0.03 M sodium phosphate ($NaPO_4$) containing 1.0%

Triton® X-100 (TX-100) (J. T. Baker Inc., Philipsburg, N.J.) (pH 6.0) by stirring at room temperature for 60 min. Cells containing the UspA2 protein were pelleted by centrifugation at 13,700×g for 30 min at 4° C. Following centrifugation, the pellet was resuspended in 2 liters of pH 8.0, 0.03 M Tris (hydroxymethyl)aminomethane-HCl (Tris-HCl) containing 1.0% TX-100 and stirred overnight at 4° C. to extract the UspA2 protein. Cells were pelleted by centrifugation at 13,700×g for 30 min at 4° C. The supernatant, containing the UspA2 protein, was collected and further clarified by sequential microfiltration through a 0.8 µm membrane (CN.8, Nalge, Rochester, N.Y.) then a 0.45 µm membrane (cellulose acetate, low protein binding, Corning, Corning, N.Y.).

The entire filtered crude extract preparation was loaded onto a 50×217 mm (~200 ml) TMAE column [650(S), 0.025-0.4 mm, EM Separations, Gibbstown, N.J.] equilibrated with pH 8.0, 0.03 M Tris-HCl buffer containing 0.1% TX-100 (THT). The column was washed with 400 ml of equilibration buffer followed by 600 ml of 0.25 M NaCl in 0.03 M THT. UspA2 was subsequently eluted with 800 ml of 1.0 M NaCl in 0.03 M THT. Fractions were screened for UspA2 by SDS-PAGE and pooled. Pooled fractions (~750 ml), containing UspA2, were concentrated approximately two-fold by ultrafiltration using an Amicon stirred cell (Amicon Corp., Beverly, Mass.) with a YM-100 membrane under nitrogen pressure. The TMAE concentrate was split into two 175 ml aliquots and each aliquot buffer exchanged by passage over a 50×280 mm (~550 ml) Sephadex G-25 (Coarse) column (Pharmacia Biotech, Piscataway, N.J.) equilibrated with pH 7.0, 10 mM $NaPO_4$ containing 0.1% TX-100 (10 mM PT). The buffer exchanged material was subsequently loaded onto a 50×217 mm (~425 ml) ceramic hydroxyapatite column (Type I, 40 µm, Bio-Rad) equilibrated with 10 mM PT. The column was washed with 450 ml of the equilibration buffer followed by 900 ml of pH 7.0, 0.1M $NaPO_4$ containing 0.1% TX-100. UspA2 was then eluted with a linear pH 7.0 $NaPO_4$ concentration gradient between 0.1 and 0.2 M $NaPO_4$ containing 0.1% TX-100. An additional volume of pH 7.0, 0.2 M $NaPO_4$ containing 0.1% TX-100 was applied to the column and collected to maximize the recovery of UspA2. Fractions were screened for UspA2 by SDS-PAGE and pooled. The column was then washed with 900 ml of pH 7.0, 0.5 M $NaPO_4$ containing 0.1% TX-100. The fractions from this wash were screened for UspA1 by SDS-PAGE, pooled, and stored at 4° C. This pool was used for the purification of UspA1.

Purification of UspA1. The UspA1 enriched fractions collected during four separate purifications of UspA2 were pooled. The combined UspA1 pools were concentrated approximately threefold by ultrafiltration using an Amicon stirred cell with a YM-100 membrane under nitrogen pressure. The UspA1 concentrate was split into two 175 ml aliquots and the buffer exchanged by passage over a 50×280 mm (~550 ml) Sephadex G-25 column equilibrated with 10 mM PT. The buffer exchanged material was subsequently loaded onto a 50×217 mm (~425 ml) ceramic hydroxyapatite column (Bio-Rad) equilibrated with 10 mM PT. The column was washed with 450 ml of the equilibration buffer followed by 900 ml of pH 7.0, 0.25 M $NaPO_4$ containing 0.1% TX-100. UspA1 was subsequently eluted with a linear $NaPO_4$ gradient of pH 7.0, 0.25-0.5 M $NaPO_4$ containing 0.1% TX-100. The fractions containing UspA1 were identified by SDS-PAGE and pooled.

SDS-PAGE and Western blot Analysis. SDS-PAGE was carried out as described by Laemmli (1970) using 4 to 20% (w/v) gradient acrylamide gels (Integrated Separation Systems (ISS), Natick, Mass.). Proteins were visualized by staining the gels with Coomassie Brilliant Blue R250. Gels were scanned using a Personal Densitometer SI (Molecular Dynamics Inc., Sunnyvale, Calif.) and molecular weights were estimated with the Fragment Analysis software (version 1.1) using the prestained molecular weight markers from ISS as standards. Transfer of proteins to polyvinylidene difluoride (PVDF) membranes was accomplished with a semi-dry electroblotter and electroblot buffers (ISS). The membranes were probed with protein specific antisera or MAb's followed by goat anti-mouse alkaline phosphatase conjugate as the secondary antibody (BioSource International, Camarillo, Calif.). Western blots were developed with the BCIP/NBT Phosphatase Substrate System (Kirkegaard and Perry Laboratories, Gaithersburg, Md.).

Protein Estimation. Protein concentrations were estimated by the BCA assay (Pierce, Rockford, Ill.), using bovine serum albumin as the standard.

Enzymatic and Chemical Cleavages of UspA2 and UspA1.

(i) CNBr Cleavage. Approximately 0.3 mg of the purified protein was precipitated with 90% (v/v) ethanol and the pellet resuspended in 100 µl of 88% (v/v) formic acid containing 12 M urea. Following resuspension, 100 µl of 88% (v/v) formic acid containing 2 M CNBr (Sigma, St. Louis, Mo.) was added and the mixture incubated overnight at room temperature in the dark.

(ii) Trypsin and Chymotrypsin Cleavage. Approximately 2 mg of the purified protein was precipitated with 90% (v/v) ethanol and the pellet resuspended in a total volume of 1 ml of phosphate-buffered saline (PBS) containing 0.1% TX-100. This preparation was added directly to a vial containing 25 µg of either trypsin or chymotrypsin (Boehringer Mannheim, Indianapolis, Ind.). The reaction mixture was incubated for 48 h at 37° C.

(iii) Endoproteinase Lys-C Cleavage. Approximately 2 mg of the purified protein was precipitated with 90% (v/v) ethanol and the pellet resuspended in a total volume of 1.0 ml of PBS containing 0.1% TX-100. This preparation was added directly to a vial containing 15 µg of endoproteinase Lys-C (Boehringer Mannheim). The reaction mixture was incubated for 48 h at 37° C.

(iv) Separation of Peptides. The above cleavage reaction mixtures were centrifuged in an Eppendorf centrifuge at 12,000 rpm for 5 min and the supernatant loaded directly onto a Vydac Protein C4 HPLC column (The Separations Group, Hesperia, Calif.). The solvents used were 0.1% (v/v) aqueous trifluoroacetic acid (TFA) [Solvent A] and acetonitrile:$H_2O$:TFA, 80:20:0.1 (v/v/v) [Solvent B] at a flow rate of 1.0 ml/min. Following the initial wash with Solvent A, the peptides were eluted with a linear gradient between 0 and 100% of Solvent B and detected by absorbance at 220 nm. Suitable fractions were collected, dried in a Speed-Vac concentrator (Jouan Inc., Winchester, Va.) and resuspended in distilled water. The fractions were separated by SDS-PAGE in 10 to 18% (w/v, acrylamide) gradient gels (ISS) in a Tris-Tricine buffer system (Schägger and von Jagow, 1987). The fractions containing a single peptide band were submitted directly for N-terminal sequence analysis. Fractions displaying multiple peptide bands in SDS-PAGE were electrophoretically transferred onto a PVDF membrane as described above. The membrane was stained with Coomassie Brilliant Blue R-250 and the individual bands excised before submitting them for N-terminal sequence analysis (Matsudaira, 1987).

Determination of subunit size. Determination of molecular weight by Matrix Assisted Laser Desorption/Ionization-Time of Flight (MALDI-TOF) mass spectrometry (Hillenkamp and Karas, 1990) was done on a Lasermat 2000 Mass Analyzer (Finnigan Mat, Hemel Hempstead, UK) with 3,5-dimethoxy- 4-hydroxy-cinnamic acid as the matrix. Cold ethanol precipitation was done on samples containing ≧0.1% (v/v) TX-100 to remove the detergent. The final ethanol concentration was 90% (v/v). The precipitated protein was resuspended in water.

Determination of aggregate sizes by gel filtration chromatography. Approximately 1 mg of the purified protein was precipitated with 90% (v/v) ethanol and the pellet resuspended in a total volume of 1.0 ml of PBS containing 0.1% TX-100. Two hundred microliters of the preparation were applied to a Superose-6 HR 10/30 gel filtration column (10× 30 mm, Pharmacia) equilibrated in PBS/0.1% TX-100 at a flow rate of 0.5 ml/min. The column was calibrated using the HMW Calibration Kit (Pharmacia) which contains aldolase with a size of 158,000, catalase with a size of 232,000; ferritin with a size of 440,000; thyroglobulin with a size of 669,000; and blue dextran with sizes between 2000 and 2,000,000.

Amino Acid Sequence Analysis. N-terminal sequence analysis was carried out using an Applied Biosystems Model 477A Protein/Peptide Sequencer equipped with an on-line Model 120A PTH Analyzer (Applied Biosystems, Foster City, Calif.). The phenylthiohydantoin (PTH) derivatives were identified by reversed-phase HPLC using a Brownlee PTH C-18 column (particle size 5 μm, 2.1 mm i.d.×22 cm 1; Applied Biosystems).

Immunizations. Female BALB/c mice (Taconic Farms, Germantown, N.Y.), age 6-8 weeks, were immunized subcutaneously with two doses of UspA1 or UspA2 four weeks apart. To prepare the vaccine, purified UspA1 or UspA2 was added to aluminum phosphate, and the mixture rotated overnight at 4° C. 3-O-deacylated monophosphoryl lipid A (MPL) (Ribi ImmunoChem Research, Inc.) was added just prior to administration. Each dose of vaccine contained 5 μg of purified protein, 100 μg of aluminum phosphate and 50 μg of MPL resuspended in a 200 μl volume. Control mice were injected with 5 μg of $CRM_{197}$ with the same adjuvants. Serum samples were collected before the first vaccination and two weeks after the second immunization. Mice were housed in a specific-pathogen free facility and provided water and food ad libitum.

Monoclonal antibodies. The 17C7 MAb was secreted by a hybridoma (ATCC HB11093). MAbs 13-1, 29-31, 45-2, and 6-3 were prepared as previously described (Chen et al., 1995).

Murine model of *M. catarrhalis* pulmonary clearance. This model was performed as described previously (Chen et al., 1995).

Enzyme linked immunosorbent assay (ELISA) procedures. Two different ELISA procedures were used. One was used to examine the reactivity of sera to whole bacterial cells and the other the reactivity to the purified proteins.

For the whole cell ELISA, the bacteria were grown overnight on Mueller-Hinton agar and swabbed off the plate into PBS. The turbidity of the cells was adjusted to 0.10 at 600 nm and 100 μl added to the wells of a 96 well Nunc F Immunoplate (Nunc, Roskilde, Denmark). The cells were dried overnight at 37° C., sealed with a mylar plate sealer and stored at 4° C. until needed. On the day of the assay, the residual protein binding sites were blocked by adding 5% non-fat dry milk in PBS with 0.1% Tween 20 (Bovine Lacto Transfer Technique Optimizer [BLOTTO]) and incubating 37° C. for one hour. The blocking solution was then removed and 100 μl of sera serially diluted in the wells with blotto. The sera were allowed to incubate for 1 h at 37° C. The plate wells were soaked with 300 ml PBS containing 0.1% Tween 20 for 30 seconds and washed 3 times for 5 seconds with a Skatron plate washer and then incubated 1 hr at 37° C. with goat anti-mouse IgG conjugated to alkaline phosphatase (Bio-Source) diluted 1:1000 in blotto. After washing, the plates were developed at room temperature with 100 μl per well of 1 mg/ml p-nitrophenyl phosphate dissolved in diethanolamine buffer. Development was stopped by adding 50 μl of 3N NaOH to each well. The absorbance of each well was read at 405 nm and titers calculated by linear regression. The titer was reported as the inverse of the dilution extrapolated to an absorption value of 0.10 units.

For the ELISA against the purified proteins, the proteins were diluted to a concentration of 5 μg/ml in a 50 mM sodium carbonate buffer (pH 9.8) containing 0.02% sodium azide (Sigma Chemical Co.). One hundred microliters were added to each well of a 96 well E.I.A./R.I.A medium binding ELISA plate (Costar Corp., Cambridge, Mass.) and incubated for 16 hours at 4° C. The plates were washed and subsequently treated the same as described for whole cell ELISA procedure.

Complement-dependent bactericidal assay. For this assay, 20 μl of the bacterial suspension containing approximately 1200 cfu bacteria in PBS supplemented with 0.1 mM $CaCl_2$: $MgCl_2$ and 0.1% gelatin (PCMG) were mixed with 20 μl of serum diluted in PCMG and incubated for 30 min at 4° C. Complement, prepared as previously described (Chen et al., 1996), was added to a concentration of 20%, mixed, and incubated 30 min at 35° C. The assay was stopped by diluting with 200 μl of cold, 4° C., PCMG. 50 μl of this suspension was spread onto Mueller-Hinton plates. Relative killing was calculated as the percent reduction in cfu in the sample relative to that in a sample in which heat inactivated complement replaced active complement.

Inhibition of bacterial adherence to HEp-2 cells. The effect of specific antibodies on bacterial adherence to HEp-2 cells was examined. A total of $5 \times 10^4$ HEp-2 cells in 300 μl of RPMI-10 were added to a sterile 8-well Lab-Tek chamber slide (Nunc, Inc., Naperville, Ill.) and incubated overnight in a 5% $CO_2$ incubator to obtain a monolayer of cells on the slide. The slide was washed with PBS and incubated with 300 μl of bacterial suspension ($A_{550}$=0.5) or with a bacterial suspension that had been incubated with antisera (1:100) at 37° C. for 1 h. The slides were then washed with PBS and stained with the Difco quick stain following the manufacturer's instructions. The slide was viewed and photographed using a light microscope equipped with a camera (Nikon Microphot-SA, Nikon, Tokyo, Japan).

Protein interaction with fibronectin and vitronectin. The interactions of purified UspA1 and UspA2 with fibronectin were examined by dot blot. Human plasma fibronectin (Sigma Chemical Co., St. Louis, Mo.) was applied to a nitrocellulose membrane, and the membrane blocked with blotto for 1 h at room temperature. The blot was then washed with PBS and incubated with purified UspA1 or UspA2 (2 μg/ml in blotto) overnight at 4° C. After three washes with PBS, the membrane was incubated with the MAb 17C7 diluted in blotto for 2 h at room temperature and then with goat anti-mouse immunoglobulin conjugated to alkaline phosphatase (BIO-RAD Lab. Hercules, Calif.) (1:2,000 in PBS with 5% dry milk, 2 h, room temperature). The membrane was finally developed with a substrate solution containing nitroblue tetrazolium and 5-bromo-chloro-3-indolyl phosphate in 0.1 M tris-HCl buffer (pH 9.8).

Interaction with vitronectin was examined by a similar procedure. The purified UspA1 and UspA2 were spotted onto the nitrocellulose membrane and the membrane blocked with blotto. The membrane was then incubated sequentially with human plasma vitronectin (GIBCO BRL, Grand Island, N.Y., 1 μg/ml in blotto), rabbit anti-human vitronectin serum (GIBCO BRL), goat anti-rabbit IgG-alkaline phosphatase conjugate and substrate.

Figure 7:
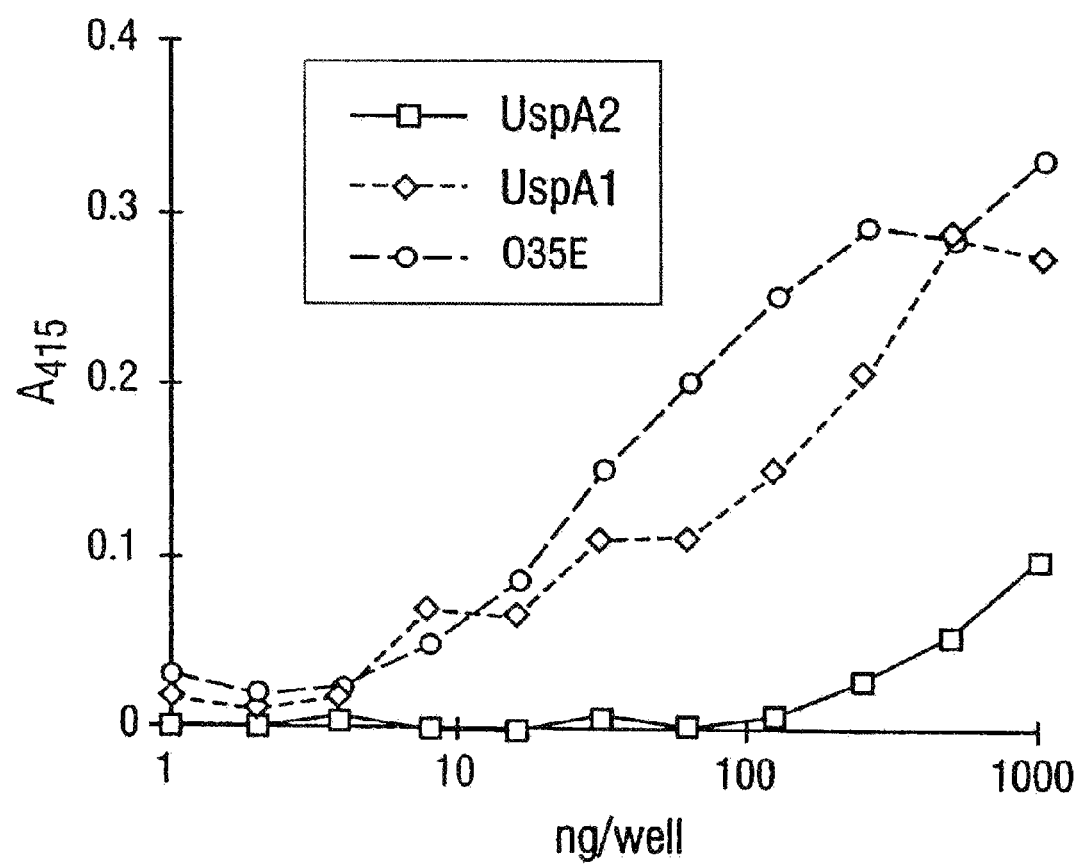
FIG. 7. Interaction of purified UspA1 and UspA2 with HEp-2 cells as determined by ELISA. HEp-2 cell monolayers cultured in 96-well plate were incubated with serially diluted UspA1 or UspA2. O35E bacterial strain was used as the positive control. The bacteria were diluted analogous to the proteins beginning with a suspension with an $A_{550}$ of 1.0. The bound proteins or attached bacteria were detected with a 1:1 mixed antisera to UspA1 and UspA2 as described in the methods.

Interaction with HEp-2 cells by the purified protein. Each well of a 96 well cell culture plate (Costar Corp., Cambridge, Mass.) was seeded with $5\times10^4$ HEp-2 cells in 0.2 ml RPMI containing 10% fetal calf serum and the plate incubated overnight in a 37° C. incubator containing 5% $CO_2$. Purified UspA1 or UspA2 (1 to 1,000 ng) in blotto was added and incubated at 37° C. for 2 h. The plate was washed with PBS, and incubated with the 1:1 mixed mouse antisera to either UspA1 or UspA2 (1:1000 dilution in PBS containing 5% dry milk), the plate was washed and incubated with rabbit anti-mouse IgG conjugated to horseradish peroxidase (1:5,000 in PBS containing 5% dry milk) (Brookwood Biomedical, Birmingham, Ala.) at room temperature for 1 h. Finally, the plate was washed and developed with a substrate solution containing 2,2'-azino-bis-(3-ethyl-benzthiazoline-6-sulfonic acid) at 0.3 mg/ml in pH 4.0 citrate buffer containing 0.03% hydrogen peroxide (KPL, Gaithersburg, Md.). Whole bacteria of strain O35E were included as a positive control. The highest concentration of the bacteria tested had an optical density of $A_{550}=1.0$. The abscissa for the bacterial data shown in FIG. 7 plots the values for three fold dilutions of the bacterial suspension.

Results

Figure 6:
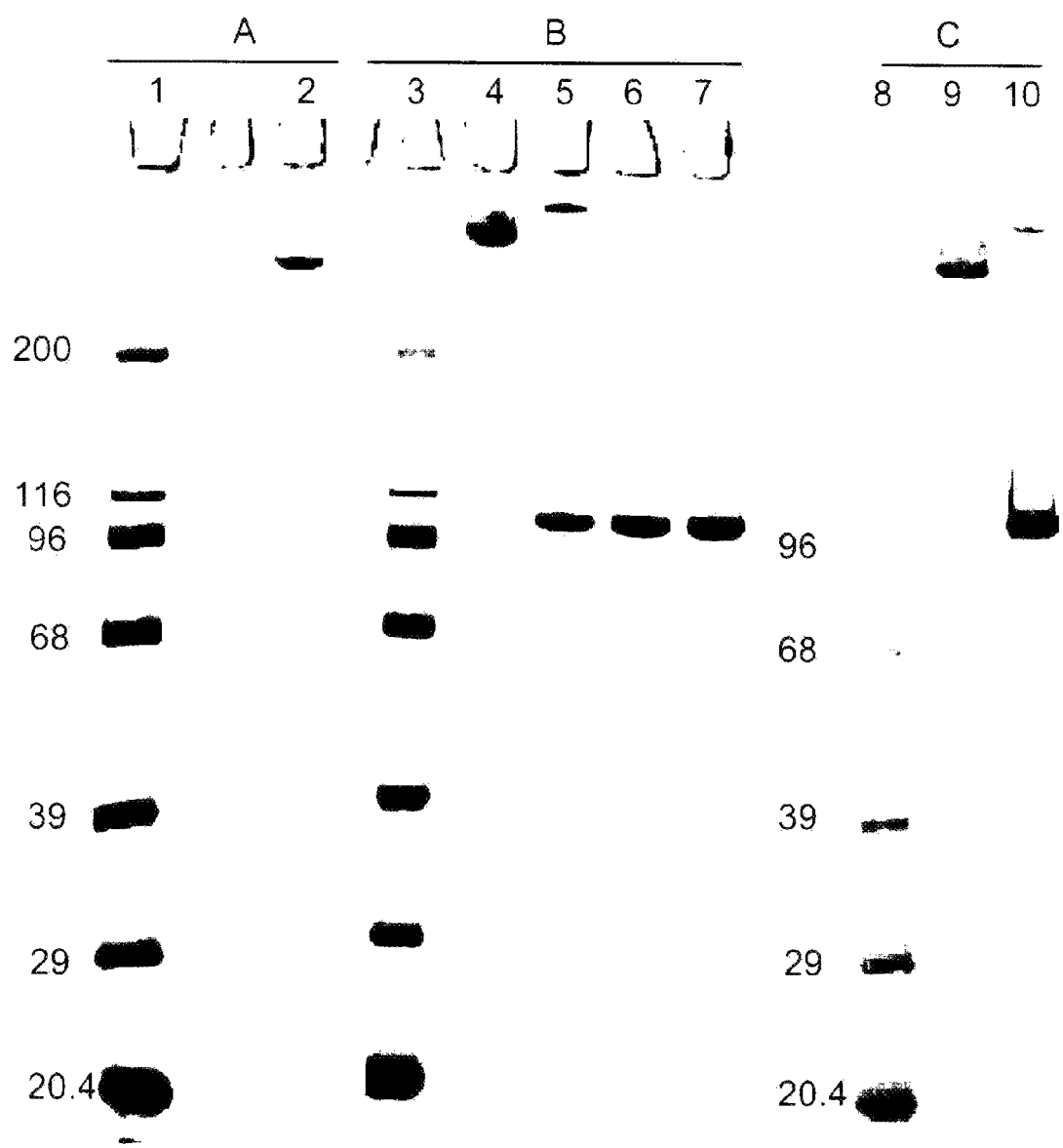
FIGS. 6A-6C. SDS-PAGE and westerns of purified proteins.

Purification of UspA1 and UspA2. The inventors developed a large-scale, high yield process for extracting and purifying UspA2 from a pellet of *M. catarrhalis* cells. The method consisted of three critical steps. First the UspA2 protein was extracted from the bacteria with pH 8.0, 0.03 M THT. Second, the cell extract was applied to a TMAE column and the UspA2 protein eluted with NaCl. Finally, the enriched fractions from the TMAE chromatography were applied to a ceramic hydroxyapatite column and the UspA2 eluted with a linear $NaPO_4$ gradient. A yield of 250 mg of purified UspA2 was typically obtained from ~400 g wet weight of *M. catarrhalis* O35E strain cells. A single band was seen for the UspA2 in SDS-PAGE gels by Coomassie blue staining. It corresponded to a molecular size of 240,000 and contained greater than 95% of the protein based on scanning densitometry (FIG. 6A). A second band reacting with the 17C7 MAb at approximately 125,000 could be detected in the UspA2 preparation by western but not by Coomassie blue staining (FIG. 6C). The cells need not be lysed to achieve this high yield, which suggested this protein is present in large amounts on the surface of the bacterium.

A method for the purification of the UspA1 protein was also developed. This protein co-purified with UspA2 through the initial extraction and TMAE chromatography steps. Following hydroxyapatite chromatography, however, UspA1 remained bound to the column and had to be eluted at the higher salt concentration of 500 mM $NaPO_4$. The crude UspA1 preparation obtained in this step was reapplied and eluted from the hydroxyapatite column using a linear sodium phosphate gradient. A total of 80 mg of purified UspA1 was isolated from 1.6 kg wet wt. of *M. catarrhalis* O35E strain cells. UspA1 purified using this method migrated at three different apparent sizes on SDS-PAGE depending on the method of sample preparation. Unheated samples exhibited a single band at ~280,000, whereas samples heated at 100° C. for 3 min resulted in an apparent molecular weight shift to 350,000. Prolonged heating at 100° C. resulted in a shift of the 350,000 band to one at 100,000 (FIG. 6B). Following heating of the sample for 7 min at 100° C., the band at 100,000 contained greater than 95% of the protein based on scanning densitometry of the Coomassie stained gel. In contrast, UspA2 migrated at 240,000 regardless of the duration of the heating when examined by SDS-PAGE. The different migration behaviors indicated the preparations contained two distinctly different proteins Molecular Weight Determinations. MALDI-TOF mass spectrometric analysis for determination of molecular weight of UspA2 using 3,5-dimethoxy-4-hydroxy-cinnamic acid matrix in presence of 70% (v/v) aqueous acetonitrile and 0.1% TFA resulted in the identification of a predominant species with average molecular mass of 59,518 Da. In addition to the expected $[M+H]^+$ and $[M+2H]^{2+}$ molecular ions, the $[2M+H]^+$ and $[3M+H]^+$ ions were also observed. The latter two ions were consistent with the dimer and the trimer species. Using similar conditions, the inventors were unable to determine the mass of UspA1.

To determine the molecular sizes of the purified proteins in solution, UspA1 and UspA2 were independently run on a Superose-6 HR 10/30 gel filtration column (optimal separation range: 5,000-5,000,000) calibrated with molecular weight standards. Purified UspA1 exhibited a native molecular size of 1,150,000 and UspA2 a molecular size of 830,000. These sizes, however, may be affected by the presence of TX-100.

N-terminal Sequence Analysis of Internal UspA1 and UspA2 Peptides. All attempts to determine the N-terminal sequences of both UspA and UspA1 proved unsuccessful. No sequence could be determined. This suggested two things. First, the N-terminus of both proteins were blocked, and, second, neither protein preparation contained contaminating proteins that were not N-terminally blocked.

Thus, to confirm that the primary sequence of purified UspA1 and UspA2 corresponded to that deduced from their respective gene sequences, internal peptide fragments were generated and subjected to N-terminal sequence analysis. Tables X and XI show the N-terminal sequences obtained for fragments generated from the digestion of the UspA2 and UspA1 proteins, respectively. The sequences matching the primary amino acid sequence deduced from the respective gene sequences are indicated for each fragment. The UspA2 fragments #3 and #4 exhibited sequence similarity with residues 505-515 and 605-614 respectively of the amino acid sequence deduced from the UspA1 gene. In Table XII, UspA1 fragment #3 exhibited sequence similarity with residues #278-294 of the UspA2 primary sequence. These sequences corresponded with the domains within UspA1 and UspA2 that share 93% sequence identity. The remainder of the sequences, however, were unique to the respective proteins.

TABLE X

N-terminal sequences of internal UspA2 peptide cleavage fragments

| UspA2 Fragment Sequence[a] | Match[b] | Cleavage |
|---|---|---|
| 1) LLAEQQLNG SEQ ID NO:73 | 92-100 | Trypsin |
| 2) ALESNVEEGL SEQ ID NO:74 | 216-225 | Lys-C |
|  | 245-254 |  |
|  | 274-283 |  |
| 3) ALESNVEEGLLDLS SEQ ID NO:75 | 274-288 | Trypsin |
|  | *505-515 |  |
| 4) AKASAANTDR SEQ ID NO:76 | 378-387 | Chymotrypsin |
|  | *605-614 |  |
| 5) AATAADAITKNGN SEQ ID NO:77 | 439-450 | Chymotrypsin |
| 6) SITDLGTKVDGFDGR SEQ ID NO:78 | 458-472 | Lys-C |

TABLE X-continued

N-terminal sequences of internal UspA2 peptide cleavage fragments

| UspA2 Fragment Sequence[a] | Match[b] | Cleavage |
|---|---|---|
| 7) VD̲ALXTKVNALDXKVN SEQ ID NO:79 | 473-488 | Trypsin |
| 8) AAQAALSGLFV̲PYSVGKFNATAALGGYGSK SEQ ID NO:80 | 506-535 | CNBr |

[a]Underlined residues denote mismatch with the nucleotide derived amino acid sequence. Ambiguous residues whose identity could not be verified are denoted by the letter X.
[b]Asterisk (*) indicates match with UspA1. Without asterisk indicates matches with nucleotide derived amino acid sequence of UspA2.

TABLE XI

N-terminal sequences of internal UspA1 peptide cleavage fragments

| UspA1 Fragment Sequence[a] | Match[b] | Cleavage |
|---|---|---|
| 1) LENNVEEP̲EXLNLS | 456-468 | Lys-C |
| 2) DQKADI | 473-478 | Trypsin |
| 3) NNVEEGLLDLSGRLIDQK | 504-521 *278-294 | Lys-C |
| 4) VAE̲GFEIF | 690-697 | Trypsin |
| 5) AGIATNKQELILQNDRLNRI | 701-720 | Lys-C |

[a]As per Table X. X denotes an unidentified amino acid residue.
[b]Asterisk (*) indicates match with UspA2. Without asterisk indicates matches with nucleotide derived amino acid sequence of UspA1.

Reactivity of MAbs with UspA1 and UspA2. The western blot analysis of purified UspA1 and UspA2 revealed that both proteins reacted strongly with the MAb 17C7 described by Helminen et al. (1994) (FIG. 7). The reactivity of the proteins with other MAbs was also investigated. The data in Table XII show that, whether assayed by ELISA or western, the MAbs 13-1, 29-31 and 45-2 only reacted with UspA2, the MAbs 7D7, 29C6, 11A6 and 12D5 only reacted with UspA1, while 17C7 and 6-3 reacted with both UspA1 and UspA2. All the MAbs shown in Table XIII bind to whole bacteria when examined by ELISA. These results indicated that UspA2 was exposed on the surface of the bacterium.

TABLE XII

Summary of reactivity of monoclonal antibodies with purified UspA1, UspA2 and whole bacteria of strain O35E

| | | Reactivity | | |
|---|---|---|---|---|
| mAb | Isotype | Whole bacterium[a] | Purified UspA1[b] | Purified UspA2[b] |
| 13-1 | IgG1κ | + | − | + |
| 29-31 | IgG1λ | + | − | + |
| 45-2 | IgG2a | + | − | + |
| 17C7 | IgG2a | + | + | + |
| 6-3 | IgM | + | + | + |
| 7D7 | IgG2b | + | + | − |
| 29C6 | IgG1 | + | + | − |
| 11A6 | IgA | + | + | − |
| 12D5 | IgG1 | + | + | − |

[a]Determined by whole cell ELISA.
[b]Determined by ELISA and western blot.

TABLE XIII

Cross-reactivity of antibodies to UspA1 and UspA2 proteins

| | Geometric mean ELISA titer[b] to | |
|---|---|---|
| Antiserum to | UspA1 | UspA2 |
| UspA1[a] | 740,642[c] | 10,748[c] |
| UspA2[a] | 19,120[d] | 37,615[d] |

[a]The preparation of the sera are described in the text.
[b]ELISA titers are for total IgG and IgM antibodies for sera pooled from ten mice.
[c]The difference in titer of the anti-UspA1 with the two purified proteins was statistically different by the Wilcoxon signed rank test (p = 0.0002).
[d]The difference in titer of the anti-UspA2 with the two purified proteins was statistically different by the Wilcoxon signed rank test (p = 0.01).

Immunogenicity and antibody cross-reactivity. Antisera to the purified UspA1 and UspA2 proteins were generated in mice. The titers of antigen specific antibodies (IgG and IgM) as well as the cross-reactive antibodies in these sera were determined by an ELISA assay using each of the purified proteins (Table XIII). Both proteins elicited antibody titers that were greater against themselves than against the heterologous protein. Thus, the reactivities of both the MAbs (Table XII) as well as the polyclonal antibodies indicate that the proteins possessed both shared and non-shared B-cell epitopes.

Antibody reactivity to whole bacterial cells and bactericidal activity. Antisera to the UspA1 and UspA2 were assayed by whole cell ELISA against the homologous O35E strain and several heterologous isolates (Table XIV). The antibodies to UspA1 and to UspA2 reacted strongest with the O35E strain. The reactivity of the sera toward the heterologous isolates indicated they bound antibodies elicited by both UspA1 and UspA2.

TABLE XIV

ELISA and complement mediated bactericidal titers toward whole bacterial cells of multiple isolates of M. catarrhalis elicited by purified UspA1 and purified UspA2

| | Whole cell ELISA[a] | | Bactericidal titer[b] | |
|---|---|---|---|---|
| Isolate | anti-UspA1[a] | anti-UspA2[a] | anti-UspA1 | anti-UspA2 |
| O35E | 195,261 | 133,492 | 400 | 800 |
| 430-345 | 12,693 | 18,217 | 400 | 400 |
| 1230-359 | 7,873 | 13,772 | 400 | 400 |
| TTA24 | 14,341 | 7,770 | 800 | 800 |

[a]Titer determined for pool of sera from ten mice. The titer of the sera drawn before the first immunization was less than 50 for all isolates.
[b]Bactericidal titers were determined as the inverse of the highest serum dilution killing greater than 50% of the bacteria. The titers for the sera from mice immunized contemporaneously with $CRM_{197}$ were less than 100.

The bactericidal activities of the antisera to UspA1 and UspA2 were determined against O35E and other isolates as well (Table XIV). Both sera had bactericidal titers ranging from 400-800 against O35E and the disease isolates. Anti-$CRM_{197}$ serum, the negative control, as well as sera drawn before immunization, had a titers of <100 against all the strains. These results were consistent with the previous observation that the epitopes shared by the two proteins are highly conserved among isolates and the antibodies toward those isolates are bactericidal.

Pulmonary challenges. Immunized mice were given a pulmonary challenge with the homologous O35E strain or the heterologous TTA24 strain. Relative to the control mice immunized with CRM₁₉₇, enhanced clearance of both strains was observed regardless of whether the mice were immunized with UspA1 or UspA2 (Table XV). No statistical difference p>0.05) was seen between the groups of mice immunized with UspA1 and with UspA2.

TABLE XV

Pulmonary clearance of *M. catarrhalis* by mice immunized with purified UspA1 and UspA2

| Study | Immunogen | Challenge strain | % clearance[a] | p[a] |
|---|---|---|---|---|
| 1 | UspA1 | O35E | 49.0 | 0.013 |
|   | UspA2 |  | 31.8 | 0.05 |
|   | CRM₁₉₇ |  | 0 | — |
| 2 | UspA1 | TTA24 | 54.6 | 0.02 |
|   | UspA2 |  | 66.6 | 0.0003 |
|   | CRM₁₉₇ |  | 0 | — |

[a]Challenge method described in text. Numbers are the percentage of bacteria cleared from the immunized mice compared to control mice which were immunized with CRM₁₉₇.

Interaction of purified proteins with HEp-2 cells. The purified UspA1 and UspA2 were tested for their ability to interact with HEp-2 cell monolayer in a 96-well plate using an ELISA. Protein binding to the HEp-2 cells was detected with a 1:1 mix of the mouse antisera to UspA1 and UspA2. Purified UspA1 bound to HEp-2 cells at concentrations above 10 ng. A weak binding by the UspA2 was detected at concentrations above 100 ng (FIG. 7). The attachment of O35E bacteria to HEp-2 cells was used as a positive control. This result, plus the data showing that the anti-UspA1 antibodies inhibited attachment of the bacteria to HEp2 cells, suggests UspA1 plays an important role in bacterial attachment which also suggested that UspA1 was exposed on the bacterial surface.

Figure 8:
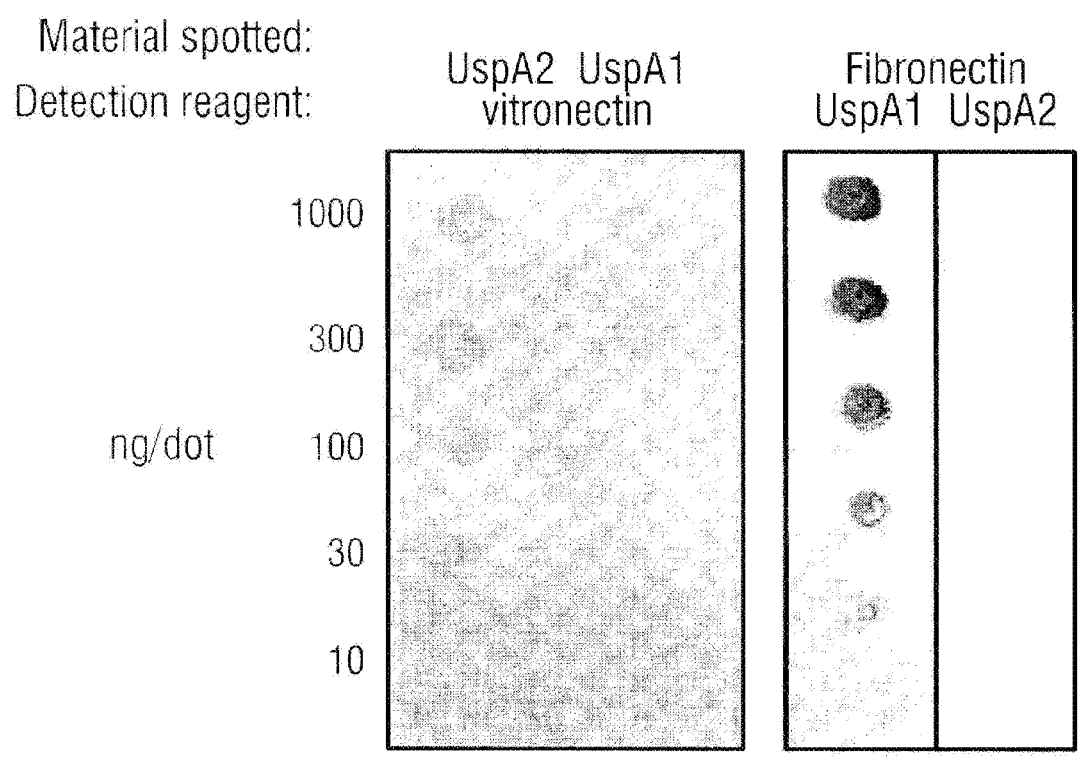
FIG. 8. Interaction with fibronectin and vitronectin determined by dot blot. The bound vitronectin was detected with rabbit polyclonal antibodies, the protein bound to the fibronectin was detected with pooled sera made against the UspA1 and UspA2.
Figure 9A:
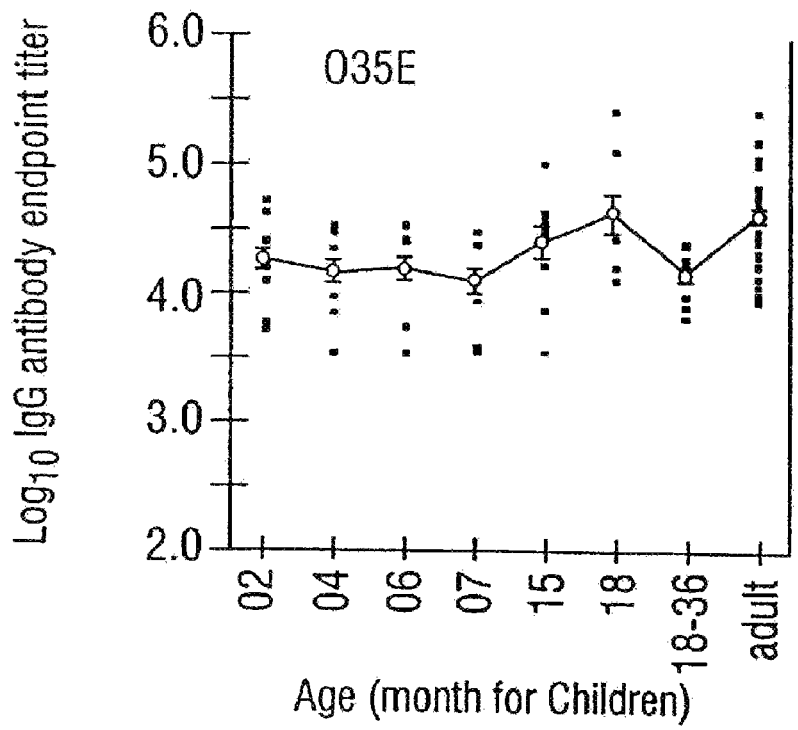
FIG. 9A-9F. The levels of antibodies to the protein UspA1, UspA2 and M. catarrhalis O35E strain in normal human sera. Data are the $\log_{10}$ transformed end-point titers of the IgG (FIGS. 9A-9C) and IgA (FIGS. 9D-9F) antibodies determined by ELISA. The individual titers were plotted according to age group and the geometric mean titer for each age group linked by a solid line. Sera for the 2-18 month old children were consecutive samples from a group of ten children.
Figure 9B:
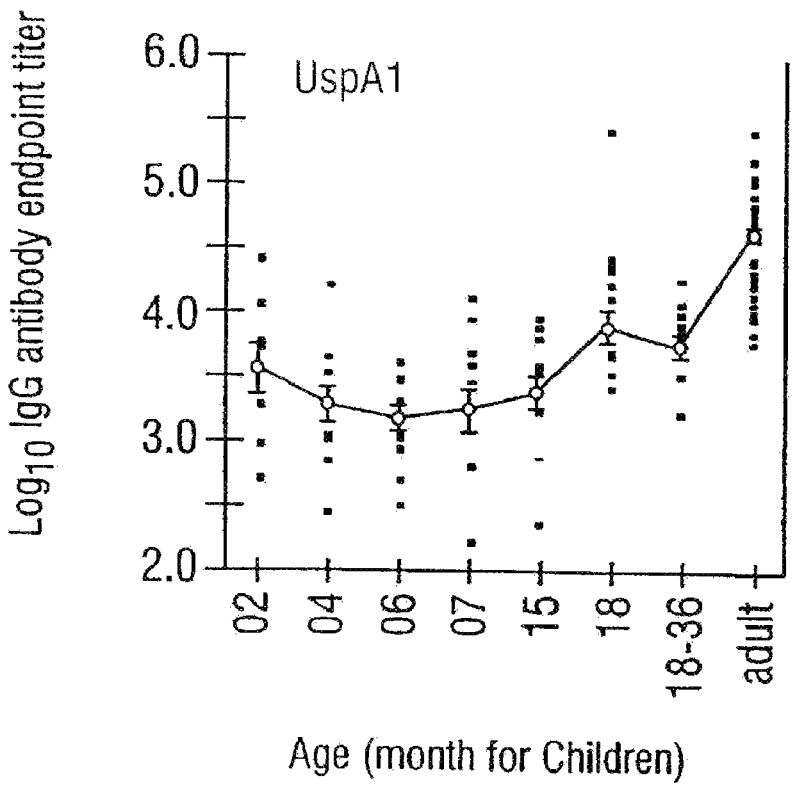
Figure 9C:
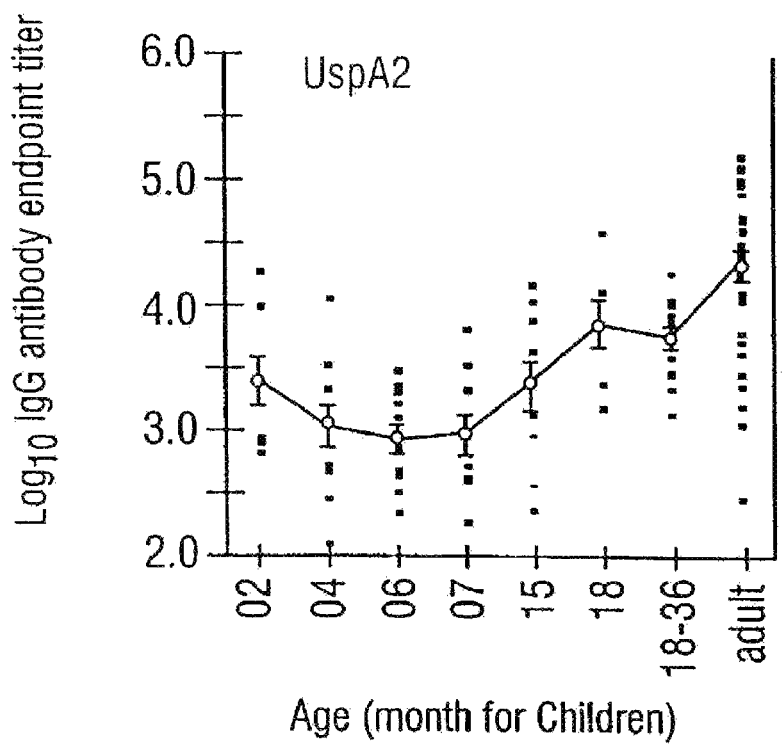
Figure 9D:
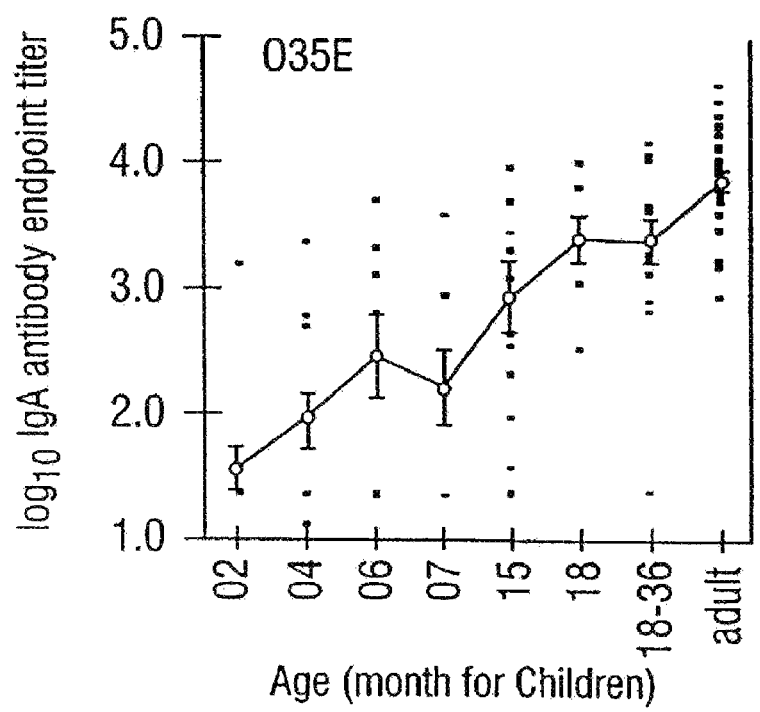
Figure 9E:
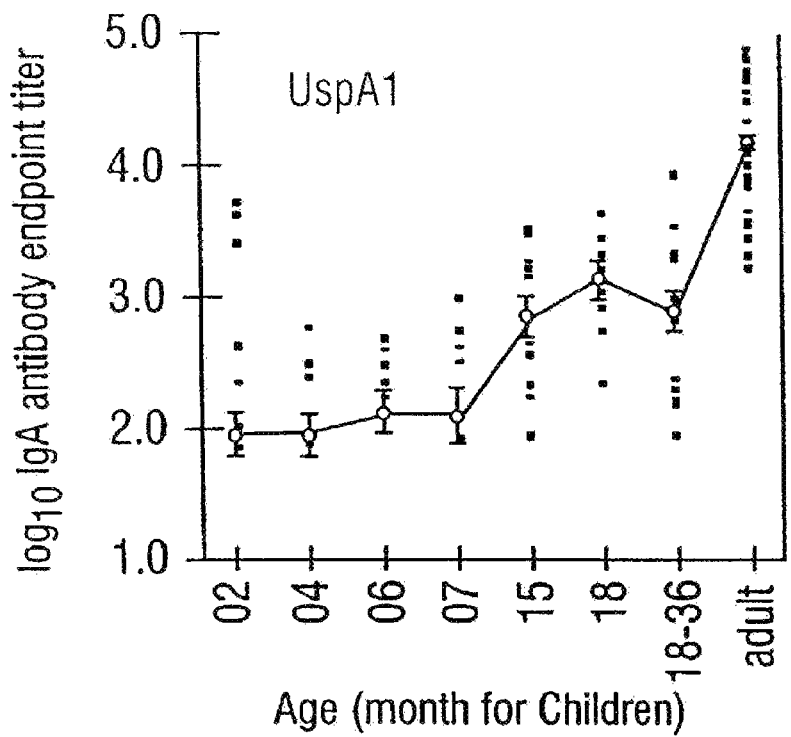
Figure 9F:
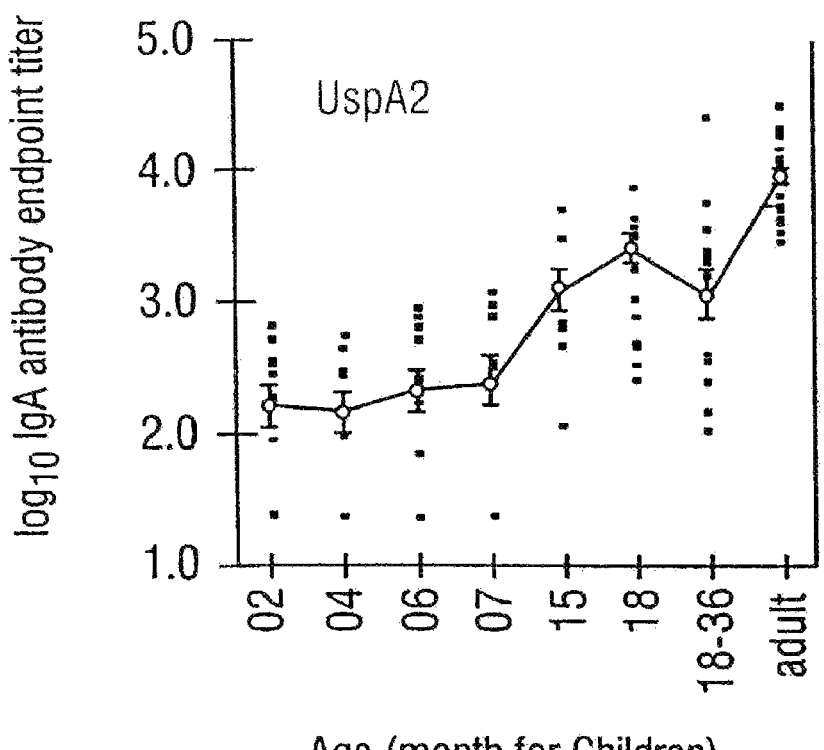

Interaction of purified proteins with fibronectin and vitronectin. The purified proteins were assayed for their ability to interact with fibronectin and vitronectin by dot blot assays. Human plasma fibronectin immobilized on a nitrocellulose membrane bound purified UspA1 but not UspA2 (FIG. 8), while UspA2 immobilized on the nitrocellulose membrane was capable of binding vitronectin (FIG. 8). Vitronectin binding by the UspA1 was also detected, but the reactivity was weaker. Collagen (type IV), porcine mucin (type III), fetuin and heparin were also tested for interaction with purified UspA1 and purified UspA2, but these did not exhibit detectable binding.

Discussion

Previous UspA purification attempts yielded preparations containing multiple high molecular weight protein bands by SDS-PAGE and western blot. Because each of the bands reacted with the "UspA specific" MAb 17C7, it was thought they represented multiple forms of the UspA protein (Chen et al., 1996). However, the inventors have discovered that there are two distinct proteins, UspA1 and UspA2, that share an epitope recognized by the 17C7 MAb. These two proteins are encoded by different genes. This study shows that UspA1 and UspA2 can be separated from one another. The isolated proteins had different SDS-PAGE mobility characteristics, different reactivity with a set of monoclonal antibodies, and different internal peptide sequences. The results, however, were consistent with the proteins sharing a portion of their peptide sequences, including the MAb 17C7 epitope. The separation of the proteins from one another has allowed the inventors to further demonstrate how the proteins were different as well as examine their biochemical, functional, and immunological characteristics.

In solution, the purified proteins appear to be homopolymers of their respective subunits held together by strong non-covalent forces. This is indicated by the fact that UspA2 lacks any cysteines and treatment of both proteins with reducing agents did not alter their mobilities in SDS-PAGE. Both gene sequences possess leucine zipper motifs that might mediate coil-coil interactions (O'Shea et al., 1991). Even so, it was surprising that the non-covalent bonds of both proteins were not only strong enough to resist dissociation by the conditions normally used to prepare samples for SDS-PAGE, but also high concentrations of chaotropic agents such as urea (Klingman and Murphy, 1994) and guanidine HCl. Of the two proteins, UspA2 appeared to be less tightly aggregated, this was indicated by the fact that its subunit size of 59,500 Da could be determined by mass spectrometry. UspA1, however, was recalcitrant to dissociation by all the methods tried, and this may be the reason its size could not be determined by mass spectrometry. In SDS-PAGE, the dominant UspA2 migrated with an apparent size of 240,000 while a far smaller portion migrated at about 125,000 and could only be detected by western analysis. The mobility of UspA1, however, varied depending on how long the sample was heated. The smallest form was about 100,000. This was consistent with the size of the gene product missing from the uspA1 mutant but not with the size predicted from the gene sequence of 88,000 Da. In solution, both proteins formed larger aggregates than those seen by SDS-PAGE. Their sizes, as measured by gel filtration chromatography, were 1,150,000 and 830,000 for UspA1 and UspA2 respectively. If the proteins behave this way in vivo, UspA1 and UspA2 likely occur as large molecular complexes on the bacterial surface of the bacterium.

The results of the N-terminal amino acid sequence analyses of the UspA2 and UspA1 derived peptides (Tables X and XI) were in agreement with the protein sequences derived from the respective gene sequences. This confirmed that the purified UspA1 and UspA2 proteins were the products of the respective uspA1 and uspA2 genes. Further, the experimental and theoretical amino acid compositions of UspA1 and UspA2 were consistent, given the size of the proteins and the accuracy of the amino acid determination. There was, however, a discrepancy between the size determined by mass spectrometry of 59,518 and the size indicated from the gene sequence for UspA2 of 62,483. This discrepancy suggested that this protein either undergoes post-translational processing or proteolytic degradation.

The data also suggest that both proteins are exposed on the bacterial surface. That at least one of the proteins is exposed is evident from the finding that the MAb 17C7 and polyclonal sera react with whole cells. The reactivities of the UspA2 specific monoclonal antibodies 13-1, 29-31 and 45-2 with the bacterial cells in the whole cell ELISA provided evidence that the UspA2 is a surface protein (Table XII). The reactivities of the UspA1 specific MAbs 7D7, 29C6, 11A6 and 12D5 with the bacterial cells in the whole cell ELISA provided evidence that the UspA1 is a surface protein (Table XII). Further evidence for surface exposure of UspA1 was indicated by the inhibitory effect of the antiserum on bacterial attachment to HEp-2 cells. The sera to the UspA2 lacked this activity. Thus, both UspA1 and UspA2 appeared to be surface exposed on the bacterium.

Surface exposure of the proteins is probably important for the two proteins' functions. One function for UspA1 appears to be meditation of adherence to host tissues. The evidence for this was that UspA1 antibodies inhibited bacterial binding to HEp-2 cells and the purified protein itself bound to the cells. The relevance of binding to HEp-2 cells is that they are epithelial cells derived from the larynx, a common site of *M.* catarrhalis colonization (Schalen et al., 1992). This confirms the inventors findings that mutants that do not express UspA1 fail to bind epithelial cells. The inventors' also showed that UspA1 binds fibronectin. Fibronectin has been reported to be a host receptor for other pathogens (Ljungh and Wadstrom, 1995; Westerlund and Korhonen, 1993). Examination of the gene sequence, however, failed to reveal any similarity with the fibronectin binding motifs reported for Gram positive organisms (Westerlund and Korhonen, 1993). Thus, it is fairly clear that UspA1 plays a role in host adherence, possibly via cell associated fibronectin.

The function of UspA2 is less certain. Antibodies toward it did not block adherence to the HEp-2 or Chang cell lines, nor did the purified protein bind to those cells. Yet, UspA2 bound vitronectin strongly. Pathogen binding of vitronectin has been linked to host cell adherence (Gomez-Duarte et al., 1997; Limper et al., 1993); however, van Dijk and his co-workers have reported that vitronectin binding by *M. catarrhalis* may be used by the bacteria to subvert host defenses (Verdiun et al., 1994). The soluble form of vitronectin, known as complement factor S, regulates formation of the membrane attack complex (Su, 1996). They suggest that the binding of vitronectin to the *M. catarrhalis* surface inhibits the formation of the membrane attack complex, rendering the bacteria resistant to the complement dependent killing activity of the sera. They have also described two types of human isolates: one that binds vitronectin and is resistant to the lytic activity of the serum and the other that does not bind vitronectin and is serum sensitive (Hol et al., 1993). It must be noted, however, that vitronectin, like all the extracellular matrix proteins, has many forms and serves multiple functions in the host (Preissner, 1991; Seiffert, 1997). Thus, the interaction of both UspA1 and UspA2 with the extracellular matrix proteins fibronectin and vitronectin may serve the bacterium in ways beyond subverting host defenses or as receptors for bacterial adhesion.

Even though the two proteins share epitopes and sequences, they have different biochemical activities and likely serve different biological functions. If an immune response to the respective protein interferes with its function, it ought to be considered as a vaccine candidate. The results of the immunological studies in mice indicated that both proteins would be good vaccine candidates. Mice immunized with either UspA1 or UspA2 developed high antibody titers toward the homologous and heterologous bacterial isolates. Further, the sera from these mice had complement dependent bactericidal activity toward all the isolates tested. In addition, immunized mice exhibited enhanced pulmonary clearance of the homologous isolate and heterologous isolates. It is important to note that antibodies elicited by the proteins were partially cross-reactive. This was expected since both react with the 17C7 MAb and share amino acid sequence.

Example V

The Level and Bactericidal Capacity of Child and Adult Human Antibodies Directed against the Proteins UspA1 and UspA2

To determine if humans have naturally acquired antibodies to the UspA1 and UspA2 of the *M. catarrhalis* and the biological activity of these antibodies if present, sera from healthy humans of various ages was examined using both ELISA and a bactericidal assay. It was found that healthy people have naturally acquired antibodies to both UspA1 and UspA2 in their sera, and the level of these antibodies and their bactericidal capacity were age-dependent. These results also indicate that naturally acquired antibodies to UspA1 and UspA2 are biologically functional, and thus support their use as vaccine candidates to prevent *M. catarrhalis* disease.

Material and Methods

Bacteria. The *M. catarrhalis* strains O35E and TTA24 were as described in Example I. An ATCC strain (ATCC 25238) and three other clinical isolates from the inventors' collection were also used.

Human sera. Fifty-eight serum samples were collected from a group of ten children at 2, 4, 6, 7, 15 and 18 months of age who had received routine childhood immunizations. Individual sera from twenty-six adults and fifteen additional children 18-36 months of age were also assayed. All sera were obtained from clinically healthy individuals. Information on *M. catarrhalis* colonization and infection of these subjects was not collected. The sera were stored at −70° C.

Purification of UspA1 and UspA2. Purified UspA1 and UspA2 were made from the O35E strain of *M. catarrhalis* as described in Example IV herein. Each protein preparation contained greater than 95% of the specific protein based on densitometric scanning of Coomassie brilliant blue stained SDS-PAGE. Based on western blot analysis using monoclonal antibodies, each purified protein contained no detectable contamination of the other.

Purification of UspA1 and UspA2 specific antibodies from human plasma. Human plasmas from two healthy adults were obtained from the American Red Cross (Rochester, N.Y.) and pooled. The antibodies were precipitated by adding ammonium sulfate to 50% saturation. The precipitate was collected by centrifugation and dialyzed against PBS. A nitrocellulose membrane (2×3 inches) was incubated with UspA1 or UspA2 at 0.5 mg/ml in PBS containing 0.1% (vol/vol) Triton X-100 for 1 h at room temperature, washed twice with PBS and residual binding sites on the membrane blocked with 5% (wt/vol) dry milk in PBS for 2 h at room temperature. The membrane was then sequentially washed twice with PBS, 100 mM glycine (pH 2.5) and finally with PBS before incubation with the dialyzed antibody preparation. After incubating for 4 h at 4° C., the membrane was washed again with PBS, and then 10 mM Tris buffer (pH 8.0) containing 1 M sodium chloride to remove non-specific proteins. The bound antibodies were eluted by incubation in 5 ml of 100 mM glycine (pH 2.5) for 2 min with shaking. One ml of Tris-HCl (1M, pH 8.0) was immediately added to the eluate to neutralize the pH. The eluted antibodies were dialyzed against PBS and stored at −20° C.

Enzyme-linked immunosorbent assay (ELISA). Antibody titers to the O35E and other *M. catarrhalis* strains were determined by a whole-cell ELISA as previously described using biotin-labeled rabbit anti-human IgG or IgA antibodies (Brookwood Biomedical, Birmingham, Ala.) (Chen et al., 1996). Antibody titers to UspA1 and UspA2 were determined by a similar method except that the plates were coated with 0.1 µg of purified protein in 100 µg of PBS per well overnight at room temperature. The IgG subclass antibodies to UspA1 or UspA2 were determined using sheep anti-human IgG subclass antibodies conjugated to alkaline phosphatase (The Binding Site Ltd., San Diego, Calif.). The antibody end point titer was defined as the highest serum dilution giving an $A_{415}$ greater than three times that of the control. The control wells received all treatments except human sera and usually had absorbance values ranging from 0.03 to 0.06.

The specificity of biotin-labeled rabbit anti-human IgG and IgA antibodies was determined against purified human IgG, IgM and IgA (Pierce, Rockford, Ill.) by ELISA. No cross-reactivity was found. The assay sensitivity determined by testing against purified human antibodies of appropriate isotype in an ELISA was 15 and 60 ng/ml in the IgG and IgA assays, respectively. Likewise, the specificity of the human IgG subclass antibody assays was confirmed in ELISA against purified human myeloma IgG subclass proteins (ICN Biomedicals, Inc., Irvine, Calif.), and the assay sensitivity was 15 ng/ml in the IgG1, IgG3 and IgG4 assays, and 120 ng/ml in the IgG2 assay. Two control sera were included to control for assay to assay variation.

Complement dependent bactericidal assay. The bactericidal activity of the human sera was determined as described previously (Chen et al., 1996). In some studies, the sera were absorbed with purified UspA1 or UspA2 prior to the assay. The absorption of specific antibodies from these sera was accomplished by adding the purified proteins to 20 or 50 µg/ml final concentration. The final serum dilution was 1:10. The mixtures were incubated for 2 h at 4° C. and the precipitate removed by micro-centrifugation. The purified human antibodies specific for UspA1 and UspA2 were assayed against five M. catarrhalis strains in a similar manner.

Statistics. Statistical analysis was performed on logarithmic transformed titers using JMP software (SAS institute, Cary, N.C.). To allow transformation, a value of one half the lowest serum dilution was assigned to sera which contained no detectable titers. Comparison of IgG levels among the age groups was done by analysis of variance, and the relationship of antibody titer and the bactericidal titer was determined by logistic regression. A p value less than 0.05 was considered significant.

Results

Comparison of serum IgG and IgA titers to UspA1 and UspA2 in children and adults. The IgG and IgA antibody titers in the sera from ten children collected longitudinally between 2-18 months of age, as well as the random samples from fifteen 18-36 month old children and twenty-six adults were determined against the whole bacterial cells of the O35E strain, the purified UspA1 and the purified UspA2 by ELISA. IgG titers to all three antigens were detected in almost all the sera (FIG. 9). The IgG titers to UspA1 and UspA2 exhibited strong age-dependent variation when compared to IgG titers to the O35E bacterium (FIG. 9). The adult sera had significantly higher IgG titers to the purified proteins than sera from children of various age groups (p<0.01). Sera from children at 6-7 months of age had the lowest IgG titers to UspA proteins and the mean titer at this age was significantly lower than that at 2 months of age (p<0.05).

The level of IgA antibodies to UspA1, UspA2 and O35E bacterial cells were age dependent (FIG. 9). A serum IgA titer against the UspA1 and UspA2 was detected in all twenty-six adults and children of 18-36 months of age. For children less than 18 months of age, the proportion exhibiting antigen specific IgA titers increased with age. The mean IgA titers to UspA1, UspA2 or O35E bacterium in these sera were low for the first 7 months of age but gradually increased thereafter (FIG. 9).

Figure 10A:
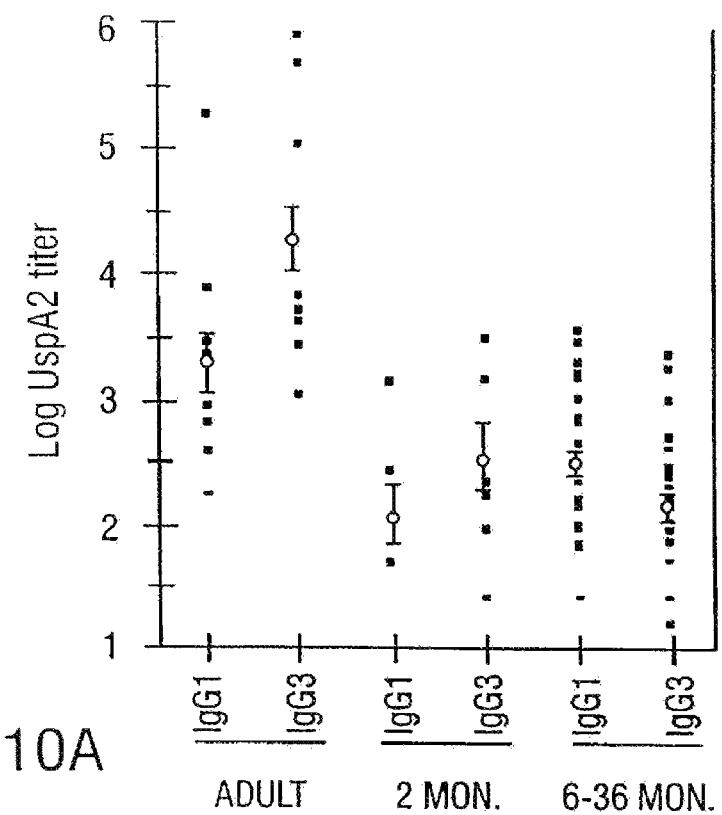
FIG. 10A-10B. Subclass distribution of IgG antibodies to UspA1 and UspA2 in normal human sera.
Figure 10B:
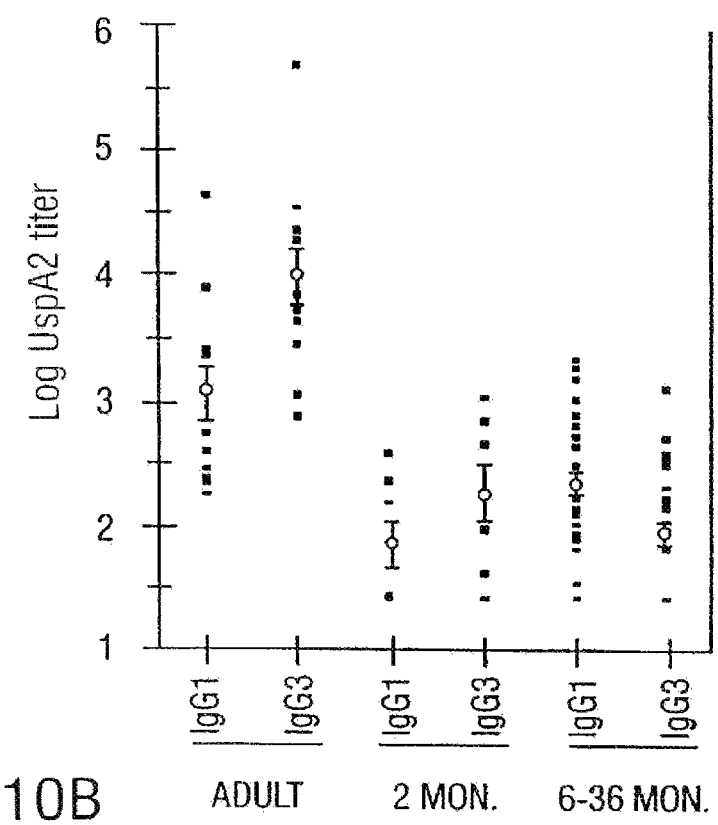

Age-dependent subclass distribution of IgG antibodies to UspA1 and UspA2. The IgG subclass titers to the UspA1 and UspA2 antigens were determined on sera from ten adult sera and thirty-five children's sera. The subclass distribution was found to be age-dependent. The most prominent antibodies to the UspA1 and UspA2 antigens were of the IgG1 and IgG3 subclasses, which were detected in almost all sera. The IgG2 and IgG4 titers were either undetectable or extremely low. Therefore, only data on IgG1 and IgG3 subclasses are reported (FIG. 10). The IgG3 titers against UspA1 or UspA2 in the adult sera were significantly higher than the IgG1 titers (p<0.05). The same subclass profile was seen in the sera from the 2 month old children, although the difference between IgG1 and IgG3 titers did not reach statistical significance, probably because of the smaller sample size. Sera from children between 4 and 36 months of age all had a similar subclass profile which was different from that of the adults and 2 month old children. The IgG1 titers in children's sera were either higher than or equivalent to the IgG3 titers. The mean IgG1 titer to either UspA1 or UspA2 was significantly higher than IgG3 titer to the same antigens in these children's sera (p<0.05).

Figure 11A:
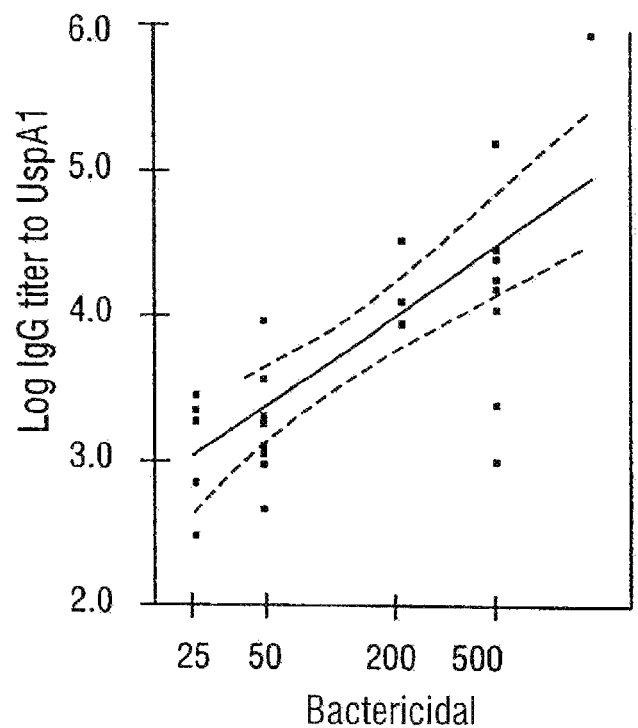
FIG. 11A-11B. Relationship of serum IgG titers to UspA1 (FIG. 11A) and UspA2 (FIG. 11B) with the bactericidal titer against the O35E strain determined by logistic regression ($p<0.05$). The solid line indicates the linear relationship between the IgG titer and bactericidal titer. Broken lines represent the 95% confidence intervals of the linear fit.
Figure 11B:
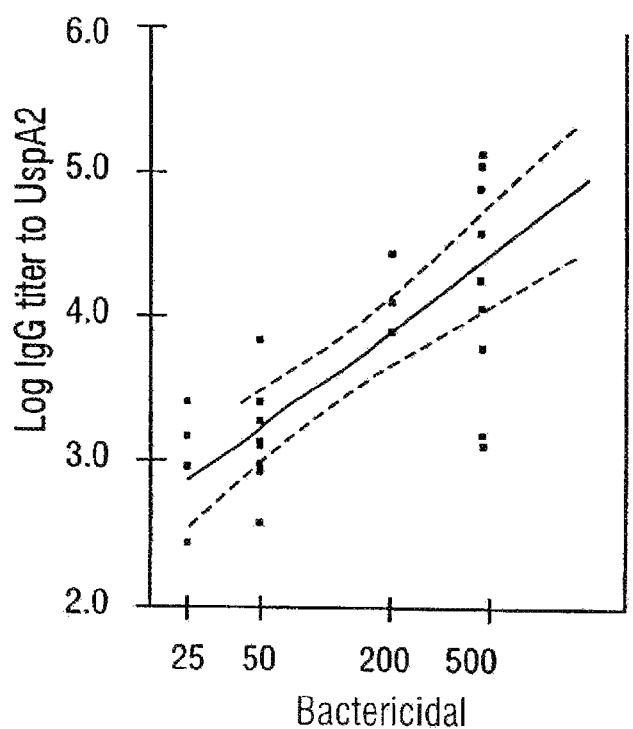

Bactericidal activity. The bactericidal titers of seventeen sera representing different age groups were determined (Table XVI). All the adult sera and three out of five sera from the two month old children which had high IgG titers to the UspA proteins had strong bactericidal activity. Sera from 6 month old children had the least bactericidal activity. All five sera from this age group had a marginal bactericidal titer of 50, the lowest dilution assayed. The bactericidal activity of the sera from 18 to 36 month old children was highly variable with titers ranging from less than 50 to 500. There was a significant linear relationship between the bactericidal titers and the IgG antibody titers against both UspA1 and UspA2 by logistic regression analysis (p<0.01) (FIG. 11).

TABLE XVI

The level of IgG antibodies to UspA1 and UspA2 from normal human serum and the serum bactericidal activity

| Subject[a] | Age | ELISA IgG titer[b] UspA1 | UspA2 | BC titer[c] |
|---|---|---|---|---|
| 1 | 2 month | 17,127 | 6,268 | 500 |
|   | 6 month | 4,273 | 1,363 | 50 |
|   | 15 month | 798 | 250 | <50 |
| 2 | 2 month | 12,078 | 12,244 | 500 |
|   | 6 month | 1,357 | 878 | 50 |
|   | 18 month | 14,041 | 14,488 | 200 |
| 3 | 2 month | 30,283 | 20,362 | 500 |
|   | 6 month | 1,077 | 1,947 | 50 |
|   | 18 month | 2,478 | 1,475 | <50 |
| 4 | 2 month | 2,086 | 869 | <50 |
|   | 6 month | 530 | 802 | 50 |
|   | 18 month | 9,767 | 8,591 | 200 |
| 5 | 2 month | 3,233 | 2,655 | <50 |
|   | 6 month | 2,246 | 360 | 50 |
|   | 18 month | 26,693 | 43,703 | 500 |
| 6 | 1.5-3 year | 4,036 | 2,686 | 50 |
| 7 | 1.5-3 year | 2,037 | 1,251 | 50 |
| 8 | 1.5-3 year | 341 | 251 | <50 |
| 9 | 1.5-3 year | 2,538 | 1,200 | 500 |
| 10 | 1.5-3 year | 1078 | 1,370 | 500 |
| 11 | 1.5-3 year | 1,265 | 953 | 50 |
| 12 | adult | 161,750 | 87,180 | 450 |
| 13 | adult | 873,680 | 248,290 | >1350 |
| 14 | adult | 154,650 | 146,900 | 450 |
| 15 | adult | 10,330 | 7,860 | 50 |
| 16 | adult | 35,780 | 31,230 | 150 |
| 17 | adult | 19,130 | 132,200 | 450 |

[a]Three consecutive samples from subjects 1 through 5 were collected at the stated ages.
[b]ELISA end point titers to purified UspA1 or UspA2 from the O35E strain were determined as the highest serum dilution giving an $A_{415}$ greater than three times the background.
[c]BC titers: bactericidal titer assayed against the O35E strain. Sera were assayed at 1:50, 100, 200, and 500. Bactericidal titer was determined as the highest serum dilution resulting in killing of 50% or more of the bacteria relative to the control. Control bacteria were incubated with test serum and heat inactivated complement serum.

Bactericidal activity of sera absorbed with purified UspA1 or UspA2. Because normal human sera contain antibodies to numerous antigens of M. catarrhalis as indicated by western blot, an absorption method was used to determine the contribution of UspA1 and UspA2 specific antibodies towards the bactericidal activity. Six adult sera were absorbed with purified UspA1 or UspA2, and the change in ELISA reactivity to UspA proteins determined. A reduction in ELISA reactivity was seen for all the sera after absorption (Table XVII). Further, absorption with one protein resulted in a reduction of IgG titers to the other protein. Reduction of UspA2 reactivity was of the same degree regardless of whether the absorbent was UspA1 or UspA2. In contrast, there was less reduction in UspA1 reactivity after absorption with UspA2 than with UspA1 (Table XVII). This indicated that antibodies to UspA1 and UspA2 were partially cross-reactive.

TABLE XVII

ELISA titer of adult sera before and after absorption[a]

| Absorbent | #1 | #2 | #3 | #4 | #5 | #6 |
|---|---|---|---|---|---|---|
| | IgG titers to UspA1 in sample[b] | | | | | |
| saline | 161,750 | 873,680 | 154,650 | 10,330 | 35,780 | 19,130 |
| UspA1 | 2,450 | 2,210 | 3,160 | 1,650 | <500 | 3,010 |
| UspA2 | 42,620 | 90,150 | 33,570 | 6,420 | 3,490 | 4,130 |
| | IgG titers to UspA2[b] | | | | | |
| saline | 87,180 | 248,290 | 146,900 | 7,860 | 31,230 | 13,200 |
| UspA1 | 2,800 | 2,120 | 2,700 | 2,220 | <500 | <500 |
| UspA2 | <500 | 1,820 | 3,010 | 2,960 | <500 | <500 |

[a]Absorption: An aliquot of adult serum was diluted and added with purified UspA1 or UspA2 from O35E strain to a final 50 µg/ml protein concentration and final 1:10 serum dilution. The mixtures were incubated at 4° C. for 2 h, and precipitates removed by microcentrifugation.
[b]IgG titers against the UspA1 and UspA2 proteins were end point titers determined with a starting serum dilution of 1:500.

The bactericidal titers of the absorbed sera were determined and compared with those seen before absorption (Table XVIII). Absorption with either UspA1 or UspA2 resulted in complete loss of bactericidal activity (<50) for all six sera when assayed against the O35E strain, the strain from which the purified proteins were made (Table XVIII). The bactericidal activity of the absorbed sera was also reduced by at least three fold when assayed against the a heterologous strain 1230-359. Absorption using UspA1 resulted in greater reduction of the bactericidal titer against the heterologous strain in 3 out of 6 samples compared to absorptions using UspA2 (Table XVIII). This result was consistent with the difference in the reductions of ELISA titers to the UspA1 after absorption with the two proteins. Absorption using the combined proteins UspA1 and UspA2 did not result in further reduction of the bactericidal activity compared to UspA1 alone. All six human sera contained antibodies to a 74 kDa OMP from M. catarrhalis as determined by western blot analysis, and absorption using the purified 74 kDa protein did not affect the bactericidal activity of either the O35E strain or the 1230-357 strain. This indicated that antibodies to the UspA proteins were the major source of the bactericidal activity against M. catarrhalis in adult sera.

TABLE XVIII

Bactericidal titer of the adult human sera before and after absorption[a]

| Adsorbent | #1 | #2 | #3 | #4 | #5 | #6 |
|---|---|---|---|---|---|---|
| | Bactericidal titer to O35E strain in sample[b] | | | | | |
| saline | 450 | >1350 | 450 | 50 | 150 | 450 |
| UspA1 | <50 | <50 | <50 | <50 | <50 | <50 |
| UspA2 | <50 | 150 | <50 | <50 | <50 | <50 |

TABLE XVIII-continued

Bactericidal titer of the adult human sera before and after absorption[a]

| Adsorbent | #1 | #2 | #3 | #4 | #5 | #6 |
|---|---|---|---|---|---|---|
| | Bactericidal titer to 1230-359 strain[b] | | | | | |
| saline | 450 | 4050 | >1350 | 150 | 150 | 450 |
| UspA1 | 50 | 150 | <50 | <50 | 50 | 150 |
| UspA2 | 150 | 1350 | 450 | <50 | 50 | 50 |

[a]Sera were the same as those described in Table XVII.
[b]Bactericidal titer: The bactericidal activity was measured against the O35E or 1230-359 strains with 3-fold diluted sera starting at 1:50. The highest serum dilution resulting in 50% or greater killing was determined as the bactericidal titer. The purified UspA1 and UspA2 proteins used for absorption were made from the O35E strain.

Because only small volumes of the children sera were available, absorption of these sera was done using a mixture of UspA1 and UspA2 proteins. Absorption resulted in the complete loss or a significant reduction of bactericidal activity in four out of seven sera (Table XIX). The four sera including three from two month old children all had an initial bactericidal titer of 200 or greater prior to absorption. The other three sera, which did not show a change in bactericidal titer upon absorption, all had a marginal titer of 50 before absorption. The reduction in ELISA reactivity to the UspA proteins after absorption confirmed that the antibody concentration had been reduced. This suggested that antibodies specific for the UspA1 and UspA2 proteins in children's sera were also a major source of the bactericidal activity towards M. catarrhalis.

TABLE XIX

Bactericidal activity of children's sera before and after absorption with pooled purified UspA1 and UspA2[a]

| Sample | Age (months) | Unabsorbed serum | | Absorbed serum | |
|---|---|---|---|---|---|
| | | $A_{415}$[b] | BC titer[c] | $A_{415}$[b] | BC titer[c] |
| 1 | 2 | 0.84 | 200 | 0.29 | <50 |
| 2 | 2 | 0.93 | 200 | 0.19 | <50 |
| 3 | 2 | 0.98 | 500 | 0.38 | 50 |
| 4 | 18 | 0.88 | 200 | 0.43 | 50 |
| 5 | 15 | 0.66 | 50 | 0.25 | 50 |
| 6 | 18 | 0.62 | 50 | 0.32 | 50 |
| 7 | 15 | 0.68 | 50 | 0.35 | 50 |

[a]Absorption: Each serum was absorbed with a mixture of UspA1 and UspA2 proteins from O35E strain at final protein concentrations of 200, 50 or 20 µg/ml. The same result was seen for all three absorptions of each sample. Only the data from the assay using 20 µg/ml of protein are shown.
[b]$A_{415}$: The absorbance at 415 nm in ELISA using the mixture of UspA1 and UspA2 as detection antigen. Sera were tested at a 1:300 dilution.
[c]BC titer: Highest serum dilution resulting in 50% or greater killing of the O35E strain in the assay. Sera were assayed at dilutions 1:50, 200, and 500.

Affinity purified antibodies to UspA1 and UspA2: To confirm their cross-reactivity and bactericidal activity, antibodies to UspA1 or UspA2 from adult plasma were isolated by an affinity purification procedure. The purified antibodies reacted specifically with the UspA1 and the UspA2 proteins but not with non-UspA proteins in the O35E lysates in a western blot assay. The purified antibodies to one protein also reacted to the other with almost equivalent titer in ELISA (Table XX). Both antibody preparations exhibited reactivity with five M. catarrhalis strains in the whole-cell ELISA and bactericidal assay (Table XXI). The bactericidal titers against all five M. catarrhalis strains ranged between 400 and 800, which was equivalent to 0.25-0.50 µg/ml of the protein in the purified antibody preparations (Table XXI).

TABLE XX

Cross-reactivity of affinity purified human antibodies to UspA1 and UspA2 in ELISA

| Antibodies purified to[a] | IgG titers against[b] | |
|---|---|---|
| | UspA1 | UspA2 |
| UspA1 | 50,468 | 20,088 |
| UspA2 | 53,106 | 52,834 |

[a]The antibodies were purified from plasma pooled from two healthy adults by immune elution using purified UspA1 or UspA2 from the O35E strain immobilized on nitrocellulose membrane.
[b]ELISA end point titers are the highest antibody dilutions giving an $A_{415}$ greater than three times the background.

TABLE XXI

Whole cell ELISA titer and bactericidal titer of affinity purified human antibodies to UspA1 and UspA2[a]

| Assay | Whole cell ELISA titer[b] | | BC titer[c] | |
|---|---|---|---|---|
| strain | Ab to UspA1 | Ab to UspA2 | Ab to UspA1 | Ab to UspA2 |
| O35E | 12,553 | 9,939 | 400 | 800 |
| ATCC25238 | 30,843 | 29,512 | 400 | 400 |
| TTA24 | 51,511 | 57,045 | 800 | 800 |
| 216:96 | 31,140 | 23,109 | 400 | 400 |
| 1230-359 | 8,495 | 16,458 | 800 | 800 |

[a]The purified antibody preparations were the same as described in Table XX. The specific reactivities of the purified antibodies to UspA proteins, but not other outer membrane proteins, were confirmed by western blots.
[b]ELISA end point titers are the highest antibody dilutions giving an $A_{415}$ greater than three times the background when assayed against whole bacterial cells.
[c]BC titer: Highest antibody dilution resulting in 50% or greater killing of the bacterial inoculum in the assay. Antibodies (120 μg/ml) were assayed at dilutions 1:100, 200, 400, and 800.

Discussion

Previous studies examining human antibodies to *M. catarrhalis* whole cells or outer membrane proteins usually focused on a single age group. Further, the biological function of the antibodies was left largely undetermined (Chapman et al., 1985), and the antigens eliciting the functional antibodies were not identified. Thus, these previous studies did not provide information as to the role of naturally acquired antibodies in protection against *M. catarrhalis* diseases, nor did they provide clear information as to what antigens are suitable for vaccine development. The data from this study indicate that the IgG antibodies to UspA1 and UspA2 are present in normal human sera and their levels are age-dependent. These antibodies are an important source of serum bactericidal activity in both children and adults.

These data indicated that most children had serum IgG antibodies to both UspA1 and UspA2 at two months of age although the level varied from individual to individual, and the IgG subclass profile in these infant sera was similar to that in adult sera. The infant sera had bactericidal activity. The absorption studies suggested that the bulk of the bactericidal antibodies in these sera were directed against the UspA1 and the UspA2 proteins. These results suggest that the IgG antibodies detected in the two month old children are of maternal origin. This is consistent with the report that umbilical cord serum contains high titers of antibodies to an extract of *M. catarrhalis* whole cells (Ejlertsen et al., 1994b).

Due to the lack of clinical information on the study subjects and small number of subjects examined in this study, it could not be determined whether maternal antibodies against UspA, although bactericidal in vitro, were protective in young children. However, at two months of age the children had significantly higher serum IgG titers against the UspA proteins and only a few of these children had a low level of IgA antibodies to *M. catarrhalis* as compared to children at 15-18 months of age. If serum IgA reflects prior mucosal exposure to the bacterium, then most of the children are not infected by *M. catarrhalis* in the first few months of age. One of the reasons may be that the maternal antibodies present in the young children protect them from infection at this age. This is consistent with the finding that young children seldom carry this bacterium and do not develop *M. catarrhalis* disease during the first months of life (Ejlertsen et al., 1994a).

Children may become susceptible to *M. catarrhalis* infection as maternal antibodies wane. In this study, the sera from 6 to 7 month old children had the lowest level of IgG antibodies to the UspA proteins and barely detectable bactericidal titers against whole cells of *M. catarrhalis*. By 15 months of age, nearly all children had serum IgA antibodies to the UspA proteins, and the level of IgA antibodies had significantly increased along with the level of IgG antibodies and bactericidal activity when compared with children of 6 to 7 months of age. This suggested that these children had been exposed to the bacterium and mounted an antibody response. The fifteen sera from the group of 18-36 month old children all had IgG and IgA titers to the UspA proteins and the bactericidal titers varied greatly. The UspA specific IgG antibodies in the older children's sera had different characteristics than the antibodies from the two month old children. First, the IgG1 antibody titer was significantly higher than the IgG3 titer in children's sera, while the opposite was true for the 2 month old children (FIG. 10). Second, most sera from 2 month old children had bactericidal activity, while bactericidal activity was barely detectable in the sera from children of 6 months or older. The low antibody level and the low serum bactericidal activity seen in children between 6-36 months of age is consistent with the epidemiological findings that children of this age group have the highest colonization rate and highest incidence of *M. catarrhalis* disease (Bluestone, 1986; Ejlertsen et al., 1994b; Leinonen et al., 1981; Roitt et al., 1985; Ruuskanen and Heikkinen, 1994; Sethi et al., 1995; Teele et al., 1989).

Adults, a population usually resistant to *M. catarrhalis* infections (Catlin, 1990; Ejlertsen et al., 1994a), were found to have consistently higher levels of IgG antibodies to the UspA proteins as well as higher serum bactericidal activity than children. The bactericidal activity of the adult sera was clearly antibody-mediated since immunoglobulin depleted sera had no activity (Chen et al., 1996), and the antibodies purified from adult plasma exhibited complement dependent bactericidal activity. The antibodies purified from human sera using UspA1 or UspA2 from a single isolate exhibited killing against multiple strains. This result indicates that humans developed bactericidal antibodies toward the conserved epitopes of UspA proteins in response to natural infections.

In all adult samples, the IgG antibodies were primarily of the IgG1 and IgG3 subclasses with IgG3 being higher. This is consistent with previous reports that the IgG3 subclass is a major constituent of the immune response to *M. catarrhalis* in adults and children greater than 4 years of age, but not in younger children (Carson et al., 1994; Goldblatt et al., 1990). Of the four IgG subclasses in humans, IgG3 constitutes only a minor component of the total immunoglobulin in serum. However, IgG3 antibody has the highest affinity to interact with Cl q, the initial step in the classic complement pathway leading to elimination of the bacterium by both complement-dependent killing and opsono-phagocytosis (Roitt et al., 1985). Since IgG3 antibody is efficiently transferred across the placenta, it may also confer protective immunity to infants. The data from this study indicate that IgG3 antibody to the UspA proteins is an important component of the immune response to natural infection and has in vitro biological activity.

As clinical information related to *M. catarrhalis* infection was not collected for the study subjects, it is unknown how the antibodies to UspA1 or UspA2 were induced. When antibodies made against the UspA proteins in guinea pigs were tested for reactivity with other bacterial species, including *Pseudomonas aeruginosa, Neisseria meningitidis, Neisseria gonorrhoeae, Bordetella pertussis, Escherichia coli*, and nontypable *Haemophilus influenzae* by western blot, no reactivity was detected. This suggests that the antibodies were elicited as a specific response to the UspA antigens of *M. catarrhalis*. This is consistent with the high colonization rate and the endemic nature of this organism in human populations. Since the affinity purified antibodies to the two UspA proteins were cross-reactive, it could not be determined whether the human antibodies were elicited by one or both proteins. It seemed clear that the shared sequence between these two proteins was the main target of the bactericidal antibodies.

In summary, this study demonstrated that antibodies to the two UspA proteins are present in nearly all humans regardless of age. The overall level and subclass distribution of these antibodies, however, were age-dependent. IgG antibodies against UspA1 and UspA2 were cross-reactive, and are a major source of serum bactericidal activity in adults. The level of these antibodies and serum bactericidal activity appears to correlate with age-dependent resistance to *M. catarrhalis* infection. Since humans make an antibody response to many other *M. catarrhalis* antigens in addition to UspA1 and UspA2 after natural infection, it remains to be determined if immunization with one or both UspA proteins will confer adequate protection in susceptible populations.

Example VI

UspA2 as a Carrier for Oligosaccharides

UspA2 as a Pneumococcal Saccharide Carrier.

This study demonstrates that UspA2 can serve as a carrier for a pneumococcal saccharide. A seven valent pneumococcal polysaccharide was conjugated to UspA2 by reductive amination. Swiss Webster mice were immunized on wk 0 and wk 4 and a final bleed taken on wk 6. Each mouse was immunized subcutaneously (s.c.) in the abdomen with 1 µg carbohydrate per dose with aluminum phosphate as the adjuvant. A group of mice was immunized with the PP7F-CRM conjugate as a control. The data for the sera from the 6 wk bleed are shown in Table XXII, Table XXIII, and Table XXIV. The conjugate elicited antibodies against both the polysaccharide as well as bactericidal antibodies to *M. catarrhalis*. These results demonstrate that UspA2 can serve a carrier for eliciting antibodies to this pneumococcal saccharide and retain its immunogenicity to UspA2.

TABLE XXII

Titers elicited by 7F conjugates to the pneumococcal polysaccharide 7F

| Antigen | IgG ELISA titer to Pn Ps 7F* |
| --- | --- |
| PP7F-UspA2 mix | <100 |
| PP7F-UspA2 conjugate | 9,514 |
| PP7F-CRM conjugate | 61,333 |

*Pool of sera from five mice.

TABLE XXIII

ELISA titers of sera against whole cells of three *M. catarrhalis* isolates

| Immunogen | Strain Tested | | |
| --- | --- | --- | --- |
| Group[1] | 035E | 430-345 | 1230-359 |
| PP7F-UspA2[2] mix | 51,409 | 4,407 | 9,124 |
| PP7F CRM conjugate | 56 | 49 | 47 |
| PP7F UspA2 conjugate | 31,111 | 3,529 | 8,310 |

[1]Vaccine group consists of 5 Swiss-Webster mice. Each group immunized at wk 0 and wk 3 and serum collected at wk 6.

[2]Vaccine composed of 1 µg Pneumo Type 7F and 1 µg UspA2 adjuvanted with aluminum phosphate.

TABLE XXIV

Complement dependent bactericidal antibodies against three *M. catarrhalis* isolates

| Immunogen | Strain Tested | | |
| --- | --- | --- | --- |
| Group[1] | 035E | 430-345 | 1230-359 |
| PP7F-UspA2 mix | 400 | 400 | 400 |
| PP7F CRM conjugate | <100 | <100 | <100 |
| PP7F UspA2 conjugate | 400 | 400 | 200 |

[1]$BC_{50}$ titer is highest serum dilution at which >50% of bacteria were killed as compared to serum from wk 0 mice. The most concentrated serum tested was a 1:100 dilution.

UspA2 as an *Haemophilus* b Oligosaccharide Carrier.

This study demonstrates that UspA2 can serve as a carrier for an *Haemophilus influenzae* type b oligosaccharide (HbO). An HbO sample (average DP=24) was conjugated to UspA2 by aqueous reductive amination in the presence of 0.1% Triton X-100. The ratio of the HbO to UspA2 was 2:1 by weight. Conjugation was allowed to proceed for 3 days at 35° C. and the conjugate diafiltered using an Amicon 100K cutoff membrane. The conjugate ratio (mg carbohydrate/mg UspA2) was 0.43:1. The carbohydrate was determined by orcinal assay and the protein by Lowry. The number of hydroxy-ethyl lysines was determined by amino acid analysis and found to be 12.6.

The immunogenicity of the conjugate was examined by immunizing Swiss-Webster mice. The mice were immunized twice on wk 0 and wk 4 with 1 µg of carbohydrate. No adjuvant was used with the conjugate, but was used with UspA2. The sera were pooled and titered. The reactivity toward HbPS by the radioantigen binding assay (RABA) was similar to that seen when HbO is conjugated to $CRM_{197}$ (Table XXV). The whole cell titer toward the homologous *M. catarrhalis* isolate (O35E) was similar to that seen for non-conjugated USpA2 (Table XXVI), as were the bactericidal titers (Table XXVII). Thus, when a carbohydrate antigen that typically elicits a RABA titer less than 0.10 is conjugated to UspA2, it becomes immunogenic.

TABLE XXV

Comparison of immunogenicity of HbO conjugated to UspA2 to HbO conjugated to $CRM_{197}$ to *Haemophilus* b polysaccharide by Radioantigen Binding Assay (RABA)

| Week | HbO-$CRM_{197}$ | Hbo-UspA2 |
|---|---|---|
| 0 | <0.10 | <0.10 |
| 3 | 2.51 | 2.87 |
| 4 | 4.46 | 3.56 |
| 6 | 58.66 | 18.92 |

TABLE XXVI

Comparison of immunogenicity of HbO-UspA2 conjugate with non-conjugated UspA2 by ELISA against whole cell of the O35E isolate to *M. catarrhalis*

| Week | UspA2[a] | Hbo-UspA2 |
|---|---|---|
| 0 | <50 | <50 |
| 4 | 54,284 | 17,424 |
| 6 | 345,057 | 561,513 |

[a]5 μg UspA2 adjuvanted with 500 μg aluminum phosphate.

TABLE XXVII

Bactericidal of sera toward two *M. catarrhalis* isolates.

| Isolate | UspA2[a] | Hbo-UspA2 |
|---|---|---|
| O35E | 4,500 | >4,500 |
| 345 | n.d. | 450 |

[a]5 μg UspA2 adjuvanted with 500 μg aluminum phosphate.
n.d. = not determined

Example VII

Association of Mouse Serum Sensitivity with Expression of Mutant Forms of UspA2

When bacteria are killed in the presence of serum that lack specific antibodies toward them, it is called "serum sensitivity." In the case of *M. catarrhalis*, the mutants lacking an intact UspA2 protein have been found to be serum sensitive. These mutants were constructed so that one (O35E.1; refer to Example IX for a description of isolates O35E.1, O35E.2 and O35E.12) did not express UspA1, one (O35E.2) did not express UspA2, and one (O35E.12) did not express either protein based on a lack of reactivity with the 17C7 monoclonal antibody. The O35E.2 and O35E.12, however, expressed a smaller truncated form UspA2 (tUspA2) that reacts with antibodies prepared by immunizing mice with purified UspA2. The tUspA2 could be detected in a western blot of bacterial lysates using either polyclonal anti-UspA2 sera or the MAb 13-1. The size of the smaller form was consistent with the gene truncation used for the construction of the two mutants.

This bactericidal capacity was tested by mixing the non-immune mouse sera, a 1:5 dilution of human complement and a suspension of bacteria (Approx. 1000 cfu) in the wells of a microtiter plate. The mouse sera were tested at both a 1:50 and 1:100 dilution. The number of surviving bacteria was then determined by spreading a dilution of this bacterial suspension on agar growth medium. The killing was considered significant when fewer than 50% viable bacteria as cfu's were recovered relative to the samples without mouse sera. Killing by the non-immune sera was seen only for the mutants lacking a "complete" UspA2 (Table XXVIII).

TABLE XXVIII

Bactericidal activity of the pre-immune sera from Balb/c mice

| Mutant | Proteins Expressed | Bactericidal Activity of Normal Mouse Sera |
|---|---|---|
| O35E | UspA1 & UspA2 | − |
| O35E.1 | UspA2 | − |
| O35E.2 | UspA1 & tUspA2 | + |
| O35E.12 | tUspA2 | + |

Example VIII

Identification of a Decapeptide Epitope in UspA1 that Binds MAb 17C7

It was clear from the work with different strains of *M. catarrhalis* and analyses of their protein sequences of UspA1 that certain epitopic regions must exist which are similar, if not identical, in all of the strains and provide the basis of the immunogenic response in humans. In order to identify such immunogenic epitope(s), peptides spanning the UspA1 region known to contain the binding site for MAb 17C7 were prepared and examined for their ability to bind to MAb 17C7.

Figure 12:
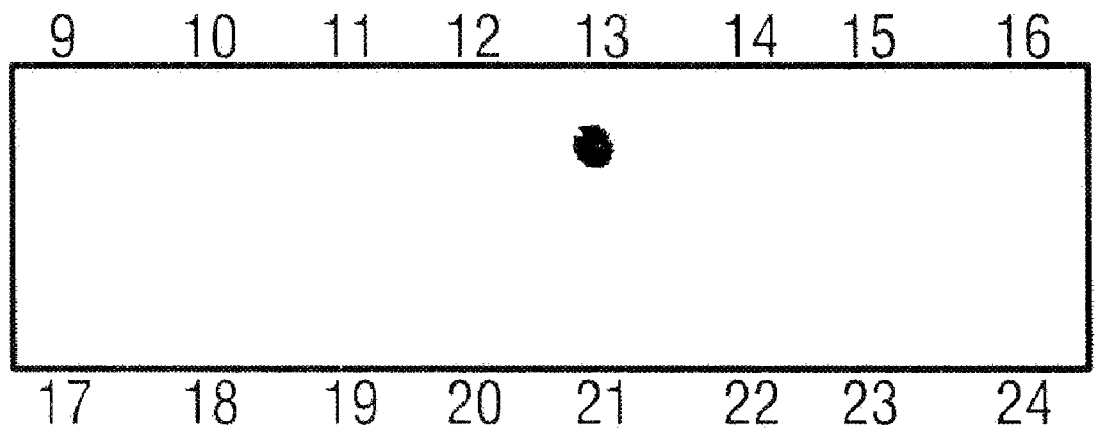
FIG. 12. Schematic drawing showing the relative positions of decapeptides 10-24 within the region of UspA1 and UspA2 which binds to MAb 17C7.

Specifically, overlapping synthetic decapeptides, as shown in Table XXIX and FIG. 12, that were N-terminally bound to a membrane composed of derivatized cellulose were obtained from Research Genetics Inc. (Huntsville, Ala.). After five washes with PBS-Tween containing 5% (w/v) non-fat dry milk, the membrane was subsequently incubated with MAb 17C7 (in the form of hybridoma culture supernatant) overnight at 4° C. Following three washes with PBS-Tween, the membrane was incubated overnight at 4° C. with gentle rocking with $10^6$ cpm of radioiodinated (specific activity $2 \times 10^7$ cpm/μg protein), affinity-purified goat anti-mouse immunoglobulin. The membrane was then washed as before and exposed to X-ray film (Fuji RX safety film, Fuji Industries, Tokyo, Japan).

TABLE XXIX

Decapeptides Used to Identify Binding Site for MAb 17C7

| PEPTIDE # | PEPTIDE SEQUENCE | |
|---|---|---|
| 9 | SGRLLDQKAD | SEQ ID NO:81 |
| 10 | QKADIDNNIN | SEQ ID NO:82 |
| 11 | NNINNIYELA | SEQ ID NO:83 |
| 12 | NNIYELAQQQ | SEQ ID NO:84 |
| 13 | YELAQQQDQH | SEQ ID NO:18 |
| 14 | AQQQDQHSSD | SEQ ID NO:85 |
| 15 | QDQHSSDIKT | SEQ ID NO:86 |
| 16 | HSSDIKTLKN | SEQ ID NO:87 |
| 17 | DIKTLKNNVE | SEQ ID NO:88 |
| 18 | TLKNNVEEGL | SEQ ID NO:89 |
| 19 | EEGLLDLSGR | SEQ ID NO:90 |
| 20 | LSGRLIDQKA | SEQ ID NO:91 |
| 21 | DQKADIAKNQ | SEQ ID NO:92 |
| 22 | AKNQADIAQN | SEQ ID NO:93 |
| 23 | IAQNQTDIQD | SEQ ID NO:94 |
| 24 | DIQDLAAYNE | SEQ ID NO:95 |

Figure 13:
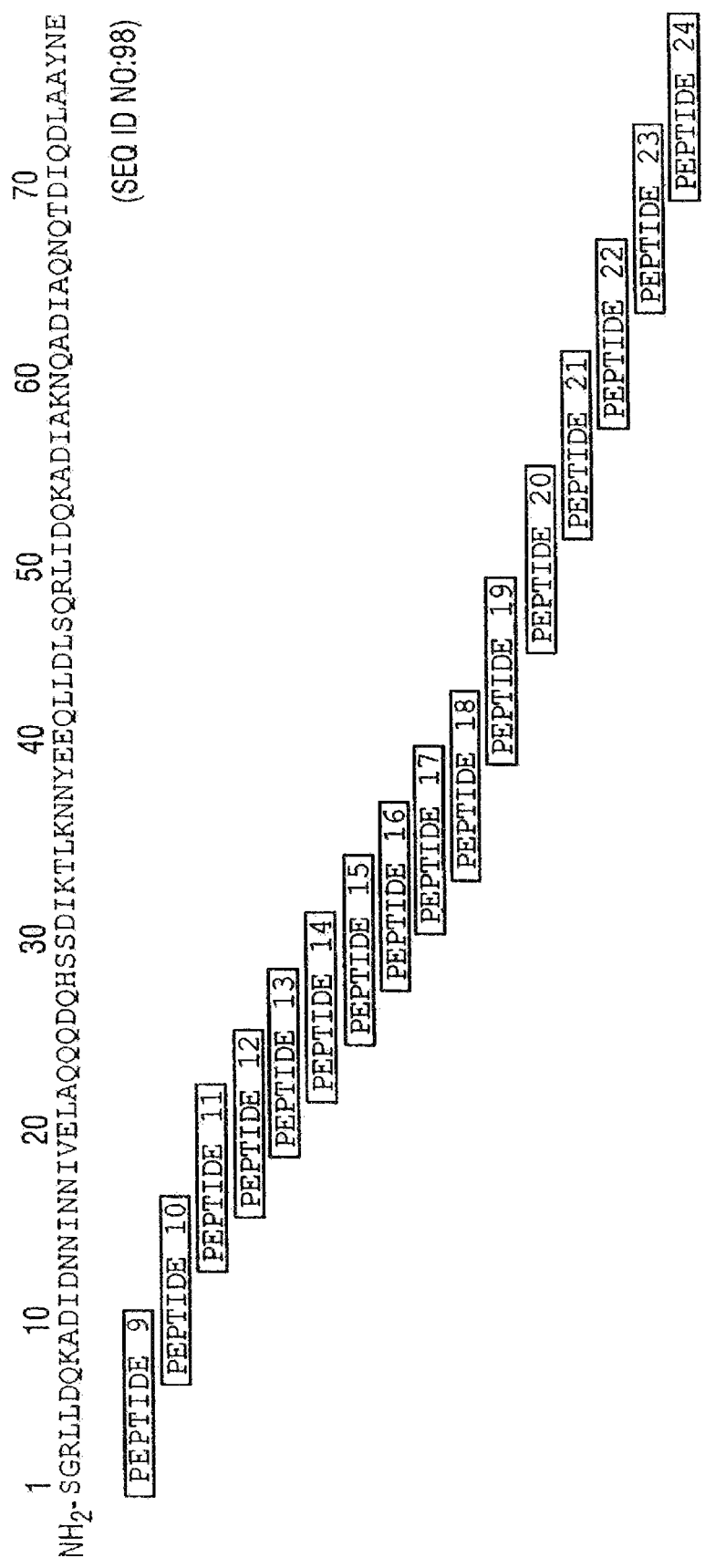
FIG. 13. Western dot blot analysis demonstrating reactivity of decapeptides 10-24 with MAb 17C7.

It is clear from the dot blot results shown in the autoradiograph (FIG. 13) that peptide 13, YELAQQQDQH (SEQ ID NO:18) exhibited optimal binding of MAb 17C7 with peptide 14 (SEQ ID NO:85) exhibiting less than optimal binding.

This same peptide (SEQ ID NO:18) is present in UspA2 which explains why both proteins bind to MAb 17C7.

Interestingly, peptide 12 shows no binding and binding by peptides 15, 16, 19, 22, 23 is probably non-specific. Thus, a comparison of peptides 12, 13, and 14 yields the conclusion that the 7-mer AQQQDQH (SEQ ID NO:17) is an essential epitope for MAb 17C7 to bind to UspA1 and UspA2. This conclusion is in agreement with the current understanding that an immunogenic epitope may comprise as few as five, six or seven amino acid residues.

Example IX

Phenotypic Effect of Isogenic uspA1 and uspA2 Mutations on M. catarrhalis Strain O35E Materials and Methods Bacterial strains, plasmids and growth conditions. The bacterial strains and plasmids used in this study are listed in Table XXX. M. catarrhalis strains were routinely grown at 37° C. on Brain-Heart Infusion (BHI) agar plates (Difco Laboratories, Detroit, Mich.) in an atmosphere of 95% air-5% $CO_2$ supplemented, when necessary, with kanamycin (20 µg/ml) (Sigma Chemicals Co., St. Louis, Mo.) or chloramphenicol (0.5 µg/ml) (Sigma), or in BHI broth. The BHI broth used to grow M. catarrhalis cells for attachment assays was sterilized by filtration. Escherichia coli strains were cultured on Luria-Bertani (LB) agar plates (Maniatis et al., 1982) supplemented, when necessary, with ampicillin (100 µg/ml), kanamycin (30 µg/ml), or chloramphenicol (30 µg/ml).

TABLE XXX

Bacterial Strains and Plasmids Used in this Study

| Strain or plasmid | Description | Source or reference |
|---|---|---|
| *M. catarrhalis* | | |
| O35E | Wild-type isolate from middle ear fluid | Helminen et al., 1994 |
| O35E.1 | Isogenic mutant of O35E with a kan cartridge in the uspA1 structural gene | Aebi et al., 1997 |
| O35E.2 | Isogenic mutant of O35E with a kan cartridge in the uspA2 structural gene | Aebi et al., 1997 |
| O35E.12 | Isogenic mutant of O35E with a kan cartridge in the uspA2 structural gene and a cat cartridge in the uspA1 structural gene | This study |
| P-44 | Wild-type isolate that exhibits rapid hemagglutination | Soto-Hernandez et al., 1989 |
| P-48 | Wild-type isolate that exhibits slow hemagglutination | Soto-Hernandez et al., 1989 |
| *Escherichia coli* | | |
| DH5α | Host for cloning studies | Stratagene |
| Plasmids | | |
| pBluescript II | Cloning vector; Amp$^r$ | Stratagene |
| pUSPA1 | pBluescript II SK+ with a 2.7 kb insert containing most of the uspA1 gene of M. catarrhalis strain O35E | Aebi et al., 1997 |
| pUSPA1CAT | pUSPA1 with a cat cartridge replacing the 0.6 kb BglII fragment of the uspA1 gene | This study |

Characterization of outer membrane proteins. Whole cell lysates and outer membrane vesicles of M. catarrhalis strains were prepared as described (Murphy and Loeb, 1989; Patrick et al., 1987). Proteins present in these preparations were resolved by SDS-PAGE and detected by staining with Coomassie blue or by western blot analysis as described (Helminen et al., 1993a).

Monoclonal antibodies (MAbs). MAb 17C7, a murine IgG antibody that reacts with a conserved epitope of both UspA1 and UspA2 from M. catarrhalis strain O35E, as described in earlier examples herein, was used for immunologic detection of these proteins. MAb 17C7 was used in the form of hybridoma culture supernatant fluid in western blot analysis and in the indirect antibody-accessibility assay. MAb 3F12, an IgG MAb specific for the major outer membrane protein of Haemophilus ducreyi (Klesney-Tait et al., 1997), was used as a negative control in the indirect antibody-accessibility assay.

Molecular cloning methods. Chromosomal DNA of M. catarrhalis strain O35E was used as the template in a polymerase chain reaction (PCR™) system together with oligonucleotide primers derived from either just after the start of the strain O35E uspA1 open reading frame (i.e., P1 in FIG. 14) or just after the end of this open reading frame (i.e., P2 in FIG. 14). These primers were designed to contain a BamHI restriction site at their 5'-end. The sequence of these primers was:

P1—5'-CGGGATCCGTGAAGAAAAATGCCG-CAGGT-3' (SEQ ID NO:96);

P2—5'-CGGGATCCCGTCGCAAGCCGATTG-3' (SEQ ID NO:97).

DNA fragments were amplified using a PTC 100 Programmable Thermal Controller (MJ Research, Inc., Cambridge, Mass.) and the GeneAmp PCR™ kit (Roche Molecular Systems, Inc., Branchburg, N.J.). PCR™ products were extracted from 0.7% agarose gel slices using the Qiaex Gel Extraction Kit (Qiagen, Inc., Chadsworth, Calif.) and digested with BamHI (New England Biolabs, Inc., Beverly, Mass.) for subsequent ligation into the BamHI site of pBluescript TI SK+ (Stratagene, La Jolla, Calif.). Ligation reactions were performed with overnight incubation at 16° C. using T4 DNA ligase (Gibco BRL, Inc., Gaithersburg, Md.). Competent E. coli DH5α cells were transformed with the ligation reaction mixture according to a standard heat-shock procedure (Sambrook et al., 1989) and the desired recombinants were selected by culturing in the presence of an appropriate antimicrobial compound. The 1.3 kb chloramphenicol (cat) resistance cartridge was prepared by excision (using BamHI) from pUCΔECAT (Wyeth-Lederle, Rochester, N.Y.). The cat cartridge was subsequently ligated into BglII restriction sites located in the mid-portion of cloned segment from the uspA1 gene and, after transformation of competent E. coli DH5 cells, recombinant clones were identified by selection on solidified media containing chloramphenicol.

Transformation of M. catarrhalis. The electroporation method used for transformation of M. catarrhalis strain O35E has been described in detail (Helminen et al., 1993b). Briefly, a 30-ml portion of a logarithmic-phase broth culture (109 colony forming units [cfu]/ml) was harvested by centrifugation, washed three times with 10% (v/v) glycerol in distilled water, and resuspended in 100 µl of the same solution. A 20-µl portion of these cells was electroporated with 5 µg of linear DNA (i.e., the truncated uspA1 gene containing the cat cartridge) in 5 µl of water in a microelectroporation chamber (Cel-Porator Electroporation system; Bethesda Research Laboratories, Gaithersburg, Md.) by applying a field strength of 16.2 kV over a distance of 0.15 cm. Following electroporation, the cell suspension was transferred to 1 ml of BHI broth and incubated with shaking at 37° C. for 90 min. Ten 100-μl portions were then spread on BHI agar plates containing the appropriate antimicrobial compound.

Southern blot analysis. Chromosomal DNA purified from wild-type and mutant *M. catarrhalis* strains strains was digested with either PvuII or HindIII (New England Biolabs) and Southern blot analysis was performed as described (Sambrook et al., 1989). Double-stranded DNA probes were labeled with $^{32}$P by using the Random Primed DNA Labeling Kit (Boehringer-Mannheim, Indianapolis, Ind.).

Indirect antibody-accessibility assay. Overnight BHI broth cultures of *M. catarrhalis* strain O35E and its isogenic mutants were diluted in PBS buffer containing 10% (v/v) fetal bovine serum and 0.025% (w/v) sodium azide (PBS-FBS-A) to density of 110 Klett units (ca. $10^9$ cfu/ml) as measured with a Klett-Summerson colorimeter (Klett Manufacturing Co., New York, N.Y.). Portions (100 μl) of this suspension were added to 1 ml of MAb 17C7 or MAb 3F12 culture supernatant. After incubation at 4° C. for one hour with gentle agitation, the bacterial cells were washed once and suspended in 1 ml of PBS-FBS-A. Affinity-purified goat anti-mouse immunoglobulin, radiolabeled with $^{125}$I to a specific activity of $10^8$ cpm per μg, was added and the mixture was incubated for one hour at 4° C. with gentle agitation. The cells were then washed four times with 1 ml of PBS-FBS-A, suspended in 500 μl of triple detergent (Helminen et al., 1993a) and transferred to glass tubes. The radioactivity present in each sample was measured by using a gamma counter.

Autoagglutination and hemagglutination assays. The ability of *M. catarrhalis* strains to autoagglutinate was assessed using bacterial cells grown overnight on a BHI agar plate. These cells were resuspended in PBS to a turbidity of 400 Klett units in a glass tube and subsequently allowed to stand at room temperature for ten minutes at which time the turbidity of this suspension was again determined. Rapid and slow autoagglutination were defined as turbidities of less that and greater than 200 Klett units, respectively, after 10 minutes. The hemagglutination slide assay using heparinized human group 0 Rh$^+$ erythrocytes was performed as previously described (Soto-Hernandez et al., 1989).

Serum bactericidal assay. Complement-sufficient normal adult human serum was prepared by standard methods. Complement inactivation was achieved by heating the serum for 30 min at 56° C. A *M. catarrhalis* broth culture in early logarithmic phase was diluted in Veronal-buffered saline containing 0.10% (w/v) gelatin (GVBS) to a concentration of $1-2\times10^5$ cfu/ml, and 20 μl portions were added to 20 μl of native or heat-inactivated normal human serum together with 160 μl of Veronal-buffered saline containing 5 mM MgCl$_2$ and 1.5 mM CaCl$_2$. This mixture was incubated at 37° C. in a stationary water bath. At time 0 and at 15 and 30 min, 10 μl aliquots were removed, suspended in 75 μl of BHI broth and spread onto prewarmed BHI agar plates.

Adherence assay. A method used to measure adherence of *Haemophilus influenzae* to Chang conjunctival cells in vitro (St. Geme III and Falkow, 1990) was adapted for use with *M. catarrhalis*. Briefly, 2-3×10$^5$ HEp-2 cells (ATCC CCL 23) or Chang conjunctival cells (ATCC CCL 20.2) were seeded into each well in a 24-well tissue culture plate (Corning-Costar) and incubated for 24 h before use. A 0.3 ml volume from an antibiotic-free overnight culture of *M. catarrhalis* was inoculated into 10 ml of fresh BHI medium lacking antibiotics and this culture was subsequently allowed to grow to a concentration of approximately 5×10$^8$ cfu/ml (120 Klett units) with shaking in a gyrotory water bath. The culture was harvested by centrifugation at 6,000×g at 4-8° C. for 10 min. The supernatant was discarded and a Pasteur pipet was used to gently resuspend the bacterial cells in 5 ml of pH 7.4 phosphate-buffered saline (PBS) or PBS containing 0.15% (w/v) gelatin (PBS-G). The bacterial cells were centrifuged again and this final pellet was gently resuspended in 6-8 ml of PBS or PBS-G.

Portions (25 μl) of this suspension ($10^7$ CFU) were inoculated into the wells of a 24-well tissue culture plate containing monolayers of HEp-2 or Chang cells. These tissue culture plates were centrifuged for 5 min at 165×g and then incubated for 30 min at 37° C. Non-adherent bacteria were removed by rinsing the wells gently five times with PBS or PBS-G, and the epithelial cells were then released from the plastic support by adding 200 μl of PBS containing 0.05% trypsin and 0.02% EDTA. This cell suspension was serially diluted in PBS or PBS-G and spread onto BHI plates to determine the number of viable *M. catarrhalis* present. Adherence was expressed as the percentage of bacteria attached to the human cells relative to the original inoculum added to the well.

Results

Construction of an isogenic *M. catarrhalis* mutant lacking expression of both UspA1 and UspA2. Construction of *M. catarrhalis* mutants lacking the ability to express either UspA1 (mutant strain O35E.1) or UspA2 (mutant strain O35E.2) has been described in previous examples (Aebi et al., 1997). For constructing a double mutant that lacked expression of both UspA1 and UspA2, the 0.6 kb BglII fragment of pUSPA1 (FIG. 14A) was replaced by a cat cassette, yielding the recombinant plasmid pUSPA1CAT. Using the primers P1 and P2, the 3.2 kb insert of pUSPA1CAT was amplified by PCR™. This PCR™ product was used to electroporate the kanamycin-resistant uspA2 strain O35E.2 and yielded the chloramphenicol- and kanamycin-resistant transformant O35E.12, a putative uspA1 uspA2 double mutant.

Southern blot analysis was used to confirm that strains O35E.1, O35E.2, and O35E.12 were isogenic mutants and that allelic exchange had occurred properly, resulting in replacement of the wild-type uspA1 or uspA2 gene, or both, with the mutated allele. Chromosomal DNA preparations from the wild-type parent strain O35E, the uspA1 mutant O35E.1, the uspA2 mutant O35E.2, and the putative uspA1 uspA2 mutant strain O35E.12 were digested to completion with PvuII and probed in Southern blot analysis with DNA fragments derived from these two *M. catarrhalis* genes or with the kan cartridge. For probing with the cat cartridge, chromosomal DNA from strain O35E.12 was digested with HindIII.

Figure 14A:
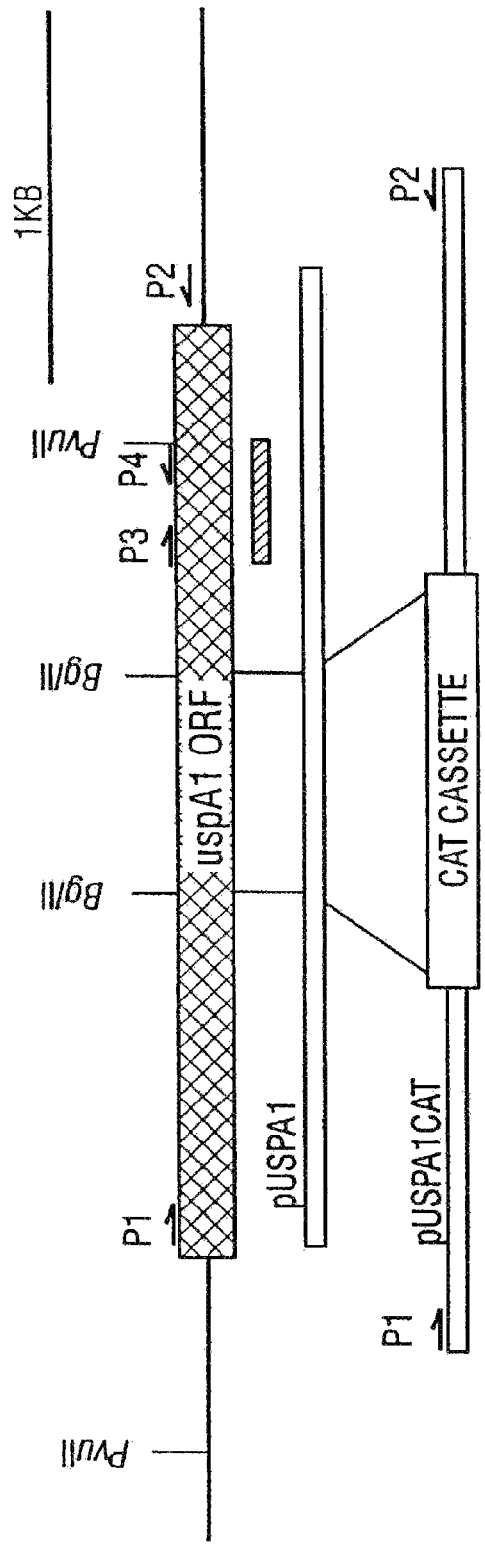
FIG. 14A-14B. Partial restriction enzyme map of the uspA1 (FIG. 14A) and uspA2 (FIG. 14B) genes from M. catarrhalis strain O35E and the mutated versions of these genes. The shaded boxes indicate the open reading frame of each gene. Relevant restriction sites are indicated. PCR™ primer sites (P1-P6) are indicated by arrows. The DNA fragments containing the partial uspA1 and uspA2 open reading frames that were derived from M. catarrhalis strain O35E chromosomal DNA by PCR™ and cloned into pBluescriptII SK+ are indicated by black bars. Dotted lines connect corresponding restriction sites on these DNA inserts and the chromosome. Open bars indicate the location of the kanamycin or chloramphenicol cassettes, respectively. The DNA probes specific for uspA1 or uspA2 are indicated by the appropriate cross-hatched bars and were amplified by PCR™ from M. catarrhalis strain O35E chromosomal DNA by the use of the oligonucleotide primer pairs
Figure 14B:
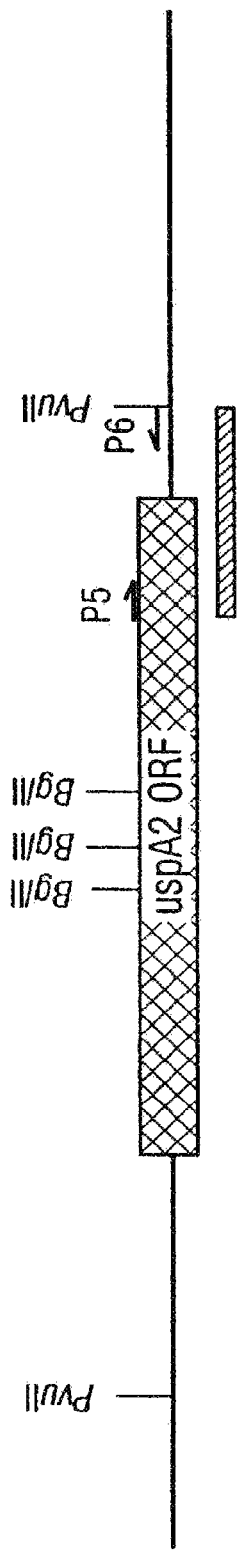

The uspA1-specific DNA probe was obtained by PCR™-based amplification of *M. catarrhalis* strain O35E chromosomal DNA using the primers P3 and P4 (FIG. 14A). A 500-bp uspA2-specific DNA fragment was amplified from O35E chromosomal DNA by PCR™ with the primers P5 and P6 (FIG. 14B). Use of these two gene-specific probes together with the kan and cat cartridges in Southern blot analysis confirmed that strain O35E.12 was a uspA1 uspA2 double mutant.

Characterization of selected proteins expressed by the wild-type and mutant *M. catarrhalis* strains. Proteins present in outer membrane vesicles extracted from the wild-type and these three mutant strains were resolved by SDS-PAGE and either stained with Coomassie blue (FIG. 15A) or probed with MAb 17C7 in western blot analysis (FIG. 15B). The wild-type parent strain O35E possessed a very high molecular weight band detectable by Coomassie blue staining (FIG. 15A, lane 1, closed arrow) that was also similarly abundant in the uspA1 mutant O35E.1 (FIG. 15A, lane 2). The uspA2 mutant O35E.2 (FIG. 15A, lane 3) had a much reduced level of expression of a band in this same region of the gel; this band was not visible at all in the uspA1 uspA2 double mutant O35E.12 (FIG. 2, panel A, lane 4).

Western blot analysis revealed that the wild-type strain (FIG. 15B, lane 1) expressed abundant amounts of MAb 17C7-reactive antigen, most of which had a very high molecular weight, in excess of 220,000. The wild-type strain also exhibited discrete antigens with apparent molecular weights of approximately 120,000 and 85,000 which bound this MAb (FIG. 15B, lane 1, open and closed arrows, respectively). The uspA1 mutant O35E.1 (FIG. 15B, lane 2) lacked expression of the 120 kDa antigen, which was proposed to be the monomeric form of UspA1, but still expressed the 85 kDa antigen. The amount of very high molecular weight MAb 17C7-reactive antigen expressed by this uspA1 mutant appeared to be equivalent to that expressed by the wild-type strain. The uspA2 mutant O35E.2 (FIG. 15B, lane 3) expressed the 120 kDa antigen but lacked expression of the 85 kDa antigen which was proposed to be the monomeric form of the UspA2 protein. In contrast to the uspA1 mutant, the uspA2 mutant had relatively little very high molecular weight antigen reactive with MAb 17C7. Finally, the uspA1 uspA2 double mutant O35E.12 (FIG. 15B, lane 4) expressed no detectable MAb 17C7-reactive antigens.

Binding of MAb 17C7 to whole cells of the wild-type and mutant strains. The indirect antibody-accessibility assay was used to determine whether both UspA1 and UspA2 are exposed on the surface of M. catarrhalis and accessible to antibody. Whole cells of both the wild-type strain O35E and the uspA1 mutant O35E.1 bound similar amounts of MAb 17C7 (Table XXXI). This result suggested that UspA2 is expressed on the surface of M. catarrhalis, or at least on the surface of the uspA1 mutant. The uspA2 mutant O35E.2 bound substantially less MAb 17C7 than did the wild-type strain, but the level of binding was still at least an order of magnitude greater than that obtained with an irrelevant IgG Mab directed against a H. ducreyi outer membrane protein (Table XXXI). As expected from the western blot analysis, the uspA1 uspA2 double mutant O35E.12 did not bind MAb 17C7 at a level greater than obtained with the negative controls involving the H. ducreyi-specific MAb (Table XXXI).

TABLE XXXI

Binding of MAb 17C7 to the Surface of Wild-Type and Mutant Strains of M. catarrhalis

| Strain | Binding[a] of MAb 17C7 | MAb 3F12b |
|---|---|---|
| O35E (wild-type) | 145,583[c] | 4,924 |
| O35E.1 (uspA1 mutant) | 154,119 | 4,208 |
| O35E.2 (uspA2 mutant) | 96,721 | 4,455 |
| O35E.12 (uspA1 uspA2 double mutant) | 6,081 | 3,997 |

[a]Counts per min of $^{125}$I-labeled goat anti-mouse immunoglobulin bound to MAbs attached to the bacterial cell surface, as determined in the indirect antibody-accessibility assay.
[b]MAb 3F12, a murine IgG antibody specific for a H. ducreyi outer membrane protein (Klesney-Tait et al., 1997), was included as a negative control.
[c]The values represent the mean of two independent studies.

Characterization of the growth, autoagglutination, and hemagglutination properties of the wild-type and mutant strains. The colony morphology of these three mutant strains grown on BHI agar plates did not differ from that of the wild-type strain parent strain. Similarly, the rate and extent of growth of all four of these strains in BHI broth were very similar if not identical (FIG. 16). In an autoagglutination assay performed as described in above in the Materials and Methods section of this example, all four strains exhibited the same rate of autoagglutination. Finally, there was no detectable difference between the wild-type parent and the three mutants in a hemagglutination assay using human group O erythrocytes (Soto-Hernandez et al., 1989). Control hemagglutination studies were performed using a pair of M. catarrhalis isolates (i.e., strains P-44 and P48) previously characterized as having rapid or slow rates, respectively, of hemagglutination (Soto-Hernandez et al., 1989).

Effect of the uspA1 and uspA2 mutations on the ability of M. catarrhalis to adhere to human cells. Preliminary studies revealed that the wild-type M. catarrhalis strain O35E adhered readily to HeLa cells, HEp-2 cells, and Chang conjunctival cells in vitro. To determine whether lack of expression of UspA1 or UspA2 affected this adherence ability, the wild-type and the three mutant strains were first used in an attachment assay with Hep-2 cells. In this set of studies, PBS was used as the diluent for washing the HEp-2 cell monolayers and for serial dilution of the trysinized HEp-2 cell monolayer at the completion of the assay. Both the wild-type strain and the uspA2 mutant O35E.2 exhibited similar levels of attachment to HEp-2 monolayers (Table XXXI). The uspA1 mutant O35E.1, however, was less able to adhere to these HEp-2 cells; lack of expression of UspA1 reduced the level of attachment by approximately six-fold (Table XXXII). The uspA1 uspA2 double mutant O35E.12 exhibited a similarly reduced level of attachment (Table XXXII).

TABLE XXXII

Adherence of Wild-Type and Mutant Strains of M. catarrhalis to HEp-2 and Chang Conjunctival Cells in vitro

| | Adherence[a] to | |
|---|---|---|
| Strain | HEp-2 cells[b] | Chang cells[c] |
| O35E (wild-type) | 14.7 ± 4.9 | 51.4 ± 30.8 |
| O35E.1 (uspA1 mutant) | 2.4 ± 0.9 (0.006[d]) | 0.8 ± 0.5 (0.002[d]) |
| O35E.2 (uspA2 mutant) | 19.1 ± 7.0 (0.213[d]) | 55.9 ± 16.7 (0.728[d]) |
| O35E.12 (uspA1 uspA2 double mutant) | 2.3 ± 1.8 (0.011[d]) | 0.6 ± 0.2 (0.002[d]) |

[a]Adherence is expressed as the percentage of the original inoculum that was adherent to the human epithelial cells at the end of the 30 min incubation period. Each number represents the mean (±S.D.) of two independent studies.
[b]PBS was used for washing of the monolayers and for serial dilutions of adherent M. catarrhalis.
[c]PBS-G was used for washing of the monolayers and for serial dilutions of adherent M. catarrhalis.
[d]P value when compared to the wild-type strain O35E using the two-tailed Student t-test.

Control studies revealed, however, that M. catarrhalis cells did not survive well in the PBS used for washing of the HEp-2 monolayer and serial dilution of the attached M. catarrhalis organisms. When $10^8$ CFU of the wild-type and mutant M. catarrhalis strains were suspended in PBS, serially diluted, and allowed to stand for 30 min on ice, the viable number of bacteria decreased to $10^7$ CFU. In contrast, when PBS containing 0.15% (w/v) gelatin (PBS-G) was used for this same type of experiment, there was no reduction in the viability of these M. catarrhalis strains over the duration of the experiment. When the HEp-2 cell-based attachment studies were repeated using PBS-G for washing the HEp-2 cell monolayer and as the diluent, there was only a three-fold reduction in adherence of the uspA1 mutant relative to that obtained with the wild-type parent strain. This finding suggested that the original six-fold difference in attachment ability observed between the wild-type and uspA1 mutant strain may have been attributable in part to viability problems caused by the use of the PBS wash and diluent.

Subsequent studies using Chang conjunctival cells as the target for bacterial attachment together with a PBS-G wash and diluent revealed a substantial difference in the attachment abilities of the wild-type strain and the uspA1 mutant (Table XXXII). Whereas the wild-type and uspA2 mutant exhibited similar levels of attachment to the Chang cells, the extent of attachment of the uspA1 mutant was nearly two orders of magnitude less than that of the wild-type parent strain. The uspA1 uspA2 double mutant also exhibited a much reduced level of attachment similar to obtained with the uspA1 mutant (Table XXXII).

Effect of the uspA1 and uspA2 mutations on serum resistance of *M. catarrhalis*. Similar to the majority of disease isolates of *M. catarrhalis* (Hol et al., 1993; 1995; Verduin et al., 1994), the wild-type strain O35E was resistant to killing by normal human serum in vitro (Helminen et al., 1993b). To examine the effect of the lack of expression of UspA1 or UspA2 on serum resistance, the wild-type strain and the three mutant strains were tested in a serum bactericidal assay. Both the wild-type strain (FIG. 17, closed diamonds) and the uspA1 mutant O35E.1 (FIG. 17, closed triangles) were able to grow in the presence of normal human serum, indicating that lack of expression of UspA1 did not adversely affect the ability of strain O35E.1 to resist killing by normal human serum. However, both the uspA2 mutant O35E.2 (FIG. 17, closed circles) and the uspA1 uspA2 double mutant O35E.12 (FIG. 17, closed squares), having in common the lack of expression of UspA2, were readily killed by normal human serum. Heat-based inactivation of the complement system present in this normal human serum eliminated the ability of this serum to kill these latter two mutants (FIG. 17, open circles and squares).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

EPO Appl. Publ. No. 0036776

U.S. Pat. No. 5,552,146

U.S. Pat. No. 5,310,687

U.S. Pat. No. 5,238,808

U.S. Pat. No. 5,221,605

U.S. Pat. No. 4,608,251

U.S. Pat. No. 4,603,102

U.S. Pat. No. 4,601,903

U.S. Pat. No. 4,599,231

U.S. Pat. No. 4,599,230

U.S. Pat. No. 4,596,792

U.S. Pat. No. 4,578,770

U.S. Pat. No. 4,554,101

U.S. Pat. No. 4,452,901

U.S. Pat. No. 4,367,110

U.S. Pat. No. 4,358,535

U.S. Pat. No. 4,196,265

U.S. Pat. No. 4,174,384

U.S. Pat. No. 3,949,064

U.S. Pat. No. 3,791,932

Aebi, Stone, Beucher, Cope, Maciver, Thomas, McCracken Jr., Sparling, Hansen, "Expression of the CopB outer membrane protein by *Moraxella catarrhalis* is regulated by iron and affects iron acquisition from transferrin and lactoferrin," *Infect. Immun.,* 64:2024-2030, 1996.

Altschul, Gish, Miller, Myers and Lipman. "Basic local alignment search tool," *J. Mol. Biol.,* 215:403-410, 1990.

Baichwal and Sugden, In: *GENE TRANSFER* Kucherlapati, R., ed. New York: Plenum Press, pp. 117-148, 1986.

Barenkamp and St. Geme III, "Identification of a second family of high-molecular-weight adhesion proteins expressed by nontypable *Haemophilus influenzae," Mol. Microbiol.,* 19:1215-1223, 1996.

Bartos and Murphy, "Comparison of the outer membrane proteins of 50 strains of *Branhamella catarrhalis," J. Infect. Dis.,* 158:761-765, 1988.

Benz and Schmidt, "Cloning and expression of an adhesin (AIDA-I) involved in diffuse adherence of enteropathic *Escherichia coli," Infect. Immun.,* 57:1506-1511, 1989.

Benz and Schmidt, "Isolation and serologic characterization of AIDA-I, the adhesin mediating the diffuse adherence phenotype of the diarrhea-associated *Escherichia coli* strain 2787 (0126:H27)," *Infect. Immun.,* 60:13-18, 1992b.

Berk, *Arch. Intern. Med.,* 150:2254-2257, 1990.

Bliska, Copass, Falkow, "The *Yersinia pseudotuberculosis* adhesin YadA mediates intimate bacterial attachment to and entry into HEp-2 cells," *Infect. Immun.,* 61:3914-3921, 1993.

Bluestone, "Otitis media and sinusitis in children: role of *Branhamella catarrhalis," Drugs,* 31(Suppl. 3):132-141, 1986.

Bluestone, Stephenson, Martin, "Ten-year review of otitis media pathogens," *Pediatr. Infect. Dis. J.,* 11:S7-S11, 1992.

Bolivar et al., *Gene,* 2:95, 1977.

Brutlag et al, *CABIOS,* 6:237-245, 1990.

Campagnari, Shanks, Dyer, "Growth of *Moraxella catarrhalis* with human transferrin and lactoferrin: Expression of iron-repressible proteins without siderophore production," *Infect. Immun.,* 62:4909-4914, 1994.

Catlin, "*Branhamella catarrhalis*: an organism gaining respect as a pathogen," *Clin. Microbiol. Rev.,* 3:293-320, 1990.

Chang et al., *Nature,* 375:615, 1978.

Chapman et al., *J. Infect. Dis.,* 151:878-882, 1985.

Chen, McMichael, Vandermeid, Hahn, Smith, Eldridge, Cowell, "Antibodies to the UspA outer membrane protein of *Moraxella catarrhalis* block bacterial attachment in vitro and are protective in a murine pulmonary challenge model," *Abstracts General Meeting Amer. Soc. Microbiol.,* E-53:290, 1995.

China, Sory, N'Guyen, de Bruyere, Cornelis, "Role of YadA protein in prevention of osponization of *Yersinia enterocolitica* by C3b molecules," *Infect. Immun.,* 61:3129-3136, 1993.

Christensen, Renneberg, Bruun, Forsgren, "Serum antibody response to proteins of *Moraxella* (*Branhamella*) *catarrhalis* in patients with lower respiratory tract infection," *Clin. Diagn. Lab. Immunol.,* 2:14-17, 1995.

Coligan et al. (eds), In: *CURRENT PROTOCOLS IMMUNOLOGY*, John Wiley, New York, ch. 2.5, 1991.

Consensus, *Pediater. Infect. Dis. J.*, 8:S94-S97, 1989.

Davies and Maesen, "The epidemiology of respiratory tract pathogens in Southern Netherlands," *Eur. Respir. J.*, 1:415-420, 1988.

Devereux, Haeberli and Smithies, "A comprehensive set of sequence analysis programs for the VAX," *Nucleic Acids Res.*, 12:387-395, 1984.

Doern, *Diag. Microbiol. Infect. Dis.*, 4:191-201, 1986.

Doyle, *Peditr. Infect. Dis. J.*, 8(Suppl):S45-7, 1989.

Faden et al., *Ann. Otol. Rhinol. Layngol*, 100:612-615, 1991.

Faden et al., *Pediatr. Infect. Dis. J.*, 9:623-626, 1990.

Faden, "Comparison of the local immune response to non-typeable *Haemophilus influenzae* (nHI) and *Moraxella catarrhalis* (MC) during otitis media," In: *Advances in Mucosal Immunology*, J. Mestecky and et al. (ed.), Plemun Press, New York, p. 733-736, 1995.

Faden, Duffy, Wasielewski, Wolf, Krystofik, Tung, Tonawanda/Williamsburg Pediatrics, "Relationship between nasopharyngeal colonization and the development of otitis media in children," *J. Infect. Dis.*, 175:1440-1445, 1997.

Faden, Harabuchi, Hong, Tonawanda/Williamsburg Pediatrics, "Epidemiology of *Moraxella catarrhalis* in children during the first 2 years of life: Relationship to otitis media," *J. Infect. Dis.*, 169:1312-1317, 1994.

Faden, Hong and Murphy, "Immune response to outer membrane antigens of *Moraxella catarrhalis* in children with otitis media," *Infect. Immun.*, 60:3824-3829, 1992.

Fetrow & Bryant, *Biotechnology*, 11:479-483, 1993.

Fitzgerald, Mulcahy, Murphy, Keane, Coakley, Scott, "A 200 kDa protein is associated with haemagglutinating isolates of *Moraxella* (*Branhaemella*) *catarrhalis*," *FEMS Immunol. Med. Microbiol.*, 18:209-216, 1997.

Fleischmann, Adams, White, Clayton, Kirkness, Kerlavage, Bult, Tomb, Dougherty, Merrick, McKenney, Sutton, FitzHugh, Fields, Gocayne, Scott, Shirley, Liu, Glodek, Kelley, Weidman, Phillips, Spriggs, Hedblom, Cotton, Utterback, Hanna, Nguyen, Saudek, Brandon, Fine, Frichman, Fuhrmann, Geoghagen, Gnehm, McDonald, Small, Fraser, Smith and Venter, "Whole-genome random sequencing and assembly of *Haemophilus influenzae* Rd.," *Science*, 269:496-512, 1995.

Gefter et al., *Somatic Cell Genet.*, 3:231-236, 1977.

Gish and States, "Identification of protein coding regions by database similarity search," *Nat. genet.*, 3:266-272, 1993.

Glorioso et al., *Ann. Rev. Microbiol.* 49:675-710, 1995.

Goeddel et al., *Nature* 281:544, 1979.

Goeddel et al., *Nucleic Acids Res.*, 8:4057, 1980.

Goldblatt, Scadding, Lund, Wade, Turner, Pandey, "Association of Gm allotypes with the antibody response to the outer membrane proteins of a common upper respiratory tract organism, *Moraxella catarrhalis*," *J. Immunol.*, 153:5316-5320, 1994.

Goldblatt, Turner, and Levinsky, "*Branhamella catarrhalis*: antigenic determinants and the development of the IgG subclass response in childhood," *J. Infect. Dis.*, 162:1128-1135, 1990.

Hager, Verghese, Alvarez, Berk, "*Branhamella catarrhalis* respiratory infections," *Rev. Infect. Dis.*, 9:1140-1149, 1987.

Helminen, Beach, Maciver, Jarosik, Hansen, Leinonen, "Human immune response against outer membrane proteins of *Moraxella* (*Branhamella*) *catarrhalis* determined by immunoblotting and enzyme immunoassay," *Clin. Diagn. Lab. Immunol.*, 2:35-39, 1995.

Helminen, Maciver, Latimer, Cope. McCracken Jr., and Hansen, "A major outer membrane protein of *Moraxella catarrhalis* is a target for antibodies that enhance pulmonary clearance of the pathogen in an animal model," *Infect. Immun.*, 61:2003-2010, 1993a.

Helminen, Maciver, Latimer, Klesney-Tait, Cope, Paris, McCracken Jr., and Hansen, "A large, antigenically conserved protein on the surface of *Moraxella catarrhalis* is a target for protective antibodies," *J. Infect. Dis.*, 170:867-872, 1994.

Helminen, Maciver, Latimer, Lumbley, Cope, McCracken, Jr., and Hansen, "A mutation affecting expression of a major outer membrane protein of *Moraxella catarrhalis* alters serum resistance and survival of this organism in vivo," *J. Infect. Dis.*, 168:1194-1201, 1993b.

Hess et al., *J. Adv. Enzyme Reg.*, 7:149, 1968.

Hitzeman et al., *J. Biol. Chem.*, 255:2073, 1980.

Hol, Verduin, Van Dijke, Verhoef, Fleer, van Dijk, "Complement resistance is a virulence factor of *Branhamella* (*Moraxella*) *catarrhalis*," *FEMS Immunol. Med. Microbiol.*, 11:207-212, 1995.

Hol, Verduin, van Dijke, Verhoef, van Dijk, "Complement resistance in *Branhamella* (*Moraxella*) *catarrhalis*," *Lancet*, 341:1281, 1993.

Holland et al., *Biochemistry*, 17:4900, 1978.

Horstmann, Sievertsen, Knobloch, Fischetti, "Antiphagocytic activity of streptococcal M protein: selective binding of complement control protein factor H," *Proc. Natl. Acad. Sci. USA*, 85:1657-1661, 1988.

Hsiao, Sethi, Murphy, "Outer membrane protein CD of *Branhamella catarrhalis*—Sequence conservation in stains recovered from the human respiratory tract," *Microb. Pathog.*, 19:215-225, 1995.

Itakura et al., *Science*, 198:1056, 1977.

Jameson and Wolf, *Comput. Appl. Biosci.*, 4(1):181-186, 1988.

Jones, *Genetics*, 85:12, 1977.

Jordan, Berk, Berk, "A comparison of serum bactericidal activity and phenotypic characteristics of bacteremic, pneumonia-causing strains, and colonizing strains of *Branhamella catarrhalis*," *Am. J. Med.*, 88(5A):28S-32S, 1990.

Kimura, Gulig, McCracken, Loftus and Hansen, "A minor high-molecular-weight outer membrane protein of *Haemophilus influenzae* type b is a protective antigen," *Infect. Immun.*, 47:253-259, 1985.Kingsman et al., *Gene*, 7:141, 1979.

Klesney-Tait, Hiltke, Spinola, Radolf, Hansen, "The major outer membrane protein of *Haemophilus ducreyi* consists of two OmpA homologs," *J. Bacteriol.*, 179:1764-1773, 1997.

Klingman and Murphy, "Purification and characterization of a high-molecular-weight outer membrane protein of *Moraxella* (*Branhamella*) *catarrhalis*," *Infect. Immun.*, 62:1150-1155, 1994.

Klingman, Pye, Murphy, Hill, "Dynamics of respiratory tract colonization by *Branhamella catarrhalis* in bronchiectasis," *Am. J. Respir. Crit. Care Med.*, 152:1072-1078, 1995.

Kohler & Milstein, *Eur. J. Immunol.*, 6:511-519, 1976.

Kohler & Milstein, *Nature*, 256:495-497, 1975.

Kovatch, Wald, Michaels, "β-Lactamase-producing *Branhamella catarrhalis* causing otitis media in children," *J. Pediatr.*, 102:261-264, 1983.

Kyte & Doolittle, *J. Mol. Biol.*, 157:105-132, 1982.

Leininger, Bowen, Renauld-Mongenie, Rouse, Menozzi, Locht, Heron, Brennan, "Immunodominant domains present on the *Bordetella pertussis* vaccine component filamentous hemagglutinin," *J. Infect. Dis.*, 175:1423-1431, 1997.

Leinonen et al., *J. Infect. Dis.*, 144:570-574, 1981.

Maniatis, Fritsch and Sambrook, *Molecular Cloning: A Laboratory Manual*, Cold Spring Harbor Laboratory Press, Cold Spring Harbor, N.Y., 1982.

Marchant, *Am. J. Med.*, 88(Suppl. 5A):15S-19S, 1990.

McGehee, *Am. J. Respir. Cell Mol. Biol.*, 1:201-210, 1989.

McLeod, Ahmad, Capewell, Croughan, Calder, Seaton, "Increase in bronchopulmonary infection due to *Branhamella catarrhalis*," *Br. Med. J. [Clin. Res].*, 292:1103-1105, 1986.

Melendez & Johnson, *Rev. Infect. Dis.*, 13:428-429, 1990.

Murphy and Bartos, "Surface exposed and antigenically conserved determinants of outer membrane proteins of *Branhamella catarrhalis*," *Infect. Immun.*, 57:2938-2941, 1989.

Murphy and Loeb, "Isolation of the outer membrane of *Branhamella catarrhalis*," *Microb. Pathog.*, 6:159-174, 1989.

Murphy et al., *Am. Jrnl. Med.*, 88:5A-41S-5A-45S, 1990.

Murphy, Kirkham and Lesse, "The major heat-modifiable outer membrane protein CD is highly conserved among strains of *Branhamella catarrhalis*," *Mol. Microbiol.*, 10:87-97, 1993.

Murphy, *Pediat. Infect. Dis. J.*, 8: S75-S77, 1989.

Nicolas and Rubenstein, In: *Vectors: A survey of molecular cloning vectors and their uses*, Rodriguez and Denhardt (eds.), Stoneham: Butterworth, pp. 494-513, 1988.

Nicotra, Rivera, Liman, Wallace, "*Branhamella catarrhalis* as a lower respiratory tract pathogen in patients with chronic lung disease," *Arch. Intern. Med.*, 146:890-893, 1986.

Patrick, Kimura, Jackson, Hermanstorfer, Hood, McCracken Jr., Hansen, "Antigenic characterization of the oligosaccharide portion of the lipooligosaccharide of nontypable *Haemophilus influenzae*," *Infect. Immun.*, 55:2902-2911, 1987.

Pilz, Vocke, Heesemann, Brade, "Mechanism of YadA-mediated serum resistance of *Yersinia enterocolitica* serotype O3." *Infect. Immun.*, 60:189-195, 1992.

Reddy, Murphy, Faden, Bernstein, "Middle ear mucin glycoprotein; Purification and interaction with nontypeable *Haemophilus influenzae* and *Moraxella catarrhalis*," *Otolaryngol. Head Neck Surg.*, 116:175-180, 1997.

Ridgeway, In: Vectors: A survey of molecular cloning vectors and their uses. Stoneham: Butterworth, Rodriguez R L, Denhardt D T, ed., pp. 467-492, 1988.

Sambrook, Fritsch and Maniatis, *Molecular Cloning—A Laboratory Manual*, Cold Spring Harbor Laboratory Press, Cold Spring Harbor, N.Y., 1989.

Sarubbi et al., *Am. J. Med.*, 88(Suppl. 5A):9S-14S, 1990.

Schonheyder & Ejlertsen, *Eur. J. Clin. Microbiol. Infect. Dis.*, 8:299-300, 1989.

Shine and Dalgarno, "Determinant of cistron specificity in bacterial ribosomes," *Nature* 254:34-38, 1975.

Skurnik and Wolf-Watz, "Analysis of the yopA gene encoding the Yop1 virulence determinants of *Yersinia* spp.," *Mol. Microbiol.*, 3:517-529, 1989.

Soto-Hernandez, Holtsclaw-Berk, Harvill, Berk, "Phenotypic characteristics of *Branhamella catarrhalis* strains," *J. Clin. Microbiol.*, 27:903-908, 1989.

St. Geme III and Falkow, "*Haemophilus influenzae* adheres to and enters cultured human epithelial cells," *Infect. Immun.*, 58:4036-4044, 1990.

St. Geme III, Cutter, Barenkamp, "Characterization of the genetic locus encoding *Haemophilus influenzae* type b surface fibrils," *J. Bacteriol.*, 178:6281-6287, 1996.

Stinchcomb et al., *Nature*, 282:39, 1979.

Temin, In: *Gene Transfer*, Kucherlapati (ed.), New York: Plenum Press, pp. 149-188, 1986.

*Tissue Culture*, Academic Press, Kruse and Patterson, editors, 1973.

Tschemper et al., *Gene*, 10:157, 1980.

Unhanand et al., *J. Infect. Dis.*, 165:644-650, 1992.

Verduin, Bootsma, Hol, Fleer, Jansze, Klingman, Murphy, van Dijk, "Complement resistance in *Moraxella (Branhamella) catarrhalis* is mediated by a high-molecular-weight outer membrane protein (HMW-OMP)," *Abstracts General Meeting Amer. Soc. Microbiol.*, B137:189(Abstract), 1995.

Verduin, Jansze, Hol, Mollnes, Verhoef, van Dijk, "Differences in complement activation between complement-resistant and complement-sensitive *Moraxella (Branhamella) catarrhalis* strains occur at the level of membrane attack complex formation," *Infect. Immun.*, 62:589-595, 1994.

Verghese et al., *J. Infect. Dis.*, 162:1189-92, 1990.

Weinberger et al., *Science*, 228:740-742, 1985.

Wolf et al., *Comput. Appl. Biosci.*, 4(1):187-191, 1988.

Wright & Wallace, *Semin. Respir. Infect.*, 4:40-46, 1989.

What is claimed is:

1. An isolated nucleic acid encoding the UspA2 antigen (SEQ ID NO:15) of the *M. catarrhalis* isolate TTA37.

2. An isolated nucleic acid having the uspA2 DNA sequence (SEQ ID NO:16) of the *M. catarrhalis* isolate TTA37.

* * * * *

UNITED STATES PATENT AND TRADEMARK OFFICE
CERTIFICATE OF CORRECTION

PATENT NO. : 7,569,683 B2  Page 1 of 1
APPLICATION NO. : 12/044818
DATED : August 4, 2009
INVENTOR(S) : Eric J. Hansen et al.

It is certified that error appears in the above-identified patent and that said Letters Patent is hereby corrected as shown below:

In title page, item (73) Assignees, line 3, delete "Holding" and insert --Holdings-- therefor.

In column 1, line 6, delete "Jun. 21, 2004" and insert --March 18, 2008-- therefor.

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

PATENT NO. : 7,569,683 B2  Page 1 of 1
APPLICATION NO. : 12/044818
DATED : August 4, 2009
INVENTOR(S) : Eric J. Hansen et al.

It is certified that error appears in the above-identified patent and that said Letters Patent is hereby corrected as shown below:

In column 1, line 16, insert
--STATEMENT REGARDING FEDERALLY SPONSORED RESEARCH

This invention was made with government support under grant numbers AI-23366 and AI-36344 awarded by the National Institutes of Health. The government has certain rights in the invention.--.

Signed and Sealed this

Tenth Day of November, 2009

David J. Kappos
*Director of the United States Patent and Trademark Office*